US012168688B2

(12) United States Patent
Yang et al.

(10) Patent No.: US 12,168,688 B2
(45) **Date of Patent: *Dec. 17, 2024**

(54) ANTIBODIES AND VARIANTS THEREOF AGAINST PD-L1

(71) Applicant: NANJING LEGEND BIOTECH CO., LTD., Jiangsu (CN)

(72) Inventors: Shuai Yang, Jiangsu (CN); Chuan-Chu Chou, Westfield, NJ (US); Shu Wu, Jiangsu (CN); Liusong Yin, Jiangsu (CN); Feng Lin, Jiangsu (CN)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 583 days.

This patent is subject to a terminal disclaimer.

(21) Appl. No.: 15/733,313

(22) PCT Filed: Dec. 28, 2018

(86) PCT No.: PCT/CN2018/124925

§ 371 (c)(1),
(2) Date: Jun. 24, 2020

(87) PCT Pub. No.: WO2019/129211

PCT Pub. Date: Jul. 4, 2019

(65) Prior Publication Data

US 2022/0135687 A1 May 5, 2022

(30) Foreign Application Priority Data

Dec. 28, 2017 (WO) ................ PCT/CN2017/119505

(51) Int. Cl.
*C07K 16/28* (2006.01)
*A61P 35/00* (2006.01)

(52) U.S. Cl.
CPC .......... *C07K 16/2827* (2013.01); *A61P 35/00* (2018.01); *C07K 16/2803* (2013.01);
(Continued)

(58) Field of Classification Search
CPC ........... C07K 16/2827; C07K 16/2803; C07K 16/2818; C07K 16/2896; C07K 2317/24;
(Continued)

(56) References Cited

U.S. PATENT DOCUMENTS 3,773,919 A 11/1973 Boswell et al.
4,676,980 A 6/1987 Segal et al.
(Continued)

FOREIGN PATENT DOCUMENTS

CA 3004804 A1 5/2017
CN 101104640 A 1/2008
(Continued)

OTHER PUBLICATIONS

Chailyan, A., et al (2011) The association of heavy and light chain variable domains in antibodies: implications for antigen specificity FEBS Journal 278; 2858-2866 (Year: 2011).*
(Continued)

*Primary Examiner* — Joanne Hama
*Assistant Examiner* — Pratik Thapa
(74) *Attorney, Agent, or Firm* — Fish & Richardson P.C.

(57) ABSTRACT

The present application provides an antibody, such as a monoclonal antibody (mAb), or an antigen binding fragment thereof, that specifically recognizes PD-L1. Also provided are pharmaceutical compositions, or methods of making and using the antibody or antigen binding fragment thereof.

21 Claims, 33 Drawing Sheets

Specification includes a Sequence Listing.

(52) U.S. Cl.
CPC ...... *C07K 16/2818* (2013.01); *C07K 16/2896* (2013.01); *C07K 2317/24* (2013.01); *C07K 2317/33* (2013.01); *C07K 2317/73* (2013.01); *C07K 2317/76* (2013.01); *C07K 2317/92* (2013.01)

(58) Field of Classification Search
CPC ............ C07K 2317/33; C07K 2317/73; C07K 2317/76; C07K 2317/92; A61P 35/00; A61K 2039/505
See application file for complete search history.

(56) References Cited

U.S. PATENT DOCUMENTS

| | | | | |
|---|---|---|---|---|
| 4,816,567 | A | 3/1989 | Cabilly et al. | |
| 5,225,539 | A | 7/1993 | Winter | |
| 5,500,362 | A | 3/1996 | Robinson et al. | |
| 5,545,806 | A | 8/1996 | Lonberg et al. | |
| 5,545,807 | A | 8/1996 | Surani et al. | |
| 5,569,825 | A | 10/1996 | Lonberg et al. | |
| 5,571,894 | A | 11/1996 | Wels et al. | |
| 5,587,458 | A | 12/1996 | King et al. | |
| 5,624,821 | A | 4/1997 | Winter et al. | |
| 5,625,126 | A | 4/1997 | Lonberg et al. | |
| 5,633,425 | A | 5/1997 | Lonberg et al. | |
| 5,637,481 | A * | 6/1997 | Ledbetter | C07K 16/2827 435/69.6 |
| 5,641,870 | A | 6/1997 | Rindrknecht et al. | |
| 5,648,260 | A | 7/1997 | Winter et al. | |
| 5,661,016 | A | 8/1997 | Lonberg et al. | |
| 5,731,168 | A | 3/1998 | Carter et al. | |
| 5,750,373 | A | 5/1998 | Garrard et al. | |
| 5,770,429 | A | 6/1998 | Lonberg et al. | |
| 5,821,337 | A | 10/1998 | Carter et al. | |
| 5,869,046 | A | 2/1999 | Presta et al. | |
| 6,075,181 | A | 6/2000 | Kucherlapati et al. | |
| 6,150,584 | A | 11/2000 | Kucherlapati et al. | |
| 6,194,551 | B1 | 2/2001 | Idusogie et al. | |
| 6,602,684 | B1 | 8/2003 | Umana et al. | |
| 6,737,056 | B1 | 5/2004 | Presta | |
| 6,982,321 | B2 | 1/2006 | Winter | |
| 7,041,870 | B2 | 5/2006 | Tomizuka et al. | |
| 7,087,409 | B2 | 8/2006 | Barbas, III et al. | |
| 7,189,826 | B2 | 3/2007 | Rodman | |
| 7,332,581 | B2 | 2/2008 | Presta | |
| 7,371,826 | B2 | 5/2008 | Presta | |
| 7,371,849 | B2 | 5/2008 | Honda et al. | |
| 7,521,541 | B2 | 4/2009 | Eigenbrot et al. | |
| 7,527,791 | B2 | 5/2009 | Adams et al. | |
| 8,552,154 | B2 * | 10/2013 | Freeman | A61P 3/10 424/130.1 |
| 8,754,287 | B2 | 6/2014 | MacDonald et al. | |
| 2002/0164328 | A1 | 11/2002 | Shinkawa et al. | |
| 2003/0115614 | A1 | 6/2003 | Kanda et al. | |
| 2003/0157108 | A1 | 8/2003 | Presta | |
| 2004/0093621 | A1 | 5/2004 | Shitara et al. | |
| 2004/0109865 | A1 | 6/2004 | Niwa et al. | |
| 2004/0110282 | A1 | 6/2004 | Kanda et al. | |
| 2004/0110704 | A1 | 6/2004 | Yamane et al. | |
| 2004/0132140 | A1 | 7/2004 | Satoh et al. | |
| 2005/0014934 | A1 | 1/2005 | Hinton et al. | |
| 2005/0079574 | A1 | 4/2005 | Bond | |
| 2005/0119455 | A1 | 6/2005 | Fuh et al. | |
| 2005/0123546 | A1 | 6/2005 | Umana et al. | |
| 2005/0266000 | A1 | 12/2005 | Bond et al. | |
| 2006/0025576 | A1 | 2/2006 | Miller et al. | |
| 2007/0061900 | A1 | 3/2007 | Murphy et al. | |
| 2007/0117126 | A1 | 5/2007 | Sidhu et al. | |
| 2007/0160598 | A1 | 7/2007 | Dennis et al. | |
| 2007/0237764 | A1 | 10/2007 | Birtalan et al. | |
| 2007/0292936 | A1 | 12/2007 | Barthelemy et al. | |
| 2009/0002360 | A1 | 1/2009 | Chen et al. | |
| 2009/0307787 | A1 | 12/2009 | Grosveld et al. | |
| 2010/0122358 | A1 | 5/2010 | Brueggemann et al. | |
| 2011/0028695 | A1 | 2/2011 | Revets et al. | |
| 2015/0289489 | A1 | 10/2015 | MacDonald et al. | |
| 2017/0137517 | A1 * | 5/2017 | Bowman | A61P 35/04 |
| 2017/0204184 | A1 | 7/2017 | Zha | |
| 2018/0326054 | A1 * | 11/2018 | Codarri Deak | A61K 39/3955 |

FOREIGN PATENT DOCUMENTS

| | | | | |
|---|---|---|---|---|
| CN | 104072613 A | | 10/2014 | |
| CN | 105777906 A | | 7/2016 | |
| CN | 105968200 A | | 9/2016 | |
| CN | 107488229 | * | 12/2017 | C07K 16/468 |
| CN | 108239149 | * | 7/2018 | A61K 39/395 |
| CN | 108239149 A | | 7/2018 | |
| EP | 0404097 | | 12/1990 | |
| WO | WO 1991/010741 | | 7/1991 | |
| WO | WO 1993/001161 | | 1/1993 | |
| WO | WO 1993/008829 | | 5/1993 | |
| WO | WO 1993/011161 | | 6/1993 | |
| WO | WO 1993/016185 | | 8/1993 | |
| WO | WO 1994/029351 | | 12/1994 | |
| WO | WO 1996/033735 | | 10/1996 | |
| WO | WO 1996/034096 | | 10/1996 | |
| WO | WO 1996/034103 | | 10/1996 | |
| WO | WO1997/030087 | | 8/1997 | |
| WO | WO 1998/024893 | | 6/1998 | |
| WO | WO 1998/058964 | | 12/1998 | |
| WO | WO 1999/022764 | | 5/1999 | |
| WO | WO 1999/051642 | | 10/1999 | |
| WO | WO 2000/061739 | | 10/2000 | |
| WO | WO 2001/029246 | | 4/2001 | |
| WO | WO 2002/031140 | | 4/2002 | |
| WO | WO 2003/011878 | | 2/2003 | |
| WO | WO 2003/084570 | | 10/2003 | |
| WO | WO 2003/085107 | | 10/2003 | |
| WO | WO 2003/085119 | | 10/2003 | |
| WO | WO 2004/042072 | | 5/2004 | |
| WO | WO 2004/049794 | | 6/2004 | |
| WO | WO 2004/056312 | | 7/2004 | |
| WO | WO 2004/092219 | | 10/2004 | |
| WO | WO 2005/035586 | | 4/2005 | |
| WO | WO 2005/035778 | | 4/2005 | |
| WO | WO 2005/053742 | | 6/2005 | |
| WO | WO 2005/100402 | | 10/2005 | |
| WO | WO 2006/029879 | | 3/2006 | |
| WO | WO 2008/077546 | | 7/2008 | |
| WO | WO 2009/089004 | | 7/2009 | |
| WO | 2010077634 A1 | | 7/2010 | |
| WO | 2013079174 A1 | | 6/2013 | |
| WO | 2015112805 A1 | | 7/2015 | |
| WO | 2016000619 A1 | | 1/2016 | |
| WO | WO2017/020858 | | 2/2017 | |
| WO | 2017084495 A1 | | 5/2017 | |
| WO | 2017161976 A1 | | 9/2017 | |
| WO | WO2017/148424 | | 9/2017 | |
| WO | WO2017/181031 | | 10/2017 | |
| WO | 2017197667 A1 | | 11/2017 | |
| WO | WO2017/193032 | | 11/2017 | |
| WO | WO2017/215590 | | 12/2017 | |
| WO | WO2017/218707 | | 12/2017 | |
| WO | WO2019/129211 | | 7/2019 | |

OTHER PUBLICATIONS

Bannas P, Hambach J, Koch-Nolte F. Nanobodies and Nanobody-Based Human Heavy Chain Antibodies As Antitumor Therapeutics. Front Immunol. Nov. 22, 2017;8:1603. doi: 10.3389/fimmu.2017.01603. PMID: 29213270; PMCID: PMC5702627. (Year: 2017).*

Chichili et al. Co-targeting of PD-1 and CTLA-4 inhibitory pathways with bispecific DART® and TRIDENT™ molecules [abstract]. In: Proceedings of the American Association for Cancer Research Annual Meeting 2017; Apr. 1-5, 2017; Washington, DC. Philadelphia (PA): AACR; Cancer Res 2017;77(13 Suppl) (Year: 2017).*

Janeway CA Jr, Travers P, Walport M, et al. Immunobiology: The Immune System in Health and Disease. 5th edition. New York: Garland Science; 2001. Chapter 3 The structure of a typical anti-

(56) References Cited

OTHER PUBLICATIONS body molecule. Available from: https://www.ncbi.nlm.nih.gov/books/NBK27144/ (Year: 2001).*
Shen J, Vil MD, Jimenez X, Iacolina M, Zhang H, Zhu Z. Single variable domain-IgG fusion. A novel recombinant approach to Fc domain-containing bispecific antibodies. J Biol Chem. Apr. 21, 2006;281(16): 10706-14. doi: 10.1074/jbc.M513415200. Epub Feb. 15, 2006. PMID: 16481314. (Year: 2006).*
Chen, Yuh-Min: "Immune checkpoint inhibitors for nonsmall cell lung cancer treatment", Journal of the Chinese Medical Association, Elsevier (Singapore) PTE LTD, Hong Kong Branch, HK, vol. 80, No. 1, Sep. 29, 2016 (Sep. 29, 2016), pp. 7-14, XP029871241, ISSN: 1726-4901, DOI: 10.1016/J.JCMA.2016.08.005.
Martin J. Scott et al: "In-Format' screening of a novel bispecific antibody format reveals significant potency improvements relative to unformatted molecules", MABS, vol. 9, No. 1, Oct. 27, 2016 (Oct. 27, 2016), pp. 85-93, XP055515015, US ISSN: 1942-0862, DOI: 10.1080/19420862.2016.1249078.
International Search Report issued Mar. 27, 2019 in International Application No. PCT/CN2018/124925.
Wulfing et al., "For optimal antibody effectiveness, sometimes less is more," Nature, Feb. 1, 2023, 614(7948):416-418.
Yu et al., "Reducing affinity as a strategy to boost immunomodulatory antibody agonism," Nature, Feb. 1, 2023, 614(7948):539-547 (Author Copy, 46 pages).
Inman et al., "Atezolizumab: A PD-L1-Blocking Antibody for Bladder Cancer," Clinical Cancer Research, Apr. 15, 2017, 23(8):1886-1890 (6 pages).
EP Office Action in European Appln. No. 18894417.7, dated Jun. 15, 2023, 10 pages.
JP Office Action in Japanese Appln. No. 2020-536100, Mailed on Jun. 13, 2023, 5 pages (with English translation).
JP Office Action in Japanese Appln. No. 2020-536100, Mailed on Jan. 10, 2023, 14 pages (with English translation).

* cited by examiner

E

F

G

H

I

J

A

B

D

C

F

E

G

H

I

J

SEQUENCE LISTING

<160> NUMBER OF SEQ ID NOS: 403

<210> SEQ ID NO 1
<211> LENGTH: 115
<212> TYPE: PRT
<213> ORGANISM: Artificial Sequence
<220> FEATURE:
<223> OTHER INFORMATION: Mouse VH

<400> SEQUENCE: 1

```
Asp Val Gln Leu Gln Glu Ser Gly Pro Asp Leu Val Lys Pro Ser Gln
1               5                   10                  15
```

```
Ser Leu Ser Leu Thr Cys Thr Val Thr Gly Tyr Ser Ile Thr Ser Gly
            20                  25                  30

Tyr Thr Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Met Thr Ala Glu Asp Thr Ala Thr Tyr Tyr Cys
                85                  90                  95

Ala Arg Asn Ser Leu Phe Ala Ser Trp Gly His Gly Thr Leu Val Thr
            100                 105                 110

Val Ser Ala
        115


<210> SEQ ID NO 2
<211> LENGTH: 120
<212> TYPE: PRT
<213> ORGANISM: Artificial Sequence
<220> FEATURE:
<223> OTHER INFORMATION: Mouse VH

<400> SEQUENCE: 2

Asp Val Gln Leu Gln Gly Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asp Trp Ile Arg Gln Phe Pro Gly Asn Lys Leu Glu Trp
        35                  40                  45

Met Gly His Ile Arg Phe Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ala Arg Ser Thr Leu Ile Thr Lys Gly Phe Phe Asp Tyr Trp Gly Gln
            100                 105                 110

Gly Thr Thr Leu Thr Val Ser Ser
        115                 120


<210> SEQ ID NO 3
<211> LENGTH: 119
<212> TYPE: PRT
<213> ORGANISM: Artificial Sequence
<220> FEATURE:
<223> OTHER INFORMATION: Mouse VH

<400> SEQUENCE: 3

Gln Val Gln Leu Gln Gln Ser Gly Ala Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Ser Trp Val Lys Gln Arg Thr Gly Gln Gly Leu Glu Trp Ile
        35                  40                  45

Gly Glu Ile Phe Pro Arg Thr Ala Asn Thr Tyr Phe Asn Glu Lys Phe
    50                  55                  60

Lys Gly Lys Ala Thr Leu Thr Ala Asp Lys Ser Ser Ser Thr Ala Tyr
```

```
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Tyr Ala Leu Asp Tyr Trp Gly Gln Gly
            100                 105                 110

Thr Ser Val Thr Val Ser Ser
        115


<210> SEQ ID NO 4
<211> LENGTH: 113
<212> TYPE: PRT
<213> ORGANISM: Artificial Sequence
<220> FEATURE:
<223> OTHER INFORMATION: Mouse VH

<400> SEQUENCE: 4

Asp Val Gln Leu Leu Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Asn Leu Glu Trp
        35                  40                  45

Met Gly Ser Ile Asn Tyr Asp Gly Ser Asn Asp Tyr Asn Pro Ser Leu
    50                  55                  60

Gln Asp Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Arg Leu Asp Tyr Trp Gly Gln Gly Thr Thr Leu Ile Val Ser
            100                 105                 110

Ser


<210> SEQ ID NO 5
<211> LENGTH: 119
<212> TYPE: PRT
<213> ORGANISM: Artificial Sequence
<220> FEATURE:
<223> OTHER INFORMATION: Mouse VH

<400> SEQUENCE: 5

Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser
        115
```

<210> SEQ ID NO 6
<211> LENGTH: 121
<212> TYPE: PRT
<213> ORGANISM: Artificial Sequence
<220> FEATURE:
<223> OTHER INFORMATION: Mouse VH

<400> SEQUENCE: 6

```
Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Ser Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Asn Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Thr Gly Ile Ile Thr Val Ile Ala Thr Arg Asp Asp Tyr Trp Gly
            100                 105                 110

Gln Gly Thr Thr Leu Thr Val Ser Ser
        115                 120
```

<210> SEQ ID NO 7
<211> LENGTH: 123
<212> TYPE: PRT
<213> ORGANISM: Artificial Sequence
<220> FEATURE:
<223> OTHER INFORMATION: Mouse VH

<400> SEQUENCE: 7

```
Glu Gly Gln Leu Gln Gln Ser Gly Ala Gly Leu Val Lys Pro Gly Ala
1               5                   10                  15

Ser Val Asn Leu Ser Cys Thr Ala Ser Gly Phe Asn Ile Lys Asp Thr
            20                  25                  30

Tyr Ile His Trp Met Lys Gln Arg Pro Glu Gln Gly Leu Glu Trp Ile
        35                  40                  45

Gly Arg Ile Ala Pro Thr Asn Gly Asn Thr Lys Tyr Asp Pro Thr Phe
    50                  55                  60

Gln Gly Lys Ala Thr Ile Thr Ala Asp Ser Ser Ser Asn Thr Ala Tyr
65                  70                  75                  80

Leu Gln Val Ser Ser Leu Thr Ser Glu Asp Thr Ala Val Tyr Tyr Cys
                85                  90                  95

Ser Arg Gly Gly Ile Tyr Tyr Tyr Gly Ser His Trp Tyr Phe Asp Val
            100                 105                 110

Trp Gly Ala Gly Thr Thr Val Thr Val Ser Ser
        115                 120
```

<210> SEQ ID NO 8
<211> LENGTH: 123
<212> TYPE: PRT
<213> ORGANISM: Artificial Sequence
<220> FEATURE:
<223> OTHER INFORMATION: Mouse VH

<400> SEQUENCE: 8

```
Glu Gly Gln Leu Gln Gln Ser Gly Ala Glu Leu Val Lys Pro Gly Ala
1               5                   10                  15
```

```
Ser Val Asn Leu Ser Cys Thr Ala Ser Gly Phe Asn Ile Lys Asp Thr
            20                  25                  30

Tyr Ile His Trp Val Lys Gln Arg Pro Asp Gln Gly Leu Glu Trp Ile
        35                  40                  45

Gly Arg Ile Ala Pro Thr Asn Gly Asn Ala Lys Phe His Pro Thr Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Gly Gly Ile Tyr Tyr Tyr Gly Thr His Trp Tyr Phe Asp Val
            100                 105                 110

Trp Gly Ala Gly Thr Thr Val Thr Val Ser Ser
        115                 120


<210> SEQ ID NO 9
<211> LENGTH: 120
<212> TYPE: PRT
<213> ORGANISM: Artificial Sequence
<220> FEATURE:
<223> OTHER INFORMATION: Mouse VH

<400> SEQUENCE: 9

Gln Val Leu Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Met His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Tyr Gly Asn Tyr Gly Gly Trp Tyr Phe Asp Val Trp Gly Ala
            100                 105                 110

Gly Thr Thr Val Thr Val Ser Ser
        115                 120


<210> SEQ ID NO 10
<211> LENGTH: 119
<212> TYPE: PRT
<213> ORGANISM: Artificial Sequence
<220> FEATURE:
<223> OTHER INFORMATION: Mouse VH

<400> SEQUENCE: 10

Lys Val Gln Leu Gln Gln Ser Gly Ala Glu Leu Val Lys Pro Gly Thr
1               5                   10                  15

Ser Val Lys Leu Ser Cys Lys Ala Ser Gly Tyr Thr Phe Thr Glu Tyr
            20                  25                  30

Ile Ile Tyr Trp Ile Lys Gln Arg Ser Gly Gln Gly Leu Glu Trp Ile
        35                  40                  45

Gly Trp Phe Tyr Pro Gly Thr Gly Ser Ile Lys Tyr Asn Glu Lys Phe
    50                  55                  60

Lys Asp Lys Ala Thr Leu Thr Ala Asp Lys Ser Ser Ser Thr Val Phe
```

-continued

```
65                  70                  75                  80

Met Glu Leu Ser Arg Leu Thr Ser Glu Asp Ser Ala Val Tyr Phe Cys
                85                  90                  95

Ala Arg His Glu Glu Gly Asn Leu Trp Phe Ala Tyr Trp Gly Gln Gly
            100                 105                 110

Thr Leu Val Thr Val Ser Ala
        115


<210> SEQ ID NO 11
<211> LENGTH: 123
<212> TYPE: PRT
<213> ORGANISM: Artificial Sequence
<220> FEATURE:
<223> OTHER INFORMATION: Mouse VH

<400> SEQUENCE: 11

Glu Gly Gln Leu Gln Gln Ser Gly Ala Glu Leu Val Lys Pro Gly Ala
1               5                   10                  15

Ser Val Ile Leu Ser Cys Thr Ala Ser Gly Phe Asn Ile Lys Asp Thr
            20                  25                  30

Tyr Ile His Trp Leu Asn Gln Arg Pro Glu Gln Gly Leu Glu Trp Ile
        35                  40                  45

Gly Arg Ile Glu Pro Ala Asn Gly Asn Thr Lys Tyr Asp Pro Thr Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ser Arg Gly Gly Ile Tyr Tyr Tyr Gly Ser His Trp Tyr Phe Asp Val
            100                 105                 110

Trp Gly Ala Gly Thr Leu Val Thr Val Ser Ser
        115                 120


<210> SEQ ID NO 12
<211> LENGTH: 118
<212> TYPE: PRT
<213> ORGANISM: Artificial Sequence
<220> FEATURE:
<223> OTHER INFORMATION: Mouse VH

<400> SEQUENCE: 12

Gln Phe Gln Leu Gln Gln Ser Gly Ala Glu Leu Val Arg Pro Gly Ser
1               5                   10                  15

Ser Val Lys Ile Ser Cys Lys Ala Ser Gly Tyr Glu Phe Ser Ser Asn
            20                  25                  30

Trp Met Asn Trp Val Lys Gln Arg Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Arg Gly Lys Ala Thr Leu Thr Ser Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Gly Arg Ala Ser Phe Tyr Phe Asp Tyr Trp Gly Gln Gly Thr
            100                 105                 110

Ala Leu Thr Val Ser Ser
        115
```

<210> SEQ ID NO 13
<211> LENGTH: 119
<212> TYPE: PRT
<213> ORGANISM: Artificial Sequence
<220> FEATURE:
<223> OTHER INFORMATION: Mouse VH with CDR mutation

<400> SEQUENCE: 13

```
Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Ser Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser
        115
```

<210> SEQ ID NO 14
<211> LENGTH: 119
<212> TYPE: PRT
<213> ORGANISM: Artificial Sequence
<220> FEATURE:
<223> OTHER INFORMATION: Mouse VH with CDR mutation

<400> SEQUENCE: 14

```
Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser
        115
```

<210> SEQ ID NO 15
<211> LENGTH: 119
<212> TYPE: PRT
<213> ORGANISM: Artificial Sequence
<220> FEATURE:
<223> OTHER INFORMATION: Mouse VH with CDR mutation

<400> SEQUENCE: 15

```
Gln Val Gln Leu Gln Gln Ser Gly Asn Glu Leu Ala Arg Pro Gly Ala
```

```
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser
        115


<210> SEQ ID NO 16
<211> LENGTH: 120
<212> TYPE: PRT
<213> ORGANISM: Artificial Sequence
<220> FEATURE:
<223> OTHER INFORMATION: Humanized VH

<400> SEQUENCE: 16

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Pro Pro Gly Lys Gly Leu Glu Trp
        35                  40                  45

Ile Gly His Ile Arg Phe Ser Gly Thr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Val Thr Val Ser Ser
        115                 120


<210> SEQ ID NO 17
<211> LENGTH: 120
<212> TYPE: PRT
<213> ORGANISM: Artificial Sequence
<220> FEATURE:
<223> OTHER INFORMATION: Humanized VH

<400> SEQUENCE: 17

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Phe Pro Gly Lys Gly Leu Glu Trp
        35                  40                  45

Met Gly His Ile Arg Phe Ser Gly Thr Thr Ser Tyr Asn Pro Ser Leu
    50                  55                  60
```

Lys Ser Arg Ile Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Thr Leu Ile Thr Lys Gly Phe Phe Asp Tyr Trp Gly Gln
100 105 110

Gly Thr Leu Val Thr Val Ser Ser
115 120

<210> SEQ ID NO 18
<211> LENGTH: 120
<212> TYPE: PRT
<213> ORGANISM: Artificial Sequence
<220> FEATURE:
<223> OTHER INFORMATION: Humanized VH

<400> SEQUENCE: 18

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp
20 25 30

Phe Ala Trp Asp Trp Ile Arg Gln Phe Pro Gly Lys Gly Leu Glu Trp
35 40 45

Met Gly His Ile Arg Phe Ser Gly Thr Thr Ser Tyr Asn Pro Ser Leu
50 55 60

Lys Ser Arg Ile Thr Ile Ser Val Asp Thr Ser Lys Asn Gln Phe Phe
65 70 75 80

Leu Lys Leu Ser Ser Val Thr Ala Ala Asp Thr Ala Thr Tyr Tyr Cys
85 90 95

Ala Arg Ser Thr Leu Ile Thr Lys Gly Phe Phe Asp Tyr Trp Gly Gln
100 105 110

Gly Thr Leu Leu Thr Val Ser Ser
115 120

<210> SEQ ID NO 19
<211> LENGTH: 120
<212> TYPE: PRT
<213> ORGANISM: Artificial Sequence
<220> FEATURE:
<223> OTHER INFORMATION: Humanized VH

<400> SEQUENCE: 19

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp
20 25 30

Phe Ala Trp Asp Trp Ile Arg Gln Pro Pro Gly Lys Gly Leu Glu Trp
35 40 45

Ile Gly His Ile Arg Phe Ser Gly Thr Thr Ser Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Thr Leu Ile Thr Lys Gly Phe Phe Asp Tyr Trp Gly Gln
100 105 110

Gly Thr Leu Leu Thr Val Ser Ser
115 120

<210> SEQ ID NO 20
<211> LENGTH: 120
<212> TYPE: PRT
<213> ORGANISM: Artificial Sequence
<220> FEATURE:
<223> OTHER INFORMATION: Humanized VH

<400> SEQUENCE: 20

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Pro Pro Gly Lys Gly Leu Glu Trp
        35                  40                  45

Ile Gly His Ile Arg Phe Ser Gly Thr Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Val Thr Val Ser Ser
        115                 120
```

<210> SEQ ID NO 21
<211> LENGTH: 119
<212> TYPE: PRT
<213> ORGANISM: Artificial Sequence
<220> FEATURE:
<223> OTHER INFORMATION: Humanized VH

<400> SEQUENCE: 21

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 22
<211> LENGTH: 119
<212> TYPE: PRT
<213> ORGANISM: Artificial Sequence
<220> FEATURE:
<223> OTHER INFORMATION: Humanized VH

<400> SEQUENCE: 22

-continued

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 23
<211> LENGTH: 119
<212> TYPE: PRT
<213> ORGANISM: Artificial Sequence
<220> FEATURE:
<223> OTHER INFORMATION: Humanized VH

<400> SEQUENCE: 23

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 24
<211> LENGTH: 119
<212> TYPE: PRT
<213> ORGANISM: Artificial Sequence
<220> FEATURE:
<223> OTHER INFORMATION: Humanized VH

<400> SEQUENCE: 24

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60
```

```
Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 25
<211> LENGTH: 119
<212> TYPE: PRT
<213> ORGANISM: Artificial Sequence
<220> FEATURE:
<223> OTHER INFORMATION: Humanized VH

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 26
<211> LENGTH: 119
<212> TYPE: PRT
<213> ORGANISM: Artificial Sequence
<220> FEATURE:
<223> OTHER INFORMATION: Humanized VH

<400> SEQUENCE: 26

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
```

115

<210> SEQ ID NO 27
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 27

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 28
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 28

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 29
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 29

-continued

```
Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 30
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 30

```
Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 31
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 31

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
```

```
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 32
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 32

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 33
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ser Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110
```

```
Thr Thr Val Thr Val Ser Ser
        115


<210> SEQ ID NO 34
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ser Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 35
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 35

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ser Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 36
<211> LENGTH: 119
<212> TYPE: PRT
<213> ORGANISM: Artificial Sequence
<220> FEATURE:
<223> OTHER INFORMATION: Humanized VH with CDR2 mutation
```

<400> SEQUENCE: 36

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ser Thr Tyr Tyr Ser Glu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser
115

<210> SEQ ID NO 37
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 37

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ser Thr Tyr Tyr Ser Glu Lys Phe
50 55 60

Lys Gly Arg Val Thr Met Thr Ala Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser
115

<210> SEQ ID NO 38
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 38

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

-continued

```
Gly Glu Ile Phe Pro Arg Arg Val Ser Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 39
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 39

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115
```

<210> SEQ ID NO 40
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 40

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110
```

```
Thr Thr Val Thr Val Ser Ser
        115


<210> SEQ ID NO 41
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 41

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 42
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 42

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115


<210> SEQ ID NO 43
<211> LENGTH: 119
<212> TYPE: PRT
<213> ORGANISM: Artificial Sequence
<220> FEATURE:
<223> OTHER INFORMATION: Humanized VH with CDR2 mutation
```

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Humanized VH with CDR2 mutation

<400> SEQUENCE: 44

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser
        115

<210> SEQ ID NO 45
<211> LENGTH: 111
<212> TYPE: PRT
<213> ORGANISM: Artificial Sequence
<220> FEATURE:
<223> OTHER INFORMATION: Mouse VL

<400> SEQUENCE: 45

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

```
Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Ala Pro Tyr Thr Phe Gly Gly Gly Thr Lys Leu Glu Ile Lys
            100                 105                 110


<210> SEQ ID NO 46
<211> LENGTH: 107
<212> TYPE: PRT
<213> ORGANISM: Artificial Sequence
<220> FEATURE:
<223> OTHER INFORMATION: Mouse VL

<400> SEQUENCE: 46

Asp Ile Val Met Thr Gln Ser His Lys Phe Met Ser Thr Ser Val Gly
1               5                   10                  15

Gly Arg Val Ser Ile Thr Cys Lys Ala Ser Gln Asp Val Ser Pro Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Thr
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105


<210> SEQ ID NO 47
<211> LENGTH: 107
<212> TYPE: PRT
<213> ORGANISM: Artificial Sequence
<220> FEATURE:
<223> OTHER INFORMATION: Mouse VL

<400> SEQUENCE: 47

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Ala Phe Thr Phe Thr Ile Ser Ser Glu Gln Ala
65                  70                  75                  80

Glu Asp Leu Ala Val Tyr Tyr Cys Gln Gln His Tyr Ser Val Pro Phe
                85                  90                  95

Thr Phe Gly Gly Gly Thr Lys Leu Glu Ile Lys
            100                 105


<210> SEQ ID NO 48
<211> LENGTH: 106
<212> TYPE: PRT
```

<213> ORGANISM: Artificial Sequence
<220> FEATURE:
<223> OTHER INFORMATION: Mouse VL

<400> SEQUENCE: 48

```
Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Phe Ile Asn Tyr Met
            20                  25                  30

Tyr Trp Tyr Gln Gln Lys Pro Gly Ser Ser Pro Lys Pro Trp Ile Leu
        35                  40                  45

Arg Thr Ser Thr Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Leu Lys
            100                 105
```

<210> SEQ ID NO 49
<211> LENGTH: 107
<212> TYPE: PRT
<213> ORGANISM: Artificial Sequence
<220> FEATURE:
<223> OTHER INFORMATION: Mouse VL

<400> SEQUENCE: 49

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Ala Phe Thr Phe Thr Ile Ser Gly Glu Gln Ala
65                  70                  75                  80

Glu Asp Leu Ala Val Tyr Tyr Cys Gln Gln His Tyr Ser Ile Pro Phe
                85                  90                  95

Thr Phe Gly Gly Gly Thr Lys Leu Glu Ile Lys
            100                 105
```

<210> SEQ ID NO 50
<211> LENGTH: 108
<212> TYPE: PRT
<213> ORGANISM: Artificial Sequence
<220> FEATURE:
<223> OTHER INFORMATION: Mouse VL

<400> SEQUENCE: 50

```
Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60
```

Gly Ser Gly Ser Gly Thr Ser Tyr Ser Leu Thr Val Ser Ser Met Glu
65 70 75 80

Ala Glu Asp Ala Ala Ser Tyr Phe Cys His Gln Trp Ser Ser Tyr Pro
85 90 95

Phe Thr Phe Gly Ser Gly Thr Lys Leu Glu Ile Lys
100 105

<210> SEQ ID NO 51
<211> LENGTH: 112
<212> TYPE: PRT
<213> ORGANISM: Artificial Sequence
<220> FEATURE:
<223> OTHER INFORMATION: Mouse VL

<400> SEQUENCE: 51

Ser Val Leu Met Thr Gln Thr Pro Leu Ser Leu Pro Val Ser Leu Gly
1 5 10 15

Asp Gln Ala Ser Ile Ser Cys Arg Ser Ser Gln Asn Ile Val Tyr Ser
20 25 30

Asp Gly Asp Thr Tyr Leu Glu Trp Tyr Leu Gln Lys Pro Gly Gln Ser
35 40 45

Pro Lys Leu Leu Ile Phe Lys Val Ser Asn Arg Phe Phe Gly Val Pro
50 55 60

Asp Arg Phe Ser Gly Ser Gly Ser Gly Thr Asp Phe Thr Leu Lys Ile
65 70 75 80

Asn Arg Val Glu Ala Glu Asp Leu Gly Val Tyr Tyr Cys Phe Gln Gly
85 90 95

Ser His Val Pro Phe Thr Phe Gly Ser Gly Thr Lys Leu Glu Ile Lys
100 105 110

<210> SEQ ID NO 52
<211> LENGTH: 112
<212> TYPE: PRT
<213> ORGANISM: Artificial Sequence
<220> FEATURE:
<223> OTHER INFORMATION: Mouse VL

<400> SEQUENCE: 52

Asp Val Leu Met Asn Gln Thr Pro Leu Ser Leu Pro Val Ser Leu Gly
1 5 10 15

Asp Gln Ala Ser Ile Ser Cys Arg Ser Ser Gln Asn Ile Val Tyr Ser
20 25 30

Asp Gly Asn Thr Tyr Leu Glu Trp Tyr Leu Gln Lys Pro Gly Gln Ser
35 40 45

Pro Lys Leu Leu Ile Phe Gln Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Phe Tyr Tyr Cys Phe Gln Gly
85 90 95

Ser His Val Pro Phe Thr Phe Gly Ser Gly Thr Lys Leu Glu Ile Lys
100 105 110

<210> SEQ ID NO 53
<211> LENGTH: 107
<212> TYPE: PRT
<213> ORGANISM: Artificial Sequence
<220> FEATURE:
<223> OTHER INFORMATION: Mouse VL

<400> SEQUENCE: 53

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Gly Asn Tyr
20 25 30

Leu Asn Trp Tyr Gln Gln Lys Pro Asp Gly Thr Val Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asp Thr Phe Pro Trp
85 90 95

Thr Phe Gly Gly Gly Thr Lys Leu Glu Ile Lys
100 105

<210> SEQ ID NO 54
<211> LENGTH: 106
<212> TYPE: PRT
<213> ORGANISM: Artificial Sequence
<220> FEATURE:
<223> OTHER INFORMATION: Mouse VL

<400> SEQUENCE: 54

Gln Ile Val Leu Thr Gln Ser Pro Ala Leu Met Ser Ala Ser Pro Gly
1 5 10 15

Glu Arg Val Thr Met Thr Cys Ser Ala Ser Ser Asp Val Ser Tyr Met
20 25 30

Tyr Trp Tyr Gln Gln Lys Pro Arg Ser Ser Pro Lys Pro Trp Ile Tyr
35 40 45

Leu Thr Ser Asn Leu Ala Ser Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Thr Gly Asn Pro Leu Thr
85 90 95

Phe Gly Ala Gly Thr Lys Leu Glu Leu Lys
100 105

<210> SEQ ID NO 55
<211> LENGTH: 112
<212> TYPE: PRT
<213> ORGANISM: Artificial Sequence
<220> FEATURE:
<223> OTHER INFORMATION: Mouse VL

<400> SEQUENCE: 55

Asp Val Leu Met Thr Gln Thr Pro Leu Ser Leu Pro Val Ser Leu Gly
1 5 10 15

Asp Gln Ala Ser Ile Ser Cys Arg Ser Ser Gln Asn Ile Val Tyr Ser
20 25 30

Asp Gly Asp Thr Tyr Leu Glu Trp Tyr Leu Gln Lys Pro Gly Gln Ser
35 40 45

Pro Lys Leu Leu Ile Phe Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

```
Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110


<210> SEQ ID NO 56
<211> LENGTH: 111
<212> TYPE: PRT
<213> ORGANISM: Artificial Sequence
<220> FEATURE:
<223> OTHER INFORMATION: Mouse VL

<400> SEQUENCE: 56

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro His Thr Phe Gly Gly Gly Thr Lys Leu Glu Ile Lys
            100                 105                 110


<210> SEQ ID NO 57
<211> LENGTH: 107
<212> TYPE: PRT
<213> ORGANISM: Artificial Sequence
<220> FEATURE:
<223> OTHER INFORMATION: Mouse VL with CDR mutation

<400> SEQUENCE: 57

Asp Ile Val Met Thr Gln Ser His Lys Phe Met Ser Thr Ser Val Gly
1               5                   10                  15

Gly Arg Val Ser Ile Thr Cys Arg Ala Ser Gln Asp Val Ser Pro Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Thr
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105


<210> SEQ ID NO 58
<211> LENGTH: 107
<212> TYPE: PRT
<213> ORGANISM: Artificial Sequence
<220> FEATURE:
<223> OTHER INFORMATION: Mouse VL with CDR mutation

<400> SEQUENCE: 58
```

-continued

Asp Ile Val Met Thr Gln Ser His Lys Phe Met Ser Thr Ser Val Gly
1 5 10 15

Asp Arg Val Ser Ile Thr Cys Arg Ala Ser Gln Asp Val Ser Thr Ala
20 25 30

Val Asp Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Thr Gly
50 55 60

Ser Gly Ser Gly Thr Ala Phe Thr Phe Thr Ile Ser Gly Glu Gln Ala
65 70 75 80

Glu Asp Leu Ala Val Tyr Tyr Cys Gln Gln His Tyr Ser Ile Pro Phe
85 90 95

Thr Phe Gly Gly Gly Thr Lys Leu Glu Ile Lys
100 105

<210> SEQ ID NO 59
<211> LENGTH: 107
<212> TYPE: PRT
<213> ORGANISM: Artificial Sequence
<220> FEATURE:
<223> OTHER INFORMATION: Humanized VL

<400> SEQUENCE: 59

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Pro Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Ser Thr Pro Trp
85 90 95

Thr Phe Gly Gln Gly Thr Lys Val Glu Ile Lys
100 105

<210> SEQ ID NO 60
<211> LENGTH: 107
<212> TYPE: PRT
<213> ORGANISM: Artificial Sequence
<220> FEATURE:
<223> OTHER INFORMATION: Humanized VL

<400> SEQUENCE: 60

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Pro Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Leu Ala Leu Tyr Tyr Cys Gln Gln His Tyr Ser Thr Pro Trp
85 90 95

```
Thr Phe Gly Gln Gly Thr Lys Val Glu Ile Lys
            100                 105


<210> SEQ ID NO 61
<211> LENGTH: 107
<212> TYPE: PRT
<213> ORGANISM: Artificial Sequence
<220> FEATURE:
<223> OTHER INFORMATION: Humanized VL

<400> SEQUENCE: 61

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Leu Tyr Tyr Cys Gln Gln His Tyr Ser Thr Pro Trp
                85                  90                  95

Thr Phe Gly Gln Gly Thr Lys Leu Glu Ile Lys
            100                 105


<210> SEQ ID NO 62
<211> LENGTH: 107
<212> TYPE: PRT
<213> ORGANISM: Artificial Sequence
<220> FEATURE:
<223> OTHER INFORMATION: Humanized VL

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys
            100                 105


<210> SEQ ID NO 63
<211> LENGTH: 107
<212> TYPE: PRT
<213> ORGANISM: Artificial Sequence
<220> FEATURE:
<223> OTHER INFORMATION: Humanized VL

<400> SEQUENCE: 63

Asp Ile Gln Met Thr Gln Ser Pro Ser Ser Met Ser Ala Ser Val Gly
1               5                   10                  15
```

-continued

```
Asp Arg Val Thr Ile Thr Cys Lys Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Leu Ala Thr Tyr Tyr Cys Gln Gln His Tyr Ser Ile Pro Phe
                85                  90                  95

Thr Phe Gly Gln Gly Thr Lys Leu Glu Ile Lys
            100                 105


<210> SEQ ID NO 64
<211> LENGTH: 107
<212> TYPE: PRT
<213> ORGANISM: Artificial Sequence
<220> FEATURE:
<223> OTHER INFORMATION: Humanized VL

<400> SEQUENCE: 64

Asp Ile Gln Met Thr Gln Ser Pro Ser Ser Met Ser Thr Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Glu Gln Pro
65                  70                  75                  80

Glu Asp Leu Ala Thr Tyr Tyr Cys Gln Gln His Tyr Ser Ile Pro Phe
                85                  90                  95

Thr Phe Gly Gln Gly Thr Lys Leu Glu Ile Lys
            100                 105


<210> SEQ ID NO 65
<211> LENGTH: 107
<212> TYPE: PRT
<213> ORGANISM: Artificial Sequence
<220> FEATURE:
<223> OTHER INFORMATION: Humanized VL with CDR1 mutation

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105
```

<210> SEQ ID NO 66
<211> LENGTH: 107
<212> TYPE: PRT
<213> ORGANISM: Artificial Sequence
<220> FEATURE:
<223> OTHER INFORMATION: Humanized VL with CDR1 mutation

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Leu Tyr Tyr Cys Gln Gln His Tyr Ser Thr Pro Trp
                85                  90                  95

Thr Phe Gly Gln Gly Thr Lys Val Glu Ile Lys
            100                 105
```

<210> SEQ ID NO 67
<211> LENGTH: 107
<212> TYPE: PRT
<213> ORGANISM: Artificial Sequence
<220> FEATURE:
<223> OTHER INFORMATION: Humanized VL with CDR1 mutation

<400> SEQUENCE: 67

```
Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Leu Tyr Tyr Cys Gln Gln His Tyr Ser Thr Pro Trp
                85                  90                  95

Thr Phe Gly Gln Gly Thr Lys Leu Glu Ile Lys
            100                 105
```

<210> SEQ ID NO 68
<211> LENGTH: 107
<212> TYPE: PRT
<213> ORGANISM: Artificial Sequence
<220> FEATURE:
<223> OTHER INFORMATION: Humanized VL with CDR1 mutation

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

Val Asp Trp Tyr Gln Gln Lys Pro Gly Lys Ala Pro Lys Leu Leu Ile
35 40 45

Tyr Ser Ala Ser Tyr Arg Tyr Thr Gly Val Pro Asp Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln His Tyr Ser Ile Pro Phe
85 90 95

Thr Phe Gly Gln Gly Thr Lys Leu Glu Ile Lys
100 105

<210> SEQ ID NO 69
<211> LENGTH: 107
<212> TYPE: PRT
<213> ORGANISM: Artificial Sequence
<220> FEATURE:
<223> OTHER INFORMATION: Humanized VL with CDR1 mutation

<400> SEQUENCE: 69

Asp Ile Gln Met Thr Gln Ser Pro Ser Ser Met Ser Ala Ser Val Gly
1 5 10 15

Asp Arg Val Thr Ile Thr Cys Arg Ala Ser Gln Asp Val Ser Thr Ala
20 25 30

Val Asp Trp Tyr Gln Gln Lys Pro Gly Lys Ala Pro Lys Leu Leu Ile
35 40 45

Tyr Ser Ala Ser Tyr Arg Tyr Thr Gly Val Pro Asp Arg Phe Ser Gly
50 55 60

Ser Gly Ser Gly Thr Asp Phe Thr Phe Thr Ile Ser Ser Leu Gln Pro
65 70 75 80

Glu Asp Leu Ala Thr Tyr Tyr Cys Gln Gln His Tyr Ser Ile Pro Phe
85 90 95

Thr Phe Gly Gln Gly Thr Lys Leu Glu Ile Lys
100 105

<210> SEQ ID NO 70
<211> LENGTH: 107
<212> TYPE: PRT
<213> ORGANISM: Artificial Sequence
<220> FEATURE:
<223> OTHER INFORMATION: Humanized VL with CDR1 mutation

<400> SEQUENCE: 70

Asp Ile Gln Met Thr Gln Ser Pro Ser Ser Met Ser Thr Ser Val Gly
1 5 10 15

Asp Arg Val Thr Ile Thr Cys Arg Ala Ser Gln Asp Val Ser Thr Ala
20 25 30

Val Asp Trp Tyr Gln Gln Lys Pro Gly Lys Ala Pro Lys Leu Leu Ile
35 40 45

Tyr Ser Ala Ser Tyr Arg Tyr Thr Gly Val Pro Asp Arg Phe Ser Gly
50 55 60

Ser Gly Ser Gly Thr Asp Phe Thr Phe Thr Ile Ser Ser Glu Gln Pro
65 70 75 80

Glu Asp Leu Ala Thr Tyr Tyr Cys Gln Gln His Tyr Ser Ile Pro Phe
85 90 95

Thr Phe Gly Gln Gly Thr Lys Leu Glu Ile Lys
100 105

<210> SEQ ID NO 71

<211> LENGTH: 11
<212> TYPE: PRT
<213> ORGANISM: Artificial Sequence
<220> FEATURE:
<223> OTHER INFORMATION: Mouse VH CDR1

<400> SEQUENCE: 71

Gly Tyr Ser Ile Thr Ser Gly Tyr Thr Trp His
1 5 10

<210> SEQ ID NO 72
<211> LENGTH: 11
<212> TYPE: PRT
<213> ORGANISM: Artificial Sequence
<220> FEATURE:
<223> OTHER INFORMATION: Mouse VH CDR1

<400> SEQUENCE: 72

Gly Tyr Ser Ile Thr Ser Asp Phe Ala Trp Asp
1 5 10

<210> SEQ ID NO 73
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 73

Gly Tyr Ile Phe Thr Gly Tyr Gly Ile Ser
1 5 10

<210> SEQ ID NO 74
<211> LENGTH: 11
<212> TYPE: PRT
<213> ORGANISM: Artificial Sequence
<220> FEATURE:
<223> OTHER INFORMATION: Mouse VH CDR1

<400> SEQUENCE: 74

Gly Tyr Ser Ile Thr Ser Gly Tyr Tyr Trp Asn
1 5 10

<210> SEQ ID NO 75
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 75

Gly Tyr Ile Phe Thr Gly Tyr Gly Ile Thr
1 5 10

<210> SEQ ID NO 76
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 76

Gly Tyr Thr Phe Thr Asn Tyr Trp Ile Ser
1 5 10

<210> SEQ ID NO 77
<211> LENGTH: 10

<212> TYPE: PRT
<213> ORGANISM: Artificial Sequence
<220> FEATURE:
<223> OTHER INFORMATION: Mouse VH CDR1

<400> SEQUENCE: 77

Gly Phe Asn Ile Lys Asp Thr Tyr Ile His
1 5 10

<210> SEQ ID NO 78
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 78

Gly Phe Asn Ile Lys Asp Thr Tyr Ile His
1 5 10

<210> SEQ ID NO 79
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 79

Gly Tyr Thr Phe Thr Ser Tyr Tyr Met His
1 5 10

<210> SEQ ID NO 80
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 80

Gly Tyr Thr Phe Thr Glu Tyr Ile Ile Tyr
1 5 10

<210> SEQ ID NO 81
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 81

Gly Phe Asn Ile Lys Asp Thr Tyr Ile His
1 5 10

<210> SEQ ID NO 82
<211> LENGTH: 10
<212> TYPE: PRT
<213> ORGANISM: Artificial Sequence
<220> FEATURE:
<223> OTHER INFORMATION: Mouse VH CDR1

<400> SEQUENCE: 82

Gly Tyr Glu Phe Ser Ser Asn Trp Met Asn
1 5 10

<210> SEQ ID NO 83
<211> LENGTH: 16
<212> TYPE: PRT

<213> ORGANISM: Artificial Sequence
<220> FEATURE:
<223> OTHER INFORMATION: Mouse VH CDR2

<400> SEQUENCE: 83

Tyr Ile His Tyr Ser Gly Ser Thr Lys Tyr Asn Pro Ser Leu Lys Ser
1 5 10 15

<210> SEQ ID NO 84
<211> LENGTH: 16
<212> TYPE: PRT
<213> ORGANISM: Artificial Sequence
<220> FEATURE:
<223> OTHER INFORMATION: Mouse VH CDR2

<400> SEQUENCE: 84

His Ile Arg Phe Ser Gly Thr Thr Ser Tyr Asn Pro Ser Leu Lys Ser
1 5 10 15

<210> SEQ ID NO 85
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 85

Glu Ile Phe Pro Arg Thr Ala Asn Thr Tyr Phe Asn Glu Lys Phe Lys
1 5 10 15

Gly

<210> SEQ ID NO 86
<211> LENGTH: 16
<212> TYPE: PRT
<213> ORGANISM: Artificial Sequence
<220> FEATURE:
<223> OTHER INFORMATION: Mouse VH CDR2

<400> SEQUENCE: 86

Ser Ile Asn Tyr Asp Gly Ser Asn Asp Tyr Asn Pro Ser Leu Gln Asp
1 5 10 15

<210> SEQ ID NO 87
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 87

Glu Ile Phe Pro Arg Arg Val Asn Thr Tyr Tyr Ser Glu Lys Phe Lys
1 5 10 15

Gly

<210> SEQ ID NO 88
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 88

Asn Ile Tyr Pro Ser Asp Ser Tyr Thr Asn Tyr Asn Gln Asn Phe Lys
1 5 10 15

Asp

<210> SEQ ID NO 89
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 89

Arg Ile Ala Pro Thr Asn Gly Asn Thr Lys Tyr Asp Pro Thr Phe Gln
1 5 10 15

Gly

<210> SEQ ID NO 90
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 90

Arg Ile Ala Pro Thr Asn Gly Asn Ala Lys Phe His Pro Thr Phe Gln
1 5 10 15

Gly

<210> SEQ ID NO 91
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 91

Trp Ile Tyr Pro Gly Asn Val Asn Thr Lys Tyr Asn Glu Lys Phe Lys
1 5 10 15

Gly

<210> SEQ ID NO 92
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 92

Trp Phe Tyr Pro Gly Thr Gly Ser Ile Lys Tyr Asn Glu Lys Phe Lys
1 5 10 15

Asp

<210> SEQ ID NO 93
<211> LENGTH: 17
<212> TYPE: PRT
<213> ORGANISM: Artificial Sequence
<220> FEATURE:
<223> OTHER INFORMATION: Mouse VH CDR2

<400> SEQUENCE: 93

Arg Ile Glu Pro Ala Asn Gly Asn Thr Lys Tyr Asp Pro Thr Phe Gln
1 5 10 15

Gly

<210> SEQ ID NO 94
<211> LENGTH: 17

<212> TYPE: PRT
<213> ORGANISM: Artificial Sequence
<220> FEATURE:
<223> OTHER INFORMATION: Mouse VH CDR2

<400> SEQUENCE: 94

Gln Ile Trp Pro Gly Asp Gly Asp Thr Asn Tyr Asn Gly Lys Phe Arg
1 5 10 15

Gly

<210> SEQ ID NO 95
<211> LENGTH: 17
<212> TYPE: PRT
<213> ORGANISM: Artificial Sequence
<220> FEATURE:
<223> OTHER INFORMATION: Mouse VH CDR2 with CDR mutation

<400> SEQUENCE: 95

Glu Ile Phe Pro Arg Arg Val Ser Thr Tyr Tyr Ser Glu Lys Phe Lys
1 5 10 15

Gly

<210> SEQ ID NO 96
<211> LENGTH: 17
<212> TYPE: PRT
<213> ORGANISM: Artificial Sequence
<220> FEATURE:
<223> OTHER INFORMATION: Mouse VH CDR2 with CDR mutation

<400> SEQUENCE: 96

Glu Ile Phe Pro Arg Arg Val Ala Thr Tyr Tyr Ser Glu Lys Phe Lys
1 5 10 15

Gly

<210> SEQ ID NO 97
<211> LENGTH: 17
<212> TYPE: PRT
<213> ORGANISM: Artificial Sequence
<220> FEATURE:
<223> OTHER INFORMATION: Mouse VH CDR2 with CDR mutation

<400> SEQUENCE: 97

Glu Ile Phe Pro Arg Arg Val Gln Thr Tyr Tyr Ser Glu Lys Phe Lys
1 5 10 15

Gly

<210> SEQ ID NO 98
<211> LENGTH: 6
<212> TYPE: PRT
<213> ORGANISM: Artificial Sequence
<220> FEATURE:
<223> OTHER INFORMATION: Mouse VH CDR3

<400> SEQUENCE: 98

Asn Ser Leu Phe Ala Ser
1 5

<210> SEQ ID NO 99
<211> LENGTH: 11
<212> TYPE: PRT
<213> ORGANISM: Artificial Sequence
<220> FEATURE:
<223> OTHER INFORMATION: Mouse VH CDR3

<400> SEQUENCE: 99

Ser Thr Leu Ile Thr Lys Gly Phe Phe Asp Tyr
1 5 10

<210> SEQ ID NO 100
<211> LENGTH: 10
<212> TYPE: PRT
<213> ORGANISM: Artificial Sequence
<220> FEATURE:
<223> OTHER INFORMATION: Mouse VH CDR3

<400> SEQUENCE: 100

Asp Tyr Asp Pro Tyr Tyr Ala Leu Asp Tyr
1 5 10

<210> SEQ ID NO 101
<211> LENGTH: 4
<212> TYPE: PRT
<213> ORGANISM: Artificial Sequence
<220> FEATURE:
<223> OTHER INFORMATION: Mouse VH CDR3

<400> SEQUENCE: 101

Arg Leu Asp Tyr
1

<210> SEQ ID NO 102
<211> LENGTH: 10
<212> TYPE: PRT
<213> ORGANISM: Artificial Sequence
<220> FEATURE:
<223> OTHER INFORMATION: Mouse VH CDR3

<400> SEQUENCE: 102

Asp Tyr Asp Pro Tyr Phe Ala Leu Asp Tyr
1 5 10

<210> SEQ ID NO 103
<211> LENGTH: 12
<212> TYPE: PRT
<213> ORGANISM: Artificial Sequence
<220> FEATURE:
<223> OTHER INFORMATION: Mouse VH CDR3

<400> SEQUENCE: 103

Gly Ile Ile Thr Val Ile Ala Thr Arg Asp Asp Tyr
1 5 10

<210> SEQ ID NO 104
<211> LENGTH: 14
<212> TYPE: PRT
<213> ORGANISM: Artificial Sequence
<220> FEATURE:
<223> OTHER INFORMATION: Mouse VH CDR3

<400> SEQUENCE: 104

Gly Gly Ile Tyr Tyr Tyr Gly Ser His Trp Tyr Phe Asp Val
1 5 10

<210> SEQ ID NO 105
<211> LENGTH: 14
<212> TYPE: PRT
<213> ORGANISM: Artificial Sequence
<220> FEATURE:
<223> OTHER INFORMATION: Mouse VH CDR3

<400> SEQUENCE: 105

Gly Gly Ile Tyr Tyr Tyr Gly Thr His Trp Tyr Phe Asp Val
1 5 10

<210> SEQ ID NO 106
<211> LENGTH: 11
<212> TYPE: PRT
<213> ORGANISM: Artificial Sequence
<220> FEATURE:
<223> OTHER INFORMATION: Mouse VH CDR3

<400> SEQUENCE: 106

Tyr Gly Asn Tyr Gly Gly Trp Tyr Phe Asp Val
1 5 10

<210> SEQ ID NO 107
<211> LENGTH: 10
<212> TYPE: PRT
<213> ORGANISM: Artificial Sequence
<220> FEATURE:
<223> OTHER INFORMATION: Mouse VH CDR3

<400> SEQUENCE: 107

His Glu Glu Gly Asn Leu Trp Phe Ala Tyr
1 5 10

<210> SEQ ID NO 108
<211> LENGTH: 14
<212> TYPE: PRT
<213> ORGANISM: Artificial Sequence
<220> FEATURE:
<223> OTHER INFORMATION: Mouse VH CDR3

<400> SEQUENCE: 108

Gly Gly Ile Tyr Tyr Tyr Gly Ser His Trp Tyr Phe Asp Val
1 5 10

<210> SEQ ID NO 109
<211> LENGTH: 9
<212> TYPE: PRT
<213> ORGANISM: Artificial Sequence
<220> FEATURE:
<223> OTHER INFORMATION: Mouse VH CDR3

<400> SEQUENCE: 109

Gly Arg Ala Ser Phe Tyr Phe Asp Tyr
1 5

<210> SEQ ID NO 110
<211> LENGTH: 15
<212> TYPE: PRT
<213> ORGANISM: Artificial Sequence
<220> FEATURE:
<223> OTHER INFORMATION: Mouse VL CDR1

<400> SEQUENCE: 110

Arg Ala Ser Glu Ser Val Asp Thr Tyr Gly Asp Ser Phe Met His
1 5 10 15

<210> SEQ ID NO 111
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 111

Lys Ala Ser Gln Asp Val Ser Pro Ala Val Ala 1 5 10

<210> SEQ ID NO 112
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 112

Lys Ala Ser Gln Asp Val Ser Thr Ala Val Asp
1 5 10

<210> SEQ ID NO 113
<211> LENGTH: 10
<212> TYPE: PRT
<213> ORGANISM: Artificial Sequence
<220> FEATURE:
<223> OTHER INFORMATION: Mouse VL CDR1

<400> SEQUENCE: 113

Ser Ala Ser Ser Phe Ile Asn Tyr Met Tyr
1 5 10

<210> SEQ ID NO 114
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 114

Lys Ala Ser Gln Asp Val Ser Thr Ala Val Asp
1 5 10

<210> SEQ ID NO 115
<211> LENGTH: 12
<212> TYPE: PRT
<213> ORGANISM: Artificial Sequence
<220> FEATURE:
<223> OTHER INFORMATION: Mouse VL CDR1

<400> SEQUENCE: 115

Ser Ala Ser Ser Ser Val Ser Ser Ser Tyr Leu Tyr
1 5 10

<210> SEQ ID NO 116
<211> LENGTH: 16
<212> TYPE: PRT
<213> ORGANISM: Artificial Sequence
<220> FEATURE:
<223> OTHER INFORMATION: Mouse VL CDR1

<400> SEQUENCE: 116

Arg Ser Ser Gln Asn Ile Val Tyr Ser Asp Gly Asp Thr Tyr Leu Glu
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: Mouse VL CDR1

<400> SEQUENCE: 117

Arg Ser Ser Gln Asn Ile Val Tyr Ser Asp Gly Asn Thr Tyr Leu Glu
1 5 10 15

<210> SEQ ID NO 118
<211> LENGTH: 11
<212> TYPE: PRT
<213> ORGANISM: Artificial Sequence
<220> FEATURE:
<223> OTHER INFORMATION: Mouse VL CDR1

<400> SEQUENCE: 118

Arg Ala Ser Gln Asp Ile Gly Asn Tyr Leu Asn
1 5 10

<210> SEQ ID NO 119
<211> LENGTH: 10
<212> TYPE: PRT
<213> ORGANISM: Artificial Sequence
<220> FEATURE:
<223> OTHER INFORMATION: Mouse VL CDR1

<400> SEQUENCE: 119

Ser Ala Ser Ser Asp Val Ser Tyr Met Tyr
1 5 10

<210> SEQ ID NO 120
<211> LENGTH: 16
<212> TYPE: PRT
<213> ORGANISM: Artificial Sequence
<220> FEATURE:
<223> OTHER INFORMATION: Mouse VL CDR1

<400> SEQUENCE: 120

Arg Ser Ser Gln Asn Ile Val Tyr Ser Asp Gly Asp Thr Tyr Leu Glu
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Mouse VL CDR1

<400> SEQUENCE: 121

Arg Ala Ser Glu Ser Val Asp Asp Tyr Gly Asn Ser Phe Met His
1 5 10 15

<210> SEQ ID NO 122
<211> LENGTH: 11
<212> TYPE: PRT
<213> ORGANISM: Artificial Sequence
<220> FEATURE:
<223> OTHER INFORMATION: Mouse VL CDR1 Chimeric

<400> SEQUENCE: 122

Arg Ala Ser Gln Asp Val Ser Pro Ala Val Ala
1 5 10

<210> SEQ ID NO 123
<211> LENGTH: 11
<212> TYPE: PRT
<213> ORGANISM: Artificial Sequence
<220> FEATURE:
<223> OTHER INFORMATION: Mouse VL CDR1 Chimeric

<400> SEQUENCE: 123

Arg Ala Ser Gln Asp Val Ser Thr Ala Val Asp
1 5 10

<210> SEQ ID NO 124
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 124

Arg Ala Ser Asn Leu Glu Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 125

Trp Ala Ser Thr Arg His Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 126

Ser Ala Ser Tyr Arg Tyr Thr
1               5

<210> SEQ ID NO 127
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 127

Arg Thr Ser Thr Leu Ala Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 128

Ser Ala Ser Tyr Arg Tyr Thr
1               5

<210> SEQ ID NO 129
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 129

Ser Thr Ser Asn Leu Ala Ser
1               5

<210> SEQ ID NO 130
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 130

Lys Val Ser Asn Arg Phe Phe
1 5

<210> SEQ ID NO 131
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 131

Gln Val Ser Asn Arg Phe Ser
1 5

<210> SEQ ID NO 132
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 132

Tyr Thr Ser Arg Leu His Ser
1 5

<210> SEQ ID NO 133
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 133

Leu Thr Ser Asn Leu Ala Ser
1 5

<210> SEQ ID NO 134
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 134

Lys Val Ser Asn Arg Phe Ser
1 5

<210> SEQ ID NO 135
<211> LENGTH: 7
<212> TYPE: PRT
<213> ORGANISM: Artificial Sequence
<220> FEATURE:
<223> OTHER INFORMATION: Mouse VL CDR2

<400> SEQUENCE: 135

Arg Ala Ser Asn Leu Glu Ser
1 5

<210> SEQ ID NO 136

<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 136

Gln Gln Ser Asn Glu Ala Pro Tyr Thr
1 5

<210> SEQ ID NO 137
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 137

Gln Gln His Tyr Ser Thr Pro Trp Thr
1 5

<210> SEQ ID NO 138
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 138

Gln Gln His Tyr Ser Val Pro Phe Thr
1 5

<210> SEQ ID NO 139
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 139

Gln Gln Tyr His Ser Tyr Pro Leu Thr
1 5

<210> SEQ ID NO 140
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 140

Gln Gln His Tyr Ser Ile Pro Phe Thr
1 5

<210> SEQ ID NO 141
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 141

His Gln Trp Ser Ser Tyr Pro Phe Thr
1 5

<210> SEQ ID NO 142
<211> LENGTH: 9

<212> TYPE: PRT
<213> ORGANISM: Artificial Sequence
<220> FEATURE:
<223> OTHER INFORMATION: Mouse VL CDR3

<400> SEQUENCE: 142

Phe Gln Gly Ser His Val Pro Phe Thr
1               5

<210> SEQ ID NO 143
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 143

Phe Gln Gly Ser His Val Pro Phe Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 144

Gln Gln Gly Asp Thr Phe Pro Trp Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 145

Gln Gln Trp Thr Gly Asn Pro Leu Thr
1               5

<210> SEQ ID NO 146
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 146

Phe Gln Gly Ser His Val Pro Phe Thr
1               5

<210> SEQ ID NO 147
<211> LENGTH: 9
<212> TYPE: PRT
<213> ORGANISM: Artificial Sequence
<220> FEATURE:
<223> OTHER INFORMATION: Mouse VL CDR3

<400> SEQUENCE: 147

Gln Gln Ser Asn Glu Asp Pro His Thr
1               5

<210> SEQ ID NO 148
<211> LENGTH: 25
<212> TYPE: PRT

<213> ORGANISM: Artificial Sequence
<220> FEATURE:
<223> OTHER INFORMATION: Mouse VH FR1

<400> SEQUENCE: 148

Asp Val Gln Leu Gln Glu Ser Gly Pro Asp Leu Val Lys Pro Ser Gln
1 5 10 15

Ser Leu Ser Leu Thr Cys Thr Val Thr
20 25

<210> SEQ ID NO 149
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 149

Asp Val Gln Leu Gln Gly Ser Gly Pro Gly Leu Val Lys Pro Ser Gln
1 5 10 15

Ser Leu Ser Leu Thr Cys Thr Val Thr
20 25

<210> SEQ ID NO 150
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 150

Gln Val Gln Leu Gln Gln Ser Gly Ala Glu Leu Ala Arg Pro Gly Ala
1 5 10 15

Ser Val Arg Leu Ser Cys Lys Ala Ser
20 25

<210> SEQ ID NO 151
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 151

Asp Val Gln Leu Leu Glu Ser Gly Pro Gly Leu Val Lys Pro Ser Gln
1 5 10 15

Ser Leu Ser Leu Thr Cys Ser Val Thr
20 25

<210> SEQ ID NO 152
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 152

Gln Val Gln Leu Gln Gln Ser Gly Asn Glu Leu Ala Arg Pro Gly Ala
1 5 10 15

Ser Val Arg Leu Ser Cys Lys Ala Ser
20 25

<210> SEQ ID NO 153
<211> LENGTH: 25

<212> TYPE: PRT
<213> ORGANISM: Artificial Sequence
<220> FEATURE:
<223> OTHER INFORMATION: Mouse VH FR1

<400> SEQUENCE: 153

Gln Val Gln Leu Gln Gln Pro Gly Ala Glu Val Val Arg Pro Gly Ala
1 5 10 15

Ser Val Lys Leu Ser Cys Lys Ala Ser
20 25

<210> SEQ ID NO 154
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 154

Glu Gly Gln Leu Gln Gln Ser Gly Ala Gly Leu Val Lys Pro Gly Ala
1 5 10 15

Ser Val Asn Leu Ser Cys Thr Ala Ser
20 25

<210> SEQ ID NO 155
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 155

Glu Gly Gln Leu Gln Gln Ser Gly Ala Glu Leu Val Lys Pro Gly Ala
1 5 10 15

Ser Val Asn Leu Ser Cys Thr Ala Ser
20 25

<210> SEQ ID NO 156
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 156

Gln Val Leu Leu Gln Gln Ser Gly Pro Glu Leu Val Lys Pro Gly Ala
1 5 10 15

Ser Val Arg Ile Ser Cys Lys Ala Ser
20 25

<210> SEQ ID NO 157
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 157

Lys Val Gln Leu Gln Gln Ser Gly Ala Glu Leu Val Lys Pro Gly Thr
1 5 10 15

Ser Val Lys Leu Ser Cys Lys Ala Ser
20 25

<210> SEQ ID NO 158

<211> LENGTH: 25
<212> TYPE: PRT
<213> ORGANISM: Artificial Sequence
<220> FEATURE:
<223> OTHER INFORMATION: Mouse VH FR1

<400> SEQUENCE: 158

```
Glu Gly Gln Leu Gln Gln Ser Gly Ala Glu Leu Val Lys Pro Gly Ala
1               5                   10                  15

Ser Val Ile Leu Ser Cys Thr Ala Ser
            20                  25
```

<210> SEQ ID NO 159
<211> LENGTH: 25
<212> TYPE: PRT
<213> ORGANISM: Artificial Sequence
<220> FEATURE:
<223> OTHER INFORMATION: Mouse VH FR1

<400> SEQUENCE: 159

```
Gln Phe Gln Leu Gln Gln Ser Gly Ala Glu Leu Val Arg Pro Gly Ser
1               5                   10                  15

Ser Val Lys Ile Ser Cys Lys Ala Ser
            20                  25
```

<210> SEQ ID NO 160
<211> LENGTH: 25
<212> TYPE: PRT
<213> ORGANISM: Artificial Sequence
<220> FEATURE:
<223> OTHER INFORMATION: Humanized VH FR1

<400> SEQUENCE: 160

```
Glu Val Gln Leu Gln Glu Ser Gly Pro Gly Leu Val Lys Pro Ser Glu
1               5                   10                  15

Thr Leu Ser Leu Thr Cys Thr Val Ser
            20                  25
```

<210> SEQ ID NO 161
<211> LENGTH: 25
<212> TYPE: PRT
<213> ORGANISM: Artificial Sequence
<220> FEATURE:
<223> OTHER INFORMATION: Humanized VH FR1

<400> SEQUENCE: 161

```
Glu Val Gln Leu Val Gln Ser Gly Ala Glu Val Lys Lys Pro Gly Ala
1               5                   10                  15

Ser Val Lys Val Ser Cys Lys Ala Ser
            20                  25
```

<210> SEQ ID NO 162
<211> LENGTH: 25
<212> TYPE: PRT
<213> ORGANISM: Artificial Sequence
<220> FEATURE:
<223> OTHER INFORMATION: Humanized VH FR1

<400> SEQUENCE: 162

```
Glu Val Gln Leu Val Gln Ser Gly Ala Glu Val Lys Lys Pro Gly Ala
1               5                   10                  15

Ser Val Lys Leu Ser Cys Lys Ala Ser
            20                  25
```

<210> SEQ ID NO 163
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 163

Trp Ile Arg Gln Phe Pro Gly Asn Lys Leu Glu Trp Met Gly
1 5 10

<210> SEQ ID NO 164
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 164

Trp Ile Arg Gln Phe Pro Gly Asn Lys Leu Glu Trp Met Gly
1 5 10

<210> SEQ ID NO 165
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 165

Trp Val Lys Gln Arg Thr Gly Gln Gly Leu Glu Trp Ile Gly
1 5 10

<210> SEQ ID NO 166
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 166

Trp Ile Arg Gln Phe Pro Gly Asn Asn Leu Glu Trp Met Gly
1 5 10

<210> SEQ ID NO 167
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 167

Trp Val Arg Gln Arg Pro Gly Gln Gly Leu Glu Trp Ile Gly
1 5 10

<210> SEQ ID NO 168
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 168

Trp Val Lys Gln Arg Pro Gly Gln Gly Leu Glu Trp Ile Gly
1 5 10

<210> SEQ ID NO 169

<211> LENGTH: 14
<212> TYPE: PRT
<213> ORGANISM: Artificial Sequence
<220> FEATURE:
<223> OTHER INFORMATION: Mouse VH FR2

<400> SEQUENCE: 169

Trp Met Lys Gln Arg Pro Glu Gln Gly Leu Glu Trp Ile Gly
1 5 10

<210> SEQ ID NO 170
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 170

Trp Val Lys Gln Arg Pro Asp Gln Gly Leu Glu Trp Ile Gly
1 5 10

<210> SEQ ID NO 171
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 171

Trp Val Lys Gln Arg Pro Gly Gln Gly Leu Glu Trp Ile Gly
1 5 10

<210> SEQ ID NO 172
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 172

Trp Ile Lys Gln Arg Ser Gly Gln Gly Leu Glu Trp Ile Gly
1 5 10

<210> SEQ ID NO 173
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 173

Trp Leu Asn Gln Arg Pro Glu Gln Gly Leu Glu Trp Ile Gly
1 5 10

<210> SEQ ID NO 174
<211> LENGTH: 14
<212> TYPE: PRT
<213> ORGANISM: Artificial Sequence
<220> FEATURE:
<223> OTHER INFORMATION: Mouse VH FR2

<400> SEQUENCE: 174

Trp Val Lys Gln Arg Pro Gly Gln Ser Leu Glu Trp Ile Gly
1 5 10

<210> SEQ ID NO 175
<211> LENGTH: 14

<212> TYPE: PRT
<213> ORGANISM: Artificial Sequence
<220> FEATURE:
<223> OTHER INFORMATION: Humanized VH FR2

<400> SEQUENCE: 175

Trp Ile Arg Gln Pro Pro Gly Lys Gly Leu Glu Trp Ile Gly
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Humanized VH FR2

<400> SEQUENCE: 176

Trp Ile Arg Gln Phe Pro Gly Lys Gly Leu Glu Trp Met Gly
1               5                   10

<210> SEQ ID NO 177
<211> LENGTH: 14
<212> TYPE: PRT
<213> ORGANISM: Artificial Sequence
<220> FEATURE:
<223> OTHER INFORMATION: Humanized VH FR2

<400> SEQUENCE: 177

Trp Val Arg Gln Ala Pro Gly Gln Gly Leu Glu Trp Met Gly
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Humanized VH FR2

<400> SEQUENCE: 178

Trp Val Arg Gln Ala Pro Gly Gln Gly Leu Glu Trp Ile Gly
1               5                   10

<210> SEQ ID NO 179
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 179

Arg Phe Ser Ile Thr Arg Asp Thr Ser Lys Asn Gln Phe Phe Leu Gln
1               5                   10                  15

Leu Asn Ser Met Thr Ala Glu Asp Thr Ala Thr Tyr Tyr Cys Ala Arg
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 180

Arg Ile Ser Ile Thr Arg Asp Thr Ser Lys Asn Gln Phe Phe Leu Gln
1               5                   10                  15

Leu Asn Ser Val Thr Ser Glu Asp Thr Ala Thr Tyr Tyr Cys Ala Arg 20 25 30

<210> SEQ ID NO 181
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 181

Lys Ala Thr Leu Thr Ala Asp Lys Ser Ser Ser Thr Ala Tyr Met Glu
1 5 10 15

Leu Arg Ser Leu Thr Ser Glu Asp Ser Ala Val Tyr Phe Cys Ala Arg
20 25 30

<210> SEQ ID NO 182
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 182

Arg Ile Ser Ile Thr Arg Asp Thr Ser Lys Asn Gln Phe Phe Leu Lys
1 5 10 15

Leu Asn Ser Val Thr Thr Glu Asp Thr Ala Thr Tyr Tyr Cys Ala Arg
20 25 30

<210> SEQ ID NO 183
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 183

Arg Ala Thr Leu Thr Ala Asp Ile Ser Ser Ser Thr Ala Tyr Met Glu
1 5 10 15

Leu Arg Ser Leu Thr Ser Glu Asp Ser Ala Val Tyr Phe Cys Ala Arg
20 25 30

<210> SEQ ID NO 184
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 184

Lys Ala Thr Leu Thr Val Asp Lys Ser Ser Ser Thr Ala Tyr Met Gln
1 5 10 15

Leu Ser Ser Pro Thr Ser Glu Asp Ser Ala Val Tyr Tyr Cys Thr Thr
20 25 30

<210> SEQ ID NO 185
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 185

Lys Ala Thr Ile Thr Ala Asp Ser Ser Ser Asn Thr Ala Tyr Leu Gln
1 5 10 15

```
Val Ser Ser Leu Thr Ser Glu Asp Thr Ala Val Tyr Tyr Cys Ser Arg
            20                  25                  30


<210> SEQ ID NO 186
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 186

Lys Ala Thr Ile Thr Ala Asp Thr Ser Ser Asn Thr Ala Tyr Leu Gln
1               5                   10                  15

Leu Ser Ser Leu Thr Ser Glu Asp Thr Ala Val Tyr Tyr Cys Thr Arg
            20                  25                  30


<210> SEQ ID NO 187
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 187

Lys Ala Thr Leu Thr Ala Asp Lys Ser Ser Ser Thr Ala Tyr Met Gln
1               5                   10                  15

Leu Ser Ser Leu Thr Ser Glu Asp Ser Ala Val Tyr Phe Cys Ala Ser
            20                  25                  30


<210> SEQ ID NO 188
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 188

Lys Ala Thr Leu Thr Ala Asp Lys Ser Ser Ser Thr Val Phe Met Glu
1               5                   10                  15

Leu Ser Arg Leu Thr Ser Glu Asp Ser Ala Val Tyr Phe Cys Ala Arg
            20                  25                  30


<210> SEQ ID NO 189
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 189

Lys Ala Thr Ile Thr Ala Asp Thr Ser Ser Asn Thr Ala Tyr Leu Gln
1               5                   10                  15

Leu Thr Ser Leu Thr Ser Glu Asp Thr Ala Val Tyr Tyr Cys Ser Arg
            20                  25                  30


<210> SEQ ID NO 190
<211> LENGTH: 32
<212> TYPE: PRT
<213> ORGANISM: Artificial Sequence
<220> FEATURE:
<223> OTHER INFORMATION: Mouse VH FR3

<400> SEQUENCE: 190

Lys Ala Thr Leu Thr Ser Asp Lys Ser Ser Ser Thr Ala Tyr Met Gln
1               5                   10                  15
```

Leu Asn Ser Leu Thr Ser Glu Asp Ser Ala Val Tyr Phe Cys Ala Arg
20 25 30

<210> SEQ ID NO 191
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 191

Arg Val Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 192
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 192

Arg Ile Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 193
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 193

Arg Ile Thr Ile Ser Val Asp Thr Ser Lys Asn Gln Phe Phe Leu Lys
1 5 10 15

Leu Ser Ser Val Thr Ala Ala Asp Thr Ala Thr Tyr Tyr Cys Ala Arg
20 25 30

<210> SEQ ID NO 194
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 194

Arg Val Thr Ile Ser Arg Asp Thr Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 195
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 195

Arg Val Thr Met Thr Thr Asp Thr Ser Thr Ser Thr Ala Tyr Met Glu 1 5 10 15

Leu Arg Ser Leu Arg Ser Asp Asp Thr Ala Val Tyr Tyr Cys Ala Arg
20 25 30

<210> SEQ ID NO 196
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 196

Arg Ala Thr Leu Thr Thr Asp Thr Ser Thr Ser Thr Ala Tyr Met Glu
1 5 10 15

Leu Arg Ser Leu Arg Ser Asp Asp Thr Ala Val Tyr Phe Cys Ala Arg
20 25 30

<210> SEQ ID NO 197
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 197

Arg Ala Thr Leu Thr Ala Asp Thr Ser Thr Ser Thr Ala Tyr Met Glu
1 5 10 15

Leu Arg Ser Leu Arg Ser Asp Asp Thr Ala Val Tyr Phe Cys Ala Arg
20 25 30

<210> SEQ ID NO 198
<211> LENGTH: 32
<212> TYPE: PRT
<213> ORGANISM: Artificial Sequence
<220> FEATURE:
<223> OTHER INFORMATION: Humanized VH FR3

<400> SEQUENCE: 198

Arg Val Thr Met Thr Ala Asp Thr Ser Thr Ser Thr Ala Tyr Met Glu
1 5 10 15

Leu Arg Ser Leu Arg Ser Asp Asp Thr Ala Val Tyr Tyr Cys Ala Arg
20 25 30

<210> SEQ ID NO 199
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 199

Trp Gly His Gly Thr Leu Val Thr Val Ser Ala
1 5 10

<210> SEQ ID NO 200
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 200

Trp Gly Gln Gly Thr Thr Leu Thr Val Ser Ser
1 5 10

<210> SEQ ID NO 201
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 201

Trp Gly Gln Gly Thr Ser Val Thr Val Ser Ser
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 202

Trp Gly Gln Gly Thr Thr Leu Ile Val Ser Ser
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 203

Trp Gly Gln Gly Thr Ser Val Thr Val Ser Ser
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 204

Trp Gly Gln Gly Thr Thr Leu Thr Val Ser Ser
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 205

Trp Gly Ala Gly Thr Thr Val Thr Val Ser Ser
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 206

Trp Gly Ala Gly Thr Thr Val Thr Val Ser Ser
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 207

Trp Gly Ala Gly Thr Thr Val Thr Val Ser Ser
1 5 10

<210> SEQ ID NO 208
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 208

Trp Gly Gln Gly Thr Leu Val Thr Val Ser Ala
1 5 10

<210> SEQ ID NO 209
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 209

Trp Gly Ala Gly Thr Leu Val Thr Val Ser Ser
1 5 10

<210> SEQ ID NO 210
<211> LENGTH: 11
<212> TYPE: PRT
<213> ORGANISM: Artificial Sequence
<220> FEATURE:
<223> OTHER INFORMATION: Mouse VH FR4

<400> SEQUENCE: 210

Trp Gly Gln Gly Thr Ala Leu Thr Val Ser Ser
1 5 10

<210> SEQ ID NO 211
<211> LENGTH: 11
<212> TYPE: PRT
<213> ORGANISM: Artificial Sequence
<220> FEATURE:
<223> OTHER INFORMATION: Humanized VH FR4

<400> SEQUENCE: 211

Trp Gly Gln Gly Thr Leu Val Thr Val Ser Ser
1 5 10

<210> SEQ ID NO 212
<211> LENGTH: 11
<212> TYPE: PRT
<213> ORGANISM: Artificial Sequence
<220> FEATURE:
<223> OTHER INFORMATION: Humanized VH FR4

<400> SEQUENCE: 212

Trp Gly Gln Gly Thr Leu Leu Thr Val Ser Ser
1 5 10

<210> SEQ ID NO 213

<211> LENGTH: 11
<212> TYPE: PRT
<213> ORGANISM: Artificial Sequence
<220> FEATURE:
<223> OTHER INFORMATION: Humanized VH FR4

<400> SEQUENCE: 213

Trp Gly Gln Gly Thr Thr Val Thr Val Ser Ser
1               5                   10

<210> SEQ ID NO 214
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 214

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 215
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 215

Asp Ile Val Met Thr Gln Ser His Lys Phe Met Ser Thr Ser Val Gly
1               5                   10                  15

Gly Arg Val Ser Ile Thr Cys
            20

<210> SEQ ID NO 216
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 216

Asp Ile Val Met Thr Gln Ser His Lys Phe Met Ser Thr Ser Val Gly
1               5                   10                  15

Asp Arg Val Thr Ile Thr Cys
            20

<210> SEQ ID NO 217
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 217

Gln Ile Val Leu Thr Gln Ser Pro Ala Ile Met Ser Ala Ser Pro Gly
1               5                   10                  15

Glu Lys Val Thr Ile Ser Cys
            20

<210> SEQ ID NO 218
<211> LENGTH: 23
<212> TYPE: PRT

<213> ORGANISM: Artificial Sequence
<220> FEATURE:
<223> OTHER INFORMATION: Mouse VL FR1

<400> SEQUENCE: 218

Asp Ile Val Met Thr Gln Ser His Lys Phe Met Ser Thr Ser Val Gly
1 5 10 15

Asp Arg Val Ser Ile Thr Cys
20

<210> SEQ ID NO 219
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 219

Gln Ile Val Leu Thr Gln Ser Pro Ala Ile Met Ser Ala Ser Pro Gly
1 5 10 15

Glu Lys Val Thr Leu Thr Cys
20

<210> SEQ ID NO 220
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 220

Ser Val Leu Met Thr Gln Thr Pro Leu Ser Leu Pro Val Ser Leu Gly
1 5 10 15

Asp Gln Ala Ser Ile Ser Cys
20

<210> SEQ ID NO 221
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 221

Asp Val Leu Met Asn Gln Thr Pro Leu Ser Leu Pro Val Ser Leu Gly
1 5 10 15

Asp Gln Ala Ser Ile Ser Cys
20

<210> SEQ ID NO 222
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 222

Asp Ile Gln Met Thr Gln Thr Thr Ser Ser Leu Ser Ala Ser Leu Gly
1 5 10 15

Asp Arg Val Thr Ile Ser Cys
20

<210> SEQ ID NO 223
<211> LENGTH: 23

<212> TYPE: PRT
<213> ORGANISM: Artificial Sequence
<220> FEATURE:
<223> OTHER INFORMATION: Mouse VL FR1

<400> SEQUENCE: 223

Gln Ile Val Leu Thr Gln Ser Pro Ala Leu Met Ser Ala Ser Pro Gly
1               5                   10                  15

Glu Arg Val Thr Met Thr Cys
            20

<210> SEQ ID NO 224
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 224

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 225
<211> LENGTH: 23
<212> TYPE: PRT
<213> ORGANISM: Artificial Sequence
<220> FEATURE:
<223> OTHER INFORMATION: Mouse VL FR1

<400> SEQUENCE: 225

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 226
<211> LENGTH: 23
<212> TYPE: PRT
<213> ORGANISM: Artificial Sequence
<220> FEATURE:
<223> OTHER INFORMATION: Humanized VL FR1

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 227
<211> LENGTH: 23
<212> TYPE: PRT
<213> ORGANISM: Artificial Sequence
<220> FEATURE:
<223> OTHER INFORMATION: Humanized VL FR1

<400> SEQUENCE: 227

Asp Ile Gln Met Thr Gln Ser Pro Ser Ser Leu Ser Thr Ser Val Gly
1               5                   10                  15

Asp Arg Val Thr Ile Thr Cys
            20

<210> SEQ ID NO 228

<211> LENGTH: 23
<212> TYPE: PRT
<213> ORGANISM: Artificial Sequence
<220> FEATURE:
<223> OTHER INFORMATION: Humanized VL FR1

<400> SEQUENCE: 228

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 229
<211> LENGTH: 23
<212> TYPE: PRT
<213> ORGANISM: Artificial Sequence
<220> FEATURE:
<223> OTHER INFORMATION: Humanized VL FR1

<400> SEQUENCE: 229

Asp Ile Gln Met Thr Gln Ser Pro Ser Ser Met Ser Ala Ser Val Gly
1 5 10 15

Asp Arg Val Thr Ile Thr Cys
20

<210> SEQ ID NO 230
<211> LENGTH: 23
<212> TYPE: PRT
<213> ORGANISM: Artificial Sequence
<220> FEATURE:
<223> OTHER INFORMATION: Humanized VL FR1

<400> SEQUENCE: 230

Asp Ile Gln Met Thr Gln Ser Pro Ser Ser Met Ser Thr Ser Val Gly
1 5 10 15

Asp Arg Val Thr Ile Thr Cys
20

<210> SEQ ID NO 231
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 231

Trp Phe Gln Gln Lys Pro Gly Gln Pro Pro Lys Leu Leu Ile Tyr
1 5 10 15

<210> SEQ ID NO 232
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 232

Trp Tyr Gln Gln Lys Pro Gly Gln Ser Pro Lys Leu Leu Ile Tyr
1 5 10 15

<210> SEQ ID NO 233
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 233

Trp Tyr Gln Gln Lys Pro Gly Gln Ser Pro Lys Leu Leu Ile Tyr
1 5 10 15

<210> SEQ ID NO 234
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 234

Trp Tyr Gln Gln Lys Pro Gly Ser Ser Pro Lys Pro Trp Ile Leu
1 5 10 15

<210> SEQ ID NO 235
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 235

Trp Tyr Gln Gln Lys Pro Gly Gln Ser Pro Lys Leu Leu Ile Tyr
1 5 10 15

<210> SEQ ID NO 236
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 236

Trp Tyr Gln Gln Lys Pro Gly Ser Ser Pro Lys Leu Trp Ile Tyr
1 5 10 15

<210> SEQ ID NO 237
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 237

Trp Tyr Leu Gln Lys Pro Gly Gln Ser Pro Lys Leu Leu Ile Phe
1 5 10 15

<210> SEQ ID NO 238
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 238

Trp Tyr Leu Gln Lys Pro Gly Gln Ser Pro Lys Leu Leu Ile Phe
1 5 10 15

<210> SEQ ID NO 239
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 239

Trp Tyr Gln Gln Lys Pro Asp Gly Thr Val Lys Leu Leu Ile Tyr
1 5 10 15

<210> SEQ ID NO 240
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 240

Trp Tyr Gln Gln Lys Pro Arg Ser Ser Pro Lys Pro Trp Ile Tyr
1 5 10 15

<210> SEQ ID NO 241
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 241

Trp Tyr Leu Gln Lys Pro Gly Gln Ser Pro Lys Leu Leu Ile Phe
1 5 10 15

<210> SEQ ID NO 242
<211> LENGTH: 15
<212> TYPE: PRT
<213> ORGANISM: Artificial Sequence
<220> FEATURE:
<223> OTHER INFORMATION: Mouse VL FR2

<400> SEQUENCE: 242

Trp Tyr Gln Gln Lys Pro Gly Gln Pro Pro Lys Leu Leu Ile Tyr
1 5 10 15

<210> SEQ ID NO 243
<211> LENGTH: 15
<212> TYPE: PRT
<213> ORGANISM: Artificial Sequence
<220> FEATURE:
<223> OTHER INFORMATION: Humanized VL FR2

<400> SEQUENCE: 243

Trp Tyr Gln Gln Lys Pro Gly Lys Ala Pro Lys Leu Leu Ile Tyr
1 5 10 15

<210> SEQ ID NO 244
<211> LENGTH: 15
<212> TYPE: PRT
<213> ORGANISM: Artificial Sequence
<220> FEATURE:
<223> OTHER INFORMATION: Humanized VL FR2

<400> SEQUENCE: 244

Trp Tyr Gln Gln Lys Pro Gly Lys Ala Pro Lys Leu Leu Ile Tyr
1 5 10 15

<210> SEQ ID NO 245
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 245

-continued

```
Gly Ile Pro Ala Arg Phe Ser Gly Ser Gly Ser Arg Thr Asp Phe Thr
1               5                   10                  15

Leu Thr Ile Asn Pro Val Glu Ala Asp Asp Val Ala Thr Tyr Tyr Cys
            20                  25                  30


<210> SEQ ID NO 246
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 246

Gly Val Pro Asp Arg Phe Thr Gly Ser Gly Ser Gly Thr Asp Phe Thr
1               5                   10                  15

Leu Thr Ile Ser Ser Val Gln Thr Glu Asp Leu Ala Leu Tyr Tyr Cys
            20                  25                  30


<210> SEQ ID NO 247
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 247

Gly Val Pro Asp Arg Phe Thr Gly Ser Gly Ser Gly Thr Ala Phe Thr
1               5                   10                  15

Phe Thr Ile Ser Ser Glu Gln Ala Glu Asp Leu Ala Val Tyr Tyr Cys
            20                  25                  30


<210> SEQ ID NO 248
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 248

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30


<210> SEQ ID NO 249
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 249

Gly Val Pro Asp Arg Phe Thr Gly Ser Gly Ser Gly Thr Ala Phe Thr
1               5                   10                  15

Phe Thr Ile Ser Gly Glu Gln Ala Glu Asp Leu Ala Val Tyr Tyr Cys
            20                  25                  30


<210> SEQ ID NO 250
<211> LENGTH: 32
<212> TYPE: PRT
<213> ORGANISM: Artificial Sequence
<220> FEATURE:
<223> OTHER INFORMATION: Mouse VL FR3
```

<400> SEQUENCE: 250

Gly Val Pro Ala Arg Phe Ser Gly Ser Gly Ser Gly Thr Ser Tyr Ser
1 5 10 15

Leu Thr Val Ser Ser Met Glu Ala Glu Asp Ala Ala Ser Tyr Phe Cys
20 25 30

<210> SEQ ID NO 251
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 251

Gly Val Pro Asp Arg Phe Ser Gly Ser Gly Ser Gly Thr Asp Phe Thr
1 5 10 15

Leu Lys Ile Asn Arg Val Glu Ala Glu Asp Leu Gly Val Tyr Tyr Cys
20 25 30

<210> SEQ ID NO 252
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 252

Gly Val Pro Asp Arg Phe Ser Gly Ser Gly Ser Gly Thr Asp Phe Thr
1 5 10 15

Leu Lys Ile Ser Arg Val Glu Ala Glu Asp Leu Gly Phe Tyr Tyr Cys
20 25 30

<210> SEQ ID NO 253
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 253

Gly Val Pro Ser Arg Phe Ser Gly Ser Gly Ser Gly Thr Asp Tyr Ser
1 5 10 15

Leu Thr Ile Ser Asn Leu Glu Gln Glu Asp Ile Ala Thr Tyr Phe Cys
20 25 30

<210> SEQ ID NO 254
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 254

Gly Val Pro Ala Arg Phe Ser Gly Ser Gly Ser Gly Thr Ser Tyr Ser
1 5 10 15

Leu Thr Ile Ser Ser Met Glu Ala Glu Asp Ala Ala Thr Tyr Tyr Cys
20 25 30

<210> SEQ ID NO 255
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 255

Gly Val Pro Asp Arg Phe Ser Gly Ser Gly Ser Gly Thr Asp Phe Thr
1 5 10 15

Leu Lys Ile Ser Arg Val Glu Ala Glu Asp Leu Gly Val Tyr Tyr Cys
20 25 30

<210> SEQ ID NO 256
<211> LENGTH: 32
<212> TYPE: PRT
<213> ORGANISM: Artificial Sequence
<220> FEATURE:
<223> OTHER INFORMATION: Mouse VL FR3

<400> SEQUENCE: 256

Gly Ile Pro Val Arg Phe Ser Gly Ser Gly Ser Arg Thr Asp Phe Thr
1 5 10 15

Leu Thr Ile Asn Pro Val Glu Ala Asp Asp Val Ala Thr Tyr Tyr Cys
20 25 30

<210> SEQ ID NO 257
<211> LENGTH: 32
<212> TYPE: PRT
<213> ORGANISM: Artificial Sequence
<220> FEATURE:
<223> OTHER INFORMATION: Humanized VL FR3

<400> SEQUENCE: 257

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 258
<211> LENGTH: 32
<212> TYPE: PRT
<213> ORGANISM: Artificial Sequence
<220> FEATURE:
<223> OTHER INFORMATION: Humanized VL FR3

<400> SEQUENCE: 258

Gly Val Pro Ser Arg Phe Ser Gly Ser Gly Ser Gly Thr Asp Phe Thr
1 5 10 15

Leu Thr Ile Ser Ser Leu Gln Pro Glu Asp Leu Ala Leu Tyr Tyr Cys
20 25 30

<210> SEQ ID NO 259
<211> LENGTH: 32
<212> TYPE: PRT
<213> ORGANISM: Artificial Sequence
<220> FEATURE:
<223> OTHER INFORMATION: Humanized VL FR3

<400> SEQUENCE: 259

Gly Val Pro Ser Arg Phe Ser Gly Ser Gly Ser Gly Thr Asp Phe Thr
1 5 10 15

Leu Thr Ile Ser Ser Val Gln Pro Glu Asp Leu Ala Leu Tyr Tyr Cys
20 25 30

<210> SEQ ID NO 260
<211> LENGTH: 32
<212> TYPE: PRT
<213> ORGANISM: Artificial Sequence
<220> FEATURE:

<223> OTHER INFORMATION: Humanized VL FR3

<400> SEQUENCE: 260

Gly Val Pro Asp Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 261
<211> LENGTH: 32
<212> TYPE: PRT
<213> ORGANISM: Artificial Sequence
<220> FEATURE:
<223> OTHER INFORMATION: Humanized VL FR3

<400> SEQUENCE: 261

Gly Val Pro Asp Arg Phe Ser Gly Ser Gly Ser Gly Thr Asp Phe Thr
1 5 10 15

Phe Thr Ile Ser Ser Leu Gln Pro Glu Asp Leu Ala Thr Tyr Tyr Cys
20 25 30

<210> SEQ ID NO 262
<211> LENGTH: 32
<212> TYPE: PRT
<213> ORGANISM: Artificial Sequence
<220> FEATURE:
<223> OTHER INFORMATION: Humanized VL FR3

<400> SEQUENCE: 262

Gly Val Pro Asp Arg Phe Ser Gly Ser Gly Ser Gly Thr Asp Phe Thr
1 5 10 15

Phe Thr Ile Ser Ser Glu Gln Pro Glu Asp Leu Ala Thr Tyr Tyr Cys
20 25 30

<210> SEQ ID NO 263
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 263

Phe Gly Gly Gly Thr Lys Leu Glu Ile Lys
1 5 10

<210> SEQ ID NO 264
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 264

Phe Gly Gly Gly Thr Lys Leu Glu Ile Lys
1 5 10

<210> SEQ ID NO 265
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 265

Phe Gly Gly Gly Thr Lys Leu Glu Ile Lys 1 5 10

<210> SEQ ID NO 266
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 266

Phe Gly Ala Gly Thr Lys Leu Glu Leu Lys
1 5 10

<210> SEQ ID NO 267
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 267

Phe Gly Gly Gly Thr Lys Leu Glu Ile Lys
1 5 10

<210> SEQ ID NO 268
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 268

Phe Gly Ser Gly Thr Lys Leu Glu Ile Lys
1 5 10

<210> SEQ ID NO 269
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 269

Phe Gly Ser Gly Thr Lys Leu Glu Ile Lys
1 5 10

<210> SEQ ID NO 270
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 270

Phe Gly Ser Gly Thr Lys Leu Glu Ile Lys
1 5 10

<210> SEQ ID NO 271
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 271

Phe Gly Gly Gly Thr Lys Leu Glu Ile Lys
1 5 10

<210> SEQ ID NO 272
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 272

Phe Gly Ala Gly Thr Lys Leu Glu Leu Lys
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 273

Phe Gly Ser Gly Thr Lys Leu Glu Ile Lys
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Mouse VL FR4

<400> SEQUENCE: 274

Phe Gly Gly Gly Thr Lys Leu Glu Ile Lys
1               5                   10

<210> SEQ ID NO 275
<211> LENGTH: 10
<212> TYPE: PRT
<213> ORGANISM: Artificial Sequence
<220> FEATURE:
<223> OTHER INFORMATION: Humanized VL FR4

<400> SEQUENCE: 275

Phe Gly Gln Gly Thr Lys Val Glu Ile Lys
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Humanized VL FR4

<400> SEQUENCE: 276

Phe Gly Gln Gly Thr Lys Leu Glu Ile Lys
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Humanized VL FR4

<400> SEQUENCE: 277

Phe Gly Gln Gly Thr Lys Leu Glu Ile Lys
1               5                   10

<210> SEQ ID NO 278
<211> LENGTH: 445
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 278

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Thr Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Met Thr Ala Glu Asp Thr Ala Thr Tyr Tyr Cys
                85                  90                  95

Ala Arg Asn Ser Leu Phe Ala Ser Trp Gly His Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 279
<211> LENGTH: 450
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 279

Asp Val Gln Leu Gln Gly Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asp Trp Ile Arg Gln Phe Pro Gly Asn Lys Leu Glu Trp
        35                  40                  45

Met Gly His Ile Arg Phe Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ala Arg Ser Thr Leu Ile Thr Lys Gly Phe Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

```
Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 280
<211> LENGTH: 449
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 280

Gln Val Gln Leu Gln Gln Ser Gly Ala Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Ser Trp Val Lys Gln Arg Thr Gly Gln Gly Leu Glu Trp Ile
        35                  40                  45

Gly Glu Ile Phe Pro Arg Thr Ala Asn Thr Tyr Phe Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 281
<211> LENGTH: 443
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 281

Asp Val Gln Leu Leu Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Asn Leu Glu Trp
        35                  40                  45

Met Gly Ser Ile Asn Tyr Asp Gly Ser Asn Asp Tyr Asn Pro Ser Leu
    50                  55                  60

Gln Asp Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Arg Leu Asp Tyr Trp Gly Gln Gly Thr Thr Leu Ile Val Ser
```

```
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 282
<211> LENGTH: 449
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 282

Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
```

```
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Lys

<210> SEQ ID NO 283
<211> LENGTH: 451
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 283

```
Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Ser Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Asn Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Thr Gly Ile Ile Thr Val Ile Ala Thr Arg Asp Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 284
<211> LENGTH: 453
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 284

```
Glu Gly Gln Leu Gln Gln Ser Gly Ala Gly Leu Val Lys Pro Gly Ala
1               5                   10                  15

Ser Val Asn Leu Ser Cys Thr Ala Ser Gly Phe Asn Ile Lys Asp Thr
            20                  25                  30

Tyr Ile His Trp Met Lys Gln Arg Pro Glu Gln Gly Leu Glu Trp Ile
        35                  40                  45

Gly Arg Ile Ala Pro Thr Asn Gly Asn Thr Lys Tyr Asp Pro Thr Phe
    50                  55                  60

Gln Gly Lys Ala Thr Ile Thr Ala Asp Ser Ser Ser Asn Thr Ala Tyr
65                  70                  75                  80

Leu Gln Val Ser Ser Leu Thr Ser Glu Asp Thr Ala Val Tyr Tyr Cys
                85                  90                  95

Ser Arg Gly Gly Ile Tyr Tyr Tyr Gly Ser His Trp Tyr Phe Asp Val
            100                 105                 110

Trp Gly Ala Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 285
<211> LENGTH: 453
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 285

Glu Gly Gln Leu Gln Gln Ser Gly Ala Glu Leu Val Lys Pro Gly Ala
1               5                   10                  15

Ser Val Asn Leu Ser Cys Thr Ala Ser Gly Phe Asn Ile Lys Asp Thr
            20                  25                  30

Tyr Ile His Trp Val Lys Gln Arg Pro Asp Gln Gly Leu Glu Trp Ile
        35                  40                  45

Gly Arg Ile Ala Pro Thr Asn Gly Asn Ala Lys Phe His Pro Thr Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Gly Gly Ile Tyr Tyr Tyr Gly Thr His Trp Tyr Phe Asp Val
            100                 105                 110

Trp Gly Ala Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 286
<211> LENGTH: 450
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 286

Gln Val Leu Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Met His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60
```

-continued

```
Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Tyr Gly Asn Tyr Gly Gly Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 287
<211> LENGTH: 449
<212> TYPE: PRT

<213> ORGANISM: Artificial Sequence
<220> FEATURE:
<223> OTHER INFORMATION: Chimeric IgG1 heavy chain with N297A mutation

<400> SEQUENCE: 287

```
Lys Val Gln Leu Gln Gln Ser Gly Ala Glu Leu Val Lys Pro Gly Thr
1               5                   10                  15

Ser Val Lys Leu Ser Cys Lys Ala Ser Gly Tyr Thr Phe Thr Glu Tyr
            20                  25                  30

Ile Ile Tyr Trp Ile Lys Gln Arg Ser Gly Gln Gly Leu Glu Trp Ile
        35                  40                  45

Gly Trp Phe Tyr Pro Gly Thr Gly Ser Ile Lys Tyr Asn Glu Lys Phe
    50                  55                  60

Lys Asp Lys Ala Thr Leu Thr Ala Asp Lys Ser Ser Ser Thr Val Phe
65                  70                  75                  80

Met Glu Leu Ser Arg Leu Thr Ser Glu Asp Ser Ala Val Tyr Phe Cys
                85                  90                  95

Ala Arg His Glu Glu Gly Asn Leu Trp Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 288
<211> LENGTH: 453
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 288

Glu Gly Gln Leu Gln Gln Ser Gly Ala Glu Leu Val Lys Pro Gly Ala
1 5 10 15

Ser Val Ile Leu Ser Cys Thr Ala Ser Gly Phe Asn Ile Lys Asp Thr
20 25 30

Tyr Ile His Trp Leu Asn Gln Arg Pro Glu Gln Gly Leu Glu Trp Ile
35 40 45

Gly Arg Ile Glu Pro Ala Asn Gly Asn Thr Lys Tyr Asp Pro Thr Phe
50 55 60

Gln Gly Lys Ala Thr Ile Thr Ala Asp Thr Ser Ser Asn Thr Ala Tyr
65 70 75 80

Leu Gln Leu Thr Ser Leu Thr Ser Glu Asp Thr Ala Val Tyr Tyr Cys
85 90 95

Ser Arg Gly Gly Ile Tyr Tyr Tyr Gly Ser His Trp Tyr Phe Asp Val
100 105 110

Trp Gly Ala Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Ala Ser
290 295 300

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 289
<211> LENGTH: 448
<212> TYPE: PRT
<213> ORGANISM: Artificial Sequence
<220> FEATURE:
<223> OTHER INFORMATION: Chimeric IgG1 heavy chain with N297A mutation

<400> SEQUENCE: 289

Gln Phe Gln Leu Gln Gln Ser Gly Ala Glu Leu Val Arg Pro Gly Ser
1               5                   10                  15

Ser Val Lys Ile Ser Cys Lys Ala Ser Gly Tyr Glu Phe Ser Ser Asn
            20                  25                  30

Trp Met Asn Trp Val Lys Gln Arg Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Arg Gly Lys Ala Thr Leu Thr Ser Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Gly Arg Ala Ser Phe Tyr Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 290
<211> LENGTH: 449
<212> TYPE: PRT
<213> ORGANISM: Artificial Sequence
<220> FEATURE:
<223> OTHER INFORMATION: Chimeric IgG1 heavy chain with CDR mutation and
      with N297A mutation

<400> SEQUENCE: 290

Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Ser Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
```

115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 291
<211> LENGTH: 449
<212> TYPE: PRT
<213> ORGANISM: Artificial Sequence
<220> FEATURE:
<223> OTHER INFORMATION: Chimeric IgG1 heavy chain with CDR mutation and with N297A mutation

<400> SEQUENCE: 291

Gln Val Gln Leu Gln Gln Ser Gly Asn Glu Leu Ala Arg Pro Gly Ala
1 5 10 15

Ser Val Arg Leu Ser Cys Lys Ala Ser Gly Tyr Ile Phe Thr Gly Tyr

```
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Lys

<210> SEQ ID NO 292
<211> LENGTH: 449
<212> TYPE: PRT
<213> ORGANISM: Artificial Sequence
<220> FEATURE:
<223> OTHER INFORMATION: Chimeric IgG1 heavy chain with CDR mutation and with N297A mutation

<400> SEQUENCE: 292

```
Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 293
<211> LENGTH: 450
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 293

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Pro Pro Gly Lys Gly Leu Glu Trp
        35                  40                  45

Ile Gly His Ile Arg Phe Ser Gly Thr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 294
<211> LENGTH: 450
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 294

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Phe Pro Gly Lys Gly Leu Glu Trp
        35                  40                  45

Met Gly His Ile Arg Phe Ser Gly Thr Thr Ser Tyr Asn Pro Ser Leu
    50                  55                  60

Lys Ser Arg Ile Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 295
<211> LENGTH: 450
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 295

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Phe Pro Gly Lys Gly Leu Glu Trp
        35                  40                  45

Met Gly His Ile Arg Phe Ser Gly Thr Thr Ser Tyr Asn Pro Ser Leu
    50                  55                  60
```

```
Lys Ser Arg Ile Thr Ile Ser Val Asp Thr Ser Lys Asn Gln Phe Phe
65                  70                  75                  80

Leu Lys Leu Ser Ser Val Thr Ala Ala Asp Thr Ala Thr Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 296
<211> LENGTH: 450
<212> TYPE: PRT

<213> ORGANISM: Artificial Sequence
<220> FEATURE:
<223> OTHER INFORMATION: Humanized IgG1 heavy chain with N297A mutation

<400> SEQUENCE: 296

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Pro Pro Gly Lys Gly Leu Glu Trp
        35                  40                  45

Ile Gly His Ile Arg Phe Ser Gly Thr Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val

```
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 297
<211> LENGTH: 450
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 297

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Phe Ala Trp Asp Trp Ile Arg Gln Pro Pro Gly Lys Gly Leu Glu Trp
        35                  40                  45

Ile Gly His Ile Arg Phe Ser Gly Thr Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
```

```
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 298
<211> LENGTH: 449
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 298

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 299
<211> LENGTH: 449
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 299

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110
```

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 300
<211> LENGTH: 449
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 300

Glu Val Gln Leu Val Gln Ser Gly Ala Glu Val Lys Lys Pro Gly Ala
1 5 10 15

```
Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

```
        435                 440                 445

Lys


<210> SEQ ID NO 301
<211> LENGTH: 449
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 301

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 302
<211> LENGTH: 449
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 302

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Asn Thr Tyr Tyr Ser Glu Lys Phe
50 55 60

Lys Gly Arg Val Thr Met Thr Ala Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 303
<211> LENGTH: 449
<212> TYPE: PRT
<213> ORGANISM: Artificial Sequence
<220> FEATURE:
<223> OTHER INFORMATION: Humanized IgG1 heavy chain with N297A mutation

<400> SEQUENCE: 303

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 304
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 304

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
```

-continued

```
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 305
<211> LENGTH: 449
<212> TYPE: PRT
<213> ORGANISM: Artificial Sequence
<220> FEATURE:
```

<223> OTHER INFORMATION: Humanized IgG1 heavy chain with CDR2 mutation
and with N297A mutation

<400> SEQUENCE: 305

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 306
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and with N297A mutation

<400> SEQUENCE: 306

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Ile
35 40 45

Gly Glu Ile Phe Pro Arg Arg Val Gln Thr Tyr Tyr Ser Glu Lys Phe
50 55 60

Lys Gly Arg Ala Thr Leu Thr Ala Asp Thr Ser Thr Ser Thr Ala Tyr
65 70 75 80

Met Glu Leu Arg Ser Leu Arg Ser Asp Asp Thr Ala Val Tyr Phe Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 307
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and with N297A mutation

<400> SEQUENCE: 307

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Gln Thr Tyr Tyr Ser Glu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 308
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 308

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

```
Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 309
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 309

Glu Val Gln Leu Val Gln Ser Gly Ala Glu Val Lys Lys Pro Gly Ala
1               5                   10                  15
```

-continued

```
Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
        435                 440                 445

Lys


<210> SEQ ID NO 310
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 310

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ser Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 311
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and with N297A mutation

<400> SEQUENCE: 311

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Ile
35 40 45

Gly Glu Ile Phe Pro Arg Arg Val Ser Thr Tyr Tyr Ser Glu Lys Phe
50 55 60

Lys Gly Arg Ala Thr Leu Thr Thr Asp Thr Ser Thr Ser Thr Ala Tyr
65 70 75 80

Met Glu Leu Arg Ser Leu Arg Ser Asp Asp Thr Ala Val Tyr Phe Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 312
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
and with N297A mutation

<400> SEQUENCE: 312

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Ile
35 40 45

Gly Glu Ile Phe Pro Arg Arg Val Ser Thr Tyr Tyr Ser Glu Lys Phe
50 55 60

Lys Gly Arg Ala Thr Leu Thr Ala Asp Thr Ser Thr Ser Thr Ala Tyr
65 70 75 80

Met Glu Leu Arg Ser Leu Arg Ser Asp Asp Thr Ala Val Tyr Phe Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

-continued

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 313
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 313

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45
```

```
Gly Glu Ile Phe Pro Arg Arg Val Ser Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 314

<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
and with N297A mutation

<400> SEQUENCE: 314

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ser Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 315
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 315

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ser Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 316
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and with N297A mutation

<400> SEQUENCE: 316

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ala Thr Tyr Tyr Ser Glu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser

```
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 317
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 317

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
```

```
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 318
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
and with N297A mutation

<400> SEQUENCE: 318

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Ile
35 40 45

Gly Glu Ile Phe Pro Arg Arg Val Ala Thr Tyr Tyr Ser Glu Lys Phe
50 55 60

Lys Gly Arg Ala Thr Leu Thr Ala Asp Thr Ser Thr Ser Thr Ala Tyr
65 70 75 80

Met Glu Leu Arg Ser Leu Arg Ser Asp Asp Thr Ala Val Tyr Phe Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

-continued

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 319
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and with N297A mutation

<400> SEQUENCE: 319

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ala Thr Tyr Tyr Ser Glu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 320
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and with N297A mutation

<400> SEQUENCE: 320

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Ala Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 321
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and with N297A mutation

<400> SEQUENCE: 321

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ala Thr Tyr Tyr Ser Glu Lys Phe
50 55 60

Lys Gly Arg Val Thr Met Thr Ala Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 322
<211> LENGTH: 218
<212> TYPE: PRT
<213> ORGANISM: Artificial Sequence
<220> FEATURE:
<223> OTHER INFORMATION: Chimeric kappa light chain

<400> SEQUENCE: 322

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
            20                  25                  30
```

```
Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Ala Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 323
<211> LENGTH: 214
<212> TYPE: PRT
<213> ORGANISM: Artificial Sequence
<220> FEATURE:
<223> OTHER INFORMATION: Chimeric kappa light chain

<400> SEQUENCE: 323

Asp Ile Val Met Thr Gln Ser His Lys Phe Met Ser Thr Ser Val Gly
1               5                   10                  15

Gly Arg Val Ser Ile Thr Cys Lys Ala Ser Gln Asp Val Ser Pro Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Thr
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 324
<211> LENGTH: 214
<212> TYPE: PRT
<213> ORGANISM: Artificial Sequence
<220> FEATURE:
<223> OTHER INFORMATION: Chimeric kappa light chain

<400> SEQUENCE: 324

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Ala Phe Thr Phe Thr Ile Ser Ser Glu Gln Ala
65                  70                  75                  80

Glu Asp Leu Ala Val Tyr Tyr Cys Gln Gln His Tyr Ser Val Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 325
<211> LENGTH: 213
<212> TYPE: PRT
<213> ORGANISM: Artificial Sequence
<220> FEATURE:
<223> OTHER INFORMATION: Chimeric kappa light chain

<400> SEQUENCE: 325

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Phe Ile Asn Tyr Met
            20                  25                  30

Tyr Trp Tyr Gln Gln Lys Pro Gly Ser Ser Pro Lys Pro Trp Ile Leu
        35                  40                  45
```

```
Arg Thr Ser Thr Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 326
<211> LENGTH: 214
<212> TYPE: PRT
<213> ORGANISM: Artificial Sequence
<220> FEATURE:
<223> OTHER INFORMATION: Chimeric kappa light chain

<400> SEQUENCE: 326

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Ala Phe Thr Phe Thr Ile Ser Gly Glu Gln Ala
65                  70                  75                  80

Glu Asp Leu Ala Val Tyr Tyr Cys Gln Gln His Tyr Ser Ile Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 327
<211> LENGTH: 215
<212> TYPE: PRT
<213> ORGANISM: Artificial Sequence
<220> FEATURE:
<223> OTHER INFORMATION: Chimeric kappa light chain

<400> SEQUENCE: 327

```
Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Val Ser Ser Met Glu
65                  70                  75                  80

Ala Glu Asp Ala Ala Ser Tyr Phe Cys His Gln Trp Ser Ser Tyr Pro
                85                  90                  95

Phe Thr Phe Gly Ser Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 328
<211> LENGTH: 219
<212> TYPE: PRT
<213> ORGANISM: Artificial Sequence
<220> FEATURE:
<223> OTHER INFORMATION: Chimeric kappa light chain

<400> SEQUENCE: 328

```
Ser Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Tyr Ser
            20                  25                  30

Asp Gly Asp Thr Tyr Leu Glu Trp Tyr Leu Gln Lys Pro Gly Gln Ser
        35                  40                  45

Pro Lys Leu Leu Ile Phe Lys Val Ser Asn Arg Phe Phe Gly Val Pro
```

```
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 329
<211> LENGTH: 219
<212> TYPE: PRT
<213> ORGANISM: Artificial Sequence
<220> FEATURE:
<223> OTHER INFORMATION: Chimeric kappa light chain

<400> SEQUENCE: 329

Asp Val Leu Met Asn Gln Thr Pro Leu Ser Leu Pro Val Ser Leu Gly
1               5                   10                  15

Asp Gln Ala Ser Ile Ser Cys Arg Ser Ser Gln Asn Ile Val Tyr Ser
            20                  25                  30

Asp Gly Asn Thr Tyr Leu Glu Trp Tyr Leu Gln Lys Pro Gly Gln Ser
        35                  40                  45

Pro Lys Leu Leu Ile Phe Gln Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Phe Tyr Tyr Cys Phe Gln Gly
                85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
        195                 200                 205

Pro Val Thr Lys Ser Phe Asn Arg Gly Glu Cys
    210                 215


<210> SEQ ID NO 330
<211> LENGTH: 214
<212> TYPE: PRT
<213> ORGANISM: Artificial Sequence
<220> FEATURE:
<223> OTHER INFORMATION: Chimeric kappa light chain

<400> SEQUENCE: 330

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Gly Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 331
<211> LENGTH: 213
<212> TYPE: PRT
<213> ORGANISM: Artificial Sequence
<220> FEATURE:
<223> OTHER INFORMATION: Chimeric kappa light chain

<400> SEQUENCE: 331

Gln Ile Val Leu Thr Gln Ser Pro Ala Leu Met Ser Ala Ser Pro Gly
1               5                   10                  15

Glu Arg Val Thr Met Thr Cys Ser Ala Ser Ser Asp Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Thr Gly Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 332
<211> LENGTH: 219
<212> TYPE: PRT
<213> ORGANISM: Artificial Sequence
<220> FEATURE:
<223> OTHER INFORMATION: Chimeric kappa light chain

<400> SEQUENCE: 332

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Tyr Ser
            20                  25                  30

Asp Gly Asp Thr Tyr Leu Glu Trp Tyr Leu Gln Lys Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 333
<211> LENGTH: 218
<212> TYPE: PRT
<213> ORGANISM: Artificial Sequence
<220> FEATURE:
<223> OTHER INFORMATION: Chimeric kappa light chain

<400> SEQUENCE: 333

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro His Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 334
<211> LENGTH: 214
<212> TYPE: PRT
<213> ORGANISM: Artificial Sequence
<220> FEATURE:
<223> OTHER INFORMATION: Chimeric kappa light chain with CDR mutation

<400> SEQUENCE: 334

Asp Ile Val Met Thr Gln Ser His Lys Phe Met Ser Thr Ser Val Gly
1               5                   10                  15

Gly Arg Val Ser Ile Thr Cys Arg Ala Ser Gln Asp Val Ser Pro Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Thr
65                  70                  75                  80

```
Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 335
<211> LENGTH: 214
<212> TYPE: PRT
<213> ORGANISM: Artificial Sequence
<220> FEATURE:
<223> OTHER INFORMATION: Chimeric kappa light chain with CDR mutation

<400> SEQUENCE: 335

Asp Ile Val Met Thr Gln Ser His Lys Phe Met Ser Thr Ser Val Gly
1               5                   10                  15

Asp Arg Val Ser Ile Thr Cys Arg Ala Ser Gln Asp Val Ser Thr Ala
            20                  25                  30

Val Asp Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Ala Phe Thr Phe Thr Ile Ser Gly Glu Gln Ala
65                  70                  75                  80

Glu Asp Leu Ala Val Tyr Tyr Cys Gln Gln His Tyr Ser Ile Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 336
<211> LENGTH: 214
<212> TYPE: PRT
<213> ORGANISM: Artificial Sequence
<220> FEATURE:
<223> OTHER INFORMATION: Humanized kappa light chain

<400> SEQUENCE: 336

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 337
<211> LENGTH: 214
<212> TYPE: PRT
<213> ORGANISM: Artificial Sequence
<220> FEATURE:
<223> OTHER INFORMATION: Humanized kappa light chain

<400> SEQUENCE: 337

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Leu Tyr Tyr Cys Gln Gln His Tyr Ser Thr Pro Trp
```

```
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 338
<211> LENGTH: 214
<212> TYPE: PRT
<213> ORGANISM: Artificial Sequence
<220> FEATURE:
<223> OTHER INFORMATION: Humanized kappa light chain

<400> SEQUENCE: 338

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Leu Tyr Tyr Cys Gln Gln His Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 339
<211> LENGTH: 214
<212> TYPE: PRT
<213> ORGANISM: Artificial Sequence
<220> FEATURE:
<223> OTHER INFORMATION: Humanized kappa light chain

<400> SEQUENCE: 339

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 340
<211> LENGTH: 214
<212> TYPE: PRT
<213> ORGANISM: Artificial Sequence
<220> FEATURE:
<223> OTHER INFORMATION: Humanized kappa light chain

<400> SEQUENCE: 340

```
Asp Ile Gln Met Thr Gln Ser Pro Ser Ser Met Ser Ala Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Leu Ala Thr Tyr Tyr Cys Gln Gln His Tyr Ser Ile Pro Phe
                85                  90                  95
```

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 341
<211> LENGTH: 214
<212> TYPE: PRT
<213> ORGANISM: Artificial Sequence
<220> FEATURE:
<223> OTHER INFORMATION: Humanized kappa light chain

<400> SEQUENCE: 341

Asp Ile Gln Met Thr Gln Ser Pro Ser Ser Met Ser Thr Ser Val Gly
1               5                   10                  15

Asp Arg Val Thr Ile Thr Cys Lys Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Glu Gln Pro
65                  70                  75                  80

Glu Asp Leu Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 342
<211> LENGTH: 214
```

<212> TYPE: PRT
<213> ORGANISM: Artificial Sequence
<220> FEATURE:
<223> OTHER INFORMATION: Humanized kappa light chain with CDR1 mutation

<400> SEQUENCE: 342

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 343
<211> LENGTH: 214
<212> TYPE: PRT
<213> ORGANISM: Artificial Sequence
<220> FEATURE:
<223> OTHER INFORMATION: Humanized kappa light chain with CDR1 mutation

<400> SEQUENCE: 343

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Leu Tyr Tyr Cys Gln Gln His Tyr Ser Thr Pro Trp
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 344
<211> LENGTH: 214
<212> TYPE: PRT
<213> ORGANISM: Artificial Sequence
<220> FEATURE:
<223> OTHER INFORMATION: Humanized kappa light chain with CDR1 mutation

<400> SEQUENCE: 344

Asp Ile Gln Met Thr Gln Ser Pro Ser Ser Leu Ser Thr Ser Val Gly
1               5                   10                  15

Asp Arg Val Thr Ile Thr Cys Arg Ala Ser Gln Asp Val Ser Pro Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Leu Ala Leu Tyr Tyr Cys Gln Gln His Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 345
<211> LENGTH: 214
<212> TYPE: PRT
<213> ORGANISM: Artificial Sequence
```

<220> FEATURE:
<223> OTHER INFORMATION: Humanized kappa light chain with CDR1 mutation

<400> SEQUENCE: 345

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 346
<211> LENGTH: 214
<212> TYPE: PRT
<213> ORGANISM: Artificial Sequence
<220> FEATURE:
<223> OTHER INFORMATION: Humanized kappa light chain with CDR1 mutation

<400> SEQUENCE: 346

Asp Ile Gln Met Thr Gln Ser Pro Ser Ser Met Ser Ala Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Leu Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 347
<211> LENGTH: 214
<212> TYPE: PRT
<213> ORGANISM: Artificial Sequence
<220> FEATURE:
<223> OTHER INFORMATION: Humanized kappa light chain with CDR1 mutation

<400> SEQUENCE: 347

Asp Ile Gln Met Thr Gln Ser Pro Ser Ser Met Ser Thr Ser Val Gly
1               5                   10                  15

Asp Arg Val Thr Ile Thr Cys Arg Ala Ser Gln Asp Val Ser Thr Ala
            20                  25                  30

Val Asp Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Glu Gln Pro
65                  70                  75                  80

Glu Asp Leu Ala Thr Tyr Tyr Cys Gln Gln His Tyr Ser Ile Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 348
<211> LENGTH: 445
<212> TYPE: PRT
<213> ORGANISM: Artificial Sequence
<220> FEATURE:
<223> OTHER INFORMATION: Chimeric IgG1 heavy chain with WT constant
```

region

<400> SEQUENCE: 348

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Thr Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Met Thr Ala Glu Asp Thr Ala Thr Tyr Tyr Cys
                85                  90                  95

Ala Arg Asn Ser Leu Phe Ala Ser Trp Gly His Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 349
<211> LENGTH: 450
<212> TYPE: PRT
<213> ORGANISM: Artificial Sequence
<220> FEATURE:
<223> OTHER INFORMATION: Chimeric IgG1 heavy chain with WT constant
      region

<400> SEQUENCE: 349

Asp Val Gln Leu Gln Gly Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asp Trp Ile Arg Gln Phe Pro Gly Asn Lys Leu Glu Trp
        35                  40                  45

Met Gly His Ile Arg Phe Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ala Arg Ser Thr Leu Ile Thr Lys Gly Phe Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 350
<211> LENGTH: 449
<212> TYPE: PRT
<213> ORGANISM: Artificial Sequence
<220> FEATURE:
<223> OTHER INFORMATION: Chimeric IgG1 heavy chain with WT constant
      region

<400> SEQUENCE: 350

Gln Val Gln Leu Gln Gln Ser Gly Ala Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Ser Trp Val Lys Gln Arg Thr Gly Gln Gly Leu Glu Trp Ile
        35                  40                  45

Gly Glu Ile Phe Pro Arg Thr Ala Asn Thr Tyr Phe Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
```

```
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 351
<211> LENGTH: 443
<212> TYPE: PRT
<213> ORGANISM: Artificial Sequence
<220> FEATURE:
<223> OTHER INFORMATION: Chimeric IgG1 heavy chain with WT constant
      region

<400> SEQUENCE: 351

Asp Val Gln Leu Leu Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Asn Leu Glu Trp
        35                  40                  45

Met Gly Ser Ile Asn Tyr Asp Gly Ser Asn Asp Tyr Asn Pro Ser Leu
    50                  55                  60

Gln Asp Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Arg Leu Asp Tyr Trp Gly Gln Gly Thr Thr Leu Ile Val Ser
            100                 105                 110

Ser Ala Ser Thr Lys Gly Pro Ser Val Phe Pro Leu Ala Pro Ser Ser
```

```
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 352
<211> LENGTH: 449
<212> TYPE: PRT
<213> ORGANISM: Artificial Sequence
<220> FEATURE:
<223> OTHER INFORMATION: Chimeric IgG1 heavy chain with WT constant
      region

<400> SEQUENCE: 352

Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30
```

```
Gly Ile Thr Trp Val Arg Gln Arg Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 353
<211> LENGTH: 451
<212> TYPE: PRT
<213> ORGANISM: Artificial Sequence
<220> FEATURE:
<223> OTHER INFORMATION: Chimeric IgG1 heavy chain with WT constant region

<400> SEQUENCE: 353

Gln Val Gln Leu Gln Gln Pro Gly Ala Glu Val Val Arg Pro Gly Ala
1 5 10 15

Ser Val Lys Leu Ser Cys Lys Ala Ser Gly Tyr Thr Phe Thr Asn Tyr
20 25 30

Trp Ile Ser Trp Val Lys Gln Arg Pro Gly Gln Gly Leu Glu Trp Ile
35 40 45

Gly Asn Ile Tyr Pro Ser Asp Ser Tyr Thr Asn Tyr Asn Gln Asn Phe
50 55 60

Lys Asp Lys Ala Thr Leu Thr Val Asp Lys Ser Ser Ser Thr Ala Tyr
65 70 75 80

Met Gln Leu Ser Ser Pro Thr Ser Glu Asp Ser Ala Val Tyr Tyr Cys
85 90 95

Thr Thr Gly Ile Ile Thr Val Ile Ala Thr Arg Asp Asp Tyr Trp Gly
100 105 110

Gln Gly Thr Thr Leu Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Arg Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser

```
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 354
<211> LENGTH: 453
<212> TYPE: PRT
<213> ORGANISM: Artificial Sequence
<220> FEATURE:
<223> OTHER INFORMATION: Chimeric IgG1 heavy chain with WT constant
      region

<400> SEQUENCE: 354

Glu Gly Gln Leu Gln Gln Ser Gly Ala Gly Leu Val Lys Pro Gly Ala
1               5                   10                  15

Ser Val Asn Leu Ser Cys Thr Ala Ser Gly Phe Asn Ile Lys Asp Thr
            20                  25                  30

Tyr Ile His Trp Met Lys Gln Arg Pro Glu Gln Gly Leu Glu Trp Ile
        35                  40                  45

Gly Arg Ile Ala Pro Thr Asn Gly Asn Thr Lys Tyr Asp Pro Thr Phe
    50                  55                  60

Gln Gly Lys Ala Thr Ile Thr Ala Asp Ser Ser Ser Asn Thr Ala Tyr
65                  70                  75                  80

Leu Gln Val Ser Ser Leu Thr Ser Glu Asp Thr Ala Val Tyr Tyr Cys
                85                  90                  95

Ser Arg Gly Gly Ile Tyr Tyr Tyr Gly Ser His Trp Tyr Phe Asp Val
            100                 105                 110

Trp Gly Ala Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Asp Glu Leu Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 355
<211> LENGTH: 453
<212> TYPE: PRT
<213> ORGANISM: Artificial Sequence
<220> FEATURE:
<223> OTHER INFORMATION: Chimeric IgG1 heavy chain with WT constant region

<400> SEQUENCE: 355

Glu Gly Gln Leu Gln Gln Ser Gly Ala Glu Leu Val Lys Pro Gly Ala
1 5 10 15

Ser Val Asn Leu Ser Cys Thr Ala Ser Gly Phe Asn Ile Lys Asp Thr
20 25 30

Tyr Ile His Trp Val Lys Gln Arg Pro Asp Gln Gly Leu Glu Trp Ile
35 40 45

Gly Arg Ile Ala Pro Thr Asn Gly Asn Ala Lys Phe His Pro Thr Phe
50 55 60

Gln Gly Lys Ala Thr Ile Thr Ala Asp Thr Ser Ser Asn Thr Ala Tyr
65 70 75 80

Leu Gln Leu Ser Ser Leu Thr Ser Glu Asp Thr Ala Val Tyr Tyr Cys
85 90 95

Thr Arg Gly Gly Ile Tyr Tyr Tyr Gly Thr His Trp Tyr Phe Asp Val
100 105 110

Trp Gly Ala Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Arg Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Asp Glu Leu Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 356
<211> LENGTH: 450
<212> TYPE: PRT
<213> ORGANISM: Artificial Sequence
<220> FEATURE:
<223> OTHER INFORMATION: Chimeric IgG1 heavy chain with WT constant region

<400> SEQUENCE: 356

Gln Val Leu Leu Gln Gln Ser Gly Pro Glu Leu Val Lys Pro Gly Ala
1 5 10 15

Ser Val Arg Ile Ser Cys Lys Ala Ser Gly Tyr Thr Phe Thr Ser Tyr
20 25 30

Tyr Met His Trp Val Lys Gln Arg Pro Gly Gln Gly Leu Glu Trp Ile
35 40 45

Gly Trp Ile Tyr Pro Gly Asn Val Asn Thr Lys Tyr Asn Glu Lys Phe

```
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Tyr Gly Asn Tyr Gly Gly Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 357

<211> LENGTH: 449
<212> TYPE: PRT
<213> ORGANISM: Artificial Sequence
<220> FEATURE:
<223> OTHER INFORMATION: Chimeric IgG1 heavy chain with WT constant region

<400> SEQUENCE: 357

Lys Val Gln Leu Gln Gln Ser Gly Ala Glu Leu Val Lys Pro Gly Thr
1 5 10 15

Ser Val Lys Leu Ser Cys Lys Ala Ser Gly Tyr Thr Phe Thr Glu Tyr
20 25 30

Ile Ile Tyr Trp Ile Lys Gln Arg Ser Gly Gln Gly Leu Glu Trp Ile
35 40 45

Gly Trp Phe Tyr Pro Gly Thr Gly Ser Ile Lys Tyr Asn Glu Lys Phe
50 55 60

Lys Asp Lys Ala Thr Leu Thr Ala Asp Lys Ser Ser Ser Thr Val Phe
65 70 75 80

Met Glu Leu Ser Arg Leu Thr Ser Glu Asp Ser Ala Val Tyr Phe Cys
85 90 95

Ala Arg His Glu Glu Gly Asn Leu Trp Phe Ala Tyr Trp Gly Gln Gly
100 105 110

Thr Leu Val Thr Val Ser Ala Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu 370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 358
<211> LENGTH: 453
<212> TYPE: PRT
<213> ORGANISM: Artificial Sequence
<220> FEATURE:
<223> OTHER INFORMATION: Chimeric IgG1 heavy chain with WT constant region

<400> SEQUENCE: 358

Glu Gly Gln Leu Gln Gln Ser Gly Ala Glu Leu Val Lys Pro Gly Ala
1 5 10 15

Ser Val Ile Leu Ser Cys Thr Ala Ser Gly Phe Asn Ile Lys Asp Thr
20 25 30

Tyr Ile His Trp Leu Asn Gln Arg Pro Glu Gln Gly Leu Glu Trp Ile
35 40 45

Gly Arg Ile Glu Pro Ala Asn Gly Asn Thr Lys Tyr Asp Pro Thr Phe
50 55 60

Gln Gly Lys Ala Thr Ile Thr Ala Asp Thr Ser Ser Asn Thr Ala Tyr
65 70 75 80

Leu Gln Leu Thr Ser Leu Thr Ser Glu Asp Thr Ala Val Tyr Tyr Cys
85 90 95

Ser Arg Gly Gly Ile Tyr Tyr Tyr Gly Ser His Trp Tyr Phe Asp Val
100 105 110

Trp Gly Ala Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Arg Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val

```
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 359
<211> LENGTH: 448
<212> TYPE: PRT
<213> ORGANISM: Artificial Sequence
<220> FEATURE:
<223> OTHER INFORMATION: Chimeric IgG1 heavy chain with WT constant
      region

<400> SEQUENCE: 359

Gln Phe Gln Leu Gln Gln Ser Gly Ala Glu Leu Val Arg Pro Gly Ser
1               5                   10                  15

Ser Val Lys Ile Ser Cys Lys Ala Ser Gly Tyr Glu Phe Ser Ser Asn
            20                  25                  30

Trp Met Asn Trp Val Lys Gln Arg Pro Gly Gln Ser Leu Glu Trp Ile
        35                  40                  45

Gly Gln Ile Trp Pro Gly Asp Gly Asp Thr Asn Tyr Asn Gly Lys Phe
    50                  55                  60

Arg Gly Lys Ala Thr Leu Thr Ser Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Gly Arg Ala Ser Phe Tyr Phe Asp Tyr Trp Gly Gln Gly Thr
            100                 105                 110

Ala Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 360
<211> LENGTH: 449
<212> TYPE: PRT
<213> ORGANISM: Artificial Sequence
<220> FEATURE:
<223> OTHER INFORMATION: Chimeric IgG1 heavy chain with CDR mutation and WT constant region

<400> SEQUENCE: 360

```
Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Ser Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95
```

```
Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 361
<211> LENGTH: 449
<212> TYPE: PRT
<213> ORGANISM: Artificial Sequence
<220> FEATURE:
<223> OTHER INFORMATION: Chimeric IgG1 heavy chain with CDR mutation and WT constant region

<400> SEQUENCE: 361

```
Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 362
<211> LENGTH: 449
<212> TYPE: PRT
<213> ORGANISM: Artificial Sequence
<220> FEATURE:
<223> OTHER INFORMATION: Chimeric IgG1 heavy chain with CDR mutation and
      WT constant region

<400> SEQUENCE: 362

Gln Val Gln Leu Gln Gln Ser Gly Asn Glu Leu Ala Arg Pro Gly Ala
1               5                   10                  15

Ser Val Arg Leu Ser Cys Lys Ala Ser Gly Tyr Ile Phe Thr Gly Tyr
            20                  25                  30

Gly Ile Thr Trp Val Arg Gln Arg Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Ala Asp Ile Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 363
<211> LENGTH: 450
<212> TYPE: PRT
<213> ORGANISM: Artificial Sequence
<220> FEATURE:
<223> OTHER INFORMATION: Humanized IgG1 heavy chain with WT constant region

<400> SEQUENCE: 363

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp
20 25 30

Phe Ala Trp Asp Trp Ile Arg Gln Pro Pro Gly Lys Gly Leu Glu Trp
35 40 45

Ile Gly His Ile Arg Phe Ser Gly Thr Thr Ser Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Thr Leu Ile Thr Lys Gly Phe Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 364
<211> LENGTH: 450
<212> TYPE: PRT
<213> ORGANISM: Artificial Sequence
<220> FEATURE:
<223> OTHER INFORMATION: Humanized IgG1 heavy chain with WT constant region

<400> SEQUENCE: 364

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp
20 25 30

Phe Ala Trp Asp Trp Ile Arg Gln Phe Pro Gly Lys Gly Leu Glu Trp
35 40 45

Met Gly His Ile Arg Phe Ser Gly Thr Thr Ser Tyr Asn Pro Ser Leu
50 55 60

Lys Ser Arg Ile Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Thr Leu Ile Thr Lys Gly Phe Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 365
<211> LENGTH: 450
<212> TYPE: PRT
<213> ORGANISM: Artificial Sequence
<220> FEATURE:
<223> OTHER INFORMATION: Humanized IgG1 heavy chain with WT constant region

<400> SEQUENCE: 365

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp

```
            20                  25                  30

Phe Ala Trp Asp Trp Ile Arg Gln Phe Pro Gly Lys Gly Leu Glu Trp
        35                  40                  45

Met Gly His Ile Arg Phe Ser Gly Thr Thr Ser Tyr Asn Pro Ser Leu
    50                  55                  60

Lys Ser Arg Ile Thr Ile Ser Val Asp Thr Ser Lys Asn Gln Phe Phe
65                  70                  75                  80

Leu Lys Leu Ser Ser Val Thr Ala Ala Asp Thr Ala Thr Tyr Tyr Cys
                85                  90                  95

Ala Arg Ser Thr Leu Ile Thr Lys Gly Phe Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly Lys
450

<210> SEQ ID NO 366
<211> LENGTH: 450
<212> TYPE: PRT
<213> ORGANISM: Artificial Sequence
<220> FEATURE:
<223> OTHER INFORMATION: Humanized IgG1 heavy chain with WT constant region

<400> SEQUENCE: 366

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp
20 25 30

Phe Ala Trp Asp Trp Ile Arg Gln Pro Pro Gly Lys Gly Leu Glu Trp
35 40 45

Ile Gly His Ile Arg Phe Ser Gly Thr Thr Ser Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Thr Leu Ile Thr Lys Gly Phe Phe Asp Tyr Trp Gly Gln
100 105 110

Gly Thr Leu Leu Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr 340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 367
<211> LENGTH: 450
<212> TYPE: PRT
<213> ORGANISM: Artificial Sequence
<220> FEATURE:
<223> OTHER INFORMATION: Humanized IgG1 heavy chain with WT constant region

<400> SEQUENCE: 367

Glu Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Thr Ser Asp
20 25 30

Phe Ala Trp Asp Trp Ile Arg Gln Pro Pro Gly Lys Gly Leu Glu Trp
35 40 45

Ile Gly His Ile Arg Phe Ser Gly Thr Thr Ser Tyr Asn Pro Ser Leu
50 55 60

Lys Ser Arg Val Thr Ile Ser Arg Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Ser Thr Leu Ile Thr Lys Gly Phe Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 368
<211> LENGTH: 449
<212> TYPE: PRT
<213> ORGANISM: Artificial Sequence
<220> FEATURE:
<223> OTHER INFORMATION: Humanized IgG1 heavy chain with WT constant
      region

<400> SEQUENCE: 368

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 369
<211> LENGTH: 449
<212> TYPE: PRT
<213> ORGANISM: Artificial Sequence
<220> FEATURE:
<223> OTHER INFORMATION: Humanized IgG1 heavy chain with WT constant region

<400> SEQUENCE: 369

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Ile
35 40 45

```
Gly Glu Ile Phe Pro Arg Arg Val Asn Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 370
<211> LENGTH: 449
<212> TYPE: PRT
<213> ORGANISM: Artificial Sequence
<220> FEATURE:
<223> OTHER INFORMATION: Humanized IgG1 heavy chain with WT constant region

<400> SEQUENCE: 370

```
Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Asn Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 371
<211> LENGTH: 449
<212> TYPE: PRT
<213> ORGANISM: Artificial Sequence
<220> FEATURE:
<223> OTHER INFORMATION: Humanized IgG1 heavy chain with WT constant
      region

<400> SEQUENCE: 371

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 372
<211> LENGTH: 449
<212> TYPE: PRT
<213> ORGANISM: Artificial Sequence
<220> FEATURE:
<223> OTHER INFORMATION: Humanized IgG1 heavy chain with WT constant
      region

<400> SEQUENCE: 372

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

-continued

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 373
<211> LENGTH: 449
<212> TYPE: PRT
<213> ORGANISM: Artificial Sequence
<220> FEATURE:
<223> OTHER INFORMATION: Humanized IgG1 heavy chain with WT constant
      region

<400> SEQUENCE: 373

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Asn Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 374
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
and WT constant region

<400> SEQUENCE: 374

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 375
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 375

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 376
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 376

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Gln Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
```

```
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 377
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 377

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
```

```
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 378
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 378

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
```

```
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Gln Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Lys

<210> SEQ ID NO 379
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and WT constant region

<400> SEQUENCE: 379

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Gln Thr Tyr Tyr Ser Glu Lys Phe
50 55 60

Lys Gly Arg Val Thr Met Thr Ala Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 380
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and WT constant region

<400> SEQUENCE: 380

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ser Thr Tyr Tyr Ser Glu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 381
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 381

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ser Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 382
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
and WT constant region

<400> SEQUENCE: 382

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Ile
35 40 45

Gly Glu Ile Phe Pro Arg Arg Val Ser Thr Tyr Tyr Ser Glu Lys Phe
50 55 60

Lys Gly Arg Ala Thr Leu Thr Ala Asp Thr Ser Thr Ser Thr Ala Tyr
65 70 75 80

Met Glu Leu Arg Ser Leu Arg Ser Asp Asp Thr Ala Val Tyr Phe Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 383
<211> LENGTH: 449
<212> TYPE: PRT

<213> ORGANISM: Artificial Sequence
<220> FEATURE:
<223> OTHER INFORMATION: Humanized IgG1 heavy chain with CDR2 mutation
and WT constant region

<400> SEQUENCE: 383

Glu Val Gln Leu Val Gln Ser Gly Ala Glu Val Lys Lys Pro Gly Ala
1 5 10 15

Ser Val Lys Leu Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ser Thr Tyr Tyr Ser Glu Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

-continued

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 384
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and WT constant region

<400> SEQUENCE: 384

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ser Thr Tyr Tyr Ser Glu Lys Phe
50 55 60

Lys Gly Arg Val Thr Met Thr Ala Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 385
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 385

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ser Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

-continued

```
Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 386
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 386

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

-continued

```
Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 387
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
and WT constant region

<400> SEQUENCE: 387

-continued

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
            420                 425                 430

Ala Leu His Asn His Tyr Thr Gln Lys Ser Leu Ser Leu Ser Pro Gly
        435                 440                 445

Lys


<210> SEQ ID NO 388
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 388

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Ile
        35                  40                  45

Gly Glu Ile Phe Pro Arg Arg Val Ala Thr Tyr Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 389
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 389

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
        35                  40                  45

Gly Glu Ile Phe Pro Arg Arg Val Ala Thr Tyr Tyr Ser Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
```

225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 390
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation and WT constant region

<400> SEQUENCE: 390

Glu Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Gly Tyr
20 25 30

Gly Ile Thr Trp Val Arg Gln Ala Pro Gly Gln Gly Leu Glu Trp Met
35 40 45

Gly Glu Ile Phe Pro Arg Arg Val Ala Thr Tyr Tyr Ser Glu Lys Phe
50 55 60

Lys Gly Arg Val Thr Met Thr Ala Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Tyr Asp Pro Tyr Phe Ala Leu Asp Tyr Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu

```
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 391
<211> LENGTH: 449
<212> TYPE: PRT
<213> ORGANISM: Artificial Sequence
<220> FEATURE:
<223> OTHER INFORMATION: Humanized IgG1 heavy chain with CDR2 mutation
      and WT constant region

<400> SEQUENCE: 391

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Gly Tyr
            20                  25                  30

Gly Ile Thr Trp Val Arg Gln Ala Pro Gly Gln Gly Leu Glu Trp Met
```

-continued

```
        35                  40                  45

Gly Glu Ile Phe Pro Arg Arg Val Ala Thr Tyr Tyr Ser Glu Lys Phe
    50                  55                  60

Lys Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Pro Tyr Phe Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 392
<211> LENGTH: 330
<212> TYPE: PRT
<213> ORGANISM: Artificial Sequence
<220> FEATURE:
<223> OTHER INFORMATION: Heavy chain constant region of IgG1 with N297A
      mutation

<400> SEQUENCE: 392

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 393
<211> LENGTH: 107
<212> TYPE: PRT
<213> ORGANISM: Artificial Sequence
```

```
<220> FEATURE:
<223> OTHER INFORMATION: Light chain constant region of IgG1

<400> SEQUENCE: 393

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 394
<211> LENGTH: 330
<212> TYPE: PRT
<213> ORGANISM: Artificial Sequence
<220> FEATURE:
<223> OTHER INFORMATION: Heavy chain constant region of WT IgG1

<400> SEQUENCE: 394

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 395
<211> LENGTH: 272
<212> TYPE: PRT
<213> ORGANISM: Artificial Sequence
<220> FEATURE:
<223> OTHER INFORMATION: PD-L1

<400> SEQUENCE: 395

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
```

```
            260                 265                 270


<210> SEQ ID NO 396
<211> LENGTH: 220
<212> TYPE: PRT
<213> ORGANISM: Artificial Sequence
<220> FEATURE:
<223> OTHER INFORMATION: PD-L1 ECD

<400> SEQUENCE: 396

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220


<210> SEQ ID NO 397
<211> LENGTH: 9
<212> TYPE: PRT
<213> ORGANISM: Artificial Sequence
<220> FEATURE:
<223> OTHER INFORMATION: Peptide Linker

<400> SEQUENCE: 397

Gly Gly Gly Gly Ser Gly Gly Gly Ser
1               5


<210> SEQ ID NO 398
<211> LENGTH: 15
<212> TYPE: PRT
<213> ORGANISM: Artificial Sequence
<220> FEATURE:
<223> OTHER INFORMATION: Peptide Linker

<400> SEQUENCE: 398

Gly Gly Gly Gly Ser Gly Gly Gly Gly Ser Gly Gly Gly Gly Ser
1               5                   10                  15
```

<210> SEQ ID NO 399
<211> LENGTH: 15
<212> TYPE: PRT
<213> ORGANISM: Artificial Sequence
<220> FEATURE:
<223> OTHER INFORMATION: Peptide Linker

<400> SEQUENCE: 399

```
Glu Pro Lys Ser Ser Asp Lys Thr His Thr Ser Pro Pro Ser Pro
1               5                   10                  15
```

<210> SEQ ID NO 400
<211> LENGTH: 143
<212> TYPE: PRT
<213> ORGANISM: Artificial Sequence
<220> FEATURE:
<223> OTHER INFORMATION: human PD-1 ECD

<400> SEQUENCE: 400

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140
```

<210> SEQ ID NO 401
<211> LENGTH: 5
<212> TYPE: PRT
<213> ORGANISM: artificial
<220> FEATURE:
<223> OTHER INFORMATION: Peptide Linker

<400> SEQUENCE: 401

```
Gly Ser Gly Gly Ser
1               5
```

<210> SEQ ID NO 402
<211> LENGTH: 4
<212> TYPE: PRT
<213> ORGANISM: artificial
<220> FEATURE:
<223> OTHER INFORMATION: Peptide Linker

<400> SEQUENCE: 402

```
Gly Gly Gly Ser
1
```

<210> SEQ ID NO 403

-continued

```
<211> LENGTH: 5
<212> TYPE: PRT
<213> ORGANISM: artificial
<220> FEATURE:
<223> OTHER INFORMATION: Peptide Linker

<400> SEQUENCE: 403

Gly Gly Gly Gly Ser
1               5
```

ANTIBODIES AND VARIANTS THEREOF AGAINST PD-L1

CROSS-REFERENCE TO RELATED APPLICATION

This application is a Section 371 of International Application No. PCT/CN2018/124925, filed on Dec. 28, 2018, which published in the English language on Jul. 4, 2019 under International Publication No. WO 2019/129211 A1, which claims priority to Chinese Application No. PCT/CN2017/119505, filed on Dec. 28, 2017, the disclosures of which are incorporated herein by reference in their entirety.

REFERENCE TO SEQUENCE LISTING SUBMITTED ELECTRONICALLY

This application contains a Sequence Listing that has been submitted electronically as an ASCII text file named "51624-0024US1_ST25_SL.txt." The ASCII text file, created on Jul. 18, 2024, is 546,302 bytes in size. The material in the ASCII text file is hereby incorporated by reference in its entirety.

FIELD OF THE INVENTION

The application relates to antibodies or antigen binding fragments thereof capable binding specifically to a PD-L1 protein and uses of such agents. In some embodiments, the application relates to mouse and humanized monoclonal antibodies directed to PD-L1 and uses of these antibodies. The antibodies or antigen binding fragments thereof are useful as diagnostics and for the treatment of diseases associated with the activity and/or expression of PD-L1.

BACKGROUND OF THE INVENTION

Humoral immunity (B cell mediated) and cellular immunity (T cell mediated) are the two arms of human acquired immune system to fight against outside infections and inside pathological changes. T cells, as a crucial member in the immune system, play an essential role in the tumor immunotherapy. T cell activation is the major mechanism to eliminate cancer cells for both traditional cytokine drugs and the newly raised immune checkpoint drugs (Esther el al., *physiol,* 25(2):85-101, 2010; Drew, *Nature Reviews Cancer* 12:252-264, 2012).

There are two steps of signals for T-cell activation. The first step is the main stimulation activated by TCR recognizing antigens presented by MHC. This signal is antigen specific. The second type of signal for T-cell activation is also called co-stimulation signal (Jennifer et al., Annu Rev Immunol. 27:591-619, 2009). In contrast. T cells also receive some co-inhibitory signal. These bio-molecules that stimulate or inhibit T-cell functions are called immune checkpoint molecules. The purpose of immune checkpoint therapy is to control the stimulatory or inhibitory signal of T cells through immune checkpoints to kill tumor cells and finally cure cancer (Suzanne et al, *Cancer Cell* 27(4):450-461, 2015).

Programmed cell death 1 (PD-1) is a cell surface receptor that plays an important role in down-regulating the immune system and promoting self-tolerance by suppressing T cell inflammatory activity. PD-1 is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells) (Francisco et al., *Immunological Reviews.* 236: 219-42, 2010; Fife et al., *Annals of the New York Academy of Sciences.* 1217: 45-59, 2011). Through these mechanisms, PD-1 inhibits the immune system. This prevents autoimmune diseases, but it can also prevent the immune system from killing cancer cells. A new class of drugs that block PD-1, i.e. the PD-1 inhibitors, activate the immune system to attack tumors and are therefore used with varying success to treat some types of cancer.

A number of cancer immunotherapy agents that target the PD-1 receptor have been developed. One such anti-PD-1 antibody drug, nivolumab, (Opdivo—Bristol Myers Squibb), was approved in Japan in July 2014 and by the US FDA in December 2014 to treat metastatic melanoma. The other anti-PD-1 antibody drug is Pembrolizumab (Keytruda, MK-3475, Merck), which was approved by the FDA in Sept 2014 to treat metastatic melanoma. Pembrolizumab has been made accessible to advanced melanoma patients in the UK via UK Early Access to Medicines Scheme (EAMS) in March 2015. It is being used in clinical trials in the US for lung cancer, lymphoma, and mesothelioma. It has had measured success, with little side effects. On Oct. 2, 2015 Pembrolizumab was approved by FDA for advanced (metastatic) non-small cell lung cancer (NSCLC) patients whose disease has progressed after other treatments.

PD-1 binds two ligands. Programmed death-ligand 1 (PD-L1) and Programmed death-ligand 2 (PD-L2). PD-L1 is a single transmembrane protein of approximately 53 kDa in size and a very important immune checkpoint molecule as well. The binding of PD-L1 with PD-1 will activate the co-inhibitory signal to reduce T cell activity and proliferation. In humans PD-L1 is expressed on a number of immune cell types including activated and anergic/exhausted T cells, on naïve and activated B cells, as well as on myeloid dendritic cells (DC), monocytes and mast cells. It is also expressed on non-immune cells including islets of the pancreas. Kupffer cells of the liver, vascular endothelium and selected epithelia, for example airway epithelia and renal tubule epithelia, where its expression is enhanced during inflammatory episodes. PD-L1 expression is also found at increased levels on a number of tumors including, but not limited to breast, colon, colorectal, lung, renal, including renal cell carcinoma, gastric, bladder, non-small cell lung cancer (NSCLC), hepatocellular cancer (HCC), and pancreatic cancer, as well as melanoma. The over-expressed PD-L1 will strongly inhibit the T cell toxicity to tumor cells and help tumor cells to evade T cell surveillance and elimination (Dong et al., *Nat Med;* 8:793-800, 2002).

A PD-L1 monoclonal antibody that inhibits the binding between PD-1 and PD-L1 attenuates or blocks the down-regulation signaling which PD-L1 exerted on T-cell, and as a result restores the T cell activity to immunogen. Currently PD-L1 monoclonal antibodies are used for clinical studies to fight against many human cancers, including non-small cell lung cancer, melanoma, colorectal cancer, renal cell cancer, ovarian cancer, prostate cancer, gastric cancer and breast cancer (Julie et al., *N Engl Med* 366: 2455-2465, 2012).

The FDA approved the first anti-PD-L1 antibody drug in 2016. This drug is developed by Genentech and named atezolizumab (trade name Tecentriq) to treat advanced bladder cancer. The drug proved that this particular molecule could be successfully used in immune checkpoint therapy in a clinical stage. Pre-clinical studies had already demonstrated that antibodies against different immune checkpoint molecules could work synergistically to cure cancer (Mace et al., *Journal for Immunotherapy of cancer* 3:366,2015:

Lussier et al., *Journal for Immuno Therapy of Cancer* 3:21, 2015). There are clinical studies to test the combination therapy of PD-L1 antibodies with other immune checkpoint inhibitory monoclonal antibodies or small molecules to treat different cancers.

Durvalumab is another FDA-approved anti-PD-L1 antibody drug, developed by Medimmune/AstraZeneca. Durvalumab is approved for the treatment of patients with locally advanced or metastatic urothelial carcinoma who either have disease progression during or following platinum-containing chemotherapy or have disease progression within 12 months of neoadjuvant or adjuvant treatment with platinum-containing chemotherapy.

BRIEF SUMMARY

The application relates to targeted binding agents against a PD-L1 protein, and methods of making and using thereof.

In a general aspect, the application relates to an isolated antibody or an antigen-binding fragment thereof, comprising:

(a) a heavy chain variable domain (VH) comprising
  i. a heavy chain CDR1 comprising an amino acid sequence selected from the group consisting of SEQ ID NOs:71-82;
  ii. a heavy chain CDR2 comprising an amino acid sequence selected from the group consisting of SEQ ID NOs:83-94, respectively, wherein SEQ ID NO:87 is optionally replaced with any one of SEQ ID NOs: 95-97; and
  iii. a heavy chain CDR3 comprising an amino acid sequence selected from the group consisting of SEQ ID NOs:98-109, respectively, and (b) a light chain variable domain (VL) comprising, respectively,
  i. a light chain CDR1 comprising an amino acid sequence selected from the group consisting of SEQ ID NOs:110-121, wherein SEQ ID NO:111 is optionally replaced with SEQ ID NO:122. and SEQ ID NO:114 is optionally replaced with SEQ ID NO:123;
  ii. a light chain CDR2 comprising an amino acid sequence selected from the group consisting of SEQ ID NOs:124-135, respectively; and
  iii. a light chain CDR3 comprising an amino acid sequence selected from the group consisting of SEQ ID NOs:136-147, respectively, wherein the antibody or antigen-binding fragment is capable of specifically binding to a PD-L 1, preferably a human PD-L1.

Preferably, the $K_D$ of the binding between an antibody or antigen-binding fragment thereof of the application and the PD-L1, preferably the human PD-L1, is $10^{-7}$ M to about $10^{-12}$ M, preferably about $10^{-8}$ M to about $10^{-12}$ M, more preferably about $10^{-9}$ M to about $10^{-12}$ M or less.

An antibody or antigen-binding fragment thereof of the application can be rodent, chimeric, human, partially humanized, or fully humanized. It can also be bispecific further comprising a second antibody moiety capable of specifically binding to a second antigen, such as CTLA-4, TIGIT, TIM-3 or LAG-3. Preferably, the second antibody moiety is a single domain antibody (sdAb).

Further provided is a pharmaceutical composition comprising any one of the isolated anti-PD-L 1 antibodies or antigen binding fragments thereof of the application, and a pharmaceutical acceptable carrier.

Another aspect of the application provides a method of treating an individual having a PD-L1-related disease, comprising administering to the individual an effective amount of any one of the pharmaceutical composition described above. In some embodiments, the PD-L1 related disease is cancer. In some embodiments, the cancer is a solid tumor, such as a colon cancer. In some embodiments, the method further comprises administering to the individual an additional cancer therapy, such as a surgery, radiation, chemotherapy, immunotherapy, hormone therapy, or a combination thereof. In some embodiments, the PD-L1 related disease is a pathogenic infection. In some embodiments, the pharmaceutical composition is administered systemically, such as intravenously (i.v.). In some embodiments, the pharmaceutical composition is administered locally, such as intratumorally. In some embodiments, the individual is a human.

Other aspects. features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiments which are presently preferred. It should be understood, however, that the invention is not limited to the precise arrangements and instrumentalities shown. In the drawings:

FIG. 2A: 1H1G4D9; FIG. 2B: 18B7G2; FIG. 2C: 21D1F4D4: FIG. 2D: 25B6E5D8; FIG. 2E: 25G1F9F8; FIG. 2F: 27D3D3G2, FIG. 2G: 29A8H8C7; FIG. 2H: 30A6B2D9; FIG. 2I: 30A7B5D9: FIG. 2J: 42G2D7C3: FIG. 2K: 51F3D2G4; and FIG. 2L: 53C1F3D4.

FIG. 3A: 1H1G4D9: FIG. 3B: 21D1F4D4; FIG. 3C: 25G1F9F8; FIG. 3D: 27D3D3G2: FIG. 3E: 29A8H8C7: FIG. 3F: 30A6B2D9: FIG. 3G: 30A7B5D9: FIG. 3H: 42G2D7C3: FIG. 3I: 51F3D2G4; and FIG. 3J: 53C1F3D4.

FIG. 4A: 18B7F4G8; FIG. 4B: 27D3D3G2; FIG. 4C: 29A8H8C7: FIG. 4D: 42G2D7C3: FIG. 4E: 51F3D2G4; and FIG. 4F: 53C1F3D4, as well as Durvalumab (positive anti-PD-L1 antibody control) (FIG. 4G) and human IgG1 isotype control mAb (FIG. 4H).

FIG. 5B: 29A8H8C7; FIG. 5C: 53C1F3D4: FIG. 5E: 27D7G3D4; and FIG. 5F: 18B7F4G8, as well as Atezoluzumab (positive anti-PD-L1 antibody control) (FIGS. 5A and 5D).

FIGS. 13A-131 depict the functional activity evaluation of 6 humanized mAbs (FIGS. 13B-13C, FIGS. 13E-13F, and FIGS. 13H-131) according to embodiments of the application and Durvalumab (positive anti-PD-L1 antibody control) (FIG. 13A.

FIGS. 14A-14E depict the tumor volume of individual tumor-bearing mouse after treatment. FIG. 14F depicts the average tumor volume of five groups of tumor-bearing mice after treatment. FIG. 14G depicts the average tumor weight of five groups of tumor-bearing mice at the end of the study.

DETAILED DESCRIPTION OF THE INVENTION

Figure 1:
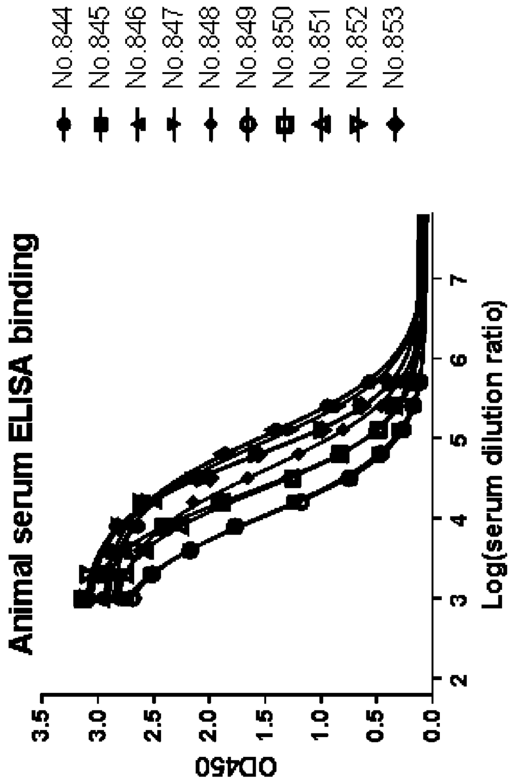
FIG. 1 depicts the immune response of immunized mice after the $4^{th}$ immunization with recombinant PD-L1 ECD protein.
Figure 2A:
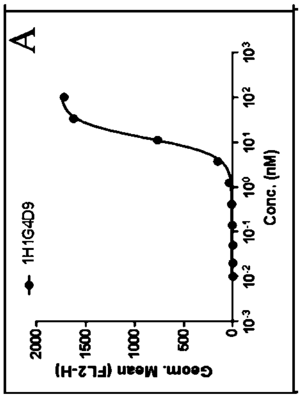
FIGS. 2A-2L depict the binding affinity between PD-L1 overexpressing stable cell line and mouse monoclonal antibodies (mAbs) according to embodiments of the application, more particularly.
Figure 2B:
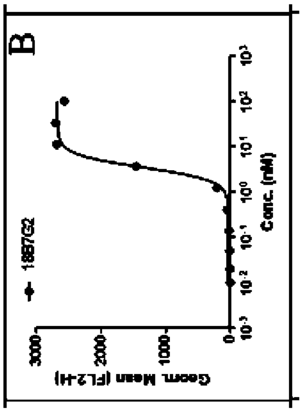
Figure 2C:
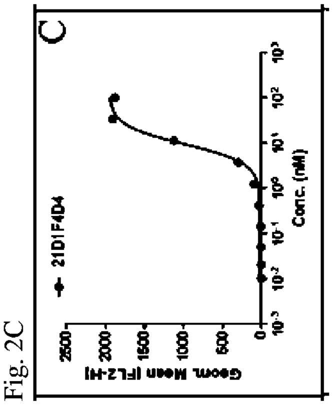
Figure 2D:
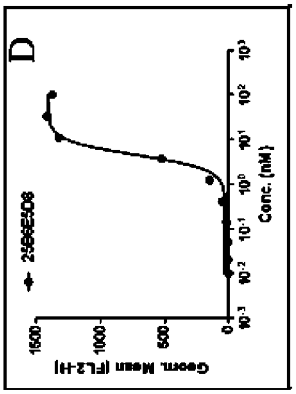
Figure 2E:
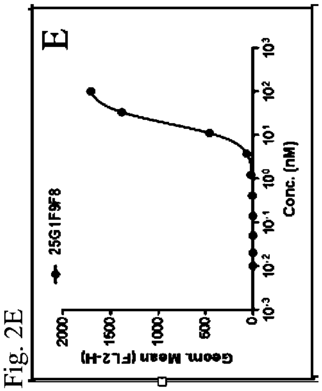
Figure 2F:
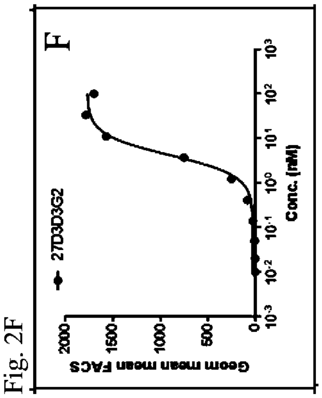
Figure 2G:
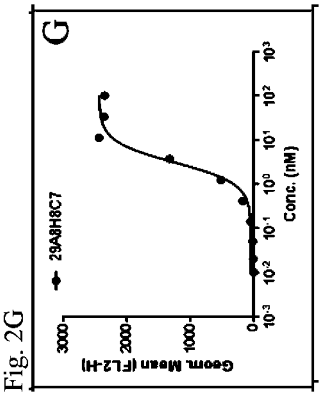
Figure 2H:
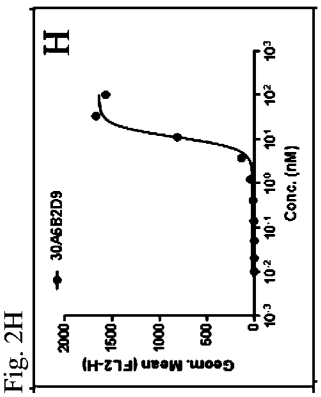
Figure 2I:
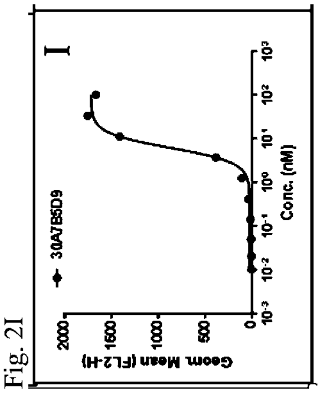
Figure 2J:
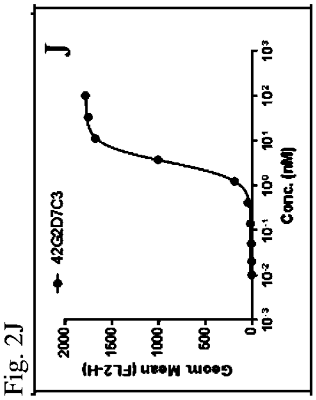
Figure 2K:
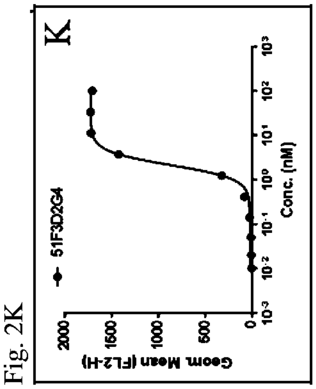
Figure 2L:
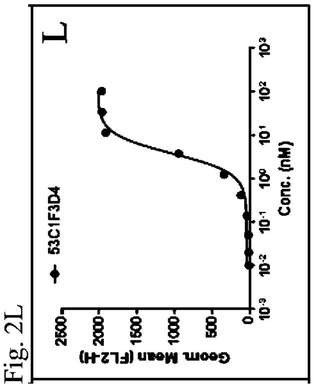
Figure 3A:
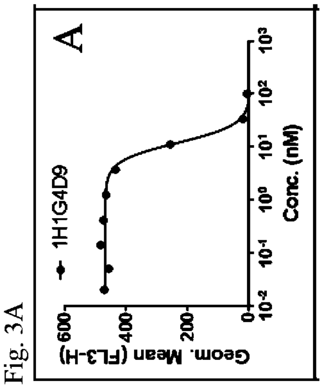
FIGS. 3A-3J depict the blocking effect of mouse mAbs according to embodiments of the application on the interaction between PD-L1 cell line and its receptor PD-1 ECD protein, more particularly.
Figure 3B:
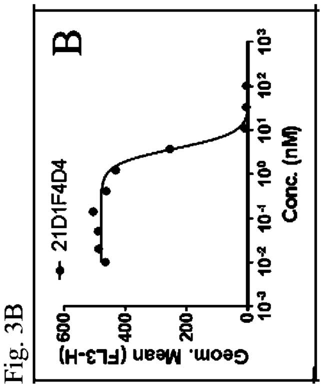
Figure 3C:
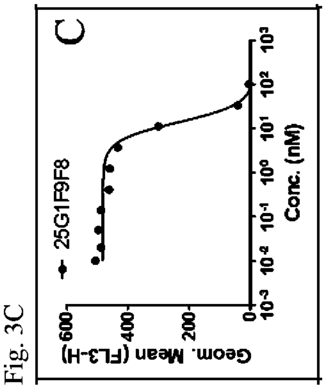
Figure 3D:
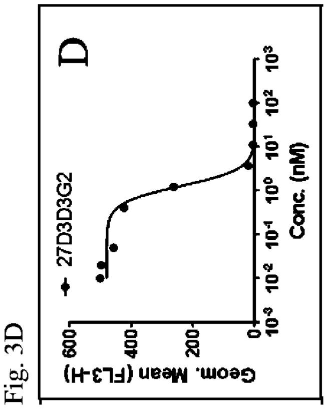
Figure 3E:
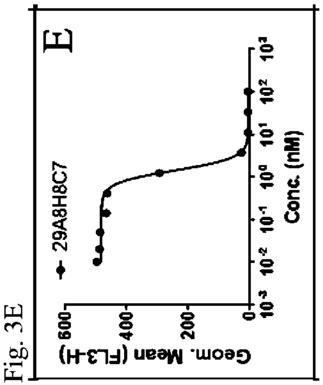
Figure 3F:
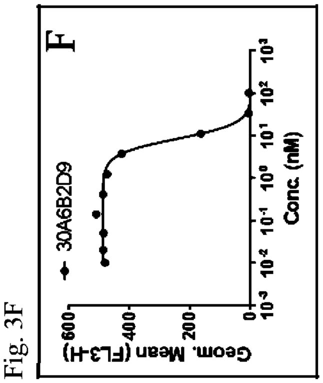
Figure 3G:
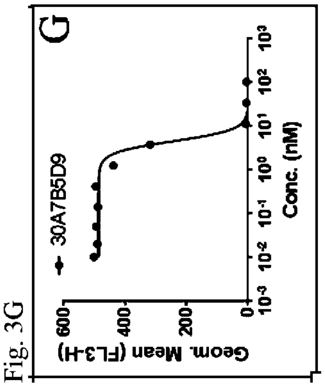
Figure 3H:
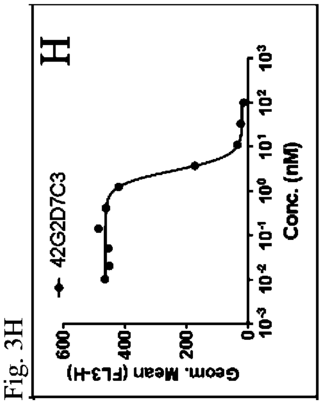
Figure 3I:
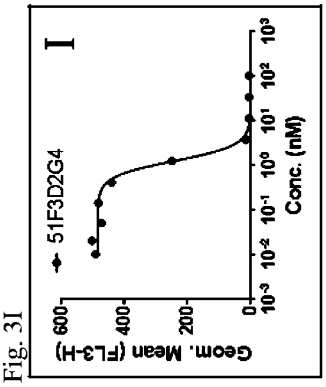
Figure 3J:
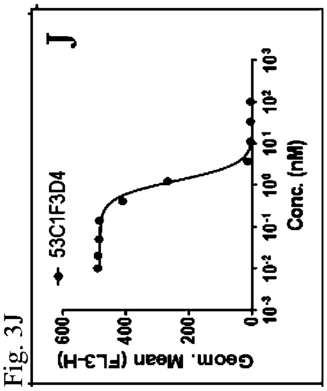
Figure 4A:
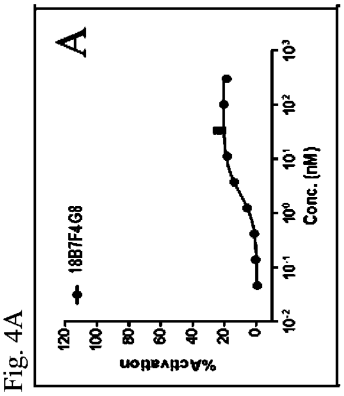
FIGS. 4A-4H depict functional activity evaluation of mouse mAbs according to embodiments of the application by PD-L1 cell-based reporter assay, more particularly.
Figure 4B:
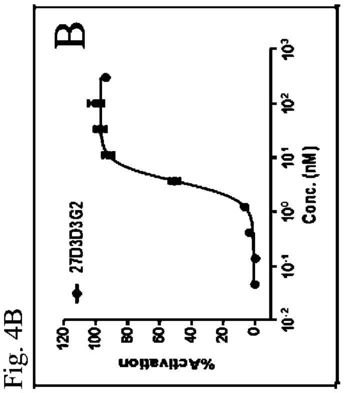
Figure 4C:
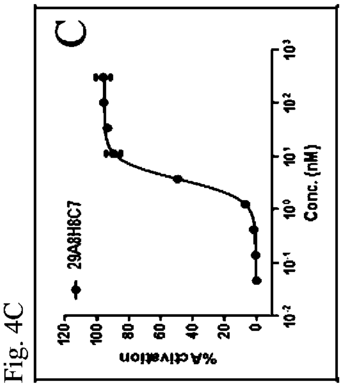
Figure 4D:
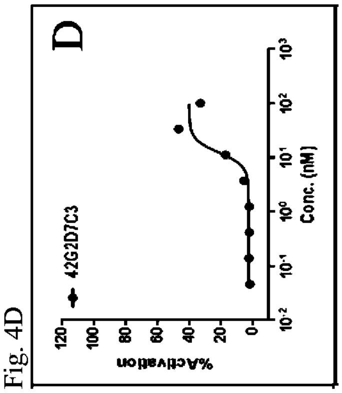
Figure 4E:
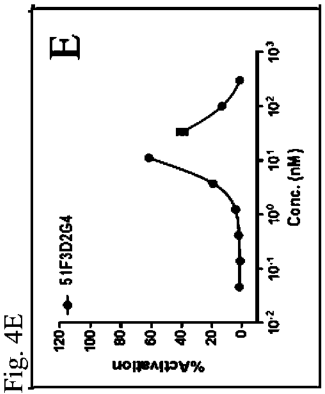
Figure 4F:
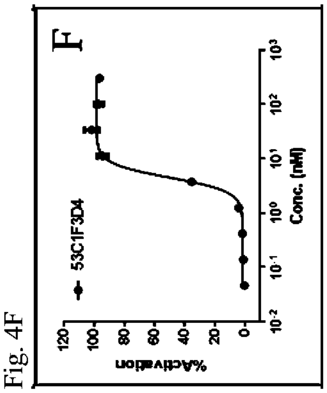
Figure 4G:
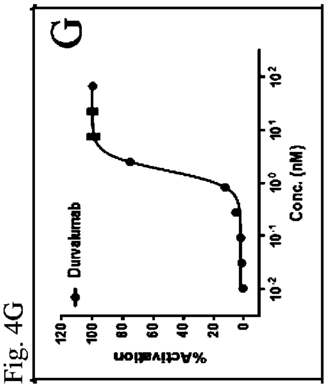
Figure 4H:
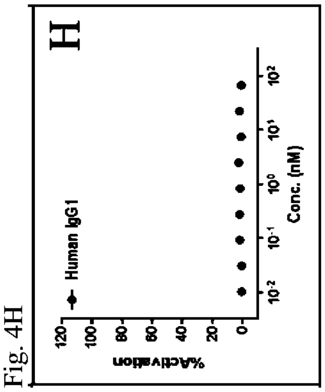
Figure 5A:
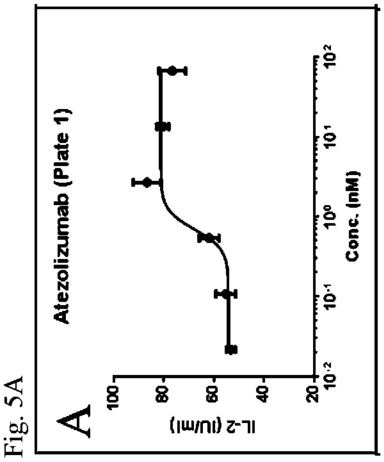
FIGS. 5A-5F depict the functional activity evaluation of mouse mAbs according to embodiments of the application by mixed lymphocyte reaction (MLR) assay, more particularly.
Figure 5B:
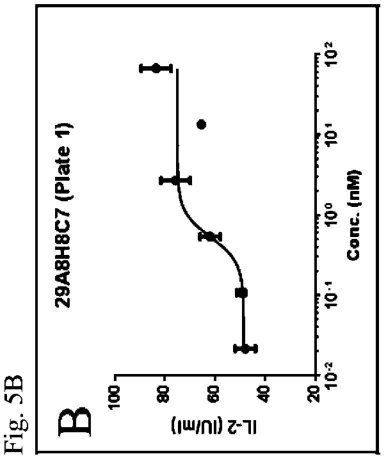
Figure 5C:
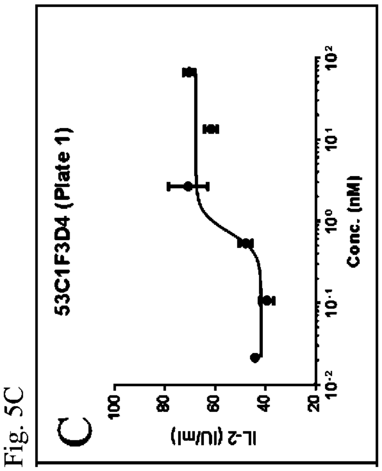
Figure 5D:
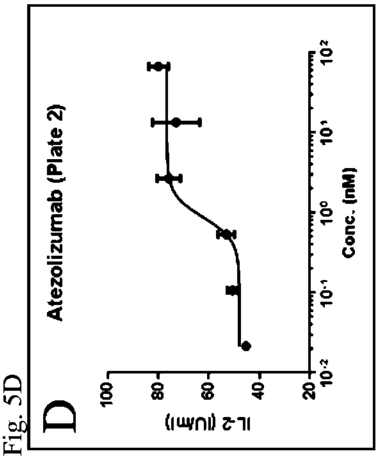
Figure 5E:
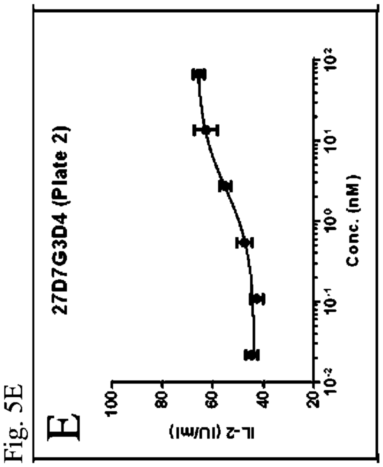
Figure 5F:
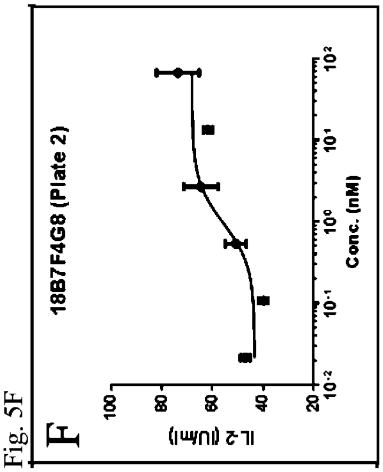
Figure 6A:
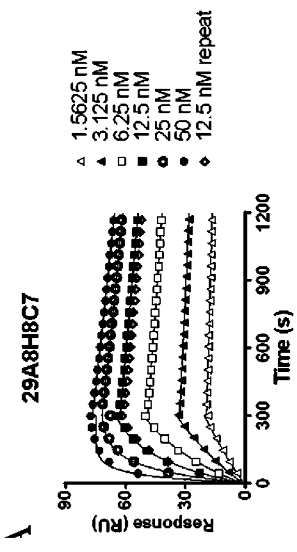
FIGS. 6A-6D depict mono-valent binding affinity determination of two mouse mAbs 29A8H8C7 (FIG. 6A) and 53C1F3D4 (FIG. 6B) according to embodiments of the application. The binding affinities of Atezolizumab (FIG. 6C) and Durvalumab (FIG. 6D) were also determined for comparison.
Figure 6B:
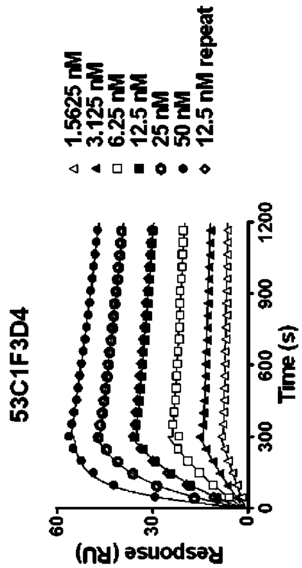
Figure 6C:
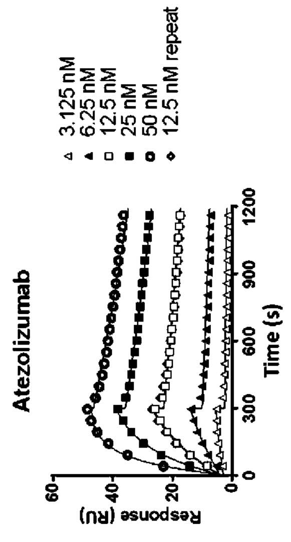
Figure 6D:
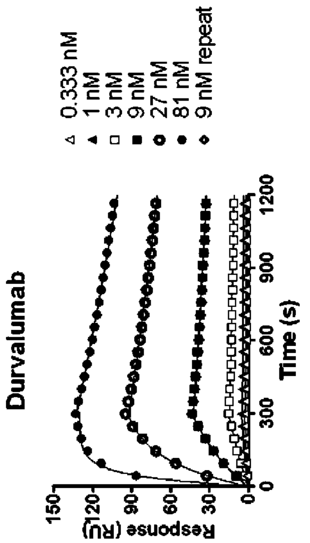
Figure 7A:
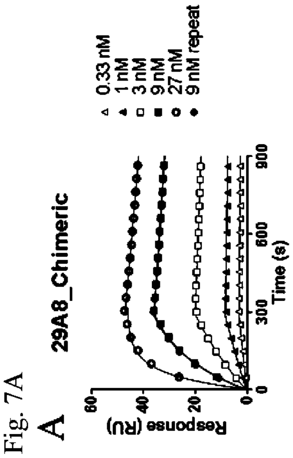
FIGS. 7A-7J depict mono-valent binding affinity determination of chimeric antibodies 29A8H8C7 (FIG. 7A) and chimeric 53C1F3D4 (FIG. 7B), 3 humanized 29A8H8C7 (FIGS. 7C-7E) and 5 humanized 53C1F3D4 (FIGS. 7F-7J) according to embodiments of the application to His-tagged human PD-L1.
Figure 7B:
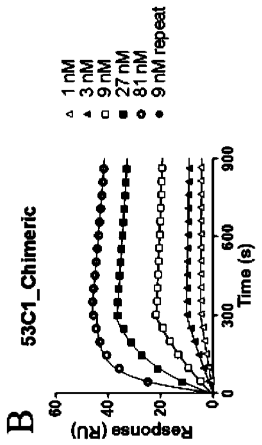
Figure 7C:
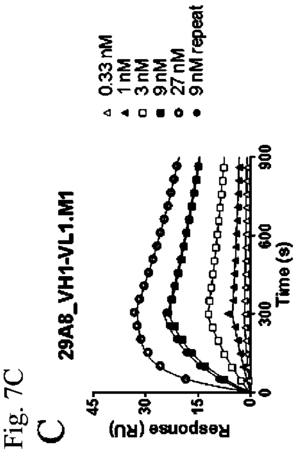
Figure 7D:
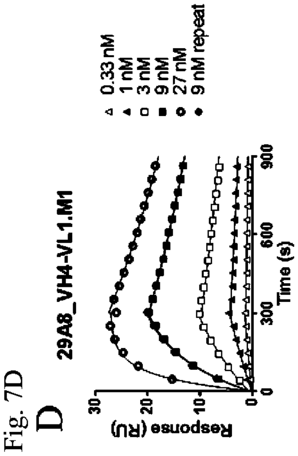
Figure 7E:
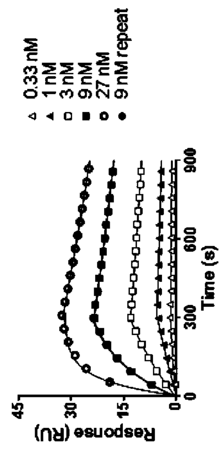
Figure 7F:
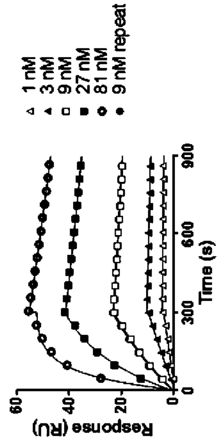
Figure 7G:
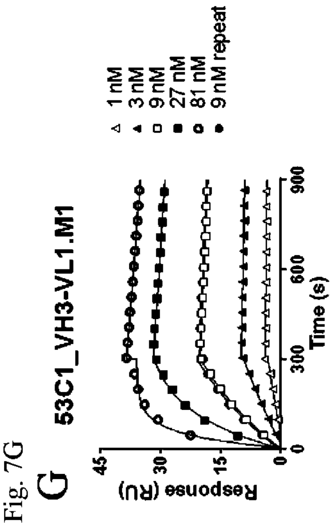
Figure 7H:
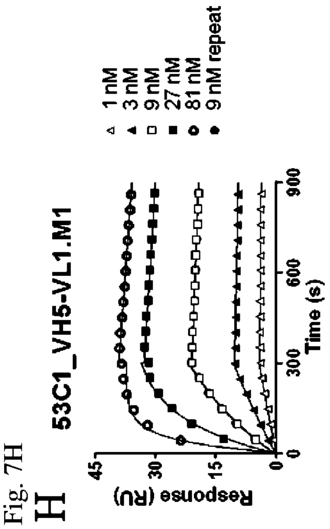
Figure 7I:
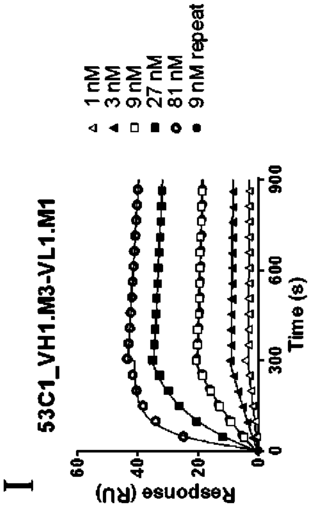
Figure 7J:
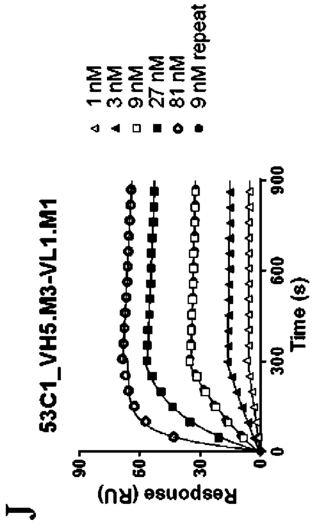
Figure 8A:
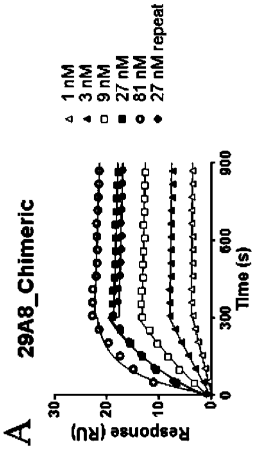
FIGS. 8A-8L depict mono-valent binding affinity determination of chimeric antibodies 29A8H8C7 (FIG. 8A) and 53C1F3D4 (FIG. 8B). 3 humanized 29A8H8C7 (FIGS. 8C-8E), 5 humanized 53C1F3D4 (FIGS. 8F-8J) according to embodiments of the application and positive control antibodies Atezolizumab (FIG. 8K) and Durvalumab (FIG. 8L) to cynomolgus PD-L1 Fc-fusion protein.
Figure 8B:
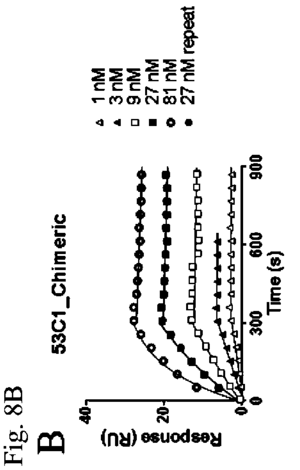
Figure 8D:
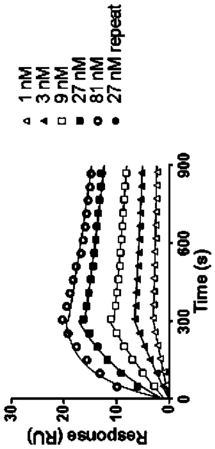
Figure 8C:
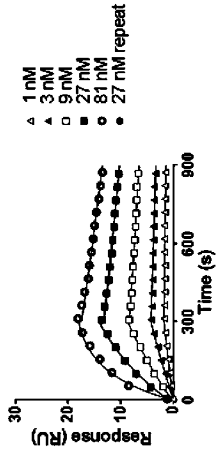
Figure 8F:
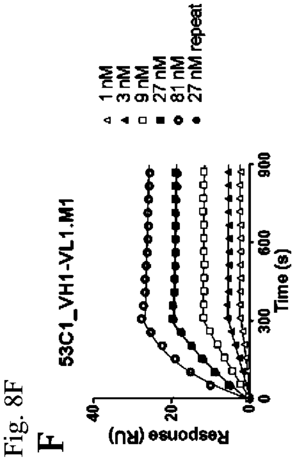
Figure 8E:
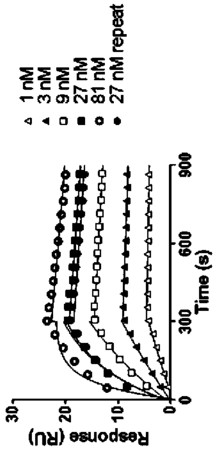
Figure 8G:
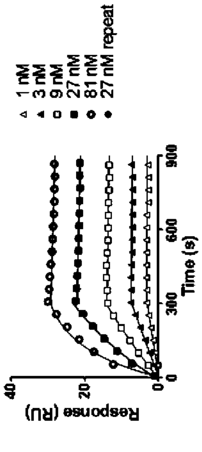
Figure 8H:
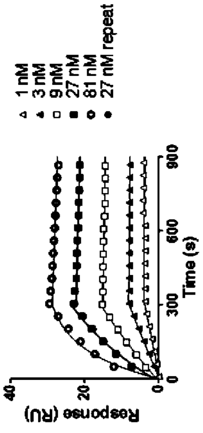
Figure 8I:
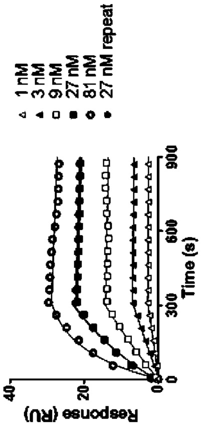
Figure 8J:
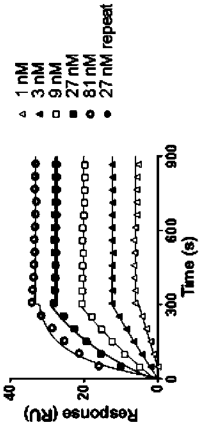
Figure 8K:
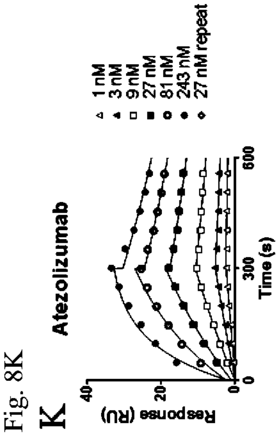
Figure 8L:
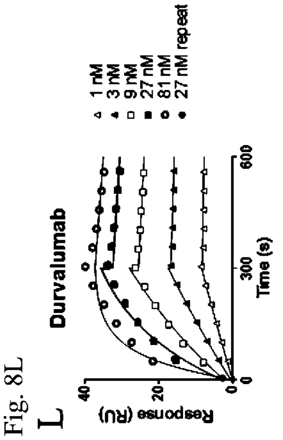
Figure 9A:
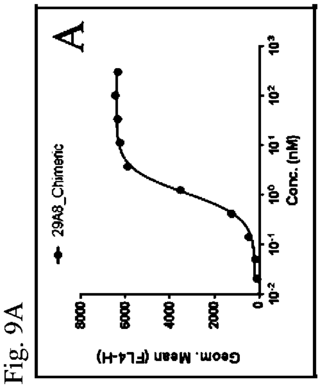
FIGS. 9A-9L depict the binding affinity between human PD-L1 overexpressing stable cell line and chimeric (FIG. 9A and FIG. 9E) or humanized antibodies (FIGS. 9B-9D and FIGS. 9F-9J) according to embodiments of the application. Durvalumab (FIG. 9K) and Atezolizumab (FIG. 9L) were used as anti-PD-L1 positive controls.
Figure 9B:
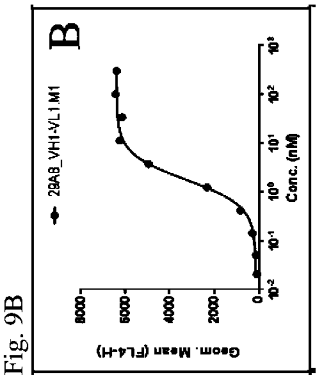
Figure 9C:
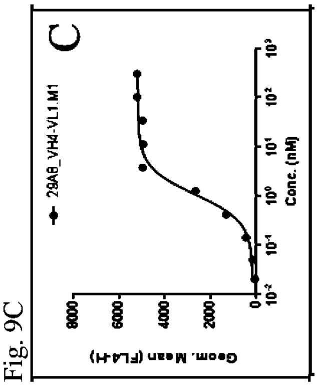
Figure 9D:
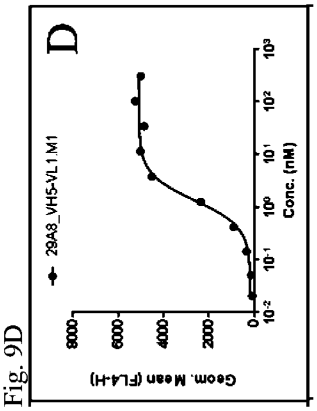
Figure 9E:
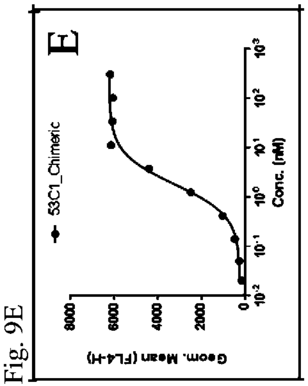
Figure 9F:
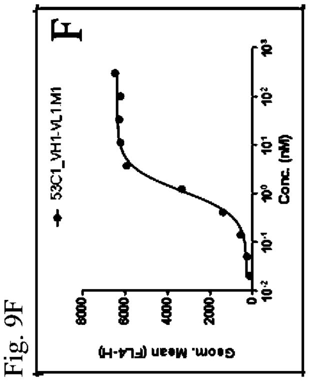
Figure 9G:
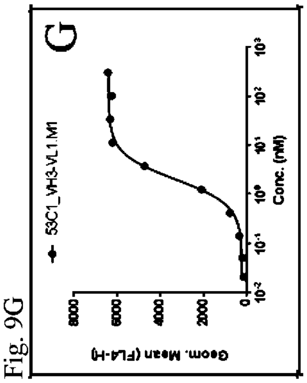
Figure 9H:
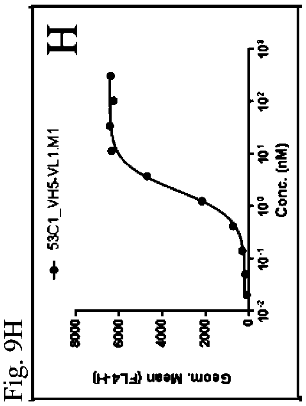
Figure 9I:
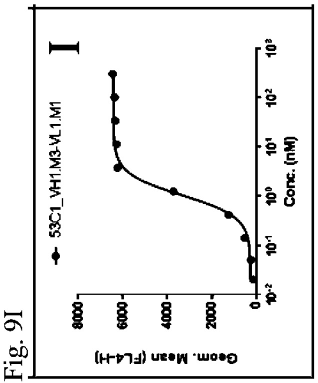
Figure 9J:
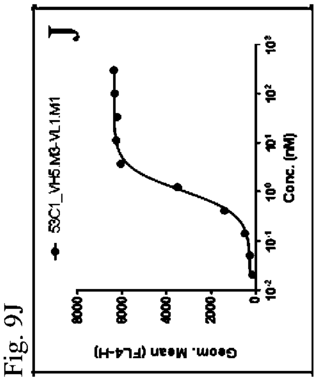
Figure 9K:
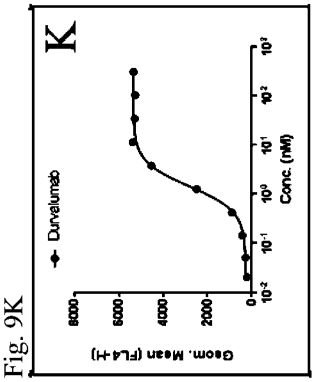
Figure 9L:
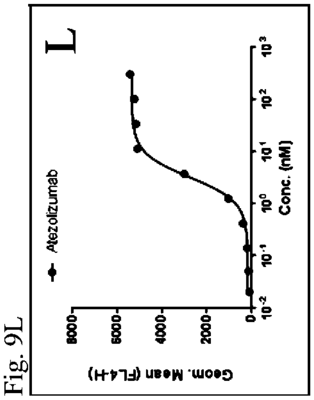
Figure 10A:
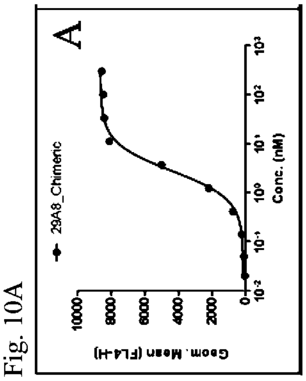
FIGS. 10A-10L depict the binding affinity between cynomolgus PD-L1 overexpressing stable cell line and chimeric (FIG. 10A and FIG. 10E) and humanized antibodies (FIGS. 10B-10D and FIGS. 10F-10J) according to embodiments of the application. Durvalumab (FIG. 10K) and Atezolizumab (FIG. 10L) were used as anti-PD-L1 positive controls.
Figure 10B:
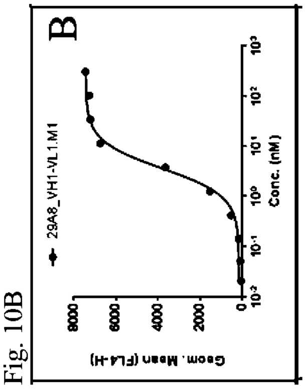
Figure 10C:
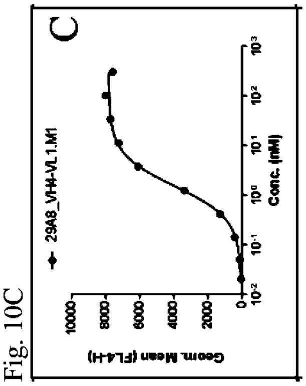
Figure 10D:
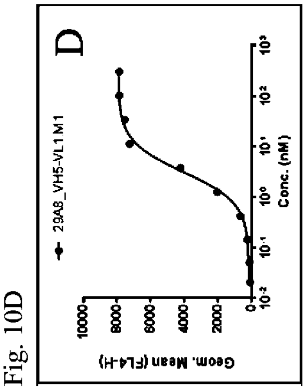
Figure 10E:
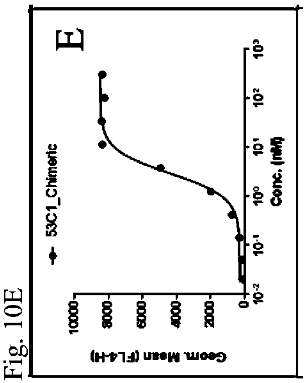
Figure 10F:
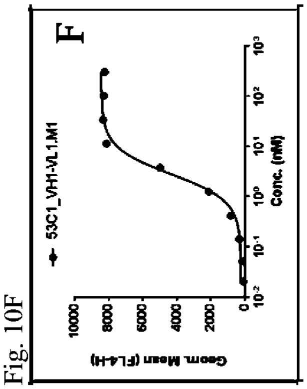
Figure 10G:
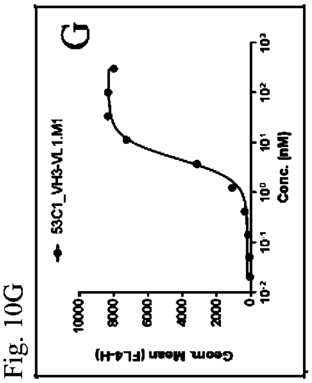
Figure 10H:
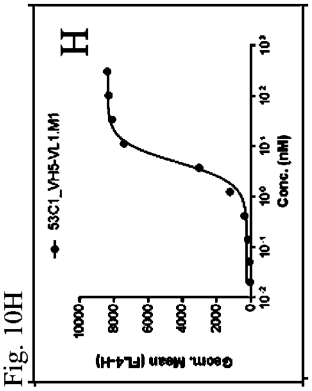
Figure 10I:
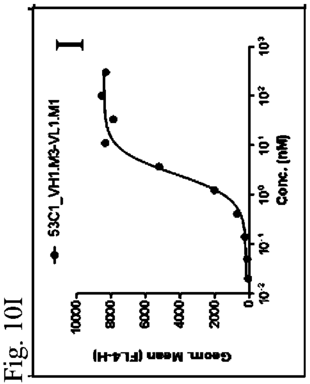
Figure 10J:
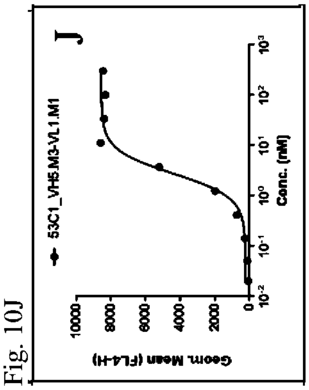
Figure 10K:
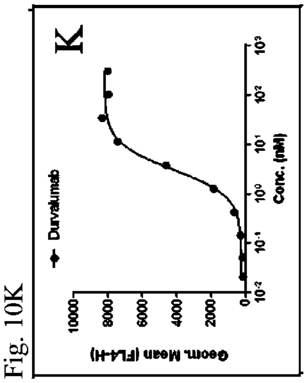
Figure 10L:
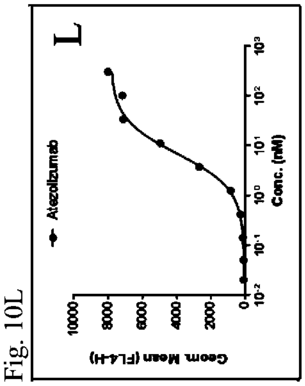
Figure 11A:
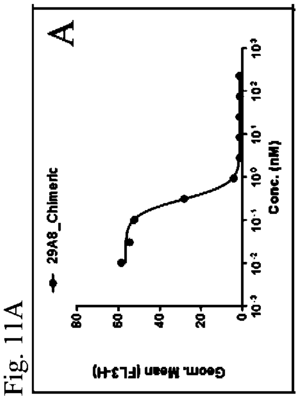
FIGS. 11A-11L depict the blocking effect of chimeric (FIG. 11A and FIG. 11E) and humanized mAbs (FIGS. 11B-11D and FIGS. 11F-11J) according to embodiments of the application on the interaction between PD-L1 cell line and its receptor PD-1 ECD protein. Durvalumab (FIG. 11K) and Atezolizumab (FIG. 11L) were used as anti-PD-L1 positive controls.
Figure 11B:
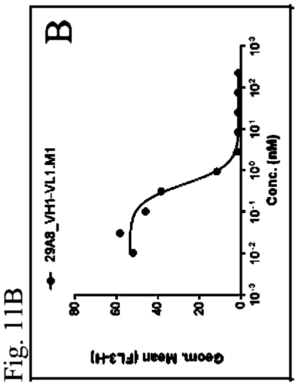
Figure 11C:
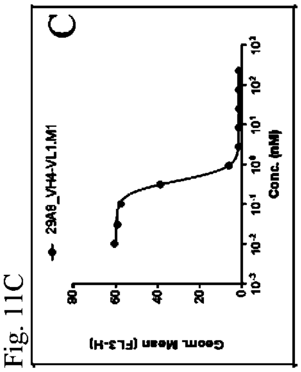
Figure 11D:
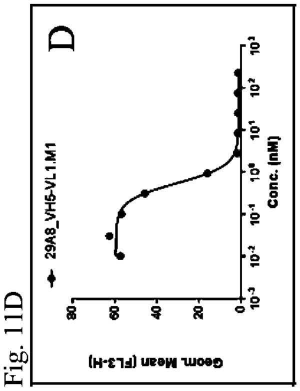
Figure 11E:
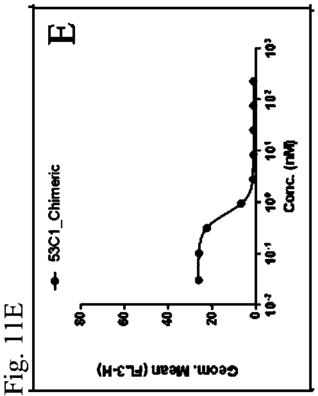
Figure 11F:
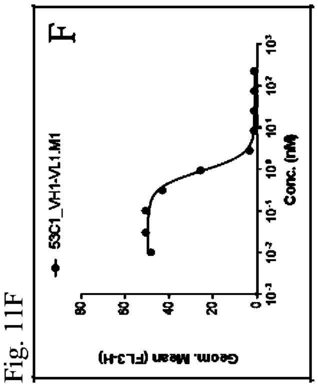
Figure 11G:
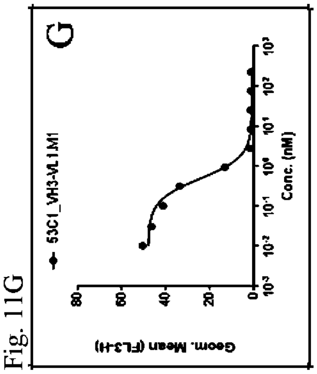
Figure 11H:
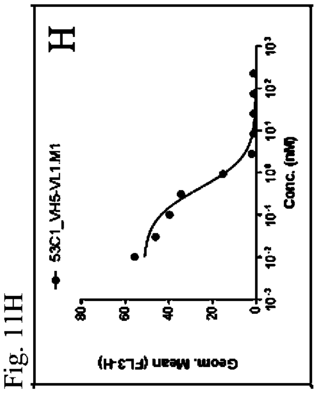
Figure 11I:
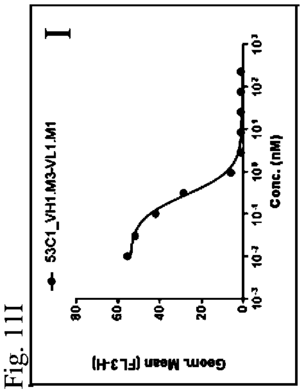
Figure 11J:
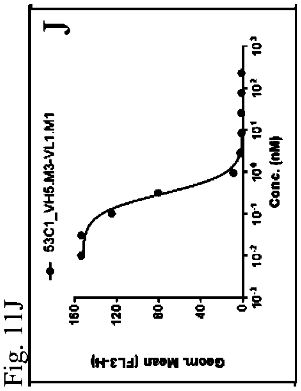
Figure 11K:
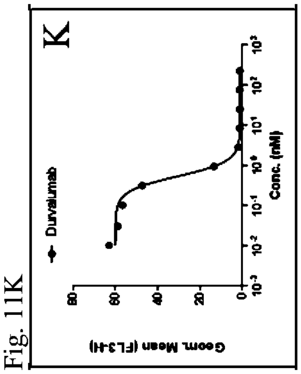
Figure 11L:
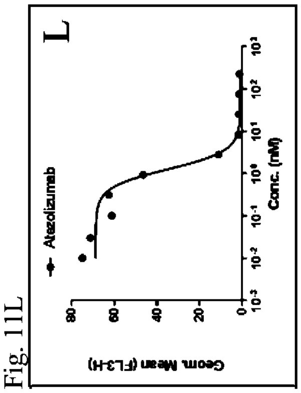
Figure 12A:
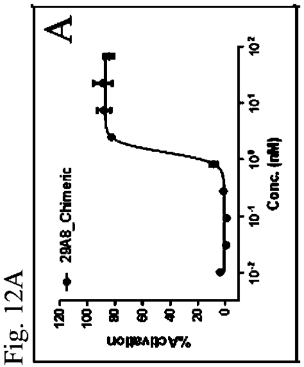
FIGS. 12A-12L depict functional activity evaluation of chimeric (FIG. 12A and FIG. 12E) and humanized mAbs (FIGS. 12B-12D and FIGS. 12F-12J) according to embodiments of the application by PD-L1 cell-based reporter assay. Durvalumab (FIG. 12K) and Atezolizumab (FIG. 12L) were used as anti-PD-L1 positive controls.
Figure 12B:
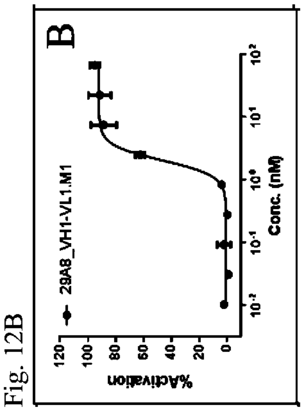
Figure 12C:
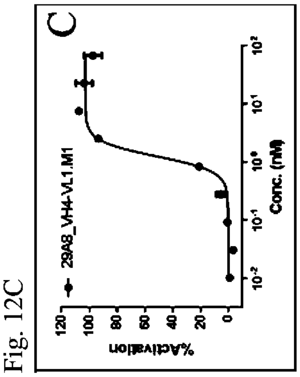
Figure 12D:
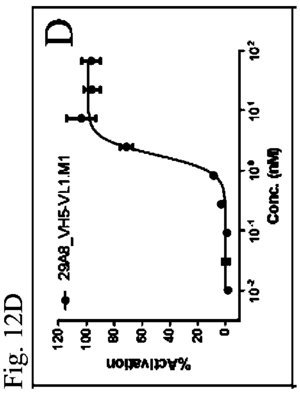
Figure 12E:
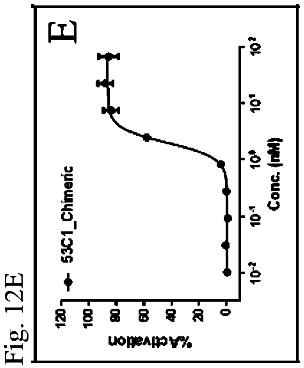
Figure 12F:
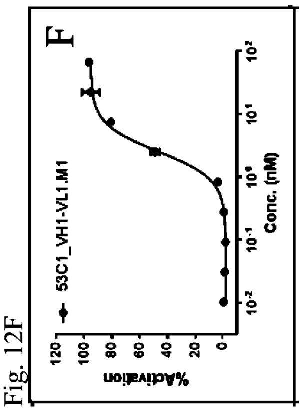
Figure 12G:
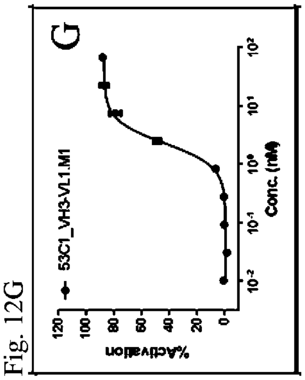
Figure 12H:
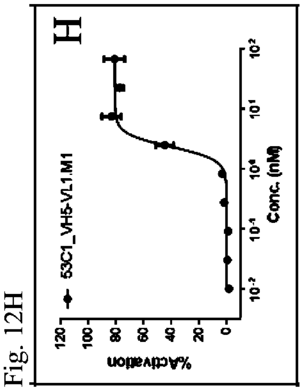
Figure 12I:
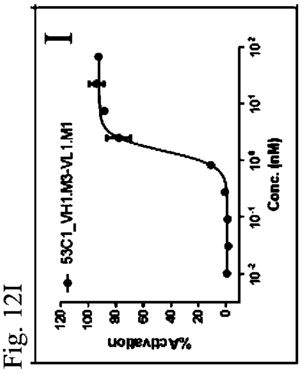
Figure 12J:
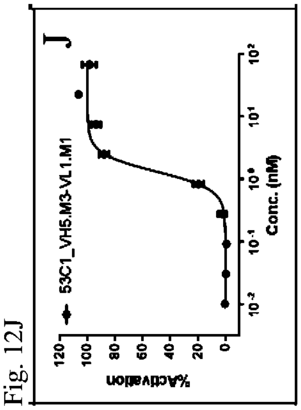
Figure 12K:
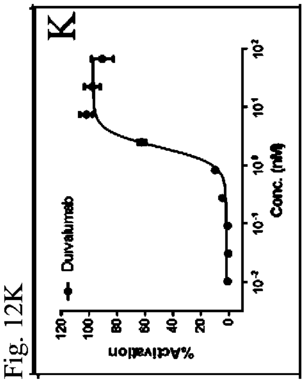
Figure 12L:
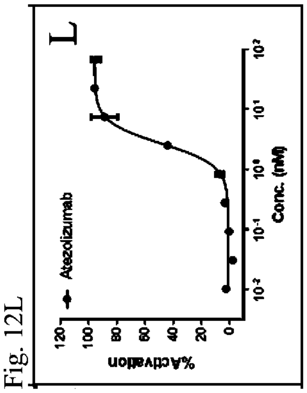
Figure 13A:
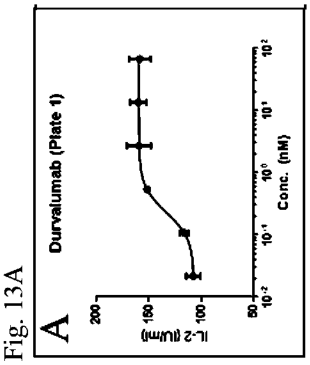
Figure 13B:
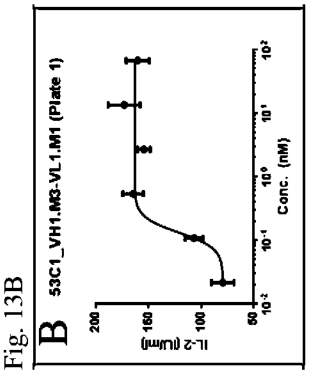
Figure 13C:
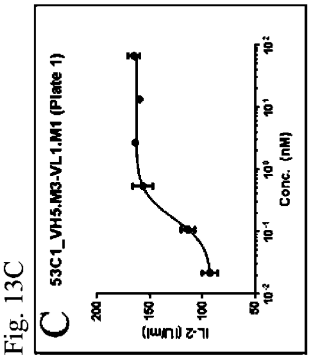
Figure 13D:
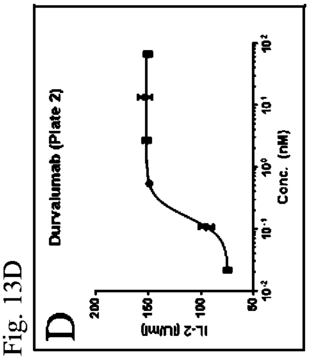
FIG. 13D, and FIG. 13G) by mixed lymphocyte reaction (MLR) assay.
Figure 13E:
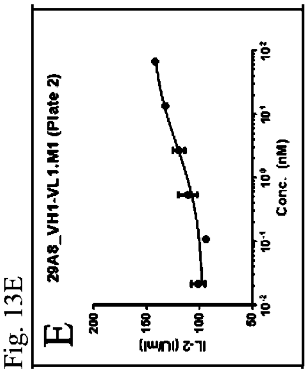
Figure 13F:
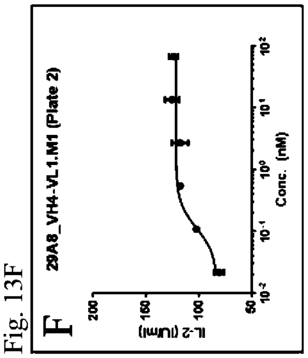
Figure 13G:
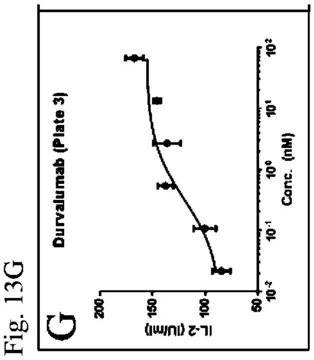
Figure 13H:
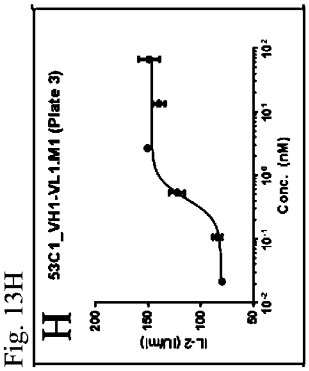
Figure 13I:
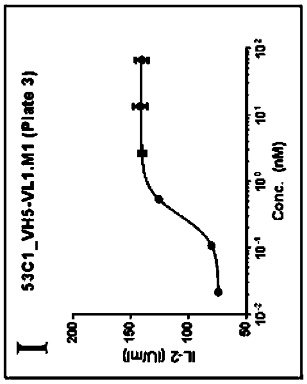
Figure 14A:
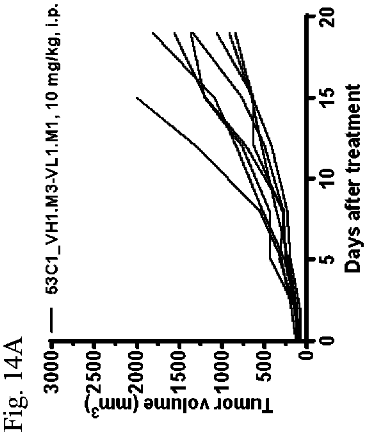
FIGS. 14A-14G depict the tumor growth after treatment with humanized antibodies according to embodiments of the application and benchmark antibody Durvalumab.
Figure 14B:
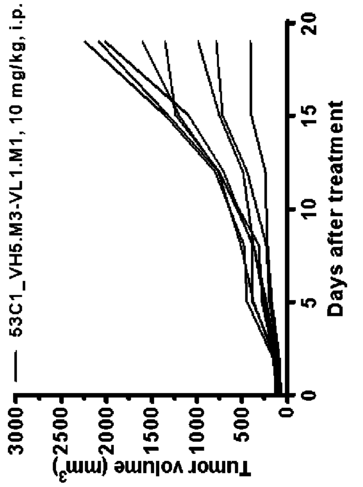
Figure 14C:
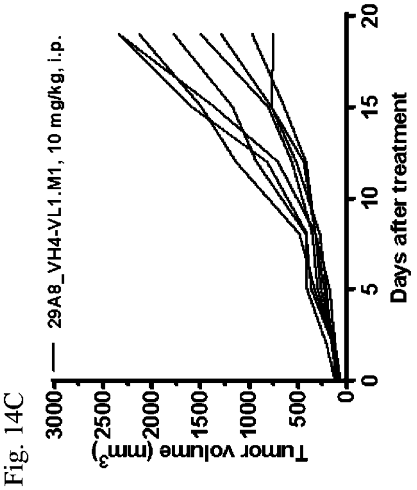
Figure 14D:
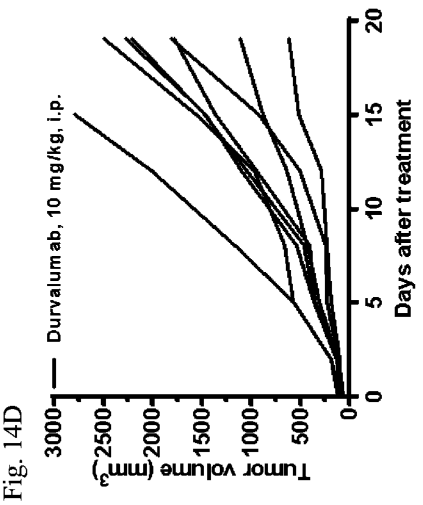
Figure 14E:
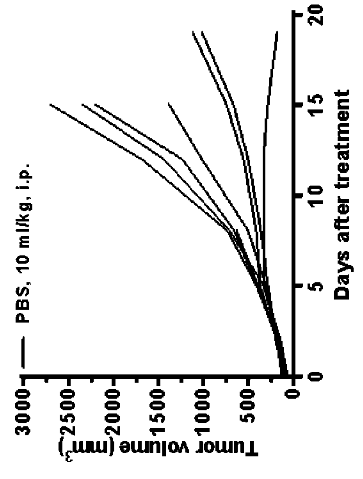
Figure 14F:
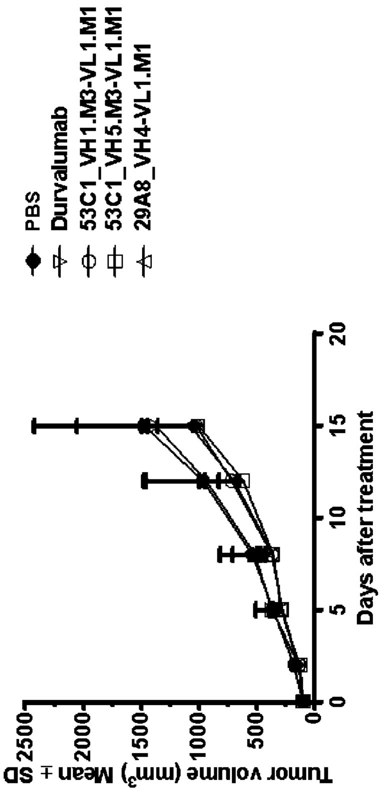
Figure 14G:
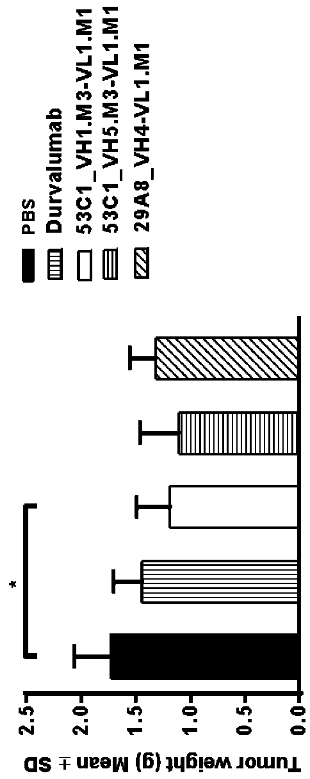

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

One skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

The application provides antibodies, particularly monoclonal antibodies (mAbs), or antigen binding fragments thereof specifically binding to PD-L1 (hereinafter also referred to as "anti-PD-L1 mAbs") and uses thereof as a new strategy to treat PD-L1-related diseases, such as cancer.

Accordingly, one aspect of the present application provides an isolated antibody, preferably monoclonal antibody, or an antigen binding fragment thereof capable of specifically recognizing PD-L1, preferably human PD-L1. The isolated anti-PD-L1 antibody can be a full-length anti-PD-L1 mAb (e.g. murine or humanized), a protein or polypeptide comprising an anti-PD-L1 mAb or an antigen binding fragment thereof fused to another antibody, such as a single domain antibody (sdAb), or an antigen-binding fragment of another antibody. The anti-PD-L1 antibody can be monospecific or multispecific, monovalent or multivalent.

Also provided are compositions (such as pharmaceutical compositions), kits and articles of manufacture comprising an isolated antibody, preferably monoclonal antibody. or an antigen binding fragment thereof of the application, as well as methods of making the isolated antibody or antigen binding fragment thereof, the compositions, kits and articles of manufacture, and methods of treating a PD-L1 related disease (such as cancer) using the compositions, kits and articles of manufacture of the application.

I. Definitions

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of “comprising”, “containing”, “including”, and “having”, whenever used herein in the context of an aspect or embodiment of the application can be replaced with the term “consisting of” or “consisting essentially of” to vary scopes of the disclosure.

As used herein, the conjunctive term “and/or” between multiple recited elements is understood as encompassing both individual and combined options. For instance, where two elements are conjoined by “and/or,” a first option refers to the applicability of the first element without the second. A second option refers to the applicability of the second element without the first. A third option refers to the applicability of the first and second elements together. Any one of these options is understood to fall within the meaning, and therefore satisfy the requirement of the term “and/or” as used herein. Concurrent applicability of more than one of the options is also understood to fall within the meaning, and therefore satisfy the requirement of the term “and/or.”

Unless otherwise stated, any numerical value, such as a concentration or a concentration range described herein, are to be understood as being modified in all instances by the term “about.” Thus, a numerical value typically includes +10% of the recited value. For example, a concentration of 1 mg/mL includes 0.9 mg/mL to 1.1 mg/mL. Likewise, a concentration range of 1 mg/mL to 10 mg/mL includes 0.9 mg/mL to 11 mg/mL. As used herein, the use of a numerical range expressly includes all possible subranges, all individual numerical values within that range, including integers within such ranges and fractions of the values unless the context clearly indicates otherwise.

The terms “Programmed cell death 1 ligand 1,” “PD-L1,” “B7 homolog 1 (B7-H1),” “PD-L1 antigen”, “PDCD1 ligand 1” and “CD274” (see, e.g., Chemnitz (2004) *J. Immunol.* 173:945-954) are used interchangeably, and include variants, isoforms, species homologs of human PD-L1, and analogs having at least one common epitope with human PD-L1 (see, e.g., Butte (2008) *Mol Immunol.* 45:3567-3572). Accordingly. an anti-PD-L1 construct of the application can, in certain embodiments, cross-react with PD-L1 from species other than human, or other proteins which are structurally related to human PD-L 1 (e.g., human PD-L1 homologs). In other embodiments, an anti-PD-L1 construct of the application can be completely specific for human PD-L1 and not exhibit species or other types of cross-reactivity.

The term “human PD-L 1” refers to a human sequence PD-L1 or a derivative thereof. For example, a human PD-L1 can have the amino acid sequence of GenBank Accession Number Q9NZQ7. A human PD-L1 can also have an amino acid sequence that differs from human PD-L1 of Genbank Accession Number Q9NZQ7 by having, for example, conserved mutations or mutations in non-conserved regions and the PD-L1 has substantially the same biological function as the human PD-L1 of Genbank Accession Number Q9NZQ7. For example, a biological function of human PD-L1 is having an epitope in the extracellular domain of PD-L1 that is specifically bound by an anti-PD-L1 construct of the instant disclosure or a biological function of human PD-L1 is modulation of T cell activity.

The term “epitope” means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term “Programmed cell death 1 (PD-1)” as used herein is intended to refer to a cell surface receptor that belongs to the immunoglobulin superfamily and is expressed on T cells and pro-B cells. An exemplary amino acid sequence of human PD-1 is disclosed at Genbank Accession Numbers NP_005009.2.

As used herein. “treatment” or “treating” is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease. preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by “treatment” is a reduction of pathological consequence of cancer. The methods of the invention contemplate any one or more of these aspects of treatment.

The term “effective amount” used herein refers to an amount of an agent or a combination of agents, sufficient to treat a specified disorder, condition or disease such as ameliorate, palliate, lessen. and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition can: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term “antibody”, “antibody moiety” or “antibody construct” is used in the broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VW) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology,* 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs" (Variable domain of the heavy chain of the Heavy chain antibody). Some $V_H$Hs can also be known as nanobodies. Camelid sdAb is one of the smallest known antigen-binding antibody fragments (see, e.g., Hamers-Casterman et al., *Nature* 363:446-8 (1993): Greenberg et al., *Nature* 374:168-73 (1995); Hassanzadeh-Ghassabeh et al., *Nanomedicine* (Lond), 8:1013-26 (2013)). A basic $V_H$H has the following structure from the N-terminus to the C-terminus: FR1-CDR1-FR2-CDR2-FR3-CDR3-FR4, in which FR 1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably. the isolated polypeptide is free of association with all other components from its production environment. Contaminant components of its production environment, such as that resulting from recombinant transfected cells, are materials that would typically interfere with research, diagnostic or therapeutic uses for the antibody, and can include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments. to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain can be referred to as "Vii" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H$H". $V_H$H is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration. connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies. i.e., the individual antibodies comprising the population are identical except for possible naturally occurring mutations and/or post-translation modifications (e.g., isomerizations, deamidations) that can be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the application can be made by a variety of techniques, including, for example, the hybridoma method (e.g., Kohler and Milstein, *Nature,* 256:495-97 (1975): Hongo et al., *Hybridoma,* 14 (3): 253-260 (1995), *Harlow et al., Antibodies: A Laboratory* Manual, (Cold Spring Harbor Laboratory Press, 2nd ed. 1988); Hammerling et al, in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991): Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004): Fellouse, *Proc. Nat'l. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096: WO 1996/33735; WO 1991/10741: Jakobovits et al., *Proc. Nat'l. Acad. Sci. USA* 90: 2551 (1993); Jakobovits et al., *Nature* 362: 255-258 (1993); Bruggemann et al., *Year in Immunol.* 7:33 (1993): U.S. Pat. Nos. 5,545,807; 5.545,806; 5,569,825; 5,625,126: 5,633,425; and 5,661,016; Marks et al., *Bio/Technology* 10: 779-783 (1992): Lonberg et al., *Nature* 368: 856-859 (1994): Morrison, Nature 368: 812-813 (1994); Fishwild et al., *Nature Biotechnol.* 14: 845-851 (1996): Neuberger, *Nature Biotechnol.* 14: 826 (1996); and Lonberg and Huszar, *Intern. Rev. Immunol.* 13: 65-93 (1995).

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_HH$) and an Fc region. The constant domains can be native sequence constant domains (e.g., human native sequence constant domains) or amino acid sequence variants thereof. In some cases, the intact antibody can have one or more effector functions.

An "antibody fragment" comprises a portion of an intact antibody, preferably the antigen binding and/or the variable region of the intact antibody. Examples of antibody fragments include, but are not limited to Fab, Fab', $F(ab')_2$ and Fv fragments; diabodies; linear antibodies (see U.S. Pat. No. 5,641,870, Example 2: Zapata et al., *Protein Eng.* 8(10): 1057-1062 [1995]): single-chain antibody molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, CH) of the heavy chain and the CHL (or CL) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_1$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody. generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161: Hollinger et al., *Proc. Nat'l. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l. Acad Sci. USA,* 81:6851-6855 (1984)). "Humanized antibody" is used as a subset of "chimeric antibodies".

"Humanized" forms of non-human (e.g., llama or camelid) antibodies are antibodies that contain minimal sequence derived from non-human immunoglobulin. In some embodiments, a humanized antibody is a human immunoglobulin (recipient antibody) in which residues from an CDR (hereinafter defined) of the recipient are replaced by residues from an CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies can comprise residues that are not found in the recipient antibody or in the donor antibody. These modifications can be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions can include one or more individual FR residue substitutions that improve antibody performance. such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example. Vaswani and Hamilton, *Ann. Allergy. Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J Mol. Biol.* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l. Acad Sci. USA.* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR 1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest,* 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda. Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| (Kabat Numbering) | | | | |
| H1 | H31-H35 | H26-H35 | H26-H32 | H30-H35 |
| (Chothia Numbering) | | | | |
| H2 | H50-H65 | H50-H58 | H53-H55 | H47-H58 |
| H3 | H95-H102 | H95-H102 | H96-H101 | H93-H101 |

HVRs can comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_H$H) are numbered according to the general numbering for VH domains given by Kabat et al. ("*Sequence of proteins of immunological interest*", US Public Health Services, NIH Bethesda, Md., Publication No. 91), as applied to $V_H$H domains from Camelids in the article of Riechmann and Muyldermans, *J. Immunol. Methods* 2000 Jun. 23: 240 (1-2): 185-195. According to this numbering, FR1 of a $V_H$H comprises the amino acid residues at positions 1-30, CDR1 of a $V_H$H comprises the amino acid residues at positions 31-35, FR2 of a $V_H$H comprises the amino acids at positions 36-49, CDR2 of a $V_H$H comprises the amino acid residues at positions 50-65, FR3 of a $V_H$H comprises the amino acid residues at positions 66-94, CDR3 of a $V_H$H comprises the amino acid residues at positions 95-102, and FR4 of a $V_H$H comprises the amino acid residues at positions 103-113. In this respect, it should be noted that—as is well known in the art for VH domains and for $V_H$H domains—the total number of amino acid residues in each of the CDRs can vary and cannot correspond to the total number of amino acid residues indicated by the Kabat numbering (that is, one or more positions according to the Kabat numbering cannot be occupied in the actual sequence, or the actual sequence can contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence can contain fewer or additional amino acids corresponding to a shortening of, or insertion into, a FR or HVR of the variable domain. For example, a heavy-chain variable domain can include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues can be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR7" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_1$ sequences is from a subgroup of variable domain sequences. Generally, the subgroup of sequences is a subgroup as in Kabat et al., *Sequences of Proteins of Immunological Interest,* 5$^{th}$ Ed. Public Health Service, National Institutes of Health, Bethesda, Md. (1991). Examples include for the $V_L$, the subgroup can be subgroup kappa I, kappa II, kappa III or kappa IV as in Kabat et al., supra. Additionally, for the VH, the subgroup can be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework can comprise the same amino acid sequence thereof, or it can contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., Bio-Technology 10:779-783 (1992) describes affinity maturation by $V_H$- and $V_L$-domain shuffling. Random mutagenesis of CDR and/or framework residues is described by, for example: Barbas et al. *Proc Nat'l. Acad Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

As use herein, the term "specifically binds," "specifically recognizes," or is "specific for" refers to measurable and reproducible interactions such as binding between a target and an antigen binding protein (such as a mAb), which is determinative of the presence of the target in the presence of a heterogeneous population of molecules including biological molecules. For example, an antigen binding protein (such as a mAb) that specifically binds a target (which can be an epitope) is an antigen binding protein (such as a mAb) that binds this target with greater affinity, avidity, more readily, and/or with greater duration than it binds other targets. In some embodiments, the extent of binding of an antigen binding protein (such as a mAb) to an unrelated target is less than about 10% of the binding of the antigen binding protein (such as a mAb) to the target as measured, e.g., by a radioimmunoassay (RIA). In some embodiments, an antigen binding protein (such as a mAb) that specifically binds a target has a dissociation constant ($K_D$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antigen binding protein specifically binds an epitope on a protein that is conserved among the protein from different species. In some embodiments, specific binding can include, but does not require, exclusive binding.

The term "specificity" refers to selective recognition of an antigen binding protein (such as a mAb) for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. That is, for example, the terms "anti-PD-L 1/PD-1," "anti-PD-1/PD-L1." "PD-L1×PD-1," "PD-1×PD-L1," "PD-1-PD-L1," and "PD-L1-PD-1" can be used interchangeably to refer to bispecific antibodies that specifically bind to both PD-L1 and PD-1. The term "monospecific" as used herein denotes an antigen binding protein (such as a mAb) that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC);

phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation comprises an N297A or DANA mutation (D265A and/or N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRL, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821.337 can be performed. Useful effector cells for such assays include peripheral blood mononuclear cells (PBMC) and natural killer (NK) cells. Alternatively, or additionally, ADCC activity of the molecule of interest can be assessed in vivo, e.g., in an animal model such as that disclosed in Clynes et al., *Proc. Nat'l. Acad. Sci. USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region can be removed, for example, during production or purification of the antibody, or by recombinantly engineering the nucleic acid encoding a heavy chain of the antibody. Accordingly. a composition of intact antibodies can comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J Immunol.* 24: 249 (1994). Methods of measuring binding to FcRn are known (see, e.g., Ghetie and Ward, *Immunol. Today* 18: (12): 592-8 (1997): Ghetie et al., Nature Biotechnology 15 (7): 637-40 (1997); Hinton et al., J. Biol. Chem. 279 (8): 6213-6 (2004): WO 2004/92219 (Hinton et al.). Binding to FcRn in vivo and serum half-life of human FcRn high-affinity binding polypeptides can be assayed. e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202: 163 (1996), can be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_D$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1}s^{-1}$.

The term equilibrium dissociation constant "$K_D$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of K presupposes that all binding agents are in solution. In the case where the antibody is tethered to a cell wall, e.g., in a yeast expression system. the corresponding equilibrium rate constant is expressed as $EC_{50}$, which gives a good approximation of $K_D$. The affinity constant, $K_a$, is the inverse of the dissociation constant, $K_D$, expressed in units of $M^{-1}$.

The dissociation constant ($K_D$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (moles per liter). An antibody or antigen-binding fragment thereof that specifically binds to a target can have a dissociation constant ($K_D$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M.

Binding specificity of the antibody or antigen-binding domain can be determined experimentally by methods known in the art. Such methods comprise, but are not limited to Western blots, ELISA-, RIA-, ECL-, IRMA-, EIA-, BIAcore-tests and peptide scans.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between PD-L1 and B7-1, or component of a process, i.e. an enzyme, cell, cell receptor or microorganism) by half. The values are typically expressed as molar concentration. $IC_{50}$ is comparable to an $EC_{50}$ for agonist drug or other substance (such as an antibody). ECs % also represents the plasma concentration required for obtaining 50% of a maximum effect in vivo. As used herein, an "$IC_{50}$" is used to indicate the effective concentration of an antibody (such as an anti-PD-L1 mAb) needed to neutralize 50% of the antigen bioactivity (such as PD-L1 bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny cannot be completely identical in nucleic acid content to a parent cell, but can contain mutations. Mutant progeny that have the same function or biological activity as screened or selected for in the originally transformed cell are included herein.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

II. Anti-PD-L1 Construct

Anti-PD-L1 Monoclonal Antibody

An isolated anti-PD-L1 construct described herein comprises a monoclonal antibody (mAb) moiety that specifically recognizes or binds to PD-L1 (or "anti-PD-L1 mAb"). In some embodiments of the invention, an isolated anti-PD-L1 construct is a full-length IgG.

PD-L1

Similar in structure to related B7 family members, PD-L1 protein contains extracellular IgV and IgC domains and a short, cytoplasmic region. PD-L1 has an intracellular domain similar to that of CD28, which lacks intrinsic catalytic activity and contains one YVKM motif able to bind PI3K, PP2A and SHP-2 and one proline-rich motif able to bind SH3 containing proteins.

An exemplary amino acid sequence of human PD-L1 is disclosed at Genbank Accession Number Q9NZQ7, within which, the region of amino acids 1-18 is the leader peptide: 19-238 is the extracellular domain: 239-259 is the transmembrane domain; and 260-290 is the cytoplasmic domain.

According to embodiments of the invention, a human PD-L1 sequence is at least 90% identical in amino acids sequence to human PD-L1 of Genbank Accession Number Q9NZQ7 and contains amino acid residues that identify the amino acid sequence as being human when compared to PD-L1 amino acid sequences of other species (e.g., murine). In some embodiments, a human PD-L1 can be at least about 95%, 96%, 97%, 98%, or 99% identical in amino acid sequence to PD-L1 of Genbank Accession Number Q9NZQ7. In some embodiments, a human PD-L1 sequence will display no more than 10 amino acid differences from the PD-L1 of Genbank Accession Number Q9NZQ7. In some embodiments, a human PD-L1 can display no more than 5, 4, 3, 2, or 1 amino acid difference from the PD-L1 of Genbank Accession Number Q9NZQ7. Percent identity can be determined as described herein. In some embodiments, an anti-PD-L1 mAb described herein specifically binds to a PD-L1 polypeptide with 100% amino acid sequence identity to the PD-L1 of Genbank Accession Number Q9NZQ7. In some embodiments, an anti-PD-L1 mAb of the application specifically binds to a PD-L1 polypeptide comprising the amino acid sequence of SEQ ID NO: 395.

In some embodiments, an anti-PD-L1 mAb of the application can cross-react with PD-L1 from species other than human, or other proteins which are structurally related to human PD-L1 (e.g., human PD-L1 homologs). In some embodiments, an anti-PD-L1 mAb of the application is completely specific for human PD-L1 and not exhibit species or other types of cross-reactivity. In some embodiments, an anti-PD-L1 mAb of the application specifically binds to a soluble isoform of human PD-L 1. In some embodiments, an anti-PD-L1 mAb of the application specifically recognizes a membrane-bound isoform of human PD-L1 (SEQ ID NO: 395).

In some embodiments, an anti-PD-L1 mAb described herein specifically recognizes or binds to the extracellular domain (ECD) of PD-L1. In some embodiments, an anti-PD-L1 mAb specifically binds to the N-terminal portion of the PD-L1 extracellular domain (ECD). In some embodiments, an anti-PD-L1 mAb specifically recognizes the C-terminal portion of the PD-L1 extracellular domain (ECD). In some embodiments, an anti-PD-L1 mAb specifically recognizes the middle portion of the PD-L1 extracellular domain (ECD). In some embodiments, the extracellular domain of PD-L1 specifically recognized by the anti-PD-L1 mAb is at least about 95%, 96%, 97%, 98%, or 99% identical in amino acid sequence to the extracellular domain of the PD-L1 of Genbank Accession Number Q9NZQ7. In some embodiments, the extracellular domain of PD-L1 specifically recognized by the anti-PD-L1 mAb is 100% identical in amino acid sequence to the extracellular domain of the PD-L1 of Genbank Accession Number Q9NZQ7. In some embodiments, the anti-PD-L1 mAb specifically recognizes a PD-L1 ECD polypeptide having the amino acid sequence of SEQ ID NO: 396.

Antibody Affinity

In some embodiments, the $K_D$ of the binding between the anti-PD-L1 mAb and PD-L1 is about $10^{-5}$ M to about $10^{-6}$ M, about $10^{-6}$ M to about $10^{-7}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-5}$ M to about $10^{-12}$ M, about $10^{-6}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-5}$ M to about $10^{-11}$ M, about $10^{-7}$ M to about $10^{-11}$ M, about $10^{-8}$ M to about $10^{-11}$ M, about $10^{-9}$ M to about $10^{-11}$ M, about $10^{-5}$ M to about $10^{-10}$ M, about $10^{-7}$ M to about $10^{-10}$ M, about $10^{-8}$ M to about $10^{-10}$ M, about $10^{-5}$ M to about $10^{-9}$ M, about $10^{-7}$ M to about $10^{-9}$ M, about $10^{-5}$ M to about $10^{-8}$ M, or about $10^{-6}$ M to about $10^{-8}$ M.

In some embodiments, the $K_{on}$ of the binding between the anti-PD-L1 mAb and PD-L1 is about $10^2$ $M^{-1}s^{-1}$ to about $10^4$ $M^{-1}s^{-1}$, about $10^4$ $M^{-1}s^{-1}$ to about $10^6$ $M^{-1}s^{-1}$, about $10^6$ $M^{-1}s^{-1}$ to about $10^7$ $M^{-1}s^{-1}$, about $10^2$ $M^{-1}s^{-1}$ to about $10^7$ $M^{-1}s^{-1}$, about $10^3$ $M^{-1}s^{-1}$ to about $10^7$ $M^{-1}s^{-1}$, about $10^4$ $M^{-1}s^{-1}$ to about $10^7$ $M^{-1}s^{-1}$, about $10^5$ $M^{-1}s^{-1}$ to about $10^7$ $M^{-1}s^{-1}$, about $10^3$ $M^{-1}s^{-1}$ to about $10^6$ $M^{-1}s^{-1}$, or about $10^4$ $M^{-1}s^{-1}$ about $10^6$ $M^{-1}s^{-1}$.

In some embodiments, the $K_{on}$ of the binding between the anti-PD-L1 mAb and PD-L1 is about 1 $s^{-1}$ to about $10^{-2}$ $s^{-1}$, about $10^{-2}$ $s^{-1}$ to about $10^{-4}$ $s^{-1}$, about $10^{-4}$ $s^{-1}$ to about $10^{-5}$ $s^{-1}$, about $10^{-5}$ $s^{-1}$ to about $10^{-6}$ $s^{-1}$, about 1 $s^{-1}$ to about $10^{-6}$ $s^{-1}$, about $10^{-2}$ $s^{-1}$ to about $10^{-6}$ $s^{-1}$, about $10^{-3}$ $s^{-1}$ to about $10^{-6}$ $s^{-1}$, about $10^{-4}$ $s^{-1}$ to about $10^{-6}$ $s^{-1}$, about $10^{-2}$ $s^{-1}$ to about $10^{-5}$ $s^{-1}$, or about $10^{-3}$ $s^{-1}$ to about 10–5 $s^{-1}$.

In some embodiments, the $IC_{50}$ of the anti-PD-L1 mAb is less than 10 nM in an amplified luminescent proximity homogeneous assay (AlphaLISA) with 0.12 nM PD-1 and 0.2 nM PD-L1. In some embodiments, the $IC_{50}$ of the anti-PD-L1 mAb is less than 500 nM in an inhibition of ligand binding by FACS analysis (competition binding assay), or cell based cytokine release assay. In some embodiments, the $IC_{50}$ of the anti-PD-L1 mAb is less than 1 nM, about 1 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM.

Chimeric or Humanized Antibodies

In some embodiments, the anti-PD-L1 antibody provided herein is a chimeric antibody. Certain chimeric antibodies are described, e.g., in U.S. Pat. No. 4,816,567; and Morrison et al., *Proc. Nat'l. Acad. Sci. USA,* 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived). e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., *Nature* 332:323-329 (1988); Queen et al., *Proc. Nat'l Acad. Sci. USA* 86:10029-10033 (1989); US Patent Nos. 5, 821,337, 7,527,791, 6,982,321, and 7,087, 409; Kashmiri et al., Methods 36:25-34 (2005) (describing SDR (a-CDR) grafting); Padlan, *Mol. Immunol.* 28:489-498 (1991) (describing "resurfacing"): Dall'Acqua et al., *Methods* 36:43-60 (2005) (describing "FR shuffling"); and Osbourn et al., *Methods* 36:61-68 (2005) and Klimka et al., *Br. J. Cancer.* 83:252-260 (2000) (describing the "guided selection" approach to FR shuffling).

Human framework regions that can be used for humanization include but are not limited to: framework regions selected using the "best-fit" method (see, e.g., Sims et a. *J Immunol.* 151:2296 (1993)); framework regions derived from the consensus sequence of human antibodies of a particular subgroup of light or heavy chain variable regions (see, e.g., Carter et al. *Proc. Nat'l. Acad. Si. USA,* 89:4285 (1992); and Presta et al. *J Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J Biol. Chem.* 272:10678-10684 (1997) and Rosok et al., *J. Biol. Chem.* 271:22611-22618 (1996)).

In some embodiments, the mAbs are modified, such as humanized, without diminishing the native affinity of the domain for antigen and while reducing its immunogenicity with respect to a heterologous species. For example, the amino acid residues of the antibody heavy chain and light chain variable domains (VH and VL) can be determined, and one or more of the mouse amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of mouse monoclonal antibodies requires the introduction and mutagenesis of a limited amount of amino acids in two chains, the light and the heavy chain and the preservation of the assembly of both chains.

Human Antibodies

In some embodiments, the anti-PD-L1 antibody, particularly mAb, provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Transgenic mice or rats capable of producing fully human single-domain antibodies are known in the art. See, e.g., US20090307787A1, U.S. Pat. No. 8,754,287, US20150289489A1, US20100122358A1. and WO2004049794.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6.075.181 and 6.150.584 describing XENOMOUSE™ technology; U.S. Pat. No. 5,770,429 describing HUMAB® technology; U.S. Pat. No. 7,041,870 describing K-M MOUSE®) technology, and U.S. Patent Application Publication No. US 2007/0061900, describing VELOCIMOUSE® technology). Human variable regions from intact antibodies generated by such animals can be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J Immunol., 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Nat'l. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein. *Histology and Histopathology,* 20(3):927-937 (2005) and Vollmers and Brandlein, *Methods and Findings in Experimental and Clinical Pharmacology,* 27(3):185-91 (2005).

Human antibodies can also be generated by isolating Fv clone variable domain sequences selected from human-derived phage display libraries. Such variable domain sequences can then be combined with a desired human constant domain. Techniques for selecting human antibodies from antibody libraries are described below.

Library-Derived Antibodies

Antibodies of the present application can be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa. NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods n Molecular Biology* 248:161-175 (Lo, ed., Human Press, Totowa, NJ, 2003); Sidhu et al., *J Mol. Biol.* 338(2): 299-310 (2004); Lee et al., *J. Mol. Biol.* 340(5): 1073-1093 (2004); *Fellouse, Proc. Nat'l. Acad. Sci. USA* 101(34): 12467-12472 (2004); and Lee et al., *J. Immunol. Methods* 284(1-2): 119-132(2004). Methods for constructing single-domain antibody libraries have been described, for example, see U.S. Pat. No. 7,371, 849.

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self-antigens without any immunization as described by Griffiths et al., *EMBO J,* 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Biological Activities

The biological activity of anti-PD-L1 mAb described herein can be determined by measuring its half maximal inhibitory concentration ($IC_{50}$), which is a measure of the effectiveness of an antibody in inhibiting a specific biological or biochemical function (such as inhibiting the binding between PD-L1 and its receptor PD-1). For example, here $IC_{50}$ can be used to indicate the effective concentration of anti-PD-L1 sdAb needed to neutralize 50% of PD-L1 bioactivity in vitro. $IC_{50}$ is comparable to an $EC_{50}$, for agonist drug or other substance (such as an antibody). $EC_{50}$ also represents the plasma concentration required for obtaining 50% of a maximum effect in vivo. $IC_{50}$ or $EC_{50}$ can be measured by assays known in the art, for example, bioassays such as inhibition of ligand binding by FACS analysis (competition binding assay), cell based cytokine release assay, or amplified luminescent proximity homogeneous assay (AlphaLISA).

For example, the blockade of ligand binding can be studied using flow cytometry (also see Example 1). CHO cells expressing human PD-L1 can be dissociated from adherent culture flasks and mixed with varying concentrations of anti-PD-L1 mAb for test, and a constant concentration of labeled-PD-1 protein (such as biotin-labeled hPD-1/Fc protein). An anti-PD-L1 antibody positive control can be employed, such as Atezolizumab. The mixture is equilibrated for 30 minutes at room temperature, washed three times with FACS buffer (PBS containing 1% BSA). Then, an antibody specifically recognizing the labeled PD-1 protein of constant concentration (such as PE/Cy5 Streptavidin secondary antibody) is added and incubated for 15 minutes at room temperature. Cells are washed with FACS buffer and analyzed by flow cytometry. Data can be analyzed with Prism (GraphPad Software, San Diego, CA) using non-linear regression to calculate $IC_{50}$. The results from the competition assay will demonstrate the ability of anti-PD-L1 mAbs in inhibiting the interaction between labeled-PD-1 and PD-L1.

The biological activity of anti-PD-L1 mAb can also be tested by PD-L1-based blockade assay for cytokine release. PD-1 signaling typically has a greater effect on cytokine production than on cellular proliferation, with significant effects on IFN-γ, TNF-α and IL-2 production. PD-1 mediated inhibitory signaling also depends on the strength of the TCR signaling, with greater inhibition delivered at low levels of TCR stimulation. This reduction can be overcome by costimulation through CD28 (Freeman et al., *J Exp. Med.* 192: 1027-34 (2000)) or the presence of IL-2 (Carter et al., *Eur. J Immunol.* 32: 634-43 (2002)). Additionally, several studies show a receptor for PD-L1 or PD-L2 that is independent of PD-1. B7.1 has already been identified as a binding partner for PD-L1 (Butte et al., *Immunity* 27: 111-22 (2007)). Chemical crosslinking studies suggest that PD-L1 and B7.1 can interact through their IgV-like domains. B7.1: PD-L1 interactions can induce an inhibitory signal into T cells. As a result, the antagonism of signaling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the application, can be combined with antagonists of other components of PD-1: PD-L1 signaling, for example, antagonist anti-PD-1 and anti-PD-L2 antibodies. Thus, blockade of PD-L1 pathways by anti-PD-L1 antibodies can be studied using a variety of bioassays that monitor T cell proliferation, IFN-γ release, or IL-2 secretion.

For examples, PD-1 Effector Cells (Jurkat cell stably transfected with human PD-1 protein and NFAT luciferase) and CHO-K1/human CD274 (CHO-K1 stably expressing human CD274) are mixed in wells. Anti-PD-L1 mAbs are added into each well at different concentrations. No antibody can be used as a background control. Negative control (such as human IgG1) and positive control (such as Atezolizumab) can be employed. After 24-hour incubation in 37° C./5% $CO_2$ incubator, medium is taken from each testing well for IL-2 secretion measurement (Cisbio). $EC_{50}$ value for each test antibody is measured, which will reflect the ability of test anti-PD-L1 mAb in blocking the interaction between PD-1 and PD-L1 on Jurkat cells, thus activating T-cell IL-2 production.

In some embodiments, an anti-PD-L1 antibody. particularly Ananta-PD-L1 mAb, of the application blocks or antagonizes signals transduced by the PD-L1 ligand. In some embodiments, an anti-PD-L1 mAb can bind to an epitope on PD-L1 so as to inhibit PD-L1 from interacting with a PD-1. In some embodiments, an anti-PD-L1 mAb can reduce the binding of PD-L1 to it receptor PD-1 by at least about any of 5%, 10%, 20%, 25%, 30%, 40%, 50%, 60%, 70%, 75%, 80%, 90%, 95%, 99% or 99.9% under conditions in which the ratio of antibody combining site to PD-L1 ligand binding site is greater than 1:1 and the concentration of antibody is greater than $10^{-8}$ M.

In some embodiments, there is provided an anti-PD-L1 mAb comprising a heavy chain variable domain (VH) with a heavy chain CDR1 comprising the amino acid sequence of any one of SEQ ID NOs:71-82. or a variant thereof comprising up to about 3 (such as about any of 1, 2, or 3) amino acid substitutions; a heavy chain CDR2 comprising the amino acid sequence of any one of SEQ ID NOs:83-97, or a variant thereof comprising up to about 3 (such as about any of 1, 2, or 3) amino acid substitutions; and a heavy CDR3 comprising the amino acid sequence of any one of SEQ ID NOs:98-109, or a variant thereof comprising up to about 3 (such as about any of 1, 2, or 3) amino acid substitutions; and a light chain variable domain (VL) with a light chain CDR1 comprising the amino acid sequence of any one of SEQ ID NOs:110-123, or a variant thereof comprising up to about 3 (such as about any of 1, 2, or 3) amino acid substitutions; a light chain CDR2 comprising the amino acid sequence of any one of SEQ ID NOs:124-135, or a variant thereof comprising up to about 3 (such as about any of 1, 2, or 3) amino acid substitutions; and a light chain CDR3 comprising the amino acid sequence of any one of SEQ ID NOs: 136-147, or a variant thereof comprising up to about 3 (such as about any of 1, 2, or 3) amino acid substitutions. In some embodiments, the K, of the binding between the anti-PD-L1 mAb and PD-L 1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 antibody is rodent, chimeric, human, partially humanized, or fully humanized.

In some embodiments, the anti-PD-L1 mAb comprises a VH CDR3 comprising the amino acid sequence of any one of SEQ ID NOs:98-109 and a VL CDR3 comprising the amino acid sequence of any one of SEQ ID NOs:136-147, and the amino acid substitutions are in CDR1 and/or CDR2 of VH and VL domains.

Thus, in some embodiments, there is provided an anti-PD-L1 mAb comprising a heavy chain variable domain (VH) with a CDR1 comprising the amino acid sequence of any one of SEQ ID NOs:71-82, or a variant thereof comprising up to about 3 (such as about any of 1, 2, or 3) amino acid substitutions; a CDR2 comprising the amino acid sequence of any one of SEQ ID NOs:83-97, or a variant thereof comprising up to about 3 (such as about any of 1, 2, or 3) amino acid substitutions; and a CDR3 comprising the amino acid sequence of any one of SEQ ID NOs:98-109; and a light chain variable domain (VL) with a CDR1 comprising the amino acid sequence of any one of SEQ ID NOs:110-123, or a variant thereof comprising up to about 3 (such as about any of 1, 2, or 3) amino acid substitutions; a CDR2 comprising the amino acid sequence of any one of SEQ ID NOs:124-135, or a variant thereof comprising up to about 3 (such as about any of 1, 2, or 3) amino acid substitutions; and a CDR3 comprising the amino acid sequence of any one of SEQ ID NOs:136-147. In some embodiments, the $K_D$ of the binding between the anti-PD-L1 mAb and PD-L1 is about $10^{-5}$ M to about $10^{-12}$ M (such as about $10^{-7}$ M to about $10^{-12}$ M, or about $10^{-8}$ M to about $10^{-12}$ M), or less. In some embodiments, the anti-PD-L1 mAb is rodent, chimeric, human, partially humanized, or fully humanized.

In some embodiments, there is provided an anti-PD-L1 mAb comprising a heavy chain variable domain (VH) with a CDR1 comprising an amino acid sequence of any one of SEQ ID NOs:71-82; a CDR2 comprising an amino acid sequence of any one of SEQ ID NOs:83-97; and a CDR3 comprising an amino acid sequence of any one of SEQ ID NOs:98-109; and a light chain variable domain (VL) with a CDR1 comprising the amino acid sequence of any one of SEQ ID NOs:110-123: a CDR2 comprising the amino acid sequence of any one of SEQ ID NOs:124-135; and a CDR3 comprising the amino acid sequence of any one of SEQ ID NOs:136-147. In some embodiments, the $K_D$ of the binding between the anti-PD-L1 mAb and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 mAb is rodent, chimeric, human, partially humanized, or fully humanized.

In some embodiments, an antibody or antigen binding fragment of the application comprises the sequences of the CDRs provided in Tables 20 and 21.

The CDRs can be combined in various pair-wise combinations to generate a number of humanized anti-PD-L1 antibodies. Humanized substitutions will be clear to those skilled in the art. For example. potentially useful humanizing substitutions can be determined by comparing the FR sequences of a naturally occurring VH or VL with the corresponding FR sequences of one or more closely related human VH or VL, then introducing one or more of such potentially useful humanizing substitutions into said VH or VL using methods known in the art (also as described herein). The humanized heavy chains and light chains are paired. The resulting humanized antibodies can be tested for their PD-L1 binding affinity, for stability, for ease and level of expression, and/or for other desired properties. An anti-PD-L1 mAb described herein can be partially or fully humanized. Preferably, the resulting humanized antibody, such as humanized mAb, or an antigen binding fragment thereof, binds to PD-L1 with $K_D$, $K_{on}$, $K_{off}$ described herein.

In some embodiments, there is provided an anti-PD-L1 humanized mAb or an antigen binding fragment thereof, comprising a VH domain comprising the amino acid sequence of any one of SEQ ID NOs:1-44, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:1-44; and a VL domain comprising the amino acid sequence of any one of SEQ ID NOs:45-70, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:45-70. In some embodiments, there is provided an anti-PD-L1 mAb comprising a VH domain comprising the amino acid sequence of any one of SEQ ID NOs:1-44, or a variant thereof comprising up to about 3 (such as about any of 1, 2, or 3) amino acid substitutions in the VH domain; and a VL domain comprising the amino acid sequence of any one of SEQ ID NOs:45-70, or a variant thereof comprising up to about 3 (such as about any of 1, 2, or 3) amino acid substitutions in the VL domain. In some embodiments, an anti-PD-L1 mAb or an antigen binding fragment thereof comprises a variant of a VH domain having the amino acid sequence of any one of SEQ ID NOs: 1-44, wherein the variant comprises amino acid substitutions in CDRs, such as the CDR1, and/or the CDR2, and/or the CDR3 of the VH; and a variant of a VL domain having the amino acid sequence of any one of SEQ ID NOs:45-70, wherein the variant comprises amino acid substitutions in CDRs, such as the CDR1, and/or the CDR2, and/or the CDR3 of any one of the VL. In some embodiments, an anti-PD-L1 mAb or an antigen binding fragment thereof comprises a variant of a VH domain having the amino acid sequence of any one of SEQ ID NOs:1-44, wherein the variant comprises amino acid substitutions in FRs, such as the FR1, and/or the FR2, and/or the FR3, and/or the FR4 of any one of the VH; and a variant of a VL domain having the amino acid sequence of any one of SEQ ID NOs:45-70, wherein the variant comprises amino acid substitutions in FRs, such as the FR1, and/or the FR2, and/or the FR3, and/or the FR4 of any one of SEQ ID NOs:45-70.

In some embodiments, there is provided an anti-PD-L1 antibody, such as an mAb (hereinafter referred to as "competing anti-PD-L1 antibody or competing anti-PD-L1 mAb"), or an antigen binding fragment thereof, that specifically binds to PD-L1 competitively with any one of the anti-PD-L1 mAb described herein. In some embodiments, competitive binding can be determined using an ELISA assay. For example, in some embodiments, there is provided an anti-PD-L1 mAb that specifically binds to PD-L1 competitively with an anti-PD-L1 mAb comprising the VH amino acid sequence of any one of SEQ ID NOs:1-44 and the VL amino acid sequence of any one of SEQ ID NOs: 45-70, respectively. For another example, in some embodiments, there is provided an anti-PD-L1 mAb that specifically binds to PD-L1 competitively with an anti-PD-L1 mAb comprising a heavy chain variable domain (VH) with a CDR1 comprising the amino acid sequence of any one of SEQ ID NOs:71-82; a CDR2 comprising the amino acid sequence of any one of SEQ ID NOs:83-97; and a CDR3 comprising the amino acid sequence of any one of SEQ ID NOs:98-109; and a light chain variable domain (VL) with a CDR 1 comprising the amino acid sequence of any one of SEQ ID NOs:110-123; a CDR2 comprising the amino acid sequence of any one of SEQ ID NOs:124-135; and a CDR3 comprising the amino acid sequence of any one of SEQ ID NOs:136-147. For another example, in some embodiments, there is provided an anti-PD-L1 mAb that specifically binds to PD-L1 competitively with any anti-PD-L1 mAb described in Tables 20 and 21. In some embodiments, the $K_D$ of the binding between the competing anti-PD-L1 mAb and PD-L1 is about $10^{-5}$ M to about $10^{-12}$ M (such as about $10^{-7}$ M to about $10^{-1}$ M, or about $10^{-8}$ M to about $10^{-12}$ M), or less. In some embodiments, the competing anti-PD-L1 mAb is rodent. chimeric, human, partially humanized, or fully humanized.

Construct Comprising the Anti-PD-L1 mAb

The anti-PD-L1 construct comprising the anti-PD-L1 mAb can be of any possible format.

In some embodiments, the anti-PD-L1 construct comprising the anti-PD-L1 mAb can further comprise additional polypeptide sequences, such as one or more antibody moieties. Such additional polypeptide sequences can or cannot change or otherwise influence the (biological) properties of the anti-PD-L1 mAb, and can or cannot add further functionality to the anti-PD-L1 mAb described herein. In some embodiments, the additional polypeptide sequences confer one or more desired properties or functionalities to the anti-PD-L1 mAb of the application. In some embodiments, the anti-PD-L1 construct is a chimeric antigen receptor (CAR) comprising an extracellular antigen binding domain comprising one or more anti-PD-L1 binding moiety described herein.

In some embodiments, the additional polypeptide sequences can be a second antibody moiety (such as sdAb, scFv) that specifically recognizes a second antigen. In some embodiments, the second antigen is not PD-L1. In some embodiments, the second antibody moiety specifically recognizes the same epitope on PD-L1 as the anti-PD-L1 mAb described herein. In some embodiments, the second antibody moiety specifically recognizes a different epitope on PD-L1 as the anti-PD-L1 mAb described herein.

In some embodiments, the additional polypeptide sequences can increase the molecule's stability, solubility, or absorption, reduce immunogenicity or toxicity, eliminate or attenuate undesirable side effects, and/or confer other advantageous properties to and/or reduce undesired properties of the anti-PD-L1 construct of the invention, compared to the anti-PD-L1 mAb described herein per se.

Full-Length IgG

In some embodiments, an anti-PD-L1 mAb is a full-length IgG. In some embodiments, the anti-PD-L1 mAb comprises the constant regions of IgG, such as any of IgG1, IgG2, IgG3, or IgG4. In some embodiments, the constant region is human constant region. In some embodiments, the constant region is human IgG1 constant region.

Thus in some embodiments, there is provided an anti-PD-L1 full-length IgG comprising a heavy chain, wherein the variable region (VH) comprises a CDR1 comprising the amino acid sequence of any one of SEQ ID NOs:71-82, or a variant thereof comprising up to about 3 (such as about any of 1, 2, or 3) amino acid substitutions; a CDR2 comprising the amino acid sequence of any one of SEQ ID NOs:83-97, or a variant thereof comprising up to about 3 (such as about any of 1, 2, or 3) amino acid substitutions; and a CDR3 comprising the amino acid sequence of any one of SEQ ID NOs:98-109, or a variant thereof comprising up to about 3 (such as about any of 1, 2, or 3) amino acid substitutions, and wherein the VH is fused to the heavy chain constant regions (hinge. $C_H1$, $C_H2$ and $C_H3$) of an immunoglobulin; and a light chain, wherein the variable region (VL) comprises a CDR1 comprising the amino acid sequence of any one of SEQ ID NOs:110-123, or a variant thereof comprising up to about 3 (such as about any of 1, 2, or 3) amino acid substitutions; a CDR2 comprising the amino acid sequence of any one of SEQ ID NOs:124-135, or a variant thereof comprising up to about 3 (such as about any of 1, 2, or 3) amino acid substitutions; and a CDR3 comprising the amino acid sequence of any one of SEQ ID NOs:136-147, or a variant thereof comprising up to about 3 (such as about any of 1, 2, or 3) amino acid substitutions, and wherein the VL is fused to the light chain constant region (CL) of an immunoglobulin. In some embodiments, there is provided an anti-PD-L1 full-length IgG comprising a heavy chain, wherein the variable region (VH) comprises a CDR1 comprising the amino acid sequence of any one of SEQ ID NOs:71-82; a CDR2 comprising the amino acid sequence of any one of SEQ ID NOs:83-97; and a CDR3 comprising the amino acid sequence of any one of SEQ ID NOs:98-109, or a variant thereof comprising up to about 3 (such as about any of 1, 2, or 3) amino acid substitutions, and wherein the VH is fused to the heavy chain constant regions (hinge, $C_H1$, $C_{H2}$ and $C_{H3}$) of an immunoglobulin; and a light chain, wherein the variable region (VL) comprises a CDR1 comprising the amino acid sequence of any one of SEQ ID NOs:110-123: a CDR2 comprising the amino acid sequence of any one of SEQ ID NOs:124-135; and a CDR3 comprising the amino acid sequence of any one of SEQ ID NOs: 136-147, or a variant thereof comprising up to about 3 (such as about any of 1, 2. or 3) amino acid substitutions, and wherein the VL is fused to the light chain constant region (CL) of an immunoglobulin. In some embodiments, the constant regions are human IgG1 constant region. In some embodiments, the $K_L$ of the binding between the full-length anti-PD-L1 IgG and PD-L1 is about $10^{-5}$ M to about $10^{-12}$ M (such as about $10^{-7}$ M to about $10^{-12}$ M, or about $10^{-8}$ M to about $10^{-12}$ M), or less. In some embodiments, the full-length anti-PD-L1 IgG is rodent, chimeric, human, partially humanized, or fully humanized.

In some embodiments, there is provided a full-length anti-PD-L1 mAb comprising the heavy chain amino acid sequence of any one of SEQ ID NOs:1-44, and light chain amino acid sequence of any one of SEQ ID NOs:45-70.

In some embodiments. there is also provided a full-length anti-PD-L1 IgG (hereinafter referred to as "competing anti-PD-L1 IgG") that specifically binds to PD-L1 competitively with any one of the full-length anti-PD-L1 IgG described herein. Competitive binding can be determined using an ELISA assay. For example, in some embodiments, there is provided an anti-PD-L1 IgG that specifically binds to PD-L1 competitively with an anti-PD-L1 IgG comprising the heavy chain amino acid sequence of any one of SEQ ID NOs:1-44, and light chain amino acid sequence of any one of SEQ ID NOs:45-70. For another example, in some embodiments, there is provided an anti-PD-L1 IgG that specifically binds to PD-L1 competitively with an anti-PD-L1 IgG comprising a heavy chain, wherein the variable region (VH) comprises a CDR1 comprising the amino acid sequence of any one of SEQ ID NOs:71-82; a CDR2 comprising the amino acid sequence of any one of SEQ ID NOs:83-97; and a CDR3 comprising the amino acid sequence of any one of SEQ ID NOs:98-109; and a light chain, wherein the variable region (VL) comprises a CDR1 comprising the amino acid sequence of any one of SEQ ID NOs:110-123: a CDR2 comprising the amino acid sequence of any one of SEQ ID NOs:124-135; and a CDR3 comprising the amino acid sequence of any one of SEQ ID NOs:136-147. In some embodiments, the $K_D$ of the binding between the competing anti-PD-L1 IgG and PD-L1 is about $10^{-5}$ M to about $10^{-12}$ M (such as about $10^{-7}$ M to about $10^{-12}$ M, or about $10^{-8}$ M to about $10^{-12}$ M) or less. In some embodiments, the competing anti-PD-L1 IgG is rodent, chimeric, human, partially humanized, or fully humanized.

Multivalent and/or Multispecific Antibodies

In some embodiments, the anti-PD-L1 construct comprises an anti-PD-L1 mAb described herein fused to one or more other antibody moiety (such as an antibody moiety that specifically recognizes another antigen). The one or more other antibody moiety can be of any antibody or antibody fragment format. such as a sdAb, a full-length antibody, a Fab, a Fab', a (Fab')2, an Fv, a single chain Fv (scFv), an scFv-scFv, a minibody, or a diabody. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046. For a review of multispecific antibodies, see Weidle et al., *Cancer Genomics Proteomics,* 10(1):1-18, 2013: Geering and Fussenegger, *Trends Biotechnol.,* 33(2):65-79, 2015: Stamova et al., *Antibodies,* 1(2): 172-198, 2012. Diabodies are antibody fragments with two antigen-binding sites that can be bivalent or bispecific. See, for example. EP 404,097; WO 1993/01161: Hudson et al., *Nat. Med.* 9:129-134 (2003); and Hollinger et al., *Proc. Nat'l. Acad. Sci. US4A* 90: 6444-6448 (1993). Triabodies and tetrabodies are also described in Hudson et al., *Nat. Med* 9:129-134 (2003). Antibody fragments can be made by various techniques, including but not limited to proteolytic digestion of an intact antibody as well as production by recombinant host cells (e.g. *E. coli* or phage), as described herein. In some embodiments, the one or more other antibody moiety is antibody mimetics, which are small engineered proteins comprising antigen-binding domains reminiscent of antibodies (Geering and Fussenegger, *Trends Biotechnol.,* 33(2):65-79, 2015). These molecules are derived from existing human scaffold proteins and comprise a single polypeptide. Exemplary antibody mimetics that can be comprised within the anti-PD-L1 construct described herein can be, but are not limited to, a designed ankyrin repeat protein (DARPin; comprising 3-5 fully synthetic ankyrin repeats flanked by N- and C-terminal Cap domains), an avidity multimer (avimer; a high-affinity protein comprising multiple A domains, each domain with low affinity for a target), or an Anticalin (based on the scaffold of lipocalins, with four accessible loops, the sequence of each can be randomized).

Techniques for making multispecific antibodies include, but are not limited to, recombinant co-expression of two immunoglobulin heavy chain-light chain pairs having different specificities (see Milstein and Cuello. *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies can also be made by engineering electrostatic steering effects for making antibody Fc-heterodimeric molecules (WO 2009/089004A1): cross-linking two or more antibodies or fragments (see, e.g., U.S. Pat. No. 4,676,980, and Brennan et al., *Science,* 229: 81 (1985)): using leucine zippers to produce bi-specific antibodies (see, e.g., Kostelny et al., *J. Immunol.* 148(5):1547-1553 (1992)): using "diabody" technology for making bispecific antibody fragments (see, e.g., Hollinger et al., *Proc. Nat'l. Acad. Sci. USA,* 90:6444-6448 (1993)); and using single-chain Fv (scFv) dimers (see, e.g., Gruber et al., *J. Immunol.,* 152:5368 (1994)); and preparing trispecific antibodies as described, e.g., in Tutt et al. *J. Immunol.* 147: 60 (1991); and creating polypeptides comprising tandem single-domain antibodies (see, e.g., U.S. Patent Application No. 20110028695; and Conrath et al. *J. Biol. Chem.,* 2001; 276(10):7346-50). Engineered antibodies with three or more functional antigen binding sites, including "Octopus antibodies," are also included herein (see, e.g., US 2006/0025576A1).

Peptide linkers

In some embodiments, the two or more antibody moieties within the anti-PD-L1 construct can be optionally connected by a peptide linker. The length, the degree of flexibility and/or other properties of the peptide linker(s) used in the anti-PD-L1 construct can have some influence on properties, including but not limited to the affinity, specificity or avidity for one or more particular antigens or epitopes. For example, longer peptide linkers can be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker can have a naturally occurring sequence, or a non-naturally occurring sequence. For example, a sequence derived from the hinge region of heavy chain only antibodies can be used as the linker. See, for example, WO1996/34103. In some embodiments, the peptide linker is a mutated human IgG1 hinge (EPKSSDKTHTSPPSP, SEQ ID NO: 399). In some embodiments, the peptide linker is a flexible linker. Exemplary flexible linkers include glycine polymers $(G)_n$, glycine-serine polymers (including, for example. $(GS)_n$, $(GSGGS)_n$ (SEQ ID NO: 401), (GGGS) (SEQ ID NO: 402), and $(GGGGS)_n$ (SEQ ID NO: 403), where n is an integer of at least one), glycine-alanine polymers, alanine-serine polymers. and other flexible linkers known in the art. In some embodiments, the peptide linker comprises the amino acid sequence of GGGGSGGGS (SEQ ID NO: 397). In some embodiments, the peptide linker comprises the amino acid sequence of SEQ ID NO: 398 (GGGGSGGGGSGGGGS).

Bispecific Antibodies

In some embodiments, an isolated antibody or antigen binding fragment of the application is a bispecific or multispecific antibody that comprises an anti-PD-L1 IgG described herein fused to a second antibody moiety, wherein the second antibody moiety binds specifically to another antigen, preferably another inhibitory immune checkpoint molecules.

In an embodiment, the other antigen is CTLA-4 and the second antibody moiety comprises an antibody or antigen binding fragment that binds specifically to CTLA-4, such as an anti-CTLA-4 mAb, preferably an anti-CTLA-4 sdAb. The isolated antibody or antigen binding fragment comprising bi-specificity against PD-L1 and CTLA-4 can be hereinafter referred to as "anti-PD-L1/CTLA-4 antibody", "anti-PD-L1/CTLA-4 construct", or "PD-L1×CTLA-4 antibody".

In an embodiment, the other antigen is TIGIT and the second antibody moiety comprises an antibody or antigen binding fragment that binds specifically to TIGIT, such as an anti-TIGIT mAb, preferably an anti-TIGIT sdAb. The isolated antibody or antigen binding fragment comprising bi-specificity against PD-L1 and TIGIT can be hereinafter referred to as "anti-PD-L1/TIGIT antibody", "anti-PD-L1/TIGIT construct", or "PD-L1×TIGIT antibody".

In an embodiment, the other antigen is TIM-3 and the second antibody moiety comprises an antibody or antigen binding fragment that binds specifically to TIM-3, such as an anti-TIM-3 mAb, preferably an anti-TIM3 sdAb. The isolated antibody or antigen binding fragment comprising bi-specificity against PD-L1 and TIM-3 can be hereinafter referred to as "anti-PD-L1/TIM-3 antibody", "anti-PD-L1/TIM-3 construct", or "PD-L1×TIM-3 antibody".

In an embodiment, the other antigen is LAG-3 and the second antibody moiety comprises an antibody or antigen binding fragment that binds specifically to LAG-3, such as an anti-LAG-3 mAb, preferably an anti-LAG-3 sdAb. The isolated antibody or antigen binding fragment having bi-specificity against PD-L1 and LAG-3 can be hereinafter referred to as "anti-PD-L1/LAG-3 antibody", "anti-PD-L1/LAG-3 construct", or "PD-L1×LAG-3 antibody".

CTLA-4, TIGIT, TIM-3 and LAG-3, similar to PD-L1, are inhibitory immune checkpoint molecules.

In some embodiments, there is provided an isolated anti-PD-L1 construct comprising a full-length IgG specifically recognizing PD-L1 and a sdAb selected from the group consisting of an anti-CTLA-4 sdAb, an anti-TIGIT sdAb, an anti-TIM-3 sdAb, and an anti-LAG-3 sdAb, wherein the anti-PD-L1 IgG comprises a heavy chain, wherein the variable region (VH) comprises a CDR1 comprising the amino acid sequence of any one of SEQ ID NOs: 71-82, or a variant thereof comprising up to about 3 (such as about any of 1, 2, or 3) amino acid substitutions; a CDR2 comprising the amino acid sequence of any one of SEQ ID NOs: 83-97, or a variant thereof comprising up to about 3 (such as about any of 1, 2, or 3) amino acid substitutions; and a CDR3 comprising the amino acid sequence of any one of SEQ ID NOs: 98-109, or a variant thereof comprising up to about 3 (such as about any of 1, 2, or 3) amino acid substitutions, and wherein the VH is fused to the heavy chain constant regions (hinge, $C_H1$, $C_H2$ and $C_H3$) of an immunoglobulin; and a light chain, wherein the variable region (VL) comprises a CDR1 comprising the amino acid sequence of any one of SEQ ID NOs: 110-123, or a variant thereof comprising up to about 3 (such as about any of 1, 2, or 3) amino acid substitutions; a CDR2 comprising the amino acid sequence of any one of SEQ ID NOs: 124-135, or a variant thereof comprising up to about 3 (such as about any of 1, 2, or 3) amino acid substitutions; and a CDR3 comprising the amino acid sequence of any one of SEQ ID NOs: 136-147, or a variant thereof comprising up to about 3 (such as about any of 1, 2, or 3) amino acid substitutions, and wherein the VL is fused to the light chain constant region (CL) of an immunoglobulin. In some embodiments, the N terminus of the sdAb is fused to the C terminus of at least one of the heavy chains of the full-length antibody specifically recognizing PD-L1. In some embodiments, the C terminus of the sdAb is fused to the N terminus of at least one of the heavy chains of the full-length antibody specifically recognizing PD-L 1. In some embodiments, the N terminus of the sdAb is fused to the C terminus of at least one of the light chains of the full-length antibody specifically recognizing PD-L1. In some embodiments, the C terminus of the sdAb is fused to the N terminus of at least one of the light chains of the full-length antibody specifically recognizing PD-L 1. In some embodiments, the full-length IgG specifically recognizing PD-L1 and the second binding moiety sdAb are optionally connected by a peptide linker. In some embodiments, the peptide linker comprises the amino acid sequence of SEQ ID NO: 397-399. In some embodiments, the $K_D$ of the binding between the anti-PD-L1 mAb and PD-L1 is about $10^{-5}$ M to about $10^{-12}$ M (such as about $10^{-7}$ M to about $10^{-12}$ M, or about $10^{-8}$ M to about $10^{-12}$ M), or less. In some embodiments, the anti-PD-L1 IgG is rodent, chimeric, human, partially humanized, or fully humanized.

In some embodiments, there is provided an anti-PD-L1 construct comprising a full-length IgG specifically recognizing PD-L1 and a sdAb selected from the group consisting of an anti-CTLA-4 sdAb, an anti-TIGIT sdAb, an anti-TIM-3 sdAb, and an anti-LAG-3 sdAb, wherein the full-length IgG comprises a VH domain comprising the amino acid sequence of any one of SEQ ID NOs:1-44, or a variant thereof having at least about 80% (such as at least about any of 80%, 85%, 90%, 91%, 92%, 93%, 94%, 95%, 96%, 97%, 98%. or 99%) sequence identify to any one of SEQ ID NOs:1-44 and wherein the VH is fused to the heavy chain constant regions (hinge, $C_H1$, $C_H2$ and $C_H3$) of an immunoglobulin; and a VL domain comprising the amino acid sequence of any one of SEQ ID NOs:45-70, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs:45-70 and wherein the VL is fused to the light chain constant regions (CL) of an immunoglobulin. In some embodiments, there is provided an isolated anti-PD-L1 construct comprising a full-length IgG specifically recognizing PD-L1 and a sdAb selected from the group consisting of an anti-CTLA-4 sdAb, an anti-TIGIT sdAb, an anti-TIM-3 sdAb, and an anti-LAG-3 sdAb, wherein the full-length IgG comprises a VH domain comprising the amino acid sequence of any one of SEQ ID NOs:1-44, or a variant thereof comprising up to about 3 (such as about any of 1, 2, or 3) amino acid substitutions in the VH domain and wherein the VH is fused to the heavy chain constant regions (hinge, $C_H1$, $C_H2$ and $C_H3$) of an immunoglobulin; and a VL domain comprising the amino acid sequence of any one of SEQ ID NOs:45-70, or a variant thereof comprising up to about 3 (such as about any of 1, 2, or 3) amino acid substitutions in the VL domain and wherein the VL is fused to the light chain constant regions (CL) of an immunoglobulin.

In some embodiments, the anti-PD-L1 full-length IgG comprising the VH domain comprising the amino acid sequence of any one of SEQ ID NOs: 1-44 or a variant thereof comprises amino acid substitutions in CDRs, such as the CDR 1, and/or the CDR2, and/or the CDR3 of any one of SEQ ID NOs:1-44, and where in the VH is fused to the heavy chain constant regions (hinge, $C_H1$, CH2 and $C_H3$) of an immunoglobulin; and the VL domain comprising the amino acid sequence of any one of SEQ ID NOs:45-70 or a variant thereof comprises amino acid substitutions in CDRs, such as the CDR1, and/or the CDR2, and/or the CDR3 of any one of SEQ ID NOs:45-70, and where in the VH fused to the light chain constant regions (CL) of an immunoglobulin. In some embodiments, the anti-PD-L1 full-length IgG comprising the VH domain comprising the amino acid sequence of any one of SEQ ID NOs:1-44 or a variant thereof comprises CDR1, CDR2, and CDR3 of any one of SEQ ID NOs:1-44, and the amino acid substitutions are in FRs, such as the FR 1, and/or the FR2, and/or the FR3, and/or the FR4 of any one of SEQ ID NOs:1-44, and wherein the VH is fused to the heavy chain constant regions (hinge, $C_H1$, $C_H2$ and $C_H3$) of an immunoglobulin; and the VL domain comprising the amino acid sequence of any one of SEQ ID NOs:45-70 or a variant thereof comprises CDR1, CDR2, and CDR3 of any one of SEQ ID NOs:45-70, and the amino acid substitutions are in FRs, such as the FR 1, and/or the FR2, and/or the FR3, and/or the FR4 of any one of SEQ ID NOs:45-70, and wherein the VL is fused to the light chain constant regions (CL) of an immunoglobulin. In some embodiments, the anti-PD-L1 full-length IgG comprising the VH domain comprising the amino acid sequence of any one of SEQ ID NOs:1-44 or a variant thereof comprises amino acid substitutions in both CDRs and FRs, and wherein the VH is fused to the heavy chain constant regions (hinge, $C_H1$, $C_12$ and $C_H3$) of an immunoglobulin; and the VL domain comprising the amino acid sequence of any one of SEQ ID NOs:45-70 or a variant thereof comprises amino acid substitutions in both CDRs and FRs, and wherein the VL is fused to the light chain constant regions (CL) of an immunoglobulin. In some embodiments, there is provided an isolated anti-PD-L1 construct comprising a full-length IgG specifically recognizing PD-L1 and a sdAb selected from the group consisting of an anti-CTLA-4 sdAb, an anti-TIGIT sdAb, an anti-TIM-3 sdAb, and an anti-LAG-3 sdAb, wherein the full-length IgG comprises a VH domain comprising the amino acid sequence of any one of SEQ ID NOs:1-44 fused to the heavy chain constant regions (hinge. $C_H1$, $C_H2$ and $C_H3$) of an immunoglobulin; and a VL domain comprising the amino acid sequence of any one of SEQ ID NOs:45-70 fused to the light chain constant regions (CL) of an immunoglobulin. In some embodiments, the N terminus of the sdAb is fused to the C terminus of at least one of the heavy chains of the full-length antibody specifically recognizing PD-L1. In some embodiments, the C terminus of the sdAb is fused to the N terminus of at least one of the heavy chains of the full-length antibody specifically recognizing PD-L1. In some embodiments, the N terminus of the sdAb is fused to the C terminus of at least one of the light chains of the full-length antibody specifically recognizing PD-L1. In some embodiments, the C terminus of the sdAb is fused to the N terminus of at least one of the light chains of the full-length antibody specifically recognizing PD-L1. In some embodiments, the full-length IgG specifically recognizing PD-L1 and the second binding moiety sdAb are optionally connected by a peptide linker. In some embodiments, the peptide linker comprises the amino acid sequence of SEQ ID NO: 397-399. In some embodiments, the $K_D$ of the binding between the anti-PD-L1 mAb and PD-L1 is about $10^{-5}$ M to about $10^{-12}$ M (such as about $10^{-7}$ M to about $10^{-12}$ M, or about $10^{-8}$ M to about $10^{-12}$ M). In some embodiments, the anti-PD-L1 mAb is rodent, chimeric, human, partially humanized, or fully humanized.

In some embodiments, there is also provided an anti-PD-L1 construct comprising a full-length IgG specifically recognizing PD-L1 (hereinafter referred to as "competing anti-PD-L1 construct") that specifically binds to PD-L1 competitively with any one of the anti-PD-L1/CTLA-4 constructs, anti-PD-L1/TIGIT constructs, anti-PD-L1/TIM-3 constructs or anti-PD-L1/LAG-3 constructs described herein.

Anti-PD-L1 Antibody Variants

In some embodiments, amino acid sequence variants of the antibodies provided herein are contemplated. For example, it can be desirable to improve the binding affinity and/or other biological properties of the antibody. Amino acid sequence variants of an antibody can be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion. insertion, and substitution can be made to arrive at the final construct, provided that the final construct possesses the desired characteristics, e.g., antigen-binding.

a) Substitution, Insertion, Deletion and Variants

In some embodiments antibody variants having one or more amino acid substitutions are provided. Sites of interest for substitutional mutagenesis include the HVRs and FRs. Conservative substitutions are shown in Table 2 under the heading of "Preferred substitutions." More substantial changes are provided in Table 2 under the heading of "exemplary substitutions." and as further described below in reference to amino acid side chain classes. Amino acid substitutions can be introduced into an antibody of interest and the products screened for a desired activity, e.g., retained/improved antigen binding, decreased immunogenicity. or improved ADCC or CDC.

TABLE 2

| Amino acid substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids can be grouped according to common side-chain properties:

(1) hydrophobic: Norleucine, Met, Ala, Val, Leu, Ile;

(2) neutral hydrophilic: Cys, Ser, Thr, Asn, Gin;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody. which can be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) can be made in HVRs, e.g., to improve antibody affinity. Such alterations can be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ. (2001)) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding can be specifically identified, e.g., using alanine scanning mutagenesis or modeling. CDR-H3 and CDR-L3 in particular are often targeted.

In some embodiments, substitutions, insertions, or deletions can occur within one or more HVRs so long as such alterations do not substantially reduce the ability of the antibody to bind antigen. For example, conservative alterations (e.g., conservative substitutions as provided herein) that do not substantially reduce binding affinity can be made in HVRs. Such alterations can be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that can be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions can be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues can be targeted or eliminated as candidates for substitution. Variants can be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an anti-PD-L1 construct provided herein is altered to increase or decrease the extent to which the construct is glycosylated. Addition or deletion of glycosylation sites to an antibody can be conveniently accomplished by altering the amino acid sequence such that one or more glycosylation sites is created or removed.

Where the anti-PD-L1 construct comprises an Fc region, the carbohydrate attached thereto can be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide can include various carbohydrates, e.g., mannose. N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-PD-L1 construct of the present application can be made in order to create antibody variants with certain improved properties.

In some embodiments. antibody variants are provided having a carbohydrate structure that lacks fucose attached (directly or indirectly) to an Fc region. For example, the amount of fucose in such antibody can be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex. hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 can also be located about ±3 amino acids upstream or downstream of position 297, i.e., between positions 294 and 300, due to minor sequence variations in antibodies. Such fucosylation variants can have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108: WO 2000/61739; WO 2001/29246; US 2003/0115614; US 2002/0164328: US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140: Okazaki et al. *J. Mol. Biol.* 336:1239-1249 (2004): Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004): Kanda. Y. et al., *Biotechnol. Bioeng.,* 94(4):680-688 (2006); and WO2003/085107).

Anti-PD-L1 construct variants are further provided with bisected oligosaccharides, e.g., in which a biantennary oligosaccharide attached to the Fc region of the antibody is bisected by GlcNAc. Such antibody variants can have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants can have improved CDC function. Such antibody variants are described, e.g., in WO 1997/30087 (Patel et al.): WO 1998/58964 (Raju, S.); and WO 1999/22764 (Raju, S.).

c) Fc Region Variants

In some embodiments, one or more amino acid modifications can be introduced into the Fc region of the anti-PD-L1 construct provided herein, thereby generating an Fc region variant. The Fc region variant can comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-PD-L1 construct variant that possesses some but not all effector functions, which make it a desirable candidate for applications in which the half-life of the anti-PD-L1 construct in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457492 (1991). Non-limiting examples of in vitro assays to assess ADCC activity oaf molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. & p. Med.* 166: 1351-1361 (1987)). Alternatively, non-radioactive assays methods can be employed (see, for example, ACTI™ non-radioactive cytotoxicity assay for flow cytometry (Cell Technology, Inc. Mountain View, CA; and CytoTox 96® non-radioactive cytotoxicity assay (Promega, Madison. WI). Useful effector cells for such assays include peripheral blood mononuclear cells (PBMC) and Natural Killer (NK) cells. Alternatively, or additionally. ADCC activity of the molecule of interest can be assessed in vivo, e.g., in an animal model such as that disclosed in Clynes et al. *Proc. Nat 7Acad & J. USA* 95:652-656 (1998). C1q binding assays can also be carried out to confirm that the antibody is unable to bind C1q and hence lacks CDC activity. See, e.g., C1q and C3c binding ELISA in WO 2006/029879 and WO 2005/100402. To assess complement activation, a CDC assay can be performed (see, for example, Gazzano-Santoro et al., *J Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments. an anti-PD-L1 construct variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551. WO 99/51642, and Idusogie et al. *J. Immunol.* 164: 4178-4184 (2000).

In some embodiments, there is provided an anti-PD-L1 construct (e.g., a HCAb) variant comprising a variant Fc region comprising one or more amino acid substitutions which increase half-life and/or improve binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter. *Nature* 322:738-40 (1988); U.S. Pat. Nos. 5,648,260; 5,624,821; and WO 94/29351 concerning other examples of Fc region variants.

Anti-PD-L1 constructs (such as full-length IgG or anti-PD-L1 IgG fused to a sdAb) comprising any of the Fc variants described herein, or combinations thereof, are contemplated.

d) Cysteine Engineered Antibody Variants

In some embodiments, it can be desirable to create cysteine engineered anti-PD-L1 constructs. e.g., "thioMAbs." in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and can be used to conjugate the antibody to other moieties, such as drug moieties or linker-drug moieties, to create an immunoconjugate, as described further herein. In some embodiments, any one or more of the following residues can be substituted with cysteine: A118 (EU numbering) of the heavy chain; and S400 (EU numbering) of the heavy chain Fc region. Cysteine engineered anti-PD-L 1 constructs can be generated as described, e.g., in U.S. Pat. No. 7,521,541.

e) Antibody Derivatives

In some embodiments, an anti-PD-L1 construct provided herein can be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers). and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water. The polymer can be of any molecular weight. and can be branched or unbranched. The number of polymers attached to the antibody can vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an anti-PD-L1 construct and nonproteinaceous moiety that can be selectively heated by exposure to radiation are provided. In some embodiments, the nonproteinaceous moiety is a carbon nanotube (Kam et al., *Proc. Nat'l. Acad. Sci. USA* 102: 11600-11605 (2005)). The radiation can be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-PD-L1 construct provided herein (such as anti-PD-L1 IgG, anti-PD-L1/CTLA-4 bispecific antibody, anti-PD-L1/TIGIT bispecific antibody, anti-PD-L1/TIM-3 bispecific antibody or anti-PD-L1/LAG-3 bispecific antibody) can be further modified to contain one or more biologically active protein, polypeptides or fragments thereof. "Bioactive" or "biologically active" as used herein means showing biological activity in the body to carry out a specific function. For example, it can mean the combination with a particular biomolecule such as protein, DNA, etc., and then promotion or inhibition of the activity of such biomolecule. In some embodiments, the bioactive protein or fragments thereof have immunostimulatory/immunoregulatory, membrane transport, or enzymatic activities.

In some embodiments, the bioactive protein or fragments thereof that can be fused with the anti-PD-L1 construct described herein is a ligand, such as lymphokines and cellular factors which interact with specific cellular receptor. Lymphokines are low molecular weight proteins which are secreted by T cells when antigens or lectins stimulate T cell growth. Examples of lymphokines include, but are not limited to, interferon-α, interferon-γ, interleukin-1 (IL-1), interleukin-2 (IL-2), interleukin-3 (IL-3), tumor necrosis factor (TNF), a colony stimulating factor (e.g. CSF-1. G-CSF or GM-CSF), chemotaxins, macrophage migration inhibitory factor (MIF), macrophage-activating factor (MAF), NK cell activating factor, T cell replacing factor, leukocyte-inhibitory factor (LIF), lymphotoxins, osteoclast-activating factor (OAF), soluble immune response suppressor (SIRS), growth-stimulating factor, monocyte growth factor, etc. Cellular factors which can be incorporated into the anti-PD-L1 fusion proteins of the invention include but are not limited to tumor necrosis factor α(TNFα), interferons (IFNs), and nerve growth factor (NGF), etc.

III. Pharmaceutical Compositions

Further provided by the present application are pharmaceutical compositions comprising any one of the anti-PD-L1 constructs comprising a full-length IgG specifically recognizing PD-L1 as described herein (such as anti-PD-L1 IgG, anti-PD-L1/CTLA-4 bispecific antibody. anti-PD-L1/TIGIT bispecific antibody, anti-PD-L1/TIM-3 bispecific antibody or anti-PD-L1/LAG-3 bispecific antibody), and optionally a pharmaceutically acceptable carrier. Pharmaceutical compositions can be prepared by mixing an anti-PD-L1 construct described herein having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions.

The pharmaceutical composition is preferably to be stable, in which the anti-PD-L1 construct comprising anti-PD-L1 mAb described here essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening. the formulation can be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of anti-PD-L1 construct described herein can comprise less than about 10% (preferably less than about 5%) of the anti-PD-L1 construct present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride: hexamethonium chloride; benzalkonium chloride, benzethonium chloride; phenol. butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine: monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers can comprise histidine and trimethylamine salts such as Tris.

Preservatives are added to retard microbial growth, and are typically present in a range from 0.2%-1.0% (w/v). The addition of a preservative can, for example, facilitate the production of a multi-use (multiple-dose) formulation. Suitable preservatives for use in the present application include octadecyldimethylbenzyl ammonium chloride: hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight. preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above), amino acids such as alanine, glycine, glutamine, asparagine, histidine, arginine, lysine, ornithine, leucine, 2-phenylalanine, glutamic acid, threonine, etc.: organic sugars or sugar alcohols such as sucrose, lactose, lactitol, trehalose, stachyose, mannose, sorbose, xylose, ribose, ribitol, myoinisitose, myoinisitol, galactose. galactitol, glycerol, cyclitols (e.g., inositol), polyethylene glycol: sulfur containing reducing agents, such as urea, glutathione, thioctic acid, sodium thioglycolate, thioglycerol, a-monothioglycerol and sodium thio sulfate; low molecular weight proteins such as human serum albumin, bovine serum albumin, gelatin or other immunoglobulins; hydrophilic polymers such as polyvinylpyrrolidone: monosaccharides (e.g., xylose, mannose, fructose, glucose: disaccharides (e.g., lactose, maltose, sucrose): trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON® polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition can be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally.

Sustained-release preparations can be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions herein can also contain more than one active compound as necessary for the particular indication being treated, preferably those with complementary activities that do not adversely affect each other. Alternatively, or in addition, the composition can comprise a cytotoxic agent, chemotherapeutic agent, cytokine, immunosuppressive agent, or growth inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* $18^{th}$ edition.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Uses or Applications

The anti-PD-L1 construct comprising mAb specifically recognizing PD-L1 as described herein (such as anti-PD-L1 full-length IgG, anti-PD-L1/CTLA-4 bispecific antibody, anti-PD-L1/TIGIT bispecific antibody, anti-PD-L1/TIM-3 bispecific antibody or anti-PD-L1/LAG-3 bispecific antibody), and the compositions (such as pharmaceutical compositions) thereof are useful for a variety of applications, such as in diagnosis, molecular assays. and therapy.

One aspect of the invention provides a method of treating a PD-L1 related disease or a condition in an individual in need thereof, comprising administering to the individual an effective amount of a pharmaceutical composition comprising the anti-PD-L1 construct described herein. In some embodiments, the PD-L1 related disease is cancer. In some embodiments, the PD-L1 related disease is pathogenic infection, such as viral infection.

The application contemplates, in part, protein constructs (such as anti-PD-L1 full-length IgG. anti-PD-L1/CTLA-4 bispecific antibody, anti-PD-L 1/TIGIT bispecific antibody, anti-PD-L1/TIM-3 bispecific antibody or anti-PD-L1/LAG-3 bispecific antibody), nucleic acid molecules and/or vectors encoding thereof, host cells comprising nucleic acid molecules and/or vectors encoding thereof, that can be administered either alone or in any combination with another therapy. and in at least some aspects, together with a pharmaceutically acceptable carrier or excipient. In some embodiments, prior to administration of the anti-PD-L1 construct, they can be combined with suitable pharmaceutical carriers and excipients that are well known in the art. The compositions prepared according to the disclosure can be used for the treatment or delaying of worsening of cancer.

In some embodiments, there is provided a method of treating cancer comprising administering to the individual an effective amount of a pharmaceutical composition comprising an isolated anti-PD-L1 construct comprising a mAb specifically recognizing PD-L1 (such as anti-PD-L1 full-length IgG, anti-PD-L1/CTLA-4 bispecific antibody, anti-PD-L1/TIGIT bispecific antibody, anti-PD-L1/TIM-3 bispecific antibody or anti-PD-L1/LAG-3 bispecific antibody). In some embodiments, the cancer is a solid tumor (such as colon cancer). In some embodiments, the pharmaceutical composition is administered systemically (such as intravenously). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer: (6) inhibiting tumor metastasis; (7) prolonging survival, (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%,o, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein can be used as a first therapy, second therapy, third therapy, or combination therapy with other types of cancer therapies known in the art, such as chemotherapy, surgery, hormone therapy, radiation, gene therapy, immunotherapy (such as T-cell therapy), bone marrow transplantation, stem cell transplantation, targeted therapy, cryotherapy, ultrasound therapy, photodynamic therapy, radio-frequency ablation or the like, in an adjuvant setting or a neoadjuvant setting (i.e., the method can be carried out before the primary/definitive therapy). In some embodiments, the method is used to treat an individual who has previously been treated. In some embodiments, the cancer has been refractory to prior therapy. In some embodiments, the method is used to treat an individual who has not previously been treated.

In some embodiments, the method is suitable for treating cancers with aberrant PD-L1 expression, activity and/or signaling include, by way of non-limiting example, melanoma, prostate cancer, lung cancer, colon cancer, gastric cancer, ovarian cancer, breast cancer, and glioblastoma.

Thus in some embodiments, there is provided a method of treating an immunotherapy-responsive solid tumor (such as carcinoma or adenocarcinoma, such as cancers with aberrant PD-L1 expression, activity and/or signaling), comprising administering to the individual an effective amount of a pharmaceutical composition comprising an isolated anti-PD-L1 construct comprising a monoclonal antibody specifically recognizing PD-L1 (such as anti-PD-L1 full-length IgG, anti-PD-L 1/CTLA-4 bispecific antibody, anti-PD-L1/TIGIT bispecific antibody, anti-PD-L 1/TIM-3 bispecific antibody or anti-PD-L1/LAG-3 bispecific antibody). In some embodiments, the cancer is a solid tumor (such as colon cancer). In some embodiments, the pharmaceutical composition is administered systemically (such as intravenously). In some embodiments, the pharmaceutical composition is administered locally (such as intratumorally). In some embodiments, the method further comprises administering to the individual an additional cancer therapy (such as surgery, radiation, chemotherapy, immunotherapy, hormone therapy, or a combination thereof). In some embodiments, the individual is a human. In some embodiments, the method of treating cancer has one or more of the following biological activities: (1) killing cancer cells (including bystander killing); (2) inhibiting proliferation of cancer cells; (3) inducing immune response in a tumor: (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of killing cancer cells mediated by the pharmaceutical composition described herein can achieve a bystander tumor cell (uninfected by the oncolytic VV) death rate of at least about any of 10%, 20%, 30%, 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks.

In some embodiments, the method is suitable for treating cancers with aberrant PD-1 or PD-L 1/PD-L2 expression, activity and/or signaling include, by way of non-limiting example, hematological cancer and/or solid tumors. Some cancers whose growth can be inhibited using the antibodies of the invention include cancers typically responsive to immunotherapy. Non-limiting examples of other cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth can be inhibited using the antibodies of the invention. Examples of other cancers that can be treated using the antibodies of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia. solid tumors of childhood. lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The application is also useful for treatment of metastatic cancers, especially metastatic cancers that express PD-L1 (Iwai et 7. (2005) *Int. Immunol.* 17:133-144).

Thus, in some embodiments, there is provided a method of treating an immunotherapy-responsive solid tumor (such as carcinoma or adenocarcinoma, such as cancers with aberrant PD-L1 expression, activity and/or signaling, and/or aberrant CTLA-4, TIGIT, TIM-3 and LAG-3 expression, activity and/or signaling), comprising administering to the individual an effective amount of a pharmaceutical composition comprising an isolated anti-PD-L1 construct comprising a full-length IgG specifically recognizing PD-L1 fused to a CTLA-4, TIGIT, TIM-3 or LAG-3 sdAb. In some embodiments, there is provided a method of treating an immunotherapy-responsive solid tumor (such as carcinoma or adenocarcinoma, such as cancers with aberrant PD-L1 expression, activity and/or signaling, and/or aberrant CTLA-4, TIGIT, TIM-3, LAG-3 expression, activity and/or signaling), comprising administering to the individual an effective amount of a pharmaceutical composition comprising an isolated anti-PD-L1 construct comprising a full-length IgG specifically recognizing PD-L1 fused to a CTLA-4, TIGIT, TIM-3 or LAG-3 sdAb.

In some embodiments, the method described herein is suitable for treating a colorectal cancer, such as adenocarcinoma, gastrointestinal carcinoid tumor, gastrointestinal stromal tumor, Leiomyosarcoma, melanoma, or squamous cell carcinoma.

Dosages and desired drug concentrations of pharmaceutical compositions of the present application can vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the anti-PD-L1 construct comprising an anti-PD-L1 mAb described herein are used, normal dosage amounts can vary from about 10 ng/kg up to about 100 mg/kg of mammal body weight or more per day, preferably about 1 mg/kg/day to 10 mg/kg/day, such as about 1-3 mg/kg/day, about 2-4 mg/kg/day, about 3-5 mg/kg/day, about 4-6 mg/kg/day, about 5-7 mg/kg/day, about 6-8 mg/kg/day, about 6-6.5 mg/kg/day, about 6.5-7 mg/kg/day, about 7-9 mg/kg/day, or about 8-10 mg/kg/day, depending upon the route of administration. It is within the scope of the present application that different formulations will be effective for different treatments and different disorders, and that administration intended to treat a specific organ or tissue can necessitate delivery in a manner different from that to another organ or tissue. Moreover, dosages can be administered by one or more separate administrations, or by continuous infusion. For repeated administrations over several days or longer, depending on the condition, the treatment is sustained until a desired suppression of disease symptoms occurs. However, other dosage regimens can be useful. The progress of this therapy is easily monitored by conventional techniques and assays.

In some embodiments, the pharmaceutical composition is administered for a single time (e.g. bolus injection). In some embodiments, the pharmaceutical composition is administered for multiple times (such as any of 2, 3, 4, 5, 6, or more times). If multiple administrations, they can be performed by the same or different routes and can take place at the same site or at alternative sites. The pharmaceutical composition can be administered twice per week, 3 times per week, 4 times per week, 5 times per week, daily, daily without break, once per week, weekly without break, once per 2 weeks, once per 3 weeks, once per month, once per 2 months, once per 3 months, once per 4 months, once per 5 months, once per 6 months, once per 7 months, once per 8 months, once per 9 months, once per 10 months, once per 11 months, or once per year. The interval between administrations can be about any one of 24h to 48h, 2 days to 3 days, 3 days to 5 days, 5 days to 1 week, 1 week to 2 weeks, 2 weeks to 1 month, 1 month to 2 months, 2 month to 3 months, 3 months to 6 months, or 6 months to a year. Intervals can also be irregular (e.g. following tumor progression). In some embodiments, there is no break in the dosing schedule. In some embodiments, the pharmaceutical composition is administered every 4 days for 4 times. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment with the anti-PD-L1 construct described herein, preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized anti-PD-L1 construct described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions can be injected using a syringe. However, other devices for administration of the pharmaceutical compositions are available such as injection devices: injector pens; auto-injector devices, needleless devices; and subcutaneous patch delivery systems.

In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., *New Eng. J. of Med.* 319: 1676 (1988)).

The anti-PD-L1 construct comprising mAb specifically recognizing PD-L1 as described herein (such as anti-PD-L1 full-length IgG, anti-PD-L1/CTLA-4 bispecific antibody. anti-PD-L1/TIGIT bispecific antibody, anti-PD-L1/TIM-3 bispecific antibody or anti-PD-L1/LAG-3 bispecific antibody), and the compositions (such as pharmaceutical compositions) thereof are also useful in diagnosis or molecular assays. For example, the antibody or antigen binding fragment can be used for the detection or quantification of PD-L1 in a biological sample, thereby detecting or monitoring the progress or treatment of a disease, such as those described above, related to PD-L1.

V. Methods of Preparation

The anti-PD-L1 construct (such as anti-PD-L1 monoclonal antibody) described herein can be prepared using any methods known in the art or as described herein. Also see Examples 1-2.

Rodent monoclonal antibodies can be obtained using methods known in the art such as by immunizing a rodent species (such as mouse or rat) and obtaining hybridomas therefrom, or by cloning a library of Fab fragment or single chain Fc (scFv) using molecular biology techniques known in the art and subsequent selection by ELISA with individual clones of unselected libraries or by using phage display.

For recombinant production of the monoclonal antibodies, the nucleic acids encoding the monoclonal antibodies are isolated or synthesized and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally. preferred host cells are of either prokaryotic or eukaryotic (generally mammalian) origin.

Embodiments

The invention provides also the following non-limiting embodiments.

Embodiment 1 comprises an isolated antibody, preferably mAb, or an antigen binding fragment thereof, comprising:

(a) a heavy chain variable domain (VH) comprising:
  i. a heavy chain CDR1 comprising the amino acid sequence of any one of SEQ ID NOs:71-82, or a variant thereof comprising up to about 3 (such as about any of 1, 2, or 3) amino acid substitutions;
  ii. a heavy chain CDR2 comprising the amino acid sequence of any one of SEQ ID NOs:83-97, or a variant thereof comprising up to about 3 (such as about any of 1, 2, or 3) amino acid substitutions; and
  iii. a heavy chain CDR3 comprising the amino acid sequence of any one of SEQ ID NOs:98-109, or a variant thereof comprising up to about 3 (such as about any of 1, 2, or 3) amino acid substitutions; and
(b) a light chain variable domain (VL) comprising:
  i. a light chain CDR1 comprising the amino acid sequence of any one of SEQ ID NOs:110-123, or a variant thereof comprising up to about 3 (such as about any of 1, 2, or 3) amino acid substitutions;
  ii. a light chain CDR2 comprising the amino acid sequence of any one of SEQ ID NOs:124-135, or a variant thereof comprising up to about 3 (such as about any of 1, 2. or 3) amino acid substitutions; and
  iii. a light chain CDR3 comprising the amino acid sequence of any one of SEQ ID NOs:136-147, or a variant thereof comprising up to about 3 (such as about any of 1, 2, or 3) amino acid substitutions, wherein the antibody or antigen-binding fragment is capable of specifically binding to a PD-L1, preferably a human PD-L1.

Embodiment 2 is an isolated antibody, preferably mAb, or an antigen binding fragment thereof, comprising (a) a heavy chain variable domain (VH) comprising:
  i. a heavy chain CDR1 comprising an amino acid sequence selected from the group consisting of SEQ ID NOs:71-82;
  ii. a heavy CDR2 comprising an amino acid sequence selected from the group consisting of SEQ ID NOs: 83-94, respectively, wherein SEQ ID NO:87 is optionally replaced with any one of SEQ ID NOs: 95-97; and
  iii. a heavy chain CDR3 comprising an amino acid sequence selected from the group consisting of SEQ ID NOs:98-109, respectively, and
(b) a light chain variable domain (VL) comprising, respectively,
  i. a light chain CDR1 comprising an amino acid sequence selected from the group consisting of SEQ ID NOs:110-121. wherein SEQ ID NO:111 is optionally replaced with SEQ ID NO:122. and SEQ ID NO:114 is optionally replaced with SEQ ID NO:123;
  ii. a light chain CDR2 comprising an amino acid sequence selected from the group consisting of SEQ ID NOs:124-135, respectively; and
  iii. a light chain CDR3 comprising an amino acid sequence selected from the group consisting of SEQ ID NOs:136-147, respectively, wherein the antibody or antigen-binding fragment is capable of specifically binding to a PD-L 1, preferably a human PD-L1.

Embodiment 3 is the isolated antibody, preferably mAb. or an antigen binding fragment thereof of embodiment 1 or 2, comprising the heavy chain CDRs of Table 20 and the respective light chain CDRs of Table 21.

Embodiment 4 is the isolated antibody, preferably mAb, or an antigen binding fragment thereof of any one of embodiments 1 to 3, comprising a VH domain comprising the amino acid sequence of any one of SEQ ID NOs:1-44, or a variant thereof having at least about 80%, at least about 90%, or at least about 95% sequence identity to any one of SEQ ID NOs:1-44; and a VL domain comprising the amino acid sequence of any one of SEQ ID NOs:45-70, or a variant thereof having at least about 80%, at least about 90%, or at least about 95% sequence identity to any one of SEQ ID NOs:45-70.

Embodiment 5 is the isolated antibody, preferably mAb. or an antigen binding fragment thereof of any one of embodiments 1 to 4, comprising a VH domain comprising an amino acid sequence of any one of SEQ ID NOs:1-44, or a variant thereof comprising up to about 3 amino acid substitutions in the VH domain; and a VL domain comprising an amino acid sequence of any one of SEQ ID NOs: 45-70, or a variant thereof comprising up to about 3 amino acid substitutions in the VL domain.

Embodiment 6 is the isolated antibody, preferably mAb, or an antigen binding fragment thereof of embodiment 5, wherein the VH domain comprises an amino acid sequence selected from the group consisting of SEQ ID NOs:1-44; and the VL domain comprises the amino acid sequence selected from the group consisting of SEQ ID NOs:45-70, respectively.

Embodiment 7 comprises an isolated antibody, preferably mAb, or an antigen binding fragment comprising:

(1) a VH comprising heavy chain CDR1, CDR2 and CDR3 sequences having the amino acid sequences of SEQ ID NOs: 75, 87 and 102, respectively, and a VL comprising light chain CDR1, CDR2 and CDR3 sequences having the amino acid sequences of SEQ ID NOs: 114, 128 and 140, respectively, wherein SEQ ID NO:87 is optionally replaced with any one of SEQ ID NOs: 95-97, and SEQ ID NO:114 is optionally replaced with SEQ ID NO: 123; or
(2) a VH comprising heavy chain CDR1, CDR2 and CDR3 sequences having the amino acid sequences of SEQ ID NOs: 72, 84 and 99, respectively, and a VL comprising light chain CDR1, CDR2 and CDR3 sequences having the amino acid sequences of SEQ ID NOs: 111, 125 and 137, respectively, wherein SEQ ID NO: 111 is optionally replaced with SEQ ID NO: 122.

Embodiment 8 is the isolated antibody, preferably mAb, or an antigen binding fragment thereof of embodiment 7, wherein the VH comprises the heavy chain CDR1, CDR2 and CDR3 sequences having the amino acid sequences of SEQ ID NOs: 72, 84 and 99, respectively, and the VL comprises the light chain CDR1, CDR2 and CDR3 sequences having the amino acid sequences of SEQ ID NOs: 122, 125 and 137, respectively.

Embodiment 9 is the isolated antibody, preferably mAb, or an antigen binding fragment thereof of embodiment 7 or 8, wherein: the VH comprises the heavy chain CDR1, CDR2 and CDR3 sequences having the amino acid sequences of SEQ ID NOs: 75, 97 and 102, respectively, and the VL comprises the light chain CDR1, CDR2 and CDR3 having the amino acid sequences of SEQ ID NOs: 123, 128 and 140, respectively.

Embodiment 10 is the isolated antibody, preferably mAb, or an antigen binding fragment thereof of any one of embodiments 1-9, wherein the $K_L$ of the binding between the antibody or antigen binding fragment and PD-L1 is about $10^{-5}$ M to about $10^{-12}$ M, about $10^{-7}$ M to about $10^{-12}$ M, or about $10^{-8}$ M to about $10^{-12}$ M or less.

Embodiment 11 is the isolated antibody, preferably mAb, or an antigen binding fragment thereof of any one of embodiments 1-10, being rodent, chimeric. human, partially humanized, or fully humanized.

Embodiment 12 is the isolated antibody, preferably mAb, or the antigen binding fragment thereof of embodiment 11, wherein the VH is fused to the heavy chain constant regions ($C_H1$, $C_H2$, and $C_H3$) of an immunoglobulin.

Embodiment 13 is the isolated antibody, preferably mAb, or an antigen binding fragment thereof of embodiment 11 or 12, wherein the VL is fused to the light chain constant region (CL) of an immunoglobulin.

Embodiment 14 is the isolated antibody, preferably mAb, of embodiment 13, comprising a constant domain of a human IgG1.

Embodiment 15 is the isolated antibody, preferably mAb, of embodiment 13 or 14, being a full-length IgG comprising the heavy chain amino acid sequence of any one of SEQ ID NOs:278-321 or 348-391, and the light chain amino acid sequences of any one of SEQ ID NOs:322-347.

Embodiment 16 is the isolated antibody, preferably mAb, or an antigen binding fragment thereof of any one of embodiments 1-15, further comprising a second antibody moiety specifically recognizing a second antigen.

Embodiment 17 is the isolated antibody, preferably mAb, or an antigen binding fragment thereof of embodiment 16, wherein the second antibody moiety is a Fab, a Fab', a (Fab')2, an Fv, a single chain Fv (scFv), an scFv-scFv, a minibody, a diabody, a sdAb, or an antibody mimetics.

Embodiment 18 is the isolated antibody, preferably mAb, or an antigen binding fragment thereof of embodiment 16 or 17, wherein the second antibody moiety is a sdAb.

Embodiment 19 is the isolated antibody, preferably mAb, or an antigen binding fragment thereof of any one of embodiments 16-18, wherein the second antibody moiety is capable of specifically binding to CTLA-4, preferably, the second antibody moiety is an sdAb capable of specifically binding to CTLA-4.

Embodiment 20 is the isolated antibody, preferably mAb, or an antigen binding fragment thereof of any one of embodiments 16-18, wherein the second antibody moiety is capable of specifically binding to TIGIT, preferably, the second antibody moiety is an sdAb capable of specifically binding to TIGIT.

Embodiment 21 is the isolated antibody. preferably mAb, or an antigen binding fragment thereof of any one of embodiments 16-18, wherein the second antibody moiety is capable of specifically binding to TIM-3, preferably, the second antibody moiety is an sdAb capable of specifically binding to TIM-3.

Embodiment 22 is the isolated antibody. preferably mAb, or an antigen binding fragment thereof of any one of embodiments 16-18, wherein the second antibody moiety is capable of specifically binding to LAG-3, preferably, the second antibody moiety is an sdAb capable of specifically binding to LAG-3.

Embodiment 23 is the isolated antibody, preferably mAb, or an antigen binding fragment thereof of any one of embodiments 19-22, wherein the amino-terminus of the heavy chain or light chain of a full-length IgG capable of specifically recognizing PD-L1 is fused, optionally via a peptide linker, to the carboxyl-terminus of the sdAb capable of specifically binding to CTLA-4, TIGIT, TIM-3 or LAG-3.

Embodiment 24 is the isolated antibody, preferably mAb, or an antigen binding fragment thereof of any one of embodiments 19-22, wherein the carboxyl-terminus of the heavy chain or light chain of a full-length IgG capable of specifically recognizing PD-L1 is fused to, optionally via a peptide linker, the amino-terminus of the sdAb capable of specifically binding to CTLA-4, TIGIT, TIM-3 or LAG-3.

Embodiment 25 is the isolated antibody or antigen-binding fragment thereof of embodiment 23 or 24, wherein the full-length IgG capable of specifically recognizing PD-L1 is fused to the sdAb capable of specifically binding to CTLA-4, TIGIT, TIM-3 or LAG-3 via a peptide linker having the amino acid sequence of one of SEQ ID NOs: 397-399.

Embodiment 26 comprises a second isolated antibody or antigen-binding fragment thereof capable of specifically binding to PD-L1 competitively with the isolated antibody or antigen-binding fragment thereof of any one of embodiments 1-25.

Embodiment 27 comprises a pharmaceutical composition comprising the isolated antibody or antigen-binding fragment thereof of any one of embodiments 1-25 or the second isolated antibody or antigen-binding fragment thereof of embodiment 26, and a pharmaceutical acceptable carrier.

Embodiment 28 is the isolated antibody or antigen-binding fragment thereof of any one of embodiments 1-25, the second isolated antibody or antigen-binding fragment thereof of embodiment 26, the pharmaceutical composition of embodiment 27 for use in treating a PD-L1 related disease in a subject in need thereof.

Embodiment 29 is the isolated antibody or antigen-binding fragment thereof or pharmaceutical composition for use of embodiment 28, wherein the PD-L1 related disease is cancer.

Embodiment 30 is the isolated antibody or antigen-binding fragment thereof or pharmaceutical composition for use of embodiment 29, wherein the cancer is a solid tumor.

Embodiment 31 is the isolated antibody or antigen-binding fragment thereof or pharmaceutical composition for use of embodiment 29, wherein the cancer is a colon cancer.

Embodiment 32 is the isolated antibody or antigen-binding fragment thereof or pharmaceutical composition for use of any one of embodiments 28-31 in combination with an additional cancer therapy.

Embodiment 33 is the isolated antibody or antigen-binding fragment thereof or pharmaceutical composition for use of embodiment 32, wherein the additional cancer therapy is a surgery, radiation, chemotherapy, immunotherapy, hormone therapy, or a combination thereof.

Embodiment 34 is the isolated antibody or antigen-binding fragment thereof or pharmaceutical composition for use of embodiment 28. wherein the PD-L1 related disease is a pathogenic infection.

Embodiment 35 is the isolated antibody or antigen-binding fragment thereof or pharmaceutical composition for use of any one of embodiments 28-34, wherein the isolated antibody or antigen-binding fragment or pharmaceutical composition is for systemic or local administration.

Embodiment 36 is the isolated antibody or antigen-binding fragment thereof or pharmaceutical composition for use of any one of embodiments 28-34. wherein the isolated antibody or antigen-binding fragment or pharmaceutical composition is for intravenous administration.

Embodiments 37 is the isolated antibody or antigen-binding fragment thereof or pharmaceutical composition for use of any one of embodiments 28-34, wherein the isolated antibody or antigen-binding fragment or pharmaceutical composition is for intratumoral administration.

Embodiment 38 is the isolated antibody or antigen-binding fragment thereof or pharmaceutical composition for use of any one of embodiments 28-37, wherein the subject is a human.

Embodiment 39 is a method of treating a PD-L1-related disease in a subject in need thereof, comprising administering to the subject an effective amount of the pharmaceutical composition of embodiment 27.

Embodiment 40 is the method of embodiment 39, wherein the PD-L1 related disease is cancer.

Embodiment 41 is the method of embodiment 40, wherein the cancer is a solid tumor.

Embodiment 42 is the method of embodiment 40 or 41, wherein the cancer is a colon cancer.

Embodiment 43 is the method of any one of embodiments 40-42, further comprising administering to the individual an additional cancer therapy.

Embodiment 44 is the method of embodiment 43, wherein the additional cancer therapy is surgery, radiation, chemotherapy, immunotherapy, hormone therapy, or a combination thereof.

Embodiment 45 is the method of embodiment 39, wherein the PD-L1 related disease is a pathogenic infection.

Embodiment 46 is the method of any one of embodiments 3945, wherein the pharmaceutical composition is administered systemically or locally.

Embodiment 47 is the method of any one of embodiments 39-45, wherein the pharmaceutical composition is administered intravenously.

Embodiment 48 is the method of any one of embodiments 39-45, wherein the pharmaceutical composition is administered intratumorally.

Embodiment 49 is the method of any one of embodiments 39-48, wherein the individual is a human.

EXAMPLES

The examples below are intended to be purely exemplary of the invention and should therefore not be considered to limit the invention in any way. The following examples and detailed description are offered by way of illustration and not by way of limitation.

Example 1: Generation of Anti-PD-L1 mAb

Immunization

Human PD-L1 extracellular domain Fc fusion protein (PD-L1-Fc) (GenScritp, Cat. No.: Z03371, SEQ ID NO: 396) was used as immunogen. For immunization, the antigen protein was formulated as an emulsion with CFA (primary immunization), or IFA (boost immunization) or no adjuvant (final boost). About 50 μg protein was mixed with Freud complete adjuvant (Sigma-Aldrich) at 1:1 ratio and used to immunize female Balb/c and C57b1/6 mice. The mice were immunized intraperitoneally afterwards with 25 μg PD-L1-Fc mixed with Freud incomplete adjuvant (Sigma-Aldrich) at 1:1 ratio every two weeks, up to 3 times. Titer of all 10 immunized mice reached above 10' (FIG. 1). Final boost was carried out using 25 μg PD-L1-Fc (no adjuvant) intraperitoneally on two mice (#848 and #853) which showed the highest titer against the antigen protein. Four days after the final boost, cell fusion was carried out.

Hybridoma Fusion and Screening

Isolated spleens of the two selected mice and the fusion partner myeloma cell (SP 2/0) were made into homogenized single cell suspension. About $8.9\times10^7$ splenocytes and $4.1\times10^7$ SP 2/0 cells were fused through electrofusion method. The fused cells were re-suspended in 100 ml DMEM/10% FBS medium containing Thymus nucleoside pyrimidine, hypoxanthine and aminopterin hybridoma selective reagents. The cell suspension was dispensed into more than fifty 96-well plates, 100 μl in each well. The cells were cultured in 37° C. incubator with 6% $CO_2$ for 7 days. The hybridoma supernatants were collected and subjected to PD-L1 binding assay and PD-1 competition assay by Enzyme Linked ImmunoSorbent Assay (ELISA), PD-1 overexpressing cell line binding by Fluorescence Activated Cell Sorting (FACS) to identify PD-L1 specific antibodies using the following methods.

PD-L1 Protein Binding Assay by ELISA

Indirect ELISA was employed to assess the binding ability of the antibodies in hybridoma supernatants to PD-L1 ECD (Acrobiosystems, Cat. No.: PD1-H5229). Recombinant PD-L 1-Fc or human IgG1 (negative control), was diluted by phosphate buffered saline (PBS) to 0.5 μg/ml, and was coated on 96-well ELISA plates (100 μl per well) at 4° C. overnight. PBST (PBS supplemented with 0.05% Tween-20) was used to wash the plates. PBST supplemented with 1% BSA was use to block the plates (200 μl per well) at 37° C. for 0.5 hour, and was discarded afterwards. Hybridoma supernatants were added in the wells (100 μl per well), and incubated at room temperature for 1 hour. The plates were washed 3 times with PBST. And goat anti-mouse IgG (Fab specific) HRP (GenScript) secondary antibody was added (100 μl per well) and incubated at 37° C. for 0.5 hour. The plates were then washed 5 times with PBST. Tetramethylbenzidine (TMB, GenScript) was added into the wells, and incubated at room temperature for 15 minutes. Hydrochloride (HCl, Sigma) stopping buffer (1 M, 50 μl per well) was added to stop the reaction and the plates were read at 450 nm using a spectrometer.

PD-1 Competition Assay by ELISA

Competition ELISA was employed to assess the ability of the antibodies in hybridoma supernatants to block the binding of PD-L1 to its receptor PD-1. Recombinant PD-1 ECD protein (GenScript Cat. No.: Z03424) was diluted by PBS to 0.5 μg/ml, and was coated on ELISA plate (100 μl per well) at 4° C. overnight. PBST were used to wash the plates. PBST supplemented with 1% BSA was use to block the plates (200 μl per well) at 37° C. for 0.5 hour, and was discarded afterwards. Hybridoma supernatants were added in the wells (50 μl per well) and non-related supernatants added to the other coated wells (50 p per well) was used as controls. Biotinylated PD-L1-Fc (0.15 μg/ml, 50 μl per well) was added into the wells afterwards. The plates were incubated at 37° C. for 1 hour, and were washed 3 times with PBST. Horseradish peroxidase (HRP)-labeled Streptavidin (SA-HRP, GenScript) was added (100 μl per well) to the wells and the plates were incubated at 37° C. for 0.5 hour. The plates were washed 5 times with PBST. TMB (GenScript) was added into the wells, and incubated at room temperature for 15 minutes. HCl (Sigma) stopping buffer (1 M, 50 μl per well) was added to stop the reaction and the plates were read at 450 nm using a spectrometer.

PD-L1 Stable Cell Line Binding by FACS

FACS was employed to assess the binding ability of the antibodies in hybridoma supernatants to the PD-L1 protein expressed on the surface of CHO cells. CHO cell overexpressing PD-L1 and the parental CHO cells were collected and washed 3 times with PBS. About $2.5\times10^5$ cells and 100 μl hybridoma supernatants were added into each well of 96-well plates, and incubated at 4° C. for 1 hour. The plates were washed 3 time using PBS. Goat anti-mouse IgG(H+L) iFluor647 (GenScript) was added to the wells, 100 μl per well, and incubated at 4° C. for 45 minutes. Cells were washed 3 times with PBS, and the signal was read by FACS BD Calibur.

Monoclonal Antibody Variable Domain Sequencing

Through the screening procedures described above, twelve PD-L1 specific monoclonal antibodies, namely 1H1G4D9, 18B7F4G8, 21D1F4D4, 25B6E5D8, 25G1F9F8, 27D3D3G2, 29A8H8C7, 30A6B2D9, 30A7B5D9, 42G2D7C3, 51F3D2G4 and 53C1F3D4, were identified. To get the variable domain sequences of the monoclonal antibodies, total RNA of the monoclones was extracted from $3\times10^6$–$5\times10^6$ of the hybridoma cells using TRIzol (Ambion). The isotype of monoclonal antibodies was determined using express mouse isotype ELISA kit (Linotyping System-HRP, Southern Biotech). Isotype specific primers and universal primers (PrimeScript™ 1st Strand cDNA Synthesis Kit, Takara) were used to reverse transcript the RNA into cDNA. The variable region DNAs of antibody heavy chain and light chain were amplified using rapid amplification of cDNA ends (RACE) polymerase chain reaction (PCR), and were subcloned into the pMD18-T vector system (Takara). Vector specific primers were used to sequence the inserted variable domain DNA. The amino acid sequences of the variable domains are shown in Tables 18 and 19.

Example 2: Mouse Monoclonal Antibody Characterization

Mouse monoclonal antibodies were produced from hybridoma culture. Properties, such as antigen binding, receptor blocking, functional activity of mouse mAbs were characterized using SPR, FACS, reporter assay and mixed lymphocyte reaction (MLR) assay.

Hybridoma Cell Culture and Mouse mAb Production

Frozen hybridoma cells were thawed rapidly and transferred to warm RPMI 1640 medium containing 10% FBS and expanded. The expanded cell culture was transferred into a roller bottle containing hybridoma cell culture medium to a final cell density of $1\text{-}2\times10^5$ cells/ml. The roller bottle was immediately placed on the roller device in a 37° C. incubator. Hybridoma cells were then cultured under 2-3 rpm rotation speed for two weeks. The hybridoma cells were spun down by centrifugation at 3,000-4,000 rpm for 15 min. The culture supernatant was filtered through 1.0 μm filter and then concentrated to 1/10 of the original volume. The concentrated supernatant can be immediately purified using 1 ml HiTrap Protein A HP column (GE healthcare) following the manufacturer's manual.

PD-L1 Stable Cell Line Binding by FACS

PD-L1 stable cell line binding activity assessment of 12 mouse mAbs was carried out using FACS. CHO-K1 cells expressing human PD-L1 (Genscript, Cat #M00543) were dissociated from adherent culture flasks and mixed with varying concentrations of antibodies. The antibody and cells were incubated for 30 minutes at room temperature, washed three times with FACS buffer (PBS containing 1% BSA). PE-labeled goat anti-mouse IgG (minimal x-reactivity) secondary antibody (BioLegend, Cat #405307) was added and incubated at room temperature for 15 minutes. Cells were washed again with FACS buffer and analyzed by FACSCalibur (BD Bioscience, San Jose, CA) and Flowjo software. Data were analyzed with Prism 6 (GraphPad Software, San Diego, CA) using non-linear regression, and $EC_{50}$ values were calculated (FIGS. 2A-2L and Table 3). Some of the mouse mAbs, namely 18B7F4G8, 29A8H8C7, 42G2D7C3, 51F3D2G4 and 53C1F3D4 showed very high affinities to the PD-L1 protein expressed on cells.

TABLE 3

Binding affinity between PD-L1 overexpressing cell line and mouse mAbs

| | Best-fit values | | | | |
|---|---|---|---|---|---|
| Sample | Bottom | Top | $LogEC_{50}$ | HillSlope | $EC_{50}$ (nM) |
| 1H1G4D9 | 12.85 | 1760 | 1.089 | 2.266 | 12.28 |
| 18B7F4G8 | 12.75 | 398.6 | −0.2089 | 2.578 | 0.62 |
| 21D1F4D4 | 24.13 | 1959 | 0.9715 | 2.055 | 9.37 |
| 25B6E5D8 | 29.44 | 1411 | 0.6535 | 2.654 | 4.50 |
| 25G1F9F8 | 8.399 | 1752 | 1.257 | 2.138 | 18.08 |
| 27D3D3G2 | 29.58 | 1773 | 0.6223 | 1.868 | 4.19 |
| 29A8H8C7 | 45.55 | 2444 | 0.4852 | 1.811 | 3.06 |
| 30A6B2D9 | 23.76 | 1639 | 1.046 | 3.256 | 11.12 |
| 30A7B5D9 | 22.88 | 1719 | 0.7868 | 2.551 | 6.12 |
| 42G2D7C3 | 11.98 | 1776 | 0.5176 | 2.235 | 3.29 |
| 51F3D2G4 | 21.09 | 1724 | 0.328 | 2.786 | 2.13 |
| 53C1F3D4 | 38.87 | 2023 | 0.5717 | 1.922 | 3.73 |

PD-L1 to PD-1 Interaction Blocking by FACS

CHO-K 1 cells expressing human PD-L1 (Genscript, Cat #M00543) were dissociated from adherent culture flasks, washed twice with wash buffer (1×PBS supplemented with 0.2% BSA) and mixed ($2\times10^5$ cells/well, 100 μl) with biotinylated PD-1 Fc fusion protein (28 μg/ml, 50 μl per well). A series of diluted mouse mAbs (concentration starting from 900 nM, 3 fold dilution, 50 μl per well) were added afterwards. The mixture was incubated at 4° C. for 30 minutes, washed twice with wash buffer, followed by the addition of PEcy5/streptavidin (1 μg/ml, 150 μl/well). The plates were again incubated at 4° C. for 30 minutes before the cells in each well were analyzed by FACSCalibur (BD Bioscience, San Jose, CA) and Flowjo software. Data were analyzed with Prism (GraphPad Software, San Diego, CA) using non-linear regression, and $EC_{50}$ values were calculated (FIGS. 3A-3J and Table 4). Some of the mouse mAbs, namely 18B7F4G8, 25B6E5D8 had no blocking effect on the binding between PD-L1 cell line and PD-1 protein, while some of the mouse mAbs, namely 27D3D3G2, 29A8H8C7, 51F3D2G4 and 53CIF3D4 could block the interaction most effectively.

TABLE 4

Blocking effect of mouse mAbs on PD-L1 cell line and PD-11 ECD.

| | Best-fit values | | | | |
|---|---|---|---|---|---|
| Sample | Bottom | Top | $LogIC_{50}$ | HillSlope | $IC_{50}$ (nM) |
| 1H1G4D9 | −4.207 | 469.5 | 1.074 | −2.52 | 11.85 |
| 18B7F4G8 | | | no blocking effect | | |
| 21D1F4D4 | −3.712 | 480.4 | 0.579 | −2.409 | 3.794 |
| 25B6E5D8 | | | no blocking effect | | |
| 25G1F9F8 | −11.67 | 482.5 | 1.139 | −2.088 | 13.76 |
| 27D3D3G2 | −0.8319 | 481 | 0.1074 | −2.228 | 1.281 |
| 29A8H8C7 | 3.803 | 482.8 | 0.1499 | −2.939 | 1.412 |
| 30A6B2D9 | −3.543 | 488.6 | 0.9218 | −2.379 | 8.352 |
| 30A7B5D9 | −1.139 | 486.1 | 0.6466 | −3.302 | 4.432 |
| 42G2D7C3 | 19.73 | 464.3 | 0.4614 | −2.591 | 2.894 |
| 51F3D2G4 | 0.08551 | 484.8 | 0.08928 | −2.476 | 1.228 |
| 53C1F3D4 | −2.682 | 483.2 | 0.1048 | −2.127 | 1.273 |

PD-L1 Cell-Based Reporter Assay

Six mouse mAbs that showed high binding activity and/or high blocking activity, namely 18B7F4G8, 27D3D3G2, 29A8H8C7, 42G2D7C3, 51F3D2G4 and 53CF13D4 were evaluated using PD-L 1 cell-based reporter assay. The effector cells contain a luciferase construct that is induced upon disruption of the PD-1/PD-L1 receptor-ligand interaction, such as when the PD-L1 cells are mixed with effector cells expressing PD-1. Thus, efficacy of inhibiting PD-L1 on CHO-K1 stable cells by anti-PD-L 1 mAbs can be assessed by measuring luciferase reporter activity. The assay was performed as follows.

On day one, PD-L1 cells were thawed in a 37° C. water bath until cells were just thawed (about 3-4 minutes), and 0.5 mL of thawed cells were transferred to 14.5 mL cell recovery medium (10% FBS/F-12). The cell suspension was mixed well by gently inverting the tube 1-2 times. The cell suspension was then transferred to a sterile reagent reservoir, and dispensed into assay plates with 25 μL of cell suspension per well. 100 μL of assay medium was added per well as blank control. 100 μL of cell recovery medium was added per well for wells serving as blank control. The plates were then lidded and incubated overnight in a $CO_2$ incubator at 37° C.

On the day of assay, fresh assay buffer (RPMI 1640+1% FBS) was prepared. An eight-point serial dilution was performed in assay buffer for each of the control anti-PD-L1 antibody (e.g., Durvalumab) and mouse mAbs. The starting concentration and dilution scheme was optimized to achieve full dose-response curves. The assay plates containing PD-L1 cells were retrieved from the $CO_2$ incubator. Ninety-five μl of medium was removed per well from all the wells. Forty μL of serial dilutions of the control anti-PD-L1 antibody, or the antigen binding protein, was added per well to wells containing PD-L1 cells. Eighty μL assay buffer was added per well to the blank control wells for each plate.

Next, PD-1 effector cells were thawed in a 37° C. water bath until cells were just thawed (about 3-4 minutes). The cell suspension was gently mixed in the vial by pipetting up and down, and 0.5 mL of the cells was added to 5.9 mL assay buffer. The cell suspension was mixed well by gently inverting the tube 1-2 times. The cell suspension was then transferred to a sterile reagent reservoir, and 40 μL of the cell suspension was dispensed to each well containing the PD-1 cells and control antibody or bispecific antigen binding protein. The plates were lidded and incubated for six hours at 37° C. in a $CO_2$ incubator.

The Luciferase Assay System was reconstituted by transferring one bottle of Buffer to the bottle containing Substrate. The system was stored at room temperature and shielded from light for same day use. After 6 hours induction, assay plates were removed from the $CO_2$ incubator and equilibrated at ambient temperature for 5-10 min. Eighty μL of reagent was added to each well. The plates were incubated for 5-10 min at ambient temperature. Luminescence was measured in GloMax® Discover System (Promega. Madison. WI) or a plate reader with glow-type luminescence reading capabilities.

Luminescence was expressed as Relative Light Unit (RLU). The RLU values of wells having diluted antibody or bispecific antigen binding protein was normalized to the RLU of no antibody or bispecific antigen binding protein control to provide Fold of Luciferase Induction. Data was graphed as RLU versus Log 10 of concentration of antibody or bispecific antigen binding protein and as Fold of Induction versus Log 10 concentration of antibody or bispecific antigen binding protein. Data were analyzed with Prism 6 (GraphPad Software, San Diego, CA) using non-linear regression, and $EC_{50}$ values were calculated (FIGS. 4A-4H and Table 5). Three antibodies. namely 27D3D3G2, 29A8H8C7 and 53C1F3D4, showed high functional activity. Mouse mAb 18B7F4G8 had a lower $EC_{50}$ value, however the percentage activation compared to the other antibodies was low, maximum 20% activation compared to the other three antibodies.

TABLE 5

Functional activity of mouse mAbs by cell-based reporter assay.

| | Best-fit values | | | | |
|---|---|---|---|---|---|
| Sample | Bottom | Top | $LogEC_{50}$ | HillSlope | $EC_{50}$ (nM) |
| 18B7F4G8 | −0.3657 | 20.56 | 0.3565 | 1.52 | 2.272 |
| 27D3D3G2 | 0.8835 | 97.2 | 0.5585 | 2.581 | 3.618 |
| 29A8H8C7 | 0.5048 | 95.38 | 0.5572 | 2.419 | 3.607 |
| 42G2D7C3 | | | not determined | | |
| 51F3D2G4 | 1.672 | 100 | 0.939 | 1.798 | 8.69 |
| 53C1F3D4 | 1.495 | 98.58 | 0.6483 | 3.358 | 4.449 |
| Durvalumab | 2.458 | 100.1 | 0.2329 | 2.919 | 1.71 |

Mixed Lymphocytes Reaction (MLR) Assay

Four mouse mAbs, namely 18B7F4G8, 27D3D3G2, 29A8H8C7 and 53C1F3D4, were evaluated for their function activity using MLR assay. Dendritic cells (DCs) and CD4+ T cells were isolated from human Peripheral blood mononuclear cells (PBMC). DCs were analyzed for their expressions of costimulatory molecules and MHC class II in FACS assay. The expression of the surface markers, i.e. CD1a, CD83, CD86, and HLA-DR was verified. A suitable ratio of CD4+ T cells and DCs were seeded into the wells of a 96-well plate and treated with the above-mentioned antibodies. Assay plate were incubated in a 37° C., 5% $CO_2$ incubator for 72 hours and the IL-2 released by cells was measured using human IL2 HTRF Kit (Cisbio, cat #64IL2PEB). Data were analyzed with Prism 6 (GraphPad Software, San Diego, CA) using non-linear regression, and $EC_{50}$ values were calculated (FIGS. 5A-5F and Table 6). According to the assay result, the functional activities of 29A8H8C7, 53C1F3D4 and 18B7F4G8 showed functional activity comparable to that of anti-PD-L1 positive control antibody Atezolizumab.

TABLE 6

Functional activity of mouse mAbs by MLR assay.

| | Best-fit values | | | | |
|---|---|---|---|---|---|
| Sample | Bottom | Top | $LogEC_{50}$ | HillSlope | $EC_{50}$ (nM) |
| Atezolizumab (Plate 1) | 54.16 | 81.27 | −0.1644 | 3.5 | 0.6848 |
| 29A8H8C7 (Plate 1) | 48.62 | 75.02 | −0.2784 | 2.727 | 0.5268 |
| 53C1F3D4 (Plate 1) | 41.65 | 67.63 | −0.1309 | 3.5 | 0.7397 |
| Atezolizumab (Plate 2) | 48.04 | 76.64 | −0.05928 | 3.048 | 0.8724 |
| 27D7G3D4 (Plate 2) | 43.47 | 66.23 | 0.399 | 1.062 | 2.506 |
| 18B7F4G8 (Plate 2) | 43.36 | 68.13 | −0.01998 | 1.654 | 0.955 |

Affinity Determination by SPR

Equilibrium dissociation constant ($K_D$) of mouse mAbs 29A8H8C7 and 53C1F3D4 was determined by surface plasmon resonance (SPR) on a Biacore™ T200 instrument. Briefly, capturing antibody (anti-mouse Fc antibody for the affinity measurement of mouse mAbs, or anti-human Fc antibody for the affinity measurement of chimeric and humanized mAbs. GE healthcare) was immobilized on a Biacore™ CM5 chip to approximately 7,000 RU using EDC-activated amine coupling chemistry. Antibody of interest (5 μg/ml) was captured for 60 seconds onto the sensor-chip surface. His-tagged PD-L1 ECD protein (ACROBiosystems) was flowed over the sensorchip surface at a series concentrations. Flow rate was 30 μl/min in all experiments. Association and dissociation phases were 5 and 15 min, respectively. The chip was regenerated using Glycine/HCl pH 1.5. Captured antibody and antigen were removed between each cycle using 50 mM HCl in order to ensure a fresh binding surface for each concentration of antigen. The resulting sensorgrams were fit globally using a 1:1 binding model in order to calculate on- and off-rates (ka and kd, respectively), as well as affinities ($K_D$). According to the result (FIGS. 6A-6D and Table 7), 29A8H8C7 and 53C1F3D4 both showed higher binding affinities to PD-L1 ECD protein than Atezolizumab and Durvalumab.

TABLE 7

Affinity determination of mouse IgGs and anti-PD-L1 control antibodies.

| Ligand | Analyte | $k_a$ (1/Ms) | $k_d$ (1/s) | $K_D$ (M) | Rmax (RU) | $Chi^2$ ($RU^2$) | U-value |
|---|---|---|---|---|---|---|---|
| 29A8H8C7 | PD-L1- | 6.20E+05 | 1.70E−04 | 2.80E−10 | 77.11 | 0.328 | 1 |
| 53C1F3D4 | His | 3.20E+05 | 1.90E−04 | 6.10E−10 | 56.83 | 0.097 | 1 |
| Durvalumab | | 3.04E+05 | 2.99E−04 | 9.84E−10 | 134.2 | 0.717 | 1 |
| Atezolizumab | | 2.92E+05 | 3.19E−04 | 1.10E−09 | 47.97 | 0.374 | 1 |

Example 3: Humanization of Mouse mAbs

Two mouse anti-PD-L1 mAbs, namely 29A8H8C7 and 53CIF3D4, were selected for humanization using CDR grafting technology (see, e.g., U.S. Pat. No. 5,225,539). Before CDR grafting was performed, several CDR residues of these antibodies were mutated to increase the humanness of the CDR or to reduce the possibility of potential post-translation modification (PTM). These mutations are: 1. Lysine 24 in CDR1 of light chain variable domain (VL) of mouse 29A8H8C7 and 53CF13D4 was mutated to Arginine (K24R) to increase humanness, resulting the VL sequences of 29A8VL.M1 and 53C1VL.M1; 2. Asparagine 57 in CDR2 of heavy chain variable domain (VH) of mouse 53C1F3D4 was mutated to Serine (N57S), Alanine (N57A) and Glutamine (N57Q), resulting the VH sequences of 53C1VH.M1, 53C1VH.M2 and 53C1VH.M3, respectively, to reduce the possibility of potential deamidation.

Chimeric IgG and mutants thereof were produced using mammalian cells. Briefly, the DNA fragments encoding heavy chain variable region (VH) were synthesized and inserted into a modified pTT5 vector that contains the DNA encoding human IgG1 heavy chain constant region (hinge, $C_H1$, $C_H2$ and $C_H3$) with effector-less mutations (constant region amino acid sequence see SEQ ID NO: 392), resulting the heavy chain expression plasmids; similarly the DNA fragment encoding light chain variable region (VL) was synthesized and inserted into a modified pTT5 vector that contains the DNA encoding human IgG1 kappa chain constant region (CL), resulting in the light chain expression plasmids. The Maxiprep plasmids were prepared.

The wild-type and mutant heavy chain and light chains were combined, resulting the wild-type chimeric IgGs and a series of mutant IgGs. For example, 29A8_chimeric is the 29A8H8C7 chimeric antibody, and was produced using the wild-type heavy chain plasmid encoding 29A8VH connected to the heavy chain constant regions with effector-less Fc mutations and the light chain plasmid encoding 29A8VL connected to the light chain constant region; 53C1_VH.M3-VL.M1 is a mutant of the chimeric 53CIF3D4, and was produced using the mutant heavy chain plasmid encoding 53C1VH.M3 connected to the heavy chain constant regions with effector-less Fc mutations and the mutant light chain plasmid encoding 53C1VL.M1 connected to the light chain constant region. The combined plasmids were used to transfect HEK293-6E cells. The transfected cells were cultured at 37° C. for 2 days. The supernatants were collected, filtered; and the secreted chimeric and mutant antibodies were subjected to SPR affinity assessment.

According to SPR affinity measurement, none of the mutations affected the binding affinity between human PD-L1 and anti-PD-L1 antibodies significantly (Table 8), therefore K24R in VL-CDR1 of both antibodies and N57Q, N57S and N57A in VH-CDR2 of 53CF13D4 could be introduced to the humanized antibodies.

TABLE 8

Affinity determination of chimeric and mutant IgGs.

| Ligand | Analyte | $k_a$ (1/Ms) | $k_d$ (1/s) | $K_D$ (M) | Rmax (RU) | $Chi^2$ ($RU^2$) | U-value |
|---|---|---|---|---|---|---|---|
| 29A8_chimeric | PD- | 5.30E+05 | 1.70E−04 | 3.20E−10 | 83.75 | 0.243 | 1 |
| 29A8_VH-VL.M1 | L1/His | 5.30E+05 | 1.50E−04 | 2.90E−10 | 96.63 | 0.394 | 1 |
| 53C1_chimeric | | 2.60E+05 | 1.90E−04 | 7.50E−10 | 45.85 | 0.056 | 1 |
| 53C1_VH.M1-VL | | 2.40E+05 | 2.10E−04 | 8.70E−10 | 51.26 | 0.078 | 1 |
| 53C1_VH.M2-VL | | 2.00E+05 | 1.60E−04 | 8.10E−10 | 50.07 | 0.05 | 1 |
| 53C1_VH.M3-VL | | 2.60E+05 | 1.40E−04 | 5.30E−10 | 40.06 | 0.043 | 1 |
| 53C1_VH-VL.M1 | | 2.60E+05 | 2.00E−04 | 7.60E−10 | 54.59 | 0.089 | 1 |
| 53C1_VH.M1-VL.M1 | | 2.40E+05 | 2.00E−04 | 8.60E−10 | 51.42 | 0.074 | 1 |
| 53C1_VH.M2-VL.M1 | | 2.00E+05 | 1.80E−04 | 9.40E−10 | 36.73 | 0.042 | 1 |
| 53C1_VH.M3-VL.M1 | | 2.60E+05 | 1.40E−04 | 5.60E−10 | 54.65 | 0.052 | 1 |

The mouse antibodies were humanized using CDR grafting technology (see, e.g., U.S. Pat. No. 5,225,539). Briefly, the variable chain sequences of the murine antibody 29A8H8C7 and 53C1F3D4 were compared to those available in the Research Collaboratory for Structural Bioinformatics (RCSB) protein databank. A homology model of 29A8H8C7 and 53C1F3D4 were generated based on the nearest VH and VK structures. Human sequences with highest identity to 29A8H8C7 and 53CIF3D4 were identified and analyzed (Foote and Winter, *J. Mol. Biol.* 224: 487499 (1992): Morea V. et al., *Methods* 20:267-279 (2000); Chothia C. et al., *J. Mol. Biol.* 186:651-663 (1985)). The most appropriate human frameworks on which to build the CDR grafted heavy and light chains were identified. For the heavy chain, the frameworks encoded by Genbank accession #CAB51716 and BAC02193, the sequences of which are incorporated herein by references, were determined to be the most appropriate for 29A8H8C7 and 53CIF3D4, respectively. For the light chain, the frameworks encoded by Genbank accession #ABA70776 and CAG27369, the sequences of which are incorporated herein by references, were determined to be the most appropriate for 29A8H8C7 and 53C1F3D4, respectively.

Straight grafts were performed to generate expression constructs for each chain. The amino acid sequences of the straightly grafted 29A8VH1. 29A8VL1, 53C1VH1 and 53C1VL1 are disclosed in the Sequence Listing (SEQ ID NOs:293, 336, 298 and 339). Straightly grafted heavy chain (SEQ ID NO: 298) and the N57Q mutant thereof, namely 53C1VH1.M3, (SEQ ID NO: 304) and the straightly grafted light chain variants with the above mentioned K24R mutations. namely 29A8VL1.M1 and 53C1VL1.M1 (SEQ ID NOs: 342 and 345) were constructed.

In case of affinity loss of the humanized antibodies, several framework residues were mutated back to their murine counterparts to restore the binding affinity of the antibodies. For the humanization of 29A8H8C7, humanized VH variants 29A8VH2, 29A8VH3, 29A8VH4 and 29A8VH5 (SEQ ID NOs: 294-297) and humanized VL variants 29A8VL2.M1 and 29A8VL3.M1 were constructed (SEQ ID NOs: 343 and 344). For the humanization of 53C1 F3D4, humanized VH variants 53C1VH2, 53C1VH3, 53C1VH4, 53C1VH5 and 53C1VH6 (SEQ ID NOs: 299-303) and the N57Q mutant thereof. namely 53C1VH2.M3, 53C1VH3.M3, 53C1VH4.M3, 53C1VH5.M3 and 53C1VH6.M3 (SEQ ID NOs: 305-309), and humanized VL variants 53C1VL2.M1 and 53C1VL3.M1 were also constructed (SEQ ID NOs: 346 and 347).

Humanized heavy chains and light chains were combined, and used to produce a series humanized antibodies. These antibodies were transiently produced using HEK293 cells and the antibodies in the supernatant were subjected to SPR affinity assessment. The binding affinities of the humanized variants are shown in Tables 9 and 10. According the affinity assessment, the humanized 29A8H8C7 had certain degree of affinity loss, whereas the binding affinity of 53CIF3D4 was retained after humanization. Three humanized variants of 429A8H8C7, namely 29A8_VH1-VL.M1, 29A8 VH4-VL.M1 and 29A8_VH5-VL2.M1 and 5 humanized variants of 53CF3D4, namely 53C1 VH1-VL8.M, 53C1_VH3-VL2.M1, 53C1_VH5-VL1.M1, 53C1 VH1.M3-VL1.ME and 53C1 VH5.M3-VL1.M1 together with the chimeric antibodies, were selected for antibody production, characterization and functional profiling. These humanized variants have either highest humanness, e.g., less back mutation, or highest binding affinity to human PD-L1 protein.

TABLE 10

Affinity assessment of humanized 29A8H8C7.

| Ligand | Analyte | $k_a$ (1/Ms) | $k_d$ (1/s) | $K_D$ (M) | Rmax (RU) | Chi$^2$ (RU$^2$) |
|---|---|---|---|---|---|---|
| 29A8_chimeric | PD-L1-His | 5.8E+05 | 1.5E−04 | 2.5E−10 | 43.02 | 0.136 |
| 29A8_VH1-VL1.M1 | | 4.7E+05 | 7.1E−04 | 1.5E−09 | 70.10 | 0.161 |

TABLE 10-continued

Affinity assessment of humanized 29A8H8C7.

| Ligand | Analyte | $k_a$ (1/Ms) | $k_d$ (1/s) | $K_D$ (M) | Rmax (RU) | Chi$^2$ (RU$^2$) |
|---|---|---|---|---|---|---|
| 29A8_VH1-VL2.M1 | | 4.7E+05 | 6.0E−04 | 1.3E−09 | 64.79 | 0.120 |
| 29A8 _VH1-VL3.M1 | | 4.6E+05 | 6.2E−04 | 1.3E−09 | 67.91 | 0.136 |
| 29A8_VH2-VL1.M1 | | 4.7E+05 | 6.1E−04 | 1.3E−09 | 64.97 | 0.096 |
| 29A8_VH2-VL2.M1 | | 4.9E+05 | 5.7E−04 | 1.2E−09 | 58.63 | 0.086 |
| 29A8_VH2-VL3.M1 | | 4.7E+05 | 6.0E−04 | 1.3E−09 | 60.45 | 0.087 |
| 29A8_VH3-VL1.M1 | | 4.8E+05 | 5.1E−04 | 1.1E−09 | 62.72 | 0.141 |
| 29A8_VH3-VL2.M1 | | 4.8E+05 | 4.4E−04 | 9.0E−10 | 61.22 | 0.099 |
| 29A8_VH3-VL3.M1 | | 5.4E+05 | 4.5E−04 | 8.3E−10 | 43.53 | 0.230 |
| 29A8_VH4-VL1.M1 | | 5.6E+05 | 6.3E−04 | 1.1E−09 | 58.32 | 0.083 |
| 29A8_VH5-VL1.M1 | | 5.5E+05 | 4.2E−04 | 7.6E−10 | 81.41 | 0.23 |

TABLE 10

Affinity assessment of humanized 53C1F3D4.

| Ligand | Analyte | $k_a$ (1/Ms) | $k_d$ (1/s) | $K_D$ (M) | Rmax (RU) | Chi$^2$ (RU$^2$) |
|---|---|---|---|---|---|---|
| 53C1_chimeric | PD-L1-His | 2.5E+05 | 1.8E−04 | 7.2E−10 | 28.39 | 0.063 |
| 53C1_VH1-VL1.M1 | | 2.4E+05 | 2.6E−04 | 1.1E−09 | 29.46 | 0.124 |
| 53C1_VH1-VL2.M1 | | 2.1E+05 | 2.6E−04 | 1.2E−09 | 59.58 | 0.188 |
| 53C1_VH1-VL3.M1 | | 2.0E+05 | 3.1E−04 | 1.5E−09 | 62.91 | 0.140 |
| 53C1_VH2-VL1.M1 | | 2.4E+05 | 2.5E−04 | 1.0E−09 | 32.49 | 0.101 |
| 53C1_VH2-VL2.M1 | | 2.2E+05 | 2.7E−04 | 1.2E−09 | 56.03 | 0.135 |
| 53C1_VH2-VL3.M1 | | 2.0E+05 | 3.0E−04 | 1.5E−09 | 65.37 | 0.126 |
| 53C1_VH3-VL1.M1 | | 3.0E+05 | 1.5E−04 | 4.9E−10 | 37.51 | 0.204 |
| 53C1_VH3-VL2.M1 | | 2.9E+05 | 1.6E−04 | 5.7E−10 | 64.90 | 0.241 |
| 53C1_VH3-VL3.M1 | | 2.6E+05 | 1.8E−04 | 6.8E−10 | 55.70 | 0.155 |
| 53C1_VH4-VL1.M1 | | 2.6E+05 | 2.0E−04 | 7.5E−10 | 43.52 | 0.012 |
| 53C1_VH5-VL1.M1 | | 3.8E+05 | 1.2E−04 | 3.1E−10 | 50.03 | 0.042 |
| 53C1_VH6-VL1.M1 | | 3.7E+05 | 1.0E−04 | 2.7E−10 | 42.4 | 0.038 |
| 53C1_VH1.M3-VL1.M1 | | 3.2E+05 | 1.0E−04 | 3.2E−10 | 47.76 | 0.025 |
| 53C1_VH3.M3-VL1.M1 | | 3.5E+05 | 7.3E−05 | 2.1E−10 | 58.38 | 0.042 |
| 53C1_VH4.M3-VL1.M1 | | 3.1E+05 | 9.8E−05 | 3.2E−10 | 48.86 | 0.028 |
| 53C1_VH5.M3-VL1.M1 | | 3.8E+05 | 6.1E−05 | 1.6E−10 | 50.47 | 0.047 |
| 53C1_VH6.M3-VL1.M1 | | 3.7E+05 | 6.3E−05 | 1.7E−10 | 59.18 | 0.050 |

Example 4: Production, Characterization and Functional Profiling of Humanized mAbs
Humanized Antibody Production The combined heavy chain and light chain plasmids encoding 2 chimeric and above-mentioned 8 humanized antibodies were used to transfect HEK293-6E cells. The transfected cells were cultured in shaking flasks at 37° C. for 6 days. The supernatants were collected, filtered and loaded onto protein A affinity column. The column was extensively washed with 1×PBS. pH 7.4 before the remaining antibody was eluted with sterile 0.1 M sodium citrate, pH 3.5. The eluted antibody solution was neutralization using 1/9 volume of the 1 M Tris-HCl, pH 9.0 buffer. The buffer of the antibodies was changed to 1×PBS, pH 7.4 or 50 mM Histine pH 6.0. The concentration was then determined through the absorbance at 280 nM (OD280). The purity was determined using sodium dodecyl sulfate polyacrylamide gel electrophoresis (SDS-PAGE) and size exclusion chromatography (SEC). The constant regions of the chimeric and humanized antibodies can be those of wild-type human IgG1 or those of human IgG1 with effector-less Fe mutations. In the interest of brevity, the following characterization assays were carried out using chimeric and humanized anti-PD-L1 with the constant regions of human IgG1 with effector-less Fc mutations.

Affinity Determination by SPR

Equilibrium dissociation constant ($K_D$) of humanized 29A8H8C7 and 53C1F3D4 to human and cynomolgus PD-L1 was determined by surface plasmon resonance (SPR) on a Biacore™ T200 instrument. For the monovalent human PD-L1 binding affinity determination, the method is similar to that described earlier, except that the capturing antibody used was anti-human Fc antibody. For cynomolgus PD-L1 binding affinity determination, cynomolgus PD-L1 Fc-fusion protein was immobilized on the sensorchip through amine coupling, and chimeric and humanized PD-L1 antibodies and benchmark antibodies Atezolizumab and Durvalumab were used as the analyte. According to the result (FIGS. 7A-7J and FIG. 8 and Tables 11 and 12), the binding affinity of 29A8H8C7 to both His-tagged human PD-L1 and cynomolgus PD-L1 Fc-fusion protein was slightly reduced, whereas the binding affinity of 53CIF3D4 was fully retained after humanization.

TABLE 11

Monovalent binding affinity of chimeric and humanized anti-PD-L1 antibodies to His-tagged human PD-L1

| Ligand | Analyte | $k_a$ (1/Ms) | $k_d$ (1/s) | $K_D$ (M) | Rmax (RU) | Chi$^2$ (RU$^2$) | U-value |
|---|---|---|---|---|---|---|---|
| 29A8_Chimeric | human | 6.40E+05 | 1.90E−04 | 3.00E−10 | 47.85 | 0.057 | 1 |
| 29A8_VH1-VL1M1 | PD-L1 | 5.90E+05 | 8.00E−04 | 1.40E−09 | 35.08 | 0.039 | 1 |
| 29A8_VH4-VL1M1 | | 6.30E+05 | 7.10E−04 | 1.10E−09 | 28.79 | 0.026 | 1 |
| 29A8_VH5-VL1M1 | | 6.20E+05 | 4.60E−04 | 7.40E−10 | 33.61 | 0.049 | 1 |
| 53C1_Chimeric | | 2.40E+05 | 1.90E−04 | 7.80E−10 | 46.99 | 0.093 | 1 |
| 53C1_VH1-VL1M | | 2.00E+05 | 2.70E−04 | 1.30E−09 | 56.61 | 0.101 | 1 |
| 53C1_VH3-VL1M | | 2.90E+05 | 1.60E−04 | 5.50E−10 | 38.93 | 0.081 | 2 |
| 53C1_VH5-VL1M | | 3.10E+05 | 1.50E−04 | 4.70E−10 | 39.51 | 0.079 | 2 |
| 53C1_VH1M3-VL1M | | 2.50E+05 | 1.40E−04 | 5.70E−10 | 43.84 | 0.083 | 2 |
| 53C1_VH5M3-VL1M | | 2.90E+05 | 1.10E−04 | 4.00E−10 | 69.01 | 0.21 | 2 |

TABLE 12

Binding affinity of chimeric and humanized anti-PD-L1 antibodies to cynomolgus PD-L1 Fc-fusion protein.

| Ligand | Analyte | $k_a$ (1/Ms) | $k_d$ (1/s) | $K_D$ (M) | Rmax (RU) | Chi$^2$ (RU$^2$) | U-value |
|---|---|---|---|---|---|---|---|
| Cynomolgus | 29A8_chimeric | 1.50E+05 | 7.30E−05 | 4.80E−10 | 23.02 | 0.131 | 9 |
| PD-L1 Fc- | 29A8_VH1-VL1.M1 | 1.10E+05 | 4.30E−04 | 4.00E−09 | 19.66 | 0.044 | 1 |
| fusion | 29A8_VH4-VL1.M1 | 1.30E+05 | 4.40E−04 | 3.30E−09 | 20.71 | 0.111 | 1 |
| protein | 29A8_VH5-VL1.M1 | 2.00E+05 | 2.00E−04 | 9.80E−10 | 23.17 | 0.248 | 4 |
| | 53C1_Chimeric | 8.70E+04 | 9.50E−05 | 1.10E−09 | 31.18 | 0.15 | 5 |
| | 53C1_VH1-VL1.M1 | 7.50E+04 | 6.40E−05 | 8.60E−10 | 32.26 | 0.072 | 5 |
| | 53C1_VH3-VL1.M1 | 9.50E+04 | 6.80E−05 | 7.10E−10 | 32.72 | 0.123 | 7 |
| | 53C1_VH5-VL1.M1 | 1.00E+05 | 8.40E−05 | 8.30E−10 | 31.62 | 0.153 | 5 |
| | 53C1_VH1.M3-VL1.M1 | 9.80E+04 | 9.40E−05 | 9.50E−10 | 32.03 | 0.16 | 5 |
| | 53C1_VH5.M3-VL1.M1 | 1.40E+05 | <1.0E−05* | <6.9E−11* | 34.28 | 0.363 | 95 |
| | Atezolizumab | 3.60E+04 | 9.90E−04 | 2.80E−08 | 35.79 | 0.241 | 1 |
| | Durvalumab | 1.90E+05 | 2.10E−04 | 1.10E−09 | 38.08 | 0.982 | 9 |

*Dissociation too slow, $k_d$ outside the range of SPR, and could not be determined accurately.

PD-L1 Stable Cell Line Binding by FACS

Human and cynomolgus PD-L1 stable cell line binding activity assessment of chimeric and humanized mAbs was carried out using FACS as described above (FIGS. 9A-9L and FIGS. 10A-10L and Tables 13 and 14). According to the results, the humanized antibodies have similar binding $EC_{50}$ values to those of their chimeric counterparts. and the binding affinities to both human and cynomolgus PD-L1 cell lines are comparable to those of the anti-PD-L1 benchmark antibodies Durvalumab and Atezolizumab.

TABLE 13

Binding affinity between human PD-L1 overexpressing cell line and chimeric and humanized mAbs

| Sample | Best-fit values | | | | |
|---|---|---|---|---|---|
| | Bottom | Top | $LogEC_{50}$ | HillSlope | $EC_{50}$ (nM) |
| 29A8_Chimeric | 188.3 | 6407 | 0.03364 | 1.726 | 1.081 |
| 29A8_VH1-VL1.M1 | 151.1 | 6399 | 0.2442 | 1.611 | 1.755 |
| 29A8_VH4-VL1.M1 | 167.1 | 5182 | 0.02287 | 1.562 | 1.054 |
| 29A8_VH5-VL1.M1 | 188.7 | 5101 | 0.1173 | 1.716 | 1.31 |
| 53C1_Chimeric | 238.7 | 6234 | 0.2538 | 1.36 | 1.794 |
| 53C1_VH1-VL1.M1 | 273.3 | 6370 | 0.05041 | 1.675 | 1.123 |
| 53C1_VH3-VL1.M1 | 216.1 | 6413 | 0.3 | 1.652 | 1.995 |
| 53C1_VH5-VL1.M1 | 189.4 | 6447 | 0.2925 | 1.641 | 1.961 |
| 53C1_VH1.M3-VL1.M1 | 273.1 | 6434 | 0.01313 | 1.954 | 1.031 |
| 53C1_VH5.M3-VL1.M1 | 264.7 | 6383 | 0.02358 | 1.754 | 1.056 |
| Durvalumab | 289.4 | 5361 | 0.1474 | 1.713 | 1.404 |
| Atezolizumab | 173.1 | 5351 | 0.5011 | 1.843 | 3.171 |

TABLE 14

Binding affinity between cynomolgus PD-L1 overexpressing cell line and chimeric and humanized mAbs

| Sample | Best-fit values | | | | |
|---|---|---|---|---|---|
| | Bottom | Top | $LogEC_{50}$ | HillSlope | $EC_{50}$ (nM) |
| 29A8_Chimeric | 152.2 | 8669 | 0.4433 | 1.503 | 2.775 |
| 29A8_VH1-VL1.M1 | 154.6 | 7466 | 0.5483 | 1.578 | 3.534 |
| 29A8_VH4-VL1.M1 | 77.01 | 7824 | 0.1731 | 1.323 | 1.490 |
| 29A8_VH5-VL1.M1 | 148.2 | 7951 | 0.4871 | 1.411 | 3.070 |

TABLE 14-continued

Binding affinity between cynomolgus PD-L1 overexpressing cell line and chimeric and humanized mAbs

| Sample | Best-fit values | | | | |
|---|---|---|---|---|---|
| | Bottom | Top | $LogEC_{50}$ | HillSlope | $EC_{50}$ (nM) |
| 53C1_Chimeric | 283 | 8490 | 0.4599 | 1.765 | 2.884 |
| 53C1_VH1-VL1.M1 | 242.1 | 8432 | 0.4407 | 1.619 | 2.759 |
| 53C1_VH3-VL1.M1 | 222.6 | 8308 | 0.6683 | 2.037 | 4.659 |
| 53C1_VH5-VL1.M1 | 249.5 | 8389 | 0.6789 | 2.059 | 4.774 |
| 53C1_VH1.M3-VL1.M1 | 204.2 | 8419 | 0.42 | 1.726 | 2.630 |
| 53C1_VH5.M3-VL1.M1 | 236.3 | 8571 | 0.4359 | 1.824 | 2.729 |
| Durvalumab | 255.8 | 8221 | 0.4869 | 1.589 | 3.069 |
| Atezolizumab | 71.42 | 7863 | 0.8319 | 1.223 | 6.791 |

PD-L1 to PD-1 Interaction Blocking by FACS

The blocking of chimeric and humanized anti-PD-L1 antibodies and benchmarks to the interaction between human PD-1 protein and human PD-L1 over expressing cell line was assessed as described above (FIGS. 11A-11L and Table 15). According to the results, the humanized antibodies have similar blocking $IC_{50}$ values to those of their chimeric counterparts, and the blocking $IC_{50}$ values are comparable to that of the anti-PD-L1 benchmark antibodies Durvalumab and lower than that of Atezolizumab.

TABLE 16

Blocking effect of chimeric and humanized mAbs on PD-L1 cell line and PD-1 ECD binding.

| Sample | Best-fit values | | | | |
|---|---|---|---|---|---|
| | Bottom | Top | $LogIC_{50}$ | HillSlope | $IC_{50}$ (nM) |
| 29A8_Chimeric | 1.271 | 56.8 | −0.5227 | −2.333 | 0.3001 |
| 29A8_VH1-VL1.M1 | 1.009 | 53.67 | −0.3349 | −1.851 | 0.4625 |
| 29A8_VH4-VL1.M1 | 1.306 | 59.59 | −0.4146 | −2.677 | 0.385 |
| 29A8_VH5-VL1.M1 | 1.137 | 59.5 | −0.2636 | −2.076 | 0.5449 |
| 53C1_Chimeric | 1.169 | 26.24 | −0.2288 | −2.715 | 0.5904 |
| 53C1_VH1-VL1.M1 | 0.9265 | 49.62 | −0.04501 | −2.111 | 0.9016 |
| 53C1_VH3-VL1.M1 | 0.8081 | 47.88 | −0.3173 | −1.567 | 0.4816 |
| 53C1_VH5-VL1.M1 | 0.1624 | 51.8 | −0.3677 | −1.146 | 0.4288 |
| 53C1_VH1.M3-VL1.M1 | 0.6388 | 54.4 | −0.5526 | −1.454 | 0.2802 |
| 53C1_VH5.M3-VL1.M1 | −0.08543 | 152.6 | −0.525 | −1.804 | 0.2985 |
| Durvalumab | 1.236 | 60.08 | −0.2767 | −2.332 | 0.5288 |
| Atezolizumab | 0.9048 | 68.85 | 0.09979 | −2.005 | 1.258 |

PD-L1 Cell-Based Reporter Assay

The functional activity of chimeric and humanized antibodies was assess and compared using PD-L1 cell-based reporter assay as described earlier (FIGS. 12A-12L and Table 16). According to the results. the humanized antibodies have similar functional activities to those of the chimeric counterparts. and the functional activities are comparable to those of the anti-PD-L1 benchmark antibodies Durvalumab and Atezolizumab.

TABLE 16

| Functional activity of mouse mAbs by cell-based reporter assay. | | | | | |
|---|---|---|---|---|---|
| | Best-fit values | | | | |
| Sample | Bottom | Top | $LogEC_{50}$ | HillSlope | $EC_{50}$ (nM) |
| 29A8_Chimeric | 0.9063 | 87.24 | 0.1285 | 4.753 | 1.344 |
| 29A8_VH1-VL1.M1 | 0.6272 | 92.19 | 0.3034 | 3.518 | 2.011 |
| 29A8_VH4-VL1.M1 | 0.2767 | 103 | 0.09214 | 3.336 | 1.236 |
| 29A8_VH5-VL1.M1 | 0.0779 | 99.1 | 0.2573 | 3.132 | 1.808 |
| 53C1_Chimeric | −0.3672 | 86.27 | 0.2959 | 3.225 | 1.977 |
| 53C1_VH1-VL1.M1 | −1.953 | 95.39 | 0.4009 | 1.961 | 2.517 |
| 53C1_VH3-VL1.M1 | −0.6545 | 87.26 | 0.3538 | 2.192 | 2.258 |
| 53C1_VH5-VL1.M1 | −0.09158 | 80.9 | 0.3674 | 3.968 | 2.33 |
| 53C1_VH1.M3-VL1.M1 | −0.7789 | 92.12 | 0.1671 | 3.272 | 1.469 |
| 53C1_VH5.M3-VL1.M1 | 0.06753 | 100 | 0.1163 | 3.036 | 1.307 |
| Durvalumab | 2.029 | 91.15 | 0.2847 | 3.379 | 1.926 |
| Atezolizumab | 1.498 | 87.61 | 0.4246 | 3.5 | 2.658 |

Mixed lymphocytes reaction (MLR) assay

Six humanized mAbs, namely 29A8 VH1-VL1.M1, 29A8_VH4-VL1.M1, 53C1_VH1-VL1.M1, 53C1_VH5-VL1.M1, 53C1_VH1.M3-VL1.M1 and 53C1_VH5.M3-VL1.M1, were evaluated for their function activity using MLR assay (FIGS. 13A-13I and Table 17). All six humanized antibodies, except 29A8_VH1-VL1.M1, showed functional activities similar to that of the benchmark antibody Durvalumab.

TABLE 17

| Functional activity of humanized mAbs by MLR assay. | | | | | |
|---|---|---|---|---|---|
| | Best-fit values | | | | |
| Sample | Bottom | Top | $LogEC_{50}$ | HillSlope | $EC_{50}$ (nM) |
| Durvalumab (Plate 1) | 107.3 | 159.7 | −0.6445 | 2.034 | 0.2267 |
| 53C1_VH1.M3-VL1.M1 (Plate 1) | 79.24 | 163.5 | −0.8825 | 3.500 | 0.1311 |
| 53Cl_VH5.M3-VL1.M1 (Plate 1) | 91.67 | 163.1 | −0.7945 | 1.94 | 0.1605 |
| Durvalumab (Plate 2) | 74.58 | 152 | −0.8079 | 2.691 | 0.1556 |
| 29A8_VH1-VL1.M1 (Plate 2) | 96.35 | 146.9 | 0.5013 | 0.7035 | 3.171 |
| 29A8_VH4-VL1.M1 (Plate 2) | 82.94 | 122 | −0.955 | 2.029 | 0.1109 |
| Durvalumab (Plate 3) | 84.34 | 156.3 | −0.4893 | 0.8964 | 0.3241 |
| 53C1_VH1-VL1.M1 (Plate 3) | 81.25 | 146.8 | −0.3687 | 2.602 | 0.4278 |
| 53C1_VH5-VL1.M1 (Plate 3) | 73.79 | 140.9 | −0.5169 | 2.173 | 0.3041 |

In Vivo Efficacy Study by Xenograft Model

The in vivo efficacy of 3 humanized mAbs, namely 29A8_VH4-VL1.M1, 53C1_VH1.M3-VL1.M1 and 53C1_VH5.M3-VL1.M1, were evaluated using xenograft model (FIGS. 14A-14G and Table 18). Benchmark antibody Durvalumab was used as a positive control. Briefly, MC38-A29-hPDL1 D13-1 cells in exponential growth phase were harvested by trypsinization and resuspended in HBSS−/− solution after cell number counting. Fifty-four (54) hPD-1 knock in mice (C57BU6 strain) (manufacturer and cat. No.) were inoculated subcutaneously in the right lower flank (near the dorsal thigh region) with a single volume of 100 μl cell suspension ($1\times10^6$ cells, cell volume: matrigel volume=1:0.8). Eventually 40 tumor-bearing mice were enrolled in the study. Since the tumor implantation, tumor size of the animals was measured twice per week in 2 dimensions using a caliper. Tumor volume, inhibition rate of tumor volume and inhibition rate of tumor growth were calculated as below:

a. Tumor volume: $V(mm^3)=(a*b^2)/2$, where "a" and "b" were the long and the short diameters of a tumor, respectively.

b. Inhibition rate of tumor volume (IRTV): IRTV=(CRTV−TRTV)/ICRTV*100° %. (TRTV: treatment group RTV; CRTV: negative control group RTV).

c. Inhibition rate of tumor growth (IRTW): IRTW=(average tumor weight of control group−average tumor weight of a treated group)/average tumor weight of control group*100%

Five (5) days after tumor inoculation, the animals were randomized into 6 groups with 8 mice each according to tumor size and animal body weight. Test or control article was administered intraperitoneally (i.p.) three times a week for 2 weeks. For ethical reason, humane euthanasia by $CO_2$ was conducted on animals that were in deteriorating condition, and/or with tumor size >3,000 $mm^3$; and/or with body weight loss over 30% of basal value. During the study, the body weights of mice were slightly increased, <30%. Tumor sizes of 6 mice in the negative PBS control group and 1 mouse in the 53C1_VH5.M3-VL1.M1 treatment group reached 3,000 $mm^3$; thus were euthanized before the study ended. So the tumor sizes were not included at day 18, which is probably the reason why the tumor growth inhibition of even the Durvalumab treatment group was not significant. Even so, two humanized antibodies. namely 53C1_VH1.M3-VL1.M1 and 53C1_VH5.M3-VL1.M1, showed better tumor growth inhibition activity than the benchmark Durvalumab.

TABLE 18

Heavy chain variable region (VH) sequences of mouse anti-PD-L1 antibodies.

| Ab | mAh | SEQ ID NO: | Sequence |
|---|---|---|---|
| Mouse | 18B7F4G8 | 1 | DVQLQESGPDLVKPSQSLSLTCTVTGYSITSGYTWHWIRQFPGNKLEWMGYIHYSGSTKYNPSLKSRFSITRDTSKNQFFLQLNSMTAEDTATYYCARNSLFASWGHGTLVTVSA |
| | 29A8H8C7 | 2 | DVQLQGSGPGLVKPSQSLSLTCTVTGYSITSDFAWDWIRQFPGNKLEWMGHIRFSGTTSYNPSLKSRISITRDTSKNQFFLQLNSVTSEDTATYYCARSTLITKGFFDYWGQGTTLTVSS |
| | 51F3D2G4 | 3 | QVQLQQSGAELARPGASVRLSCKASGYIFTGYGISWVKQRTGQGLEWIGEIFPRTANTYFNEKFKGKATLTADKSSSTAYMELRSLTSEDSAVYFCARDYDPYYALDYWGQGTSVTVSS |
| | 42G2D7D3 | 4 | DVQLLESGPGLVKPSQSLSLTCSVTGYSITSGYYWNWIRQFPGNNLEWMGSINYDGSNDYNPSLQDRISITRDTSKNQFFLKLNSVTTEDTATYYCARRLDYWGQGTTLIVSS |
| | 53C1F3D4 | 5 | QVQLQQSGNELARPGASVRLSCKASGYIFTGYGITWVRQRPGQGLEWIGEIFPRRVNTYYSEKFKGRATLTADISSSTAYMELRSLTSEDSAVYFCARDYDPYFALDYWGQGTSVTVSS |
| | 21D1F4D4 | 6 | QVQLQQPGAEVVRPGASVKLSCKASGYTFTNYWISWVKQRPGQGLEWIGNIYPSDSYTNYNQNFKDKATLTVDKSSSTAYMQLSSPTSEDSAVYYCTTGIITVIATRDDYWGQGTTLTVSS |
| | 30A6B2D9 | 7 | EGQLQQSGAGLVKPGASVNLSCTASGFNIKDTYIHWMKQRPEQGLEWIGRIAPTNGNTKYDPTFQGKATITADSSSNTAYLQVSSLTSEDTAVYYCSRGGIYYYGSHWYFDVWGAGTTVTVSS |
| | 25G1F9F8 | 8 | EGQLQQSGAELVKPGASVNLSCTASGFNIKDTYIHWVKQRPDQGLEWIGRIAPTNGNAKFHPTFQGKATITADTSSNTAYLQLSSLTSEDTAVYYCTRGGIYYYGTHWYFDVWGAGTTVTVSS |
| | 27D3D3G2 | 9 | QVLLQQSGPELVKPGASVRISCKASGYTFTSYYMHWVKQRPGQGLEWIGWIYPGNVNTKYNEKFKGKATLTADKSSSTAYMQLSSLTSEDSAVYFCASYGNYGGWYFDVWGAGTTVTVSS |
| | 30A7B5D9 | 10 | KVQLQQSGAELVKPGTSVKLSCKASGYTFTEYIIYWIKQRSGQGLEWIGWFYPGTGSIKYNEKFKDKATLTADKSSSTVFMELSRLTSEDSAVYFCAREEGNLWFAYWGQGTLVTVSA |

TABLE 18-continued

Heavy chain variable region (VH) sequences of mouse anti-PD-L1 antibodies.

| Ab | mAh | SEQ ID NO: | Sequence |
|---|---|---|---|
| | 1H1G4D9 | 11 | EGQLQQSGAELVKPGASVILSCTASGFNIKDTYIHWLNQRPEQGLEWIGRIEPANGNTKYDPTFQGKATITADTSSNTAYLQLTSLTSEDTAVYYCSRGGIYYYGSHWYFDVWGAGTLVTVSS |
| | 25B6E5D8 | 12 | QFQLQQSGAELVRPGSSVKISCKASGYEFSSNWMNWVKQRPGQSLEWIGQIWPGDGDTNYNGKFRGKATLTSDKSSSTAYMQLNSLTSEDSAVYFCARGRASFYFDYWGQGTALTVSS |
| Mouse w/CDR2 mutation | 53C1VH.M1 | 13 | QVQLQQSGNELARPGASVRLSCKASGYIFTGYGITWVRQRPGQGLEWIGEIFPRRVSTYYSEKFKGRATLTADISSSTAYMELRSLTSEDSAVYFCARDYDPYFALDYWGQGTSVTVSS |
| | 53C1VH.M2 | 14 | QVQLQQSGNELARPGASVRLSCKASGYIFTGYGITWVRQRPGQGLEWIGEIFPRRVATYYSEKFKGRATLTADISSSTAYMELRSLTSEDSAVYFCARDYDPYFALDYWGQGTSVTVSS |
| | 53C1VH.M3 | 15 | QVQLQQSGNELARPGASVRLSCKASGYIFTGYGITWVRQRPGQGLEWIGEIFPRRVQTYYSEKFKGRATLTADISSSTAYMELRSLTSEDSAVYFCARDYDPYFALDYWGQGTSVTVSS |
| Humanized | 29A8VH1 | 16 | EVQLQESGPGLVKPSETLSLTCTVSGYSITSDFAWDWIRQPPGKGLEWIGHIRFSGTTSYNPSLKSRVTISVDTSKNQFSLKLSSVTAADTAVYYCARSTLITKGFFDYWGQGTLVTVSS |
| | 29A8VH2 | 17 | EVQLQESGPGLVKPSETLSLTCTVSGYSITSDFAWDWIRQFPGKGLEWMGHIRFSGTTSYNPSLKSRITISVDTSKNQFSLKLSSVTAADTAVYYCARSTLITKGFFDYWGQGTLVTVSS |
| | 29A8VH3 | 18 | EVQLQESGPGLVKPSETLSLTCTVSGYSITSDFAWDWIRQFPGKGLEWMGHIRFSGTTSYNPSLKSRITISVDTSKNQFFLKLSSVTAADTATYYCARSTLITKGFFDYWGQGTLLTVSS |
| | 29A8VH4 | 19 | EVQLQESGPGLVKPSETLSLTCTVSGYSITSDFAWDWIRQPPGKGLEWIGHIRFSGTTSYNPSLKSRVTISVDTSKNQFSLKLSSVTAADTAVYYCARSTLITKGFFDYWGQGTLLTVSS |
| | 29A8VH5 | 20 | EVQLQESGPGLVKPSETLSLTCTVSGYSITSDFAWDWIRQPPGKGLEWIGHIRFSGTTSYNPSLKSRVTISRDTSKNQFSLKLSSVTAADTAVYYCARSTLITKGFFDYWGQGTLVTVSS |

TABLE 18-continued

Heavy chain variable region (VH) sequences of mouse anti-PD-L1 antibodies.

| Ab | mAh | SEQ ID NO: | Sequence |
|---|---|---|---|
| | 53C1VH1 | 21 | EVQLVQSGAEVKKPGASVKV SCKASGYIFTGYGITWVRQA PGQGLEWMGEIFPRRVNTYY SEKFKGRVTMTTDTSTSTAY MELRSLRSDDTAVYYCARDY DPYFALDYWGQGTTVTVSS |
| | 53C1VH2 | 22 | EVQLVQSGAEVKKPGASVKV SCKASGYIFTGYGITWVRQA PGQGLEWIGEIFPRRVNTYY SEKFKGRATLTTDTSTSTAY MELRSLRSDDTAVYFCARDY DPYFALDYWGQGTTVTVSS |
| | 53C1VH3 | 23 | EVQLVQSGAEVKKPGASVKL SCKASGYIFTGYGITWVRQA PGQGLEWIGEIFPRRVNTYY SEKFKGRATLTADTSTSTAY MELRSLRSDDTAVYFCARDY DPYFALDYWGQGTTVTVSS |
| | 53C1VH4 | 24 | EVQLVQSGAEVKKPGASVKL SCKASGYIFTGYGITWVRQA PGQGLEWMGEIFPRRVNTYY SEKFKGRVTMTTDTSTSTAY MELRSLRSDDTAVYYCARDY DPYFALDYWGQGTTVTVSS |
| | 53C1VH5 | 25 | EVQLVQSGAEVKKPGASVKV SCKASGYIFTGYGITWVRQA PGQGLEWMGEIFPRRVNTYY SEKFKGRVTMTADTSTSTAY MELRSLRSDDTAVYYCARDY DPYFALDYWGQGTTVTVSS |
| | 53C1VH6 | 26 | EVQLVQSGAEVKKPGASVKL SCKASGYIFTGYGITWVRQA PGQGLEWMGEIFPRRVNTYY SEKFKGRVTMTADTSTSTAY MELRSLRSDDTAVYYCARDY DPYFALDYWGQGTTVTVSS |
| Human-ized w/CDR2 mutation | 53C1VH1.M3 | 27 | EVQLVQSGAEVKKPGASVKV SCKASGYIFTGYGITWVRQA PGQGLEWMGEIFPRRVQTYY SEKFKGRVTMTTDTSTSTAY MELRSLRSDDTAVYYCARDY DPYFALDYWGQGTTVTVSS |
| | 53C1VH2.M3 | 28 | EVQLVQSGAEVKKPGASVKV SCKASGYIFTGYGITWVRQA PGQGLEWIGEIFPRRVQTYY SEKFKGRATLTTDTSTSTAY MELRSLRSDDTAVYFCARDY DPYFALDYWGQGTTVTVSS |
| | 53C1VH3.M3 | 29 | EVQLVQSGAEVKKPGASVKL SCKASGYIFTGYGITWVRQA PGQGLEWIGEIFPRRVQTYY SEKFKGRATLTADTSTSTAY MELRSLRSDDTAVYFCARDY DPYFALDYWGQGTTVTVSS |
| | 53C1VH4.M3 | 30 | EVQLVQSGAEVKKPGASVKL SCKASGYIFTGYGITWVRQA PGQGLEWMGEIFPRRVQTYY SEKFKGRVTMTTDTSTSTAY MELRSLRSDDTAVYYCARDY DPYFALDYWGQGTTVTVSS |
| | 53C1VH5.M3 | 31 | EVQLVQSGAEVKKPGASVKV SCKASGYIFTGYGITWVRQA PGQGLEWMGEIFPRRVQTYY SEKFKGRVTMTADTSTSTAY MELRSLRSDDTAVYYCARDY DPYFALDYWGQGTTVTVSS |
| | 53C1VH6.M3 | 32 | EVQLVQSGAEVKKPGASVKL SCKASGYIFTGYGITWVRQA PGQGLEWMGEIFPRRVQTYY SEKFKGRVTMTADTSTSTAY MELRSLRSDDTAVYYCARDY DPYFALDYWGQGTTVTVSS |
| | 53C1VH1.M1 | 33 | EVQLVQSGAEVKKPGASVKV SCKASGYIFTGYGITWVRQA PGQGLEWMGEIFPRRVSTYY SEKFKGRVTMTTDTSTSTAY MELRSLRSDDTAVYYCARDY DPYFALDYWGQGTTVTVSS |
| | 53C1VH2.M1 | 34 | EVQLVQSGAEVKKPGASVKV SCKASGYIFTGYGITWVRQA PGQGLEWIGEIFPRRVSTYY SEKFKGRATLTTDTSTSTAY MELRSLRSDDTAVYFCARDY DPYFALDYWGQGTTVTVSS |
| | 53C1VH3.M1 | 35 | EVQLVQSGAEVKKPGASVKL SCKASGYIFTGYGITWVRQA PGQGLEWIGEIFPRRVSTYY SEKFKGRATLTADTSTSTAY MELRSLRSDDTAVYFCARDY DPYFALDYWGQGTTVTVSS |
| | 53C1VH4.M1 | 36 | EVQLVQSGAEVKKPGASVKL SCKASGYIFTGYGITWVRQA PGQGLEWMGEIFPRRVSTYY SEKFKGRVTMTTDTSTSTAY MELRSLRSDDTAVYYCARDY DPYFALDYWGQGTTVTVSS |
| | 53C1VH5.M1 | 37 | EVQLVQSGAEVKKPGASVKV SCKASGYIFTGYGITWVRQA PGQGLEWMGEIFPRRVSTYY SEKFKGRVTMTADTSTSTAY MELRSLRSDDTAVYYCARDY DPYFALDYWGQGTTVTVSS |
| | 53C1VH6.M1 | 38 | EVQLVQSGAEVKKPGASVKL SCKASGYIFTGYGITWVRQA PGQGLEWMGEIFPRRVSTYY SEKFKGRVTMTADTSTSTAY MELRSLRSDDTAVYYCARDY DPYFALDYWGQGTTVTVSS |
| | 53C1VH1.M2 | 39 | EVQLVQSGAEVKKPGASVKV SCKASGYIFTGYGITWVRQA PGQGLEWMGEIFPRRVATYY SEKFKGRVTMTTDTSTSTAY MELRSLRSDDTAVYYCARDY DPYFALDYWGQGTTVTVSS |
| | 53C1VH2.M2 | 40 | EVQLVQSGAEVKKPGASVKV SCKASGYIFTGYGITWVRQA PGQGLEWIGEIFPRRVATYY SEKFKGRATLTTDTSTSTAY MELRSLRSDDTAVYFCARDY DPYFALDYWGQGTTVTVSS |
| | 53C1VH3.M2 | 41 | EVQLVQSGAEVKKPGASVKL SCKASGYIFTGYGITWVRQAP GQGLEWIGEIFPRRVATYYS EKFKGRATLTADTSTSTAYM |

TABLE 18-continued

Heavy chain variable region (VH) sequences of mouse anti-PD-L1 antibodies.

| Ab | mAh | SEQ ID NO: | Sequence |
|---|---|---|---|
| | | | ELRSLRSDDTAVYFCARDYD PYFALDYWGQGTTVTVSS |
| | 53C1VH4.M2 | 42 | EVQLVQSGAEVKKPGASVKL SCKASGYIFTGYGITWVRQA PGQGLEWMGEIFPRRVATYY SEKFKGRVTMTTDTSTSTAY MELRSLRSDDTAVYYCARDY DPYFALDYWGQGTTVTVSS |
| | 53C1VH5.M2 | 43 | EVQLVQSGAEVKKPGASVK VSCKASGYIFTGYGITWV RQAPGQGLEWMGEIFPRRVA TYYSEKFKGRVTMTADTSTS TAYMELRSLRSDDTAVYYCA RDYDPYFALDYWGQGTTVTV SS |
| | 53C1VH6.M2 | 44 | EVQLVQSGAEVKKPGASVKL SCKASGYIFTGYGITWVRQA PGQGLEWMGEIFPRRVATYY SEKFKGRVTMTADTSTSTAY MELRSLRSDDTAVYYCARDY DPYFALDYWGQGTTVTVSS |

TABLE 19

Light chain variable region (VL) sequences of mouse anti-PD-L1 antibodies.

| Ab | mAb | SEQ ID NO: | Sequence |
|---|---|---|---|
| Mouse | 18B7F4G8 | 45 | DIVLTQSPASLAVSLGQRAT ISCRASESVDTYGDSFMHWF QQKPGQPPKLLIYRASNLES GIPARFSGSGSRTDFTLTIN PVEADDVATYYCQQSNEAPY TFGGGTKLEIK |
| | 29A8H8C7 | 46 | DIVMTQSHKFMSTSVGGRVS ITCKASQDVSPAVAWYQQKP GQSPKLLIYWASTRHTGVPD RFTGSGSGTDFTLTISSVQT EDLALYYCQQHYSTPWTFGG GTKLEIK |
| | 51F3D2G4 | 47 | DIVMTQSHKFMSTSVGDRVT ITCKASQDVSTAVDWYQQKP GQSPKLLIYSASYRYTGVPD RFTGSGSGTAFTFTISSEQA EDLAVYYCQQHYSVPFTFGG GTKLEIK |
| | 42G2D7D3 | 48 | QIVLTQSPAIMSASPGEKVT ISCSASSFINYMYWYQQKPG SSPKPWILRTSTLASGVPAR FSGSGSGTSYSLTISSMEAE DAATYYCQQYHSYPLTFGAG TKLELK |
| | 53C1F3D4 | 49 | DIVMTQSHKFMSTSVGDRVS ITCKASQDVSTAVDWYQQKP GQSPKLLIYSASYRYTGVPD RFTGSGSGTAFTFTISGEQA EDLAVYYCQQHYSIPFTFGG GTKLEIK |

TABLE 19-continued

Light chain variable region (VL) sequences of mouse anti-PD-L1 antibodies.

| Ab | mAb | SEQ ID NO: | Sequence |
|---|---|---|---|
| | 21D1F4D4 | 50 | QIVLTQSPAIMSASPGEKVT LTCSASSSVSSSYLYWYQQK PGSSPKLWIYSTSNLASGVP ARFSGSGSGTSYSLTVSSME AEDAASYFCHQWSSYPFTFG SGTKLEIK |
| | 30A6B2D9 | 51 | SVLMTQTPLSLPVSLGDQAS ISCRSSQNIVYSDGDTYLEW YLQKPGQSPKLLIFKVSNRF FGVPDRFSGSGSGTDFTLKI NRVEAEDLGVYYCFQGSHVP FTFGSGTKLEIK |
| | 25G1F9F8 | 52 | DVLMNQTPLSLPVSLGDQAS ISCRSSQNIVYSDGNTYLEW YLQKPGQSPKLLIFQVSNRF SGVPDRFSGSGSGTDFTLKI SRVEAEDLGFYYCFQGSHVP FTFGSGTKLEIK |
| | 27D3D3G2 | 53 | DIQMTQTTSSLSASLGDRVT ISCRASQDIGNYLNWYQQKP DGTVKLLIYYTSRLHSGVPS RFSGSGSGTDYSLTISNLEQ EDIATYFCQQGDTFPWTFGG GTKLEIK |
| | 30A7B5D9 | 54 | QIVLTQSPALMSASPGERVT MTCSASSDVSYMYWYQQKPR SSPKPWIYLTSNLASGVPAR FSGSGSGTSYSLTISSMEAE DAATYYCQQWTGNPLTFGAG TKLELK |
| | 1H1G4D9 | 55 | DVLMTQTPLSLPVSLGDQAS ISCRSSQNIVYSDGDTYLEW YLQKPGQSPKLLIFKVSNRF SGVPDRFSGSGSGTDFTLKI SRVEAEDLGVYYCFQGSHVP FTFGSGTKLEIK |
| | 25B6E5D8 | 56 | DIVLTQSPASLAVSLGQRAT ISCRASESVDDYGNSFMHWY QQKPGQPPKLLIYRASNLES GIPVRFSGSGSRTDFTLTIN PVEADDVATYYCQQSNEDPH TFGGGTKLEIK |
| Mouse w/CDR1 mutation | 29A8VL.M1 | 57 | DIVMTQSHKFMSTSVGGRVS ITCRASQDVSPAVAWYQQKP GQSPKLLIYWASTRHTGVPD RFTGSGSGTDFTLTISSVQT EDLALYYCQQHYSTPWTFGG GTKLEIK |
| | 53C1VL.M1 | 58 | DIVMTQSHKFMSTSVGDRVS ITCRASQDVSTAVDWYQQKP GQSPKLLIYSASYRYTGVPD RFTGSGSGTAFTFTISGEQA EDLAVYYCQQHYSIPFTFGG GTKLEIK |
| Humanized | 29A8VL1 | 59 | DIQMTQSPSSLSASVGDRVT ITCKASQDVSPAVAWYQQKP GKAPKLLIYWASTRHTGVPS RFSGSGSGTDFTLTISSLQP EDFATYYCQQHYSTPWTFGQ GTKVEIK |

TABLE 19-continued

Light chain variable region (VL) sequences of mouse anti-PD-L1 antibodies.

| Ab | mAb | SEQ ID NO: | Sequence |
|---|---|---|---|
| | 29A8VL2 | 60 | DIQMTQSPSSLSASVGDRVTITCKASQDVSPAVAWYQQKPGKAPKLLIYWASTRHTGVPSRFSGSGSGTDFTLTISSLQPEDLALYYCQQHYSTPWTFGQGTKVEIK |
| | 29A8VL3 | 61 | DIQMTQSPSSLSTSVGDRVTITCKASQDVSPAVAWYQQKPGKAPKLLIYWASTRHTGVPSRFSGSGSGTDFTLTISSVQPEDLALYYCQQHYSTPWTFGQGTKLEIK |
| | 53C1VL1 | 62 | DIQMTQSPSSLSASVGDRVTITCKASQDVSTAVDWYQQKPGKAPKLLIYSASYRYTGVPDRFSGSGSGTDFTFTISSLQPEDIATYYCQQHYSIPFTFGQGTKLEIK |
| | 53C1VL2 | 63 | DIQMTQSPSSMSASVGDRVTITCKASQDVSTAVDWYQQKPGKAPKLLIYSASYRYTGVPDRFSGSGSGTDFTFTISSLQPEDLATYYCQQHYSIPFTFGQGTKLEIK |
| | 53C1VL3 | 64 | DIQMTQSPSSMSTSVGDRVTITCKASQDVSTAVDWYQQKPGKAPKLLIYSASYRYTGVPDRFSGSGSGTDFTFTISSEQPEDLATYYCQQHYSIPFTFGQGTKLEIK |
| Humanized w/CDR1 mutation | 29A8VL1.M1 | 65 | DIQMTQSPSSLSASVGDRVTITCKASQDVSPAVAWYQQKPGKAPKLLIYWASTRHTGVPSRFSGSGSGTDFTLTISSLQPEDFATYYCQQHYSTPWTFGQGTKVEIK |
| | 29A8VL2.M1 | 66 | DIQMTQSPSSLSASVGDRVTITCKASQDVSPAVAWYQQKPGKAPKLLIYWASTRHTGVPSRFSGSGSGTDFTLTISSLQPEDLALYYCQQHYSTPWTFGQGTKVEIK |
| | 29A8VL3.M1 | 67 | DIQMTQSPSSLSTSVGDRVTITCKASQDVSPAVAWYQQKPGKAPKLLIYWASTRHTGVPSRFSGSGSGTDFTLTISSVQPEDLALYYCQQHYSTPWTFGQGTKLEIK |
| | 53C1VL1.M1 | 68 | DIQMTQSPSSLSASVGDRVTITCKASQDVSTAVDWYQQKPGKAPKLLIYSASYRYTGVPDRFSGSGSGTDFTFTISSLQPEDIATYYCQQHYSIPFTFGQGTKLEIK |
| | 53C1VL2.M1 | 69 | DIQMTQSPSSMSASVGDRVTITCKASQDVSTAVDWYQQKPGKAPKLLIYSASYRYTGVPDRFSGSGSGTDFTFTISSLQPEDLATYYCQQHYSIPFTFGQGTKLEIK |
| | 53C1VL3.M1 | 70 | DIQMTQSPSSMSTSVGDRVTITCKASQDVSTAVDWYQQKPGKAPKLLIYSASYRYTGVPDRFSGSGSGTDFTFTISSEQPEDLATYYCQQHYSIPFTFGQGTKLEIK |

TABLE 20

Heavy chain variable region (VH) CDR sequences.

| Ab | mAh | ID | CDR1 | ID | CDR2 | ID | CDR3 |
|---|---|---|---|---|---|---|---|
| Mouse | 18B7F4G8 | 71 | GYSITSGYTWH | 83 | YIHYSGSTKYNPSLKS | 98 | NSLFAS |
| | 29A8H8C7 | 72 | GYSITSDFAWD | 84 | HIRFSGTTSYNPSLKS | 99 | STLITKGFFDY |
| | 51F3D2G4 | 73 | GYIFTGYGIS | 85 | EIFPRTANTYFNEKFKG | 100 | DYDPYYALDY |
| | 42G2D7D3 | 74 | GYSITSGYYWN | 86 | SINYDGSNDYNPSLQD | 101 | RLDY |
| | 53C1F3D4 | 75 | GYIFTGYGIT | 87 | EIFPRRVNTYYSEKFKG | 102 | DYDPYFALDY |
| | 21D1F4D4 | 76 | GYTFTNYWIS | 88 | NIYPSDSYTNYNQNFKD | 103 | GIITVIATRDDY |
| | 30A6B2D9 | 77 | GFNIKDTYIH | 89 | RIAPTNGNTKYDPTFQG | 104 | GGIYYYGSHWYFDV |
| | 25G1F9F8 | 78 | GFNIKDTYIH | 90 | RIAPTNGNAKFHPTFQG | 105 | GGIYYYGTHWYFDV |
| | 27D3D3G2 | 79 | GYTFTSYYMH | 91 | WIYPGNVNTKYNEKFKG | 106 | YGNYGGWYFDV |

TABLE 20-continued

Heavy chain variable region (VH) CDR sequences.

| Ab | mAh | ID | CDR1 | ID | CDR2 | ID | CDR3 |
|---|---|---|---|---|---|---|---|
| | 30A7B5D9 | 80 | GYTFTEYIIY | 92 | WFYPGTGSIKYNEKFKD | 107 | HEEGNLWFAY |
| | 1H1G4D9 | 81 | GFNIKDTYIH | 93 | RIEPANGNTKYDPTFQG | 108 | GGIYYYGSHWYFDV |
| | 25B6E5D8 | 82 | GYEFSSNWMN | 94 | QIWPGDGDTNYNGKFRG | 109 | GRASFYFDY |
| Mouse w/CDR2 mutation | 53C1VH.M1 | 75 | GYIFTGYGIT | 95 | EIFPRRVSTYYSEKFKG | 102 | DYDPYFALDY |
| | 53C1VH.M2 | 75 | GYIFTGYGIT | 96 | EIFPRRVATYYSEKFKG | 102 | DYDPYFALDY |
| | 53C1VH.M3 | 75 | GYIFTGYGIT | 97 | EIFPRRVQTYYSEKFKG | 102 | DYDPYFALDY |
| Humanized | 29A8VH1 | 72 | GYSITSDFAWD | 84 | HIRFSGTTSYNPSLKS | 99 | STLITKGFFDY |
| | 29A8VH2 | 72 | GYSITSDFAWD | 84 | HIRFSGTTSYNPSLKS | 99 | STLITKGFFDY |
| | 29A8VH3 | 72 | GYSITSDFAWD | 84 | HIRFSGTTSYNPSLKS | 99 | STLITKGFFDY |
| | 29A8VH4 | 72 | GYSITSDFAWD | 84 | HIRFSGTTSYNPSLKS | 99 | STLITKGFFDY |
| | 29A8VH5 | 72 | GYSITSDFAWD | 84 | HIRFSGTTSYNPSLKS | 99 | STLITKGFFDY |
| | 53C1VH1 | 75 | GYIFTGYGIT | 87 | EIFPRRVNTYYSEKFKG | 102 | DYDPYFALDY |

TABLE 20-continued

Heavy chain variable region (VH) CDR sequences.

| Ab | mAh | ID | CDR1 | ID | CDR2 | ID | CDR3 |
|---|---|---|---|---|---|---|---|
| | 53C1VH2 | 75 | GYIFTGYGIT | 87 | EIFPRRVNTYYSEKFKG | 102 | DYDPYFALDY |
| | 53C1VH3 | 75 | GYIFTGYGIT | 87 | EIFPRRVNTYYSEKFKG | 102 | DYDPYFALDY |
| | 53C1VH4 | 75 | GYIFTGYGIT | 87 | EIFPRRVNTYYSEKFKG | 102 | DYDPYFALDY |
| | 53C1VH5 | 75 | GYIFTGYGIT | 87 | EIFPRRVNTYYSEKFKG | 102 | DYDPYFALDY |
| | 53C1VH6 | 75 | GYIFTGYGIT | 87 | EIFPRRVNTYYSEKFKG | 102 | DYDPYFALDY |
| Humanized | 53C1VH1.M3 | 75 | GYIFTGYGIT | 97 | EIFPRRVQTYYSEKFKG | 102 | DYDPYFALDY |
| w/CDR2 mutation | 53C1VH2.M3 | 75 | GYIFTGYGIT | 97 | EIFPRRVQTYYSEKFKG | 102 | DYDPYFALDY |
| | 53C1VH3.M3 | 75 | GYIFTGYGIT | 97 | EIFPRRVQTYYSEKFKG | 102 | DYDPYFALDY |
| | 53C1VH4.M3 | 75 | GYIFTGYGIT | 97 | EIFPRRVQTYYSEKFKG | 102 | DYDPYFALDY |
| | 53C1VH5.M3 | 75 | GYIFTGYGIT | 97 | EIFPRRVQTYYSEKFKG | 102 | DYDPYFALDY |
| | 53C1VH6.M3 | 75 | GYIFTGYGIT | 97 | EIFPRRVQTYYSEKFKG | 102 | DYDPYFALDY |
| | 53C1VH1.M1 | 75 | GYIFTGYGIT | 95 | EIFPRRVSTYYSEKFKG | 102 | DYDPYFALDY |

TABLE 20-continued

| Heavy chain variable region (VH) CDR sequences. | | | | | | | |
|---|---|---|---|---|---|---|---|
| Ab | mAh | ID | CDR1 | ID | CDR2 | ID | CDR3 |
| | 53C1VH2.M1 | 75 | GYIFTGYGIT | 95 | EIFPRRVSTYYSEKFKG | 102 | DYDPYFALDY |
| | 53C1VH3.M1 | 75 | GYIFTGYGIT | 95 | EIFPRRVSTYYSEKFKG | 102 | DYDPYFALDY |
| | 53C1VH4.M1 | 75 | GYIFTGYGIT | 95 | EIFPRRVSTYYSEKFKG | 102 | DYDPYFALDY |
| | 53C1VH5.M1 | 75 | GYIFTGYGIT | 95 | EIFPRRVSTYYSEKFKG | 102 | DYDPYFALDY |
| | 53C1VH6.M1 | 75 | GYIFTGYGIT | 95 | EIFPRRVSTYYSEKFKG | 102 | DYDPYFALDY |
| | 53C1VH1.M2 | 75 | GYIFTGYGIT | 96 | EIFPRRVATYYSEKFKG | 102 | DYDPYFALDY |
| | 53C1VH2.M2 | 75 | GYIFTGYGIT | 96 | EIFPRRVATYYSEKFKG | 102 | DYDPYFALDY |
| | 53C1VH3.M2 | 75 | GYIFTGYGIT | 96 | EIFPRRVATYYSEKFKG | 102 | DYDPYFALDY |
| | 53C1VH4.M2 | 75 | GYIFTGYGIT | 96 | EIFPRRVATYYSEKFKG | 102 | DYDPYFALDY |
| | 53C1VH5.M2 | 75 | GYIFTGYGIT | 96 | EIFPRRVATYYSEKFKG | 102 | DYDPYFALDY |
| | 53C1VH6.M2 | 75 | GYIFTGYGIT | 96 | EIFPRRVATYYSEKFKG | 102 | DYDPYFALDY |

TABLE 21

| Light chain variable region (VL) CDR sequences. | | | | | | | |
|---|---|---|---|---|---|---|---|
| Ab | mAb | ID | CDR1 | ID | CDR2 | ID | CDR3 |
| Mouse | 18B7F4G8VL | 110 | RASESVDTYGDSFMH | 124 | RASNLES | 136 | QQSNEAPYT |
| | 29A8H8C7VL | 111 | KASQDVSPAVA | 125 | WASTRHT | 137 | QQHYSTPWT |
| | 51F3D2G4VL | 112 | KASQDVSTAVD | 126 | SASYRYT | 138 | QQHYSVPFT |
| | 42G2D7D3VL | 113 | SASSFINYMY | 127 | RTSTLAS | 139 | QQYHSYPLT |
| | 53C1F3D4VL | 114 | KASQDVSTAVD | 128 | SASYRYT | 140 | QQHYSIPFT |
| | 21D1F4D4VL | 115 | SASSSVSSSYLY | 129 | STSNLAS | 141 | HQWSSYPFT |
| | 30A6B2D9VL | 116 | RSSQNIVYSDGDTYLE | 130 | KVSNRFF | 142 | FQGSHVPFT |
| | 25G1F9F8VL | 117 | RSSQNIVYSDGNTYLE | 131 | QVSNRFS | 143 | FQGSHVPFT |
| | 27D3D3G2VL | 118 | RASQDIGNYLN | 132 | YTSRLHS | 144 | QQGDTFPWT |
| | 30A7B5D9VL | 119 | SASSDVSYMY | 133 | LTSNLAS | 145 | QQWTGNPLT |
| | 1H1G4D9VL | 120 | RSSQNIVYSDGDTYLE | 134 | KVSNRFS | 146 | FQGSHVPFT |
| | 25B6E5D8VL | 121 | RASESVDDYGNSFMH | 135 | RASNLES | 147 | QQSNEDPHT |
| Mutant | 29A8VL.M1 | 122 | RASQDVSPAVA | 125 | WASTRHT | 137 | QQHYSTPWT |
| Chimeric | 53C1VL.M1 | 123 | RASQDVSTAVD | 128 | SASYRYT | 140 | QQHYSIPFT |
| Humanized | 29A8VL1 | 111 | KASQDVSPAVA | 125 | WASTRHT | 137 | QQHYSTPWT |
| | 29A8VL2 | 111 | KASQDVSPAVA | 125 | WASTRHT | 137 | QQHYSTPWT |
| | 29A8VL3 | 111 | KASQDVSPAVA | 125 | WASTRHT | 137 | QQHYSTPWT |
| | 53C1VL1 | 114 | KASQDVSTAVD | 128 | SASYRYT | 140 | QQHYSIPFT |
| | 53C1VL2 | 114 | KASQDVSTAVD | 128 | SASYRYT | 140 | QQHYSIPFT |
| | 53C1VL3 | 114 | KASQDVSTAVD | 128 | SASYRYT | 140 | QQHYSIPFT |
| Humanized w/CDR1 mutation | 29A8VL1.M1 | 122 | RASQDVSPAVA | 125 | WASTRHT | 137 | QQHYSTPWT |
| | 29A8VL2.M1 | 122 | RASQDVSPAVA | 125 | WASTRHT | 137 | QQHYSTPWT |
| | 29A8VL3.M1 | 122 | RASQDVSPAVA | 125 | WASTRHT | 137 | QQHYSTPWT |
| | 53C1VL1.M1 | 123 | RASQDVSTAVD | 128 | SASYRYT | 140 | QQHYSIPFT |
| | 53C1VL2.M1 | 123 | RASQDVSTAVD | 128 | SASYRYT | 140 | QQHYSIPFT |
| | 53C1VL3.M1 | 123 | RASQDVSTAVD | 128 | SASYRYT | 140 | QQHYSIPFT |

TABLE 22

Heavy chain variable region (VH) framework (FR) sequences.

| Ab | mAb | ID | FR1 | ID | FR2 |
|---|---|---|---|---|---|
| Mouse | 18B7F4G8 | 148 | DVQLQESGPDLVKPSQSLSLTCTVT | 163 | WIRQFPGNKLEWMG |
| | 29A8H8C7 | 149 | DVQLQGSGPGLVKPSQSLSLTCTVT | 164 | WIRQFPGNKLEWMG |
| | 51F3D2G4 | 150 | QVQLQQSGAELARPGASVRLSCKAS | 165 | WVKQRTGQGLEWIG |
| | 42G2D7D3 | 151 | DVQLLESGPGLVKPSQSLSLTCSVT | 166 | WIRQFPGNNLEWMG |
| | 53C1F3D4 | 152 | QVQLQQSGNELARPGASVRLSCKAS | 167 | WVRQRPGQGLEWIG |
| | 21D1F4D4 | 153 | QVQLQQPGAEVVRPGASVKLSCKAS | 168 | WVKQRPGQGLEWIG |
| | 30A6B2D9 | 154 | EGQLQQSGAGLVKPGASVNLSCTAS | 169 | WMKQRPEQGLEWIG |
| | 25G1F9F8 | 155 | EGQLQQSGAELVKPGASVNLSCTAS | 170 | WVKQRPDQGLEWIG |
| | 27D3D3G2 | 156 | QVLLQQSGPELVKPGASVRISCKAS | 171 | WVKQRPGQGLEWIG |
| | 30A7B5D9 | 157 | KVQLQQSGAELVKPGTSVKLSCKAS | 172 | WIKQRSGQGLEWIG |
| | 1H1G4D9 | 158 | EGQLQQSGAELVKPGASVILSCTAS | 173 | WLNQRPEQGLEWIG |
| | 25B6E5D8 | 159 | QFQLQQSGAELVRPGSSVKISCKAS | 174 | WVKQRPGQSLEWIG |
| Mouse w/CDR2 mutation | 53C1VH.M1 | 152 | QVQLQQSGNELARPGASVRLSCKAS | 167 | WVRQRPGQGLEWIG |
| | 53C1VH.M2 | 152 | QVQLQQSGNELARPGASVRLSCKAS | 167 | WVRQRPGQGLEWIG |
| | 53C1VH.M3 | 152 | QVQLQQSGNELARPGASVRLSCKAS | 167 | WVRQRPGQGLEWIG |
| Humanized | 29A8VH1 | 160 | EVQLQESGPGLVKPSETLSLTCTVS | 175 | WIRQPPGKGLEWIG |
| | 29A8VH2 | 160 | EVQLQESGPGLVKPSETLSLTCTVS | 176 | WIRQFPGKGLEWMG |
| | 29A8VH3 | 160 | EVQLQESGPGLVKPSETLSLTCTVS | 176 | WIRQFPGKGLEWMG |
| | 29A8VH4 | 160 | EVQLQESGPGLVKPSETLSLTCTVS | 175 | WIRQPPGKGLEWIG |
| | 29A8VH5 | 160 | EVQLQESGPGLVKPSETLSLTCTVS | 175 | WIRQPPGKGLEWIG |
| | 53C1VH1 | 161 | EVQLVQSGAEVKKPGASVKVSCKAS | 177 | WVRQAPGQGLEWMG |
| | 53C1VH2 | 161 | EVQLVQSGAEVKKPGASVKVSCKAS | 178 | WVRQAPGQGLEWIG |
| | 53C1VH3 | 162 | EVQLVQSGAEVKKPGASVKLSCKAS | 178 | WVRQAPGQGLEWIG |
| | 53C1VH4 | 162 | EVQLVQSGAEVKKPGASVKLSCKAS | 177 | WVRQAPGQGLEWMG |
| | 53C1VH5 | 161 | EVQLVQSGAEVKKPGASVKVSCKAS | 177 | WVRQAPGQGLEWMG |
| | 53C1VH6 | 162 | EVQLVQSGAEVKKPGASVKLSCKAS | 177 | WVRQAPGQGLEWMG |
| Humanized w/CDR2 mutation | 53C1VH1.M3 | 161 | EVQLVQSGAEVKKPGASVKVSCKAS | 177 | WVRQAPGQGLEWMG |
| | 53C1VH2.M3 | 161 | EVQLVQSGAEVKKPGASVKVSCKAS | 178 | WVRQAPGQGLEWIG |
| | 53C1VH3.M3 | 162 | EVQLVQSGAEVKKPGASVKLSCKAS | 178 | WVRQAPGQGLEWIG |
| | 53C1VH4.M3 | 162 | EVQLVQSGAEVKKPGASVKLSCKAS | 177 | WVRQAPGQGLEWMG |
| | 53C1VH5.M3 | 161 | EVQLVQSGAEVKKPGASVKVSCKAS | 177 | WVRQAPGQGLEWMG |
| | 53C1VH6.M3 | 162 | EVQLVQSGAEVKKPGASVKLSCKAS | 177 | WVRQAPGQGLEWMG |
| | 53C1VH1.M1 | 161 | EVQLVQSGAEVKKPGASVKVSCKAS | 177 | WVRQAPGQGLEWMG |
| | 53C1VH2.M1 | 161 | EVQLVQSGAEVKKPGASVKVSCKAS | 178 | WVRQAPGQGLEWIG |
| | 53C1VH3.M1 | 162 | EVQLVQSGAEVKKPGASVKLSCKAS | 178 | WVRQAPGQGLEWIG |
| | 53C1VH4.M1 | 162 | EVQLVQSGAEVKKPGASVKLSCKAS | 177 | WVRQAPGQGLEWMG |
| | 53C1VH5.M1 | 161 | EVQLVQSGAEVKKPGASVKVSCKAS | 177 | WVRQAPGQGLEWMG |
| | 53C1VH6.M1 | 162 | EVQLVQSGAEVKKPGASVKLSCKAS | 177 | WVRQAPGQGLEWMG |
| | 53C1VH1.M2 | 161 | EVQLVQSGAEVKKPGASVKVSCKAS | 177 | WVRQAPGQGLEWMG |
| | 53C1VH2.M2 | 161 | EVQLVQSGAEVKKPGASVKVSCKAS | 178 | WVRQAPGQGLEWIG |
| | 53C1VH3.M2 | 162 | EVQLVQSGAEVKKPGASVKLSCKAS | 178 | WVRQAPGQGLEWIG |
| | 53C1VH4.M2 | 162 | EVQLVQSGAEVKKPGASVKLSCKAS | 177 | WVRQAPGQGLEWMG |
| | 53C1VH5.M2 | 161 | EVQLVQSGAEVKKPGASVKVSCKAS | 177 | WVRQAPGQGLEWMG |
| | 53C1VH6.M2 | 162 | EVQLVQSGAEVKKPGASVKLSCKAS | 177 | WVRQAPGQGLEWMG |

| Ab | mAb | ID | FR3 | ID | FR4 |
|---|---|---|---|---|---|
| Mouse | 18B7F4G8 | 179 | RFSITRDTSKNQFFLQLNSMTAEDTATYYCAR | 199 | WGHGTLVTVSA |
| | 29A8H8C7 | 180 | RISITRDTSKNQFFLQLNSVTSEDTATYYCAR | 200 | WGQGTTLTVSS |
| | 51F3D2G4 | 181 | KATLTADKSSSTAYMELRSLTSEDSAVYFCAR | 201 | WGQGTSVTVSS |
| | 42G2D7D3 | 182 | RISITRDTSKNQFFLKLNSVTTEDTATYYCAR | 202 | WGQGTTLIVSS |
| | 53C1F3D4 | 183 | RATLTADISSSTAYMELRSLTSEDSAVYFCAR | 203 | WGQGTSVTVSS |
| | 21D1F4D4 | 184 | KATLTVDKSSSTAYMQLSSPTSEDSAVYYCTT | 204 | WGQGTTLTVSS |
| | 30A6B2D9 | 185 | KATITADSSSNTAYLQVSSLTSEDTAVYYCSR | 205 | WGAGTTVTVSS |
| | 25G1F9F8 | 186 | KATITADTSSNTAYLQLSSLTSEDTAVYYCTR | 206 | WGAGTTVTVSS |
| | 27D3D3G2 | 187 | KATLTADKSSSTAYMQLSSLTSEDSAVYFCAS | 207 | WGAGTTVTVSS |
| | 30A7B5D9 | 188 | KATLTADKSSSTVFMELSRLTSEDSAVYFCAR | 208 | WGQGTLVTVSA |
| | 1H1G4D9 | 189 | KATITADTSSNTAYLQLTSLTSEDTAVYYCSR | 209 | WGAGTLVTVSS |
| | 25B6E5D8 | 190 | KATLTSDKSSSTAYMQLNSLTSEDSAVYFCAR | 210 | WGQGTALTVSS |
| Mouse w/CDR2 mutation | 53C1VH.M1 | 183 | RATLTADISSSTAYMELRSLTSEDSAVYFCAR | 203 | WGQGTSVTVSS |
| | 53C1VH.M2 | 183 | RATLTADISSSTAYMELRSLTSEDSAVYFCAR | 203 | WGQGTSVTVSS |
| | 53C1VH.M3 | 183 | RATLTADISSSTAYMELRSLTSEDSAVYFCAR | 203 | WGQGTSVTVSS |
| Humanized | 29A8VH1 | 191 | RVTISVDTSKNQFSLKLSSVTAADTAVYYCAR | 211 | WGQGTLVTVSS |
| | 29A8VH2 | 192 | RITISVDTSKNQFSLKLSSVTAADTAVYYCAR | 211 | WGQGTLVTVSS |
| | 29A8VH3 | 193 | RITISVDTSKNQFFLKLSSVTAADTATYYCAR | 212 | WGQGTLLTVSS |
| | 29A8VH4 | 191 | RVTISVDTSKNQFSLKLSSVTAADTAVYYCAR | 212 | WGQGTLLTVSS |
| | 29A8VH5 | 194 | RVTISRDTSKNQFSLKLSSVTAADTAVYYCAR | 212 | WGQGTLVTVSS |
| | 53C1VH1 | 195 | RVTMTTDTSTSTAYMELRSLRSDDTAVYYCAR | 213 | WGQGTTVTVSS |
| | 53C1VH2 | 196 | RATLTTDTSTSTAYMELRSLRSDDTAVYFCAR | 213 | WGQGTTVTVSS |
| | 53C1VH3 | 197 | RATLTADTSTSTAYMELRSLRSDDTAVYFCAR | 213 | WGQGTTVTVSS |
| | 53C1VH4 | 195 | RVTMTTDTSTSTAYMELRSLRSDDTAVYYCAR | 213 | WGQGTTVTVSS |

TABLE 22-continued

Heavy chain variable region (VH) framework (FR) sequences.

| | | | | | |
|---|---|---|---|---|---|
| | 53C1VH5 | 198 | RVTMTADTSTSTAYMELRSLRSDDTAVYYCAR | 213 | WGQGTTVTVSS |
| | 53C1VH6 | 198 | RVTMTADTSTSTAYMELRSLRSDDTAVYYCAR | 213 | WGQGTTVTVSS |
| Humanized w/CDR2 mutation | 53C1VH1.M3 | 195 | RVTMTTDTSTSTAYMELRSLRSDDTAVYYCAR | 213 | WGQGTTVTVSS |
| | 53C1VH2.M3 | 196 | RATLTTDTSTSTAYMELRSLRSDDTAVYFCAR | 213 | WGQGTTVTVSS |
| | 53C1VH3.M3 | 197 | RATLTADTSTSTAYMELRSLRSDDTAVYFCAR | 213 | WGQGTTVTVSS |
| | 53C1VH4.M3 | 195 | RVTMTTDTSTSTAYMELRSLRSDDTAVYYCAR | 213 | WGQGTTVTVSS |
| | 53C1VH5.M3 | 198 | RVTMTADTSTSTAYMELRSLRSDDTAVYYCAR | 213 | WGQGTTVTVSS |
| | 53C1VH6.M3 | 198 | RVTMTADTSTSTAYMELRSLRSDDTAVYYCAR | 213 | WGQGTTVTVSS |
| | 53C1VH1.M1 | 195 | RVTMTTDTSTSTAYMELRSLRSDDTAVYYCAR | 213 | WGQGTTVTVSS |
| | 53C1VH2.M1 | 196 | RATLTTDTSTSTAYMELRSLRSDDTAVYFCAR | 213 | WGQGTTVTVSS |
| | 53C1VH3.M1 | 197 | RATLTADTSTSTAYMELRSLRSDDTAVYFCAR | 213 | WGQGTTVTVSS |
| | 53C1VH4.M1 | 195 | RVTMTTDTSTSTAYMELRSLRSDDTAVYYCAR | 213 | WGQGTTVTVSS |
| | 53C1VH5.M1 | 198 | RVTMTADTSTSTAYMELRSLRSDDTAVYYCAR | 213 | WGQGTTVTVSS |
| | 53C1VH6.M1 | 198 | RVTMTADTSTSTAYMELRSLRSDDTAVYYCAR | 213 | WGQGTTVTVSS |
| | 53C1VH1.M2 | 195 | RVTMTTDTSTSTAYMELRSLRSDDTAVYYCAR | 213 | WGQGTTVTVSS |
| | 53C1VH2.M2 | 196 | RATLTTDTSTSTAYMELRSLRSDDTAVYFCAR | 213 | WGQGTTVTVSS |
| | 53C1VH3.M2 | 197 | RATLTADTSTSTAYMELRSLRSDDTAVYFCAR | 213 | WGQGTTVTVSS |
| | 53C1VH4.M2 | 195 | RVTMTTDTSTSTAYMELRSLRSDDTAVYYCAR | 213 | WGQGTTVTVSS |
| | 53C1VH5.M2 | 198 | RVTMTADTSTSTAYMELRSLRSDDTAVYYCAR | 213 | WGQGTTVTVSS |
| | 53C1VH6.M2 | 198 | RVTMTADTSTSTAYMELRSLRSDDTAVYYCAR | 213 | WGQGTTVTVSS |

TABLE 23

Light chain variable region (VL) framework (FR) sequences.

| Ab | mAb | ID | FR1 | ID | FR2 |
|---|---|---|---|---|---|
| Mouse | 18B7F4G8VL | 214 | DIVLTQSPASLAVSLGQRATISC | 231 | WFQQKPGQPPKLLIY |
| | 29A8H8C7VL | 215 | DIVMTQSHKFMSTSVGGRVSITC | 232 | WYQQKPGQSPKLLIY |
| | 51F3D2G4VL | 216 | DIVMTQSHKFMSTSVGDRVTITC | 233 | WYQQKPGQSPKLLIY |
| | 42G2D7D3VL | 217 | QIVLTQSPAIMSASPGEKVTISC | 234 | WYQQKPGSSPKPWIL |
| | 53C1F3D4VL | 218 | DIVMTQSHKFMSTSVGDRVSITC | 235 | WYQQKPGQSPKLLIY |
| | 21D1F4D4VL | 219 | QIVLTQSPAIMSASPGEKVTLTC | 236 | WYQQKPGSSPKLWIY |
| | 30A6B2D9VL | 220 | SVLMTQTPLSLPVSLGDQASISC | 237 | WYLQKPGQSPKLLIF |
| | 25G1F9F8VL | 221 | DVLMNQTPLSLPVSLGDQASISC | 238 | WYLQKPGQSPKLLIF |
| | 27D3D3G2VL | 222 | DIQMTQTTSSLSASLGDRVTISC | 239 | WYQQKPDGTVKLLIY |
| | 30A7B5D9VL | 223 | QIVLTQSPALMSASPGERVTMTC | 240 | WYQQKPRSSPKPWIY |
| | 1H1G4D9VL | 224 | DVLMTQTPLSLPVSLGDQASISC | 241 | WYLQKPGQSPKLLIF |
| | 25B6E5D8VL | 225 | DIVLTQSPASLAVSLGQRATISC | 242 | WYQQKPGQPPKLLIY |
| Mutant | 29A8VL.M1 | 215 | DIVMTQSHKFMSTSVGGRVSITC | 232 | WYQQKPGQSPKLLIY |
| Chimeric | 53C1VL.M1 | 218 | DIVMTQSHKFMSTSVGDRVSITC | 235 | WYQQKPGQSPKLLIY |
| Humanized | 29A8VL1 | 226 | DIQMTQSPSSLSASVGDRVTITC | 243 | WYQQKPGKAPKLLIY |
| | 29A8VL2 | 226 | DIQMTQSPSSLSASVGDRVTITC | 243 | WYQQKPGKAPKLLIY |
| | 29A8VL3 | 227 | DIQMTQSPSSLSTSVGDRVTITC | 243 | WYQQKPGKAPKLLIY |
| | 53C1VL1 | 228 | DIQMTQSPSSLSASVGDRVTITC | 244 | WYQQKPGKAPKLLIY |
| | 53C1VL2 | 229 | DIQMTQSPSSMSASVGDRVTITC | 244 | WYQQKPGKAPKLLIY |
| | 53C1VL3 | 230 | DIQMTQSPSSMSTSVGDRVTITC | 244 | WYQQKPGKAPKLLIY |
| Humanized w/CDR1 mutation | 29A8VL1.M1 | 226 | DIQMTQSPSSLSASVGDRVTITC | 243 | WYQQKPGKAPKLLIY |
| | 29A8VL2.M1 | 226 | DIQMTQSPSSLSASVGDRVTITC | 243 | WYQQKPGKAPKLLIY |
| | 29A8VL3.M1 | 227 | DIQMTQSPSSLSTSVGDRVTITC | 243 | WYQQKPGKAPKLLIY |
| | 53C1VL1.M1 | 228 | DIQMTQSPSSLSASVGDRVTITC | 244 | WYQQKPGKAPKLLIY |
| | 53C1VL2.M1 | 229 | DIQMTQSPSSMSASVGDRVTITC | 244 | WYQQKPGKAPKLLIY |
| | 53C1VL3.M1 | 230 | DIQMTQSPSSMSTSVGDRVTITC | 244 | WYQQKPGKAPKLLIY |

| Ab | mAb | ID | FR3 | ID | FR4 |
|---|---|---|---|---|---|
| Mouse | 18B7F4G8VL | 245 | GIPARFSGSGSRTDFTLTINPVEADDVATYYC | 263 | FGGGTKLEIK |
| | 29A8H8C7VL | 246 | GVPDRFTGSGSGTDFTLTISSVQTEDLALYYC | 264 | FGGGTKLEIK |
| | 51F3D2G4VL | 247 | GVPDRFTGSGSGTAFTFTISSEQAEDLAVYYC | 265 | FGGGTKLEIK |
| | 42G2D7D3VL | 248 | GVPARFSGSGSGTSYSLTISSMEAEDAATYYC | 266 | FGAGTKLELK |
| | 53C1F3D4VL | 249 | GVPDRFTGSGSGTAFTFTISGEQAEDLAVYYC | 267 | FGGGTKLEIK |
| | 21D1F4D4VL | 250 | GVPARFSGSGSGTSYSLTVSSMEAEDAASYFC | 268 | FGSGTKLEIK |
| | 30A6B2D9VL | 251 | GVPDRFSGSGSGTDFTLKINRVEAEDLGVYYC | 269 | FGSGTKLEIK |
| | 25G1F9F8VL | 252 | GVPDRFSGSGSGTDFTLKISRVEAEDLGFYYC | 270 | FGSGTKLEIK |
| | 27D3D3G2VL | 253 | GVPSRFSGSGSGTDYSLTISNLEQEDIATYFC | 271 | FGGGTKLEIK |
| | 30A7B5D9VL | 254 | GVPARFSGSGSGTSYSLTISSMEAEDAATYYC | 272 | FGAGTKLELK |
| | 1H1G4D9VL | 255 | GVPDRFSGSGSGTDFTLKISRVEAEDLGVYYC | 273 | FGSGTKLEIK |
| | 25B6E5D8VL | 256 | GIPVRFSGSGSRTDFTLTINPVEADDVATYYC | 274 | FGGGTKLEIK |

TABLE 23-continued

Light chain variable region (VL) framework (FR) sequences.

| | | | | | |
|---|---|---|---|---|---|
| Mutant Chimeric | 29A8VL.M1 | 246 | GVPDRFTGSGSGTDFTLTISSVQTEDLALYYC | 264 | FGGGTKLEIK |
| | 53C1VL.M1 | 249 | GVPDRFTGSGSGTAFTFTISGEQAEDLAVYYC | 267 | FGGGTKLEIK |
| Humanized | 29A8VL1 | 257 | GVPSRFSGSGSGTDFTLTISSLQPEDFATYYC | 275 | FGQGTKVEIK |
| | 29A8VL2 | 258 | GVPSRFSGSGSGTDFTLTISSLQPEDLALYYC | 275 | FGQGTKVEIK |
| | 29A8VL3 | 259 | GVPSRFSGSGSGTDFTLTISSVQPEDLALYYC | 276 | FGQGTKLEIK |
| | 53C1VL1 | 260 | GVPDRFSGSGSGTDFTFTISSLQPEDIATYYC | 277 | FGQGTKLEIK |
| | 53C1VL2 | 261 | GVPDRFSGSGSGTDFTFTISSLQPEDLATYYC | 277 | FGQGTKLEIK |
| | 53C1VL3 | 262 | GVPDRFSGSGSGTDFTFTISSEQPEDLATYYC | 277 | FGQGTKLEIK |
| Humanized w/CDR1 mutation | 29A8VL1.M1 | 257 | GVPSRFSGSGSGTDFTLTISSLQPEDFATYYC | 275 | FGQGTKVEIK |
| | 29A8VL2.M1 | 258 | GVPSRFSGSGSGTDFTLTISSLQPEDLALYYC | 275 | FGQGTKVEIK |
| | 29A8VL3.M1 | 259 | GVPSRFSGSGSGTDFTLTISSVQPEDLALYYC | 276 | FGQGTKLEIK |
| | 53C1VL1.M1 | 260 | GVPDRFSGSGSGTDFTFTISSLQPEDIATYYC | 277 | FGQGTKLEIK |
| | 53C1VL2.M1 | 261 | GVPDRFSGSGSGTDFTFTISSLQPEDLATYYC | 277 | FGQGTKLEIK |
| | 53C1VL3.M1 | 262 | GVPDRFSGSGSGTDFTFTISSEQPEDLATYYC | 277 | FGQGTKLEIK |

TABLE 24

Full-length IgG1 heavy chain sequences with effector-less Fc mutations.

| Ab | mAb | SEQ ID NO: | Sequence |
|---|---|---|---|
| Chimeric | 18B7F4G8 | 278 | DVQLQESGPDLVKPSQSLSLTCTVTGYSITSGYTWHWIRQFPGNKLEWMGYIH<br>YSGSTKYNPSLKSRFSITRDTSKNQFFLQLNSMTAEDTATYYCARNSLFASWG<br>HGTLVTVSAASTKGPSVFPLAPSSKSTSGGTAALGCLVKDYFPEPVTVSWNSG<br>ALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVS<br>HEDPEVKFNWYVDGVEVHNAKTKPREEQYASTYRVVSVLTVLHQDWLNGKEYK<br>CKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCS<br>VMHEALHNHYTQKSLSLSPGK |
| | 29A8H8C7 | 279 | DVQLQGSGPGLVKPSQSLSLTCTVTGYSITSDFAWDWIRQFPGNKLEWMGHIR<br>FSGTTSYNPSLKSRISITRDTSKNQFFLQLNSVTSEDTATYYCARSTLITKGF<br>FDYWGQGTTLTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISRTPEVTCV<br>VVDVSHEDPEVKFNWYVDGVEVENAKTKPREEQYASTYRVVSVLTVLHQDWLN<br>GKEYKCKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKSRWQQGN<br>VFSCSVMHEALHNHYTQKSLSLSPGK |
| | 51F3D2G4 | 280 | QVQLQQSGAELARPGASVRLSCKASGYIFTGYGISWVKQRTGQGLEWIGEIFP<br>RTANTYFNEKFKGKATLTADKSSSTAYMELRSLTSEDSAVYFCARDYDPYYAL<br>DYWGQGTSVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 42G2D7D3 | 281 | DVQLLESGPGLVKPSQSLSLTCSVTGYSITSGYYWNWIRQFPGNNLEWMGSIN<br>YDGSNDYNPSLQDRISITRDTSKNQFFLKLNSVTTEDTATYYCARRLDYWGQG<br>TTLIVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVE<br>PKSCDKTHTCPPCPAPELLGGPSVFLFPPKPKDTLMISRTPEVTCVVVDVSHE<br>DPEVKFNWYVDGVEVHNAKTKPREEQYASTYRVVSVLTVLHQDWLNGKEYKCK<br>VSNKALPAPIEKTISKAKGQPREPQVYTLPPSREEMTKNQVSLTCLVKGFYPS<br>DIAVEWESNGQPENNYKTTPPVLDSDGSFFLYSKLTVDKSRWQQGNVFSCSVM<br>HEALHNHYTQKSLSLSPGK |
| | 53C1F3D4 | 282 | QVQLQQSGNELARPGASVRLSCKASGYIFTGYGITWVRQRPGQGLEWIGEIFP<br>RRVNTYYSEKFKGRATLTADISSSTAYMELRSLTSEDSAVYFCARDYDPYFAL<br>DYWGQGTSVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 21D1F4D4 | 283 | QVQLQQPGAEVVRPGASVKLSCKASGYTFTNYWISWVKQRPGQGLEWIGNIYP<br>SDSYTNYNQNFKDKATLTVDKSSSTAYMQLSSPTSEDSAVYYCTTGIITVIAT<br>RDDYWGQGTTLTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSN<br>TKVDKKVEPKSCDKTHTCPPCPAPELLGGPSVFLFPPKPKDTLMISRTPEVTC |

TABLE 24-continued

Full-length IgG1 heavy chain sequences with effector-less Fc mutations.

| Ab | mAb | SEQ ID NO: | Sequence |
|---|---|---|---|
| | | | VVVDVSHEDPEVKFNWYVDGVEVHNAKTKPREEQYASTYRVVSVLTVLHQDWL NGKEYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRWQQG NVFSCSVMHEALHNHYTQKSLSLSPGK |
| | 30A6B2D9 | 284 | EGQLQQSGAGLVKPGASVNLSCTASGFNIKDTYIHWMKQRPEQGLEWIGRIAP TNGNTKYDPTFQGKATITADSSSNTAYLQVSSLTSEDTAVYYCSRGGIYYYGS HWYFDVWGAGTTVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEV TCVVVDVSHEDPEVKFNWYVDGVEVHNAKTKPREEQYASTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| | 25G1F9F8 | 285 | EGQLQQSGAELVKPGASVNLSCTASGFNIKDTYIHWVKQRPDQGLEWIGRIAP TNGNAKFHPTFQGKATITADTSSNTAYLQLSSLTSEDTAVYYCTRGGIYYYGT HWYFDVWGAGTTVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEV TCVVVDVSHEDPEVKFNWYVDGVEVHNAKTKPREEQYASTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| | 27D3D3G2 | 286 | QVLLQQSGPELVKPGASVRISCKASGYTFTSYYMHWVKQRPGQGLEWIGWIYP GNVNTKYNEKFKGKATLTADKSSSTAYMQLSSLTSEDSAVYFCASYGNYGGWY FDVWGAGTTVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYASTYRVVSVLTVLHQDWLN GKEYKCKVSNKALPAPIEKTISKAKGQPREPQVYTLPPSREEMTKNQVSLTCL VKGFYPSDIAVEWESNGQPENNYKTTPPVLDSDGSFFLYSKLTVDKSRWQQGN VFSCSVMHEALHNHYTQKSLSLSPGK |
| | 30A7B5D9 | 287 | KVQLQQSGAELVKPGTSVKLSCKASGYTFTEYIIYWIKQRSGQGLEWIGWFYP GTGSIKYNEKFKDKATLTADKSSSTVFMELSRLTSEDSAVYFCARHEEGNLWF AYWGQGTLVTVSAASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 1H1G4D9 | 288 | EGQLQQSGAELVKPGASVILSCTASGFNIKDTYIHWLNQRPEQGLEWIGRIEP ANGNTKYDPTFQGKATITADTSSNTAYLQLTSLTSEDTAVYYCSRGGIYYYGS HWYFDVWGAGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEV TCVVVDVSHEDPEVKFNWYVDGVEVHNAKTKPREEQYASTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| | 25B6E5D8 | 289 | QFQLQQSGAELVRPGSSVKISCKASGYEFSSNWMNWVKQRPGQSLEWIGQIWP GDGDTNYNGKFRGKATLTSDKSSSTAYMQLNSLTSEDSAVYFCARGRASFYFD YWGQGTALTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKV DKKVEPKSCDKTHTCPPCPAPELLGGPSVFLFPPKPKDTLMISRTPEVTCVVV DVSHEDPEVKFNWYVDGVEVHNAKTKPREEQYASTYRVVSVLTVLHQDWLNGK EYKCKVSNKALPAPIEKTISKAKGQPREPQVYTLPPSREEMTKNQVSLTCLVK GFYPSDIAVEWESNGQPENNYKTTPPVLDSDGSFFLYSKLTVDKSRWQQGNVF SCSVMHEALHNHYTQKSLSLSPGK |
| Chimeric w/CDR2 mutation | 53C1VH.M1 | 290 | QVQLQQSGNELARPGASVRLSCKASGYIFTGYGITWVRQRPGQGLEWIGEIFP RRVSTYYSEKFKGRATLTADISSSTAYMELRSLTSEDSAVYFCARDYDPYFAL DYWGQGTSVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH.M2 | 291 | QVQLQQSGNELARPGASVRLSCKASGYIFTGYGITWVRQRPGQGLEWIGEIFP RRVATYYSEKFKGRATLTADISSSTAYMELRSLTSEDSAVYFCARDYDPYFAL DYWGQGTSVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV |

TABLE 24-continued

Full-length IgG1 heavy chain sequences with effector-less Fc mutations.

| Ab | mAb | SEQ ID NO: | Sequence |
|---|---|---|---|
| | | | KGFYPSDIAVEWESNGQPENNYKTTPPVLDSDGSFFLYSKLTVDKSRWQQGNVFSCSVMHEALHNHYTQKSLSLSPGK |
| | 53C1VH.M3 | 292 | QVQLQQSGNELARPGASVRLSCKASGYIFTGYGITWVRQRPGQGLEWIGEIFPRRVQTYYSEKFKGRATLTADISSSTAYMELRSLTSEDSAVYFCARDYDPYFALDYWGQGTSVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| Humanized | 29A8VH1 | 293 | EVQLQESGPGLVKPSETLSLTCTVSGYSITSDFAWDWIRQPPGKGLEWIGHIRFSGTTSYNPSLKSRVTISVDTSKNQFSLKLSSVTAADTAVYYCARSTLITKGFFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 29A8VH2 | 294 | EVQLQESGPGLVKPSETLSLTCTVSGYSITSDFAWDWIRQFPGKGLEWMGHIRFSGTTSYNPSLKSRITISVDTSKNQFSLKLSSVTAADTAVYYCARSTLITKGFFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 29A8VH3 | 295 | EVQLQESGPGLVKPSETLSLTCTVSGYSITSDFAWDWIRQFPGKGLEWMGHIRFSGTTSYNPSLKSRITISVDTSKNQFFLKLSSVTAADTATYYCARSTLITKGFFDYWGQGTLLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 29A8VH4 | 296 | EVQLQESGPGLVKPSETLSLTCTVSGYSITSDFAWDWIRQPPGKGLEWIGHIRFSGTTSYNPSLKSRVTISVDTSKNQFSLKLSSVTAADTAVYYCARSTLITKGFFDYWGQGTLLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 29A8VH5 | 297 | EVQLQESGPGLVKPSETLSLTCTVSGYSITSDFAWDWIRQPPGKGLEWIGHIRFSGTTSYNPSLKSRVTISRDTSKNQFSLKLSSVTAADTAVYYCARSTLITKGFFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 53C1VH1 | 298 | EVQLVQSGAEVKKPGASVKVSCKASGYIFTGYGITWVRQAPGQGLEWMGEIFPRRVNTYYSEKFKGRVTMTTDTSTSTAYMELRSLRSDDTAVYYCARDYDPYFALDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 53C1VH2 | 299 | EVQLVQSGAEVKKPGASVKVSCKASGYIFTGYGITWVRQAPGQGLEWIGEIFPRRVNTYYSEKFKGRATLTTDTSTSTAYMELRSLRSDDTAVYFCARDYDPYFALDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |

TABLE 24-continued

| Full-length IgG1 heavy chain sequences with effector-less Fc mutations. | | | |
|---|---|---|---|
| Ab | mAb | SEQ ID NO: | Sequence |
| | 53C1VH3 | 300 | EVQLVQSGAEVKKPGASVKLSCKASGYIFTGYGITWVRQAPGQGLEWIGEIFP<br>RRVNTYYSEKFKGRATLTADTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH4 | 301 | EVQLVQSGAEVKKPGASVKLSCKASGYIFTGYGITWVRQAPGQGLEWMGEIFP<br>RRVNTYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH5 | 302 | EVQLVQSGAEVKKPGASVKVSCKASGYIFTGYGITWVRQAPGQGLEWMGEIFP<br>RRVNTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH6 | 303 | EVQLVQSGAEVKKPGASVKLSCKASGYIFTGYGITWVRQAPGQGLEWMGEIFP<br>RRVNTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| Humanized w/CDR2 mutation | 53C1VH1.M3 | 304 | EVQLVQSGAEVKKPGASVKVSCKASGYIFTGYGITWVRQAPGQGLEWMGEIFP<br>RRVQTYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH2.M3 | 305 | EVQLVQSGAEVKKPGASVKVSCKASGYIFTGYGITWVRQAPGQGLEWIGEIFP<br>RRVQTYYSEKFKGRATLTTDTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH3.M3 | 306 | EVQLVQSGAEVKKPGASVKLSCKASGYIFTGYGITWVRQAPGQGLEWIGEIFP<br>RRVQTYYSEKFKGRATLTADTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH4.M3 | 307 | EVQLVQSGAEVKKPGASVKLSCKASGYIFTGYGITWVRQAPGQGLEWMGEIFP<br>RRVQTYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH5.M3 | 308 | EVQLVQSGAEVKKPGASVKVSCKASGYIFTGYGITWVRQAPGQGLEWMGEIFP<br>RRVQTYYSEKFKGRVTMTADTSTSTAYMELRSLRSDDTAVYYCARDYDPYFAL |

TABLE 24-continued

Full-length IgG1 heavy chain sequences with effector-less Fc mutations.

| Ab | mAb | SEQ ID NO: | Sequence |
|---|---|---|---|
| | | | DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH6.M3 | 309 | EVQLVQSGAEVKKPGASVKLSCKASGYIFTGYGITWVRQAPGQGLEWMGEIFP<br>RRVQTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH1.M1 | 310 | EVQLVQSGAEVKKPGASVKVSCKASGYIFTGYGITWVRQAPGQGLEWMGEIFP<br>RRVSTYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH2.M1 | 311 | EVQLVQSGAEVKKPGASVKVSCKASGYIFTGYGITWVRQAPGQGLEWIGEIFP<br>RRVSTYYSEKFKGRATLTTDTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH3.M1 | 312 | EVQLVQSGAEVKKPGASVKLSCKASGYIFTGYGITWVRQAPGQGLEWIGEIFP<br>RRVSTYYSEKFKGRATLTADTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH4.M1 | 313 | EVQLVQSGAEVKKPGASVKLSCKASGYIFTGYGITWVRQAPGQGLEWMGEIFP<br>RRVSTYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH5.M1 | 314 | EVQLVQSGAEVKKPGASVKVSCKASGYIFTGYGITWVRQAPGQGLEWMGEIFP<br>RRVSTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH6.M1 | 315 | EVQLVQSGAEVKKPGASVKLSCKASGYIFTGYGITWVRQAPGQGLEWMGEIFP<br>RRVSTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV<br>VDVSHEDPEVKFNWYVDGVEVHNAKTKPREEQYASTYRVVSVLTVLHQDWLNG<br>KEYKCKVSNKALPAPIEKTISKAKGQPREPQVYTLPPSREEMTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH1.M2 | 316 | EVQLVQSGAEVKKPGASVKVSCKASGYIFTGYGITWVRQAPGQGLEWMGEIFP<br>RRVATYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKKVEPKSCDKTHTCPPCPAPELLGGPSVFLFPPKPKDTLMISRTPEVTCVV |

TABLE 24-continued

Full-length IgG1 heavy chain sequences with effector-less Fc mutations.

| Ab | mAb | SEQ ID NO: | Sequence |
|---|---|---|---|
| | | | VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH2.M2 | 317 | EVQLVQSGAEVKKPGASVKVSCKASGYIFTGYGITWVRQAPGQGLEWIGEIFP RRVATYYSEKFKGRATLTTDTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH3.M2 | 318 | EVQLVQSGAEVKKPGASVKLSCKASGYIFTGYGITWVRQAPGQGLEWIGEIFP RRVATYYSEKFKGRATLTADTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH4.M2 | 319 | EVQLVQSGAEVKKPGASVKLSCKASGYIFTGYGITWVRQAPGQGLEWMGEIFP RRVATYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH5.M2 | 320 | EVQLVQSGAEVKKPGASVKVSCKASGYIFTGYGITWVRQAPGQGLEWMGEIFP RRVATYYSEKFKGRVTMTADTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH6.M2 | 321 | EVQLVQSGAEVKKPGASVKLSCKASGYIFTGYGITWVRQAPGQGLEWMGEIFP RRVATYYSEKFKGRVTMTADTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKKVEPKSCDKTHTCPPCPAPELLGGPSVFLFPPKPKDTLMISRTPEVTCVV VDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK |

TABLE 25

Full-length kappa light chain sequences.

| Ab | mAb | SEQ ID NO: | Sequence |
|---|---|---|---|
| Chimeric | 18B7F4G8 | 322 | DIVLTQSPASLAVSLGQRATISCRASESVDTYGDSFMHWFQQKPGQPPKLLIY RASNLESGIPARFSGSGSRTDFTLTINPVEADDVATYYCQQSNEAPYTFGGGT KLEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |
| | 29A8H8C7 | 323 | DIVMTQSHKFMSTSVGGRVSITCKASQDVSPAVAWYQQKPGQSPKLLIYWAST RHTGVPDRFTGSGSGTDFTLTISSVQTEDLALYYCQQHYSTPWTFGGGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 51F3D2G4 | 324 | DIVMTQSHKFMSTSVGDRVTITCKASQDVSTAVDWYQQKPGQSPKLLIYSASY RYTGVPDRFTGSGSGTAFTFTISSEQAEDLAVYYCQQHYSVPFTFGGGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |

TABLE 25-continued

Full-length kappa light chain sequences.

| Ab | mAb | SEQ ID NO: | Sequence |
|---|---|---|---|
| | 42G2D7D3 | 325 | QIVLTQSPAIMSASPGEKVTISCSASSFINYMYWYQQKPGSSPKPWILRTSTLASGVPARFSGSGSGTSYSLTISSMEAEDAATYYCQQYHSYPLTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 53C1F3D4 | 326 | DIVMTQSHKFMSTSVGDRVSITCKASQDVSTAVDWYQQKPGQSPKLLIYSASYRYTGVPDRFTGSGSGTAFTFTISGEQAEDLAVYYCQQHYSIPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 21D1F4D4 | 327 | QIVLTQSPAIMSASPGEKVTLTCSASSSVSSSYLYWYQQKPGSSPKLWIYSTSNLASGVPARFSGSGSGTSYSLTVSSMEAEDAASYFCHQWSSYPFTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 30A6B2D9 | 328 | SVLMTQTPLSLPVSLGDQASISCRSSQNIVYSDGDTYLEWYLQKPGQSPKLLIFKVSNRFFGVPDRFSGSGSGTDFTLKINRVEAEDLGVYYCFQGSHVPFTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 25G1F9F8 | 329 | DVLMNQTPLSLPVSLGDQASISCRSSQNIVYSDGNTYLEWYLQKPGQSPKLLIFQVSNRFSGVPDRFSGSGSGTDFTLKISRVEAEDLGFYYCFQGSHVPFTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 27D3D3G2 | 330 | DIQMTQTTSSLSASLGDRVTISCRASQDIGNYLNWYQQKPDGTVKLLIYYTSRLHSGVPSRFSGSGSGTDYSLTISNLEQEDIATYFCQQGDTFPWTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 30A7B5D9 | 331 | QIVLTQSPALMSASPGERVTMTCSASSDVSYMYWYQQKPRSSPKPWIYLTSNLASGVPARFSGSGSGTSYSLTISSMEAEDAATYYCQQWTGNPLTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 1H1G4D9 | 332 | DVLMTQTPLSLPVSLGDQASISCRSSQNIVYSDGDTYLEWYLQKPGQSPKLLIFKVSNRFSGVPDRFSGSGSGTDFTLKISRVEAEDLGVYYCFQGSHVPFTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 25B6E5D8 | 333 | DIVLTQSPASLAVSLGQRATISCRASESVDDYGNSFMHWYQQKPGQPPKLLIYRASNLESGIPVRFSGSGSRTDFTLTINPVEADDVATYYCQQSNEDPHTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| chimeric with CDR1 mutation | 29A8VL.M1 | 334 | DIVMTQSHKFMSTSVGGRVSITCRASQDVSPAVAWYQQKPGQSPKLLIYWASTRHTGVPDRFTGSGSGTDFTLTISSVQTEDLALYYCQQHYSTPWTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 53C1VL.M1 | 335 | DIVMTQSHKFMSTSVGDRVSITCRASQDVSTAVDWYQQKPGQSPKLLIYSASYRYTGVPDRFTGSGSGTAFTFTISGEQAEDLAVYYCQQHYSIPFTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| humanized | 29A8VL1 | 336 | DIQMTQSPSSLSASVGDRVTITCKASQDVSPAVAWYQQKPGKAPKLLIYWASTRHTGVPSRFSGSGSGTDFTLTISSLQPEDFATYYCQQHYSTPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 29A8VL2 | 337 | DIQMTQSPSSLSASVGDRVTITCKASQDVSPAVAWYQQKPGKAPKLLIYWASTRHTGVPSRFSGSGSGTDFTLTISSLQPEDLALYYCQQHYSTPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 29A8VL3 | 338 | DIQMTQSPSSLSTSVGDRVTITCKASQDVSPAVAWYQQKPGKAPKLLIYWASTRHTGVPSRFSGSGSGTDFTLTISSVQPEDLALYYCQQHYSTPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 53C1VL1 | 339 | DIQMTQSPSSLSASVGDRVTITCKASQDVSTAVDWYQQKPGKAPKLLIYSASYRYTGVPDRFSGSGSGTDFTFTISSLQPEDIATYYCQQHYSIPFTFGQGTKLEIKRTVAAPSVFIFPPSDEQLKSGTASVVCLLNNFYPREAKVQWKVDNALQSGNS |

TABLE 25-continued

Full-length kappa light chain sequences.

| Ab | mAb | SEQ ID NO: | Sequence |
|---|---|---|---|
| | | | QESVTEQDSKDSTYSLSSTLTLSKADYEKHKVYACEVTHQGLSSPVTKSFNRG EC |
| | 53C1VL2 | 340 | DIQMTQSPSSMSASVGDRVTITCKASQDVSTAVDWYQQKPGKAPKLLIYSASY RYTGVPDRFSGSGSGTDFTFTISSLQPEDLATYYCQQHYSIPFTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 53C1VL3 | 341 | DIQMTQSPSSMSTSVGDRVTITCKASQDVSTAVDWYQQKPGKAPKLLIYSASY RYTGVPDRFSGSGSGTDFTFTISSEQPEDLATYYCQQHYSIPFTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| humanized with CDR1 mutation | 29A8VL1.M1 | 342 | DIQMTQSPSSLSASVGDRVTITCKASQDVSPAVAWYQQKPGKAPKLLIYWAST RHTGVPSRFSGSGSGTDFTLTISSLQPEDFATYYCQQHYSTPWTFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 29A8VL2.M1 | 343 | DIQMTQSPSSLSASVGDRVTITCKASQDVSPAVAWYQQKPGKAPKLLIYWAST RHTGVPSRFSGSGSGTDFTLTISSLQPEDLALYYCQQHYSTPWTFGQGTKVEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 29A8VL3.M1 | 344 | DIQMTQSPSSLSTSVGDRVTITCKASQDVSPAVAWYQQKPGKAPKLLIYWAST RHTGVPSRFSGSGSGTDFTLTISSVQPEDLALYYCQQHYSTPWTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 53C1VL1.M1 | 345 | DIQMTQSPSSLSASVGDRVTITCKASQDVSTAVDWYQQKPGKAPKLLIYSASY RYTGVPDRFSGSGSGTDFTFTISSLQPEDIATYYCQQHYSIPFTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 53C1VL2.M1 | 346 | DIQMTQSPSSMSASVGDRVTITCKASQDVSTAVDWYQQKPGKAPKLLIYSASY RYTGVPDRFSGSGSGTDFTFTISSLQPEDLATYYCQQHYSIPFTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |
| | 53C1VL3.M1 | 347 | DIQMTQSPSSMSTSVGDRVTITCKASQDVSTAVDWYQQKPGKAPKLLIYSASY RYTGVPDRFSGSGSGTDFTFTISSEQPEDLATYYCQQHYSIPFTFGQGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG EC |

TABLE 26

Full-length IgG1 heavy chain sequences with wild-type constant region sequence.

| Ab | mAb | SEQ ID NO: | Sequence |
|---|---|---|---|
| chimeric | 18B7F4G8 | 348 | DVQLQESGPDLVKPSQSLSLTCTVTGYSITSGYTWHWIRQFPGNKLEWMGYIH YSGSTKYNPSLKSRFSITRDTSKNQFFLQLNSMTAEDTATYYCARNSLFASWG HGTLVTVSAASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKR VEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFSCS VMHEALHNHYTQKSLSLSPGK |
| | 29A8H8C7 | 349 | DVQLQGSGPGLVKPSQSLSLTCTVTGYSITSDFAWDWIRQFPGNKLEWMGHIR FSGTTSYNPSLKSRISITRDTSKNQFFLQLNSVTSEDTATYYCARSTLITKGF FDYWGQGTTLTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCV VVDVSHEDPEVKFNWYVDGVEVENAKTKPREEQYNSTYRVVSVLTVLHQDWLN GKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGN VFSCSVMHEALHNHYTQKSLSLSPGK |
| | 51F3D2G4 | 350 | QVQLQQSGAELARPGASVRLSCKASGYIFTGYGISWVKQRTGQGLEWIGEIFP RTANTYFNEKFKGKATLTADKSSSTAYMELRSLTSEDSAVYFCARDYDPYYAL DYWGQGTSVTVSSASTKGPSVFPLAPSSKSTSGGTAALGCLVKDYFPEPVTVS |

TABLE 26-continued

Full-length IgG1 heavy chain sequences with wild-type constant region sequence.

| Ab | mAb | SEQ ID NO: | Sequence |
|---|---|---|---|
| | | | WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 42G2D7D3 | 351 | DVQLLESGPGLVKPSQSLSLTCSVTGYSITSGYYWNWIRQFPGNNLEWMGSIN<br>YDGSNDYNPSLQDRISITRDTSKNQFFLKLNSVTTEDTATYYCARRLDYWGQG<br>TTLIVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKRVE<br>PKSCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKCK<br>VSNKALPAPIEKTISKAKGQPREPQVYTLPPSRDELTKNQVSLTCLVKGFYPS<br>DIAVEWESNGQPENNYKTTPPVLDSDGSFFLYSKLTVDKSRWQQGNVFSCSVM<br>HEALHNHYTQKSLSLSPGK |
| | 53C1F3D4 | 352 | QVQLQQSGNELARPGASVRLSCKASGYIFTGYGITWVRQRPGQGLEWIGEIFP<br>RRVNTYYSEKFKGRATLTADISSSTAYMELRSLTSEDSAVYFCARDYDPYFAL<br>DYWGQGTSVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 21D1F4D4 | 353 | QVQLQQPGAEVVRPGASVKLSCKASGYTFTNYWISWVKQRPGQGLEWIGNIYP<br>SDSYTNYNQNFKDKATLTVDKSSSTAYMQLSSPTSEDSAVYYCTTGIITVIAT<br>RDDYWGQGTTLTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDKSRWQQG<br>NVFSCSVMHEALHNHYTQKSLSLSPGK |
| | 30A6B2D9 | 354 | EGQLQQSGAGLVKPGASVNLSCTASGFNIKDTYIHWMKQRPEQGLEWIGRIAP<br>TNGNTKYDPTFQGKATITADSSSNTAYLQVSSLTSEDTAVYYCSRGGIYYYGS<br>HWYFDVWGAGTTVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKP<br>SNTKVDKRVEPKSCDKTHTCPPCPAPELLGGPSVFLFPPKPKDTLMISRTPEV<br>TCVVVDVSHEDPEVKFNWYVDGVEVHNAKTKPREEQYNSTYRVVSVLTVLHQD<br>WLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQ<br>QGNVFSCSVMHEALHNHYTQKSLSLSPGK |
| | 25G1F9F8 | 355 | EGQLQQSGAELVKPGASVNLSCTASGFNIKDTYIHWVKQRPDQGLEWIGRIAP<br>TNGNAKFHPTFQGKATITADTSSNTAYLQLSSLTSEDTAVYYCTRGGIYYYGT<br>HWYFDVWGAGTTVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKP<br>SNTKVDKRVEPKSCDKTHTCPPCPAPELLGGPSVFLFPPKPKDTLMISRTPEV<br>TCVVVDVSHEDPEVKFNWYVDGVEVHNAKTKPREEQYNSTYRVVSVLTVLHQD<br>WLNGKEYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVDKSRWQ<br>QGNVFSCSVMHEALHNHYTQKSLSLSPGK |
| | 27D3D3G2 | 356 | QVLLQQSGPELVKPGASVRISCKASGYTFTSYYMHWVKQRPGQGLEWIGWIYP<br>GNVNTKYNEKFKGKATLTADKSSSTAYMQLSSLTSEDSAVYFCASYGNYGGWY<br>FDVWGAGTTVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSNT<br>KVDKRVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKSRWQQGN<br>VFSCSVMHEALHNHYTQKSLSLSPGK |
| | 30A7B5D9 | 357 | KVQLQQSGAELVKPGTSVKLSCKASGYTFTEYIIYWIKQRSGQGLEWIGWFYP<br>GTGSIKYNEKFKDKATLTADKSSSTVFMELSRLTSEDSAVYFCARHEEGNLWF<br>AYWGQGTLVTVSAASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 1H1G4D9 | 358 | EGQLQQSGAELVKPGASVILSCTASGFNIKDTYIHWLNQRPEQGLEWIGRIEP<br>ANGNTKYDPTFQGKATITADTSSNTAYLQLTSLTSEDTAVYYCSRGGIYYYGS<br>HWYFDVWGAGTLVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKP<br>SNTKVDKRVEPKSCDKTHTCPPCPAPELLGGPSVFLFPPKPKDTLMISRTPEV<br>TCVVVDVSHEDPEVKFNWYVDGVEVHNAKTKPREEQYNSTYRVVSVLTVLHQD |

TABLE 26-continued

Full-length IgG1 heavy chain sequences with wild-type constant region sequence.

| Ab | mAb | SEQ ID NO: | Sequence |
|---|---|---|---|
| | | | WLNGKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKSRWQ QGNVFSCSVMHEALHNHYTQKSLSLSPGK |
| | 25B6E5D8 | 359 | QFQLQQSGAELVRPGSSVKISCKASGYEFSSNWMNWVKQRPGQSLEWIGQIWP GDGDTNYNGKFRGKATLTSDKSSSTAYMQLNSLTSEDSAVYFCARGRASFYFD YWGQGTALTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQQGNVF SCSVMHEALHNHYTQKSLSLSPGK |
| chimeric with CDR2 mutation | 53C1VH.M1 | 360 | QVQLQQSGNELARPGASVRLSCKASGYIFTGYGITWVRQRPGQGLEWIGEIFP RRVSTYYSEKFKGRATLTADISSSTAYMELRSLTSEDSAVYFCARDYDPYFAL DYWGQGTSVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH.M2 | 361 | QVQLQQSGNELARPGASVRLSCKASGYIFTGYGITWVRQRPGQGLEWIGEIFP RRVATYYSEKFKGRATLTADISSSTAYMELRSLTSEDSAVYFCARDYDPYFAL DYWGQGTSVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH.M3 | 362 | QVQLQQSGNELARPGASVRLSCKASGYIFTGYGITWVRQRPGQGLEWIGEIFP RRVQTYYSEKFKGRATLTADISSSTAYMELRSLTSEDSAVYFCARDYDPYFAL DYWGQGTSVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| humanized | 29A8VH1 | 363 | EVQLQESGPGLVKPSETLSLTCTVSGYSITSDFAWDWIRQPPGKGLEWIGHIR FSGTTSYNPSLKSRVTISVDTSKNQFSLKLSSVTAADTAVYYCARSTLITKGF FDYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGN VFSCSVMHEALHNHYTQKSLSLSPGK |
| | 29A8VH2 | 364 | EVQLQESGPGLVKPSETLSLTCTVSGYSITSDFAWDWIRQFPGKGLEWMGHIR FSGTTSYNPSLKSRITISVDTSKNQFSLKLSSVTAADTAVYYCARSTLITKGF FDYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGN VFSCSVMHEALHNHYTQKSLSLSPGK |
| | 29A8VH3 | 365 | EVQLQESGPGLVKPSETLSLTCTVSGYSITSDFAWDWIRQFPGKGLEWMGHIR FSGTTSYNPSLKSRITISVDTSKNQFFLKLSSVTAADTATYYCARSTLITKGF FDYWGQGTLLTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGN VFSCSVMHEALHNHYTQKSLSLSPGK |
| | 29A8VH4 | 366 | EVQLQESGPGLVKPSETLSLTCTVSGYSITSDFAWDWIRQPPGKGLEWIGHIR FSGTTSYNPSLKSRVTISVDTSKNQFSLKLSSVTAADTAVYYCARSTLITKGF FDYWGQGTLLTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCL |

TABLE 26-continued

Full-length IgG1 heavy chain sequences with wild-type constant region sequence.

| Ab | mAb | SEQ ID NO: | Sequence |
|---|---|---|---|
| | | | VKGFYPSDIAVEWESNGQPENNYKTTPPVLDSDGSFFLYSKLTVDKSRWQQGN VFSCSVMHEALHNHYTQKSLSLSPGK |
| | 29A8VH5 | 367 | EVQLQESGPGLVKPSETLSLTCTVSGYSITSDFAWDWIRQPPGKGLEWIGHIR FSGTTSYNPSLKSRVTISRDTSKNQFSLKLSSVTAADTAVYYCARSTLITKGF FDYWGQGTLVTVSSASTKGPSVFPLAPSSKSTSGGTAALGCLVKDYFPEPVTV SWNSGALTSGVHTFPAVLQSSGLYSLSSVVTVPSSSLGTQTYICNVNHKPSNT KVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGN VFSCSVMHEALHNHYTQKSLSLSPGK |
| | 53C1VH1 | 368 | EVQLVQSGAEVKKPGASVKVSCKASGYIFTGYGITWVRQAPGQGLEWMGEIFP RRVNTYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH2 | 369 | EVQLVQSGAEVKKPGASVKVSCKASGYIFTGYGITWVRQAPGQGLEWIGEIFP RRVNTYYSEKFKGRATLTTDTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH3 | 370 | EVQLVQSGAEVKKPGASVKLSCKASGYIFTGYGITWVRQAPGQGLEWIGEIFP RRVNTYYSEKFKGRATLTADTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH4 | 371 | EVQLVQSGAEVKKPGASVKLSCKASGYIFTGYGITWVRQAPGQGLEWMGEIFP RRVNTYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH5 | 372 | EVQLVQSGAEVKKPGASVKVSCKASGYIFTGYGITWVRQAPGQGLEWMGEIFP RRVNTYYSEKFKGRVTMTADTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH6 | 373 | EVQLVQSGAEVKKPGASVKLSCKASGYIFTGYGITWVRQAPGQGLEWMGEIFP RRVNTYYSEKFKGRVTMTADTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| humanized with CDR2 mutation | 53C1VH1.M3 | 374 | EVQLVQSGAEVKKPGASVKVSCKASGYIFTGYGITWVRQAPGQGLEWMGEIFP RRVQTYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |

TABLE 26-continued

Full-length IgG1 heavy chain sequences with wild-type constant region sequence.

| Ab | mAb | SEQ ID NO: | Sequence |
|---|---|---|---|
| | 53C1VH2.M3 | 375 | EVQLVQSGAEVKKPGASVKVSCKASGYIFTGYGITWVRQAPGQGLEWIGEIFP RRVQTYYSEKFKGRATLTTDTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH3.M3 | 376 | EVQLVQSGAEVKKPGASVKLSCKASGYIFTGYGITWVRQAPGQGLEWIGEIFP RRVQTYYSEKFKGRATLTADTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH4.M3 | 377 | EVQLVQSGAEVKKPGASVKLSCKASGYIFTGYGITWVRQAPGQGLEWMGEIFP RRVQTYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH5.M3 | 378 | EVQLVQSGAEVKKPGASVKVSCKASGYIFTGYGITWVRQAPGQGLEWMGEIFP RRVQTYYSEKFKGRVTMTADTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH6.M3 | 379 | EVQLVQSGAEVKKPGASVKLSCKASGYIFTGYGITWVRQAPGQGLEWMGEIFP RRVQTYYSEKFKGRVTMTADTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH1.M1 | 380 | EVQLVQSGAEVKKPGASVKVSCKASGYIFTGYGITWVRQAPGQGLEWMGEIFP RRVSTYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH2.M1 | 381 | EVQLVQSGAEVKKPGASVKVSCKASGYIFTGYGITWVRQAPGQGLEWIGEIFP RRVSTYYSEKFKGRATLTTDTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH3.M1 | 382 | EVQLVQSGAEVKKPGASVKLSCKASGYIFTGYGITWVRQAPGQGLEWIGEIFP RRVSTYYSEKFKGRATLTADTSTSTAYMELRSLRSDDTAVYFCARDYDPYFAL DYWGQGTTVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTK VDKRVEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |
| | 53C1VH4.M1 | 383 | EVQLVQSGAEVKKPGASVKLSCKASGYIFTGYGITWVRQAPGQGLEWMGEIFP RRVSTYYSEKFKGRVTMTTDTSTSTAYMELRSLRSDDTAVYYCARDYDPYFAL DYWGQGTTVTVSSASTKGPSVFPLAPSSKSTSGGTAALGCLVKDYFPEPVTVS |

TABLE 26-continued

Full-length IgG1 heavy chain sequences with wild-type constant region sequence.

| Ab | mAb | SEQ ID NO: | Sequence |
|---|---|---|---|
| | | | WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH5.M1 | 384 | EVQLVQSGAEVKKPGASVKVSCKASGYIFTGYGITWVRQAPGQGLEWMGEIFP<br>RRVSTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH6.M1 | 385 | EVQLVQSGAEVKKPGASVKLSCKASGYIFTGYGITWVRQAPGQGLEWMGEIFP<br>RRVSTYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH1.M2 | 386 | EVQLVQSGAEVKKPGASVKVSCKASGYIFTGYGITWVRQAPGQGLEWMGEIFP<br>RRVATYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH2.M2 | 387 | EVQLVQSGAEVKKPGASVKVSCKASGYIFTGYGITWVRQAPGQGLEWIGEIFP<br>RRVATYYSEKFKGRATLTTDTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH3.M2 | 388 | EVQLVQSGAEVKKPGASVKLSCKASGYIFTGYGITWVRQAPGQGLEWIGEIFP<br>RRVATYYSEKFKGRATLTADTSTSTAYMELRSLRSDDTAVYFCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH4.M2 | 389 | EVQLVQSGAEVKKPGASVKLSCKASGYIFTGYGITWVRQAPGQGLEWMGEIFP<br>RRVATYYSEKFKGRVTMTTDTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH5.M2 | 390 | EVQLVQSGAEVKKPGASVKVSCKASGYIFTGYGITWVRQAPGQGLEWMGEIFP<br>RRVATYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG<br>KEYKCKVSNKALPAPIEKTISKAKGQPREPQVYTLPPSRDELTKNQVSLTCLV<br>KGFYPSDIAVEWESNGQPENNYKTTPPVLDSDGSFFLYSKLTVDKSRWQQGNV<br>FSCSVMHEALHNHYTQKSLSLSPGK |
| | 53C1VH6.M2 | 391 | EVQLVQSGAEVKKPGASVKLSCKASGYIFTGYGITWVRQAPGQGLEWMGEIFP<br>RRVATYYSEKFKGRVTMTADTSTSTAYMELRSLRSDDTAVYYCARDYDPYFAL<br>DYWGQGTTVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTK<br>VDKRVEPKSCDKTHTCPPCPAPELLGGPSVFLFPPKPKDTLMISRTPEVTCVV<br>VDVSHEDPEVKFNWYVDGVEVHNAKTKPREEQYNSTYRVVSVLTVLHQDWLNG |

TABLE 26-continued

| Full-length IgG1 heavy chain sequences with wild-type constant region sequence. | | | |
|---|---|---|---|
| Ab | mAb | SEQ ID NO: | Sequence |
| | | | KEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNV FSCSVMHEALHNHYTQKSLSLSPGK |

TABLE 27

| Constant Region Sequences | | |
|---|---|---|
| Constant Region | ID | Sequence |
| heavy chain constant region of IgG1 with effector-less Fc mutations | 392 | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVENAKTKPREEQYASTYRVV SVLTVLHQDWLNGKEYKCKVSNKALPAPIEK TISKAKGQPREPQVYTLPPSREEMTKNQVSL TCLVKGFYPSDIAVEWESNGQPENNYKTTPP VLDSDGSFFLYSKLTVDKSRWQQGNVFSCSV MHEALHNHYTQKSLSLSPGK |
| light chain constant region of IgG1 | 393 | RTVAAPSVFIFPPSDEQLKSGTASVVCLLNN FYPREAKVQWKVDNALQSGNSQESVTEQDSK DSTYSLSSTLTLSKADYEKEKVYACEVTHQG LSSPVTKSFNRGEC |
| heavy chain constant region of wild-type IgG1 | 394 | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKRVEPKSCDKTHTCPPCPAPELLGGPSVF LFPPKPKDTLMISRTPEVTCVVVDVSHEDPE VKFNWYVDGVEVENAKTKPREEQYNSTYRVV SVLTVLHQDWLNGKEYKCKVSNKALPAPIEK TISKAKGQPREPQVYTLPPSRDELTKNQVSL TCLVKGFYPSDIAVEWESNGQPENNYKTTPP VLDSDGSFFLYSKLTVDKSRWQQGNVFSCSV MHEALHNHYTQKSLSLSPGK |

TABLE 28

| Antigen Sequences | | |
|---|---|---|
| antigen protein | ID | sequence |
| full-length human PD-L1 | 395 | FTVTVPKDLYVVEYGSNMTIECKFPVEKQLD LAALIVYWEMEDKNIIQFVHGEEDLKVQHSS YRQRARLLKDQLSLGNAALQITDVKLQDAGV YRCMISYGGADYKRITVKVNAPYNKINQRIL |

TABLE 28-continued

| Antigen Sequences | | |
|---|---|---|
| antigen protein | ID | sequence |
| | | VVDPVTSEHELTCQAEGYPKAEVIWTSSDHQ VLSGKTTTTNSKREEKLFNVTSTLRINTTTN EIFYCTFRRLDPEENHTAELVIPELPLAHPP NERTHLVILGAILLCLGVALTFIFRLRKGRM MDVKKCGIQDTNSKKQSDTHLEET |
| human PD-L1 ECD | 396 | FTVTVPKDLYVVEYGSNMTIECKFPVEKQLD LAALIVYWEMEDKNIIQFVHGEEDLKVQHSS YRQRARLLKDQLSLGNAALQITDVKLQDAGV YRCMISYGGADYKRITVKVNAPYNKINQRIL VVDPVTSEHELTCQAEGYPKAEVIWTSSDHQ VLSGKTTTTNSKREEKLFNVTSTLRINTTTN EIFYCTFRRLDPEENHTAELVIPELPLAHPP NER |
| human PD-1 ECD | 400 | LDSPDRPWNPPTFSPALLVVTEGDNATFTCS FSNTSESFVLNWYRMSPSNQTDKLAAFPEDR SQPGQDCRERVTQLPNGRDEHMSVVRARRND SGTYLCGAISLAPKAQIKESLRAELRVTERR AEVPTAHPSPSPRPAGQFQ |

TABLE 29

| Linker Sequences | | |
|---|---|---|
| linker | ID | Sequence |
| G4SG3S | 397 | GGGGSGGGS |
| (G4S)3 | 393 | GGGGSGGGGSGGGGS |
| mutant hIgG1 hinge | 399 | EPKSSDKTHTSPPSP |

What is claimed is:

1. An antibody or an antigen-binding fragment thereof, comprising:

a heavy chain variable domain (VH) comprising a heavy chain complementarity determining region 1 (HCDR1), a HCDR2, and a HCDR3, and a light chain variable domain (VL) comprising a light chain complementarity determining region 1 (LCDR1), LCDR2, and LCDR3, wherein the HCDR1, HCDR2, HCDR3, LCDR1, LCDR2, and LCDR3 comprise the amino acid sequences of:

(1) SEQ ID NOs: 71, 83, 98,110,124, and 136, respectively;

(2) SEQ ID NOs: 72, 84, 99,111,125, and 137, respectively;

(3) SEQ ID NOs: 72, 84, 99,122,125, and 137, respectively;

(4) SEQ ID NOs: 73, 85,100,112, 126, and 138; respectively;

(5) SEQ ID NOs: 74, 86,101,113, 127, and 139; respectively;

(6) SEQ ID NOs: 75, 87,102,114, 128, and 140, respectively;

(7) SEQ ID NOs: 75, 95,102,114, 128, and 140, respectively;

(8) SEQ ID NOs: 75, 96,102,114, 128, and 140, respectively;

(9) SEQ ID NOs: 75, 97,102,114, 128, and 140, respectively;

(10) SEQ ID NOs: 75, 87,102,123, 128, and 140, respectively;

(11) SEQ ID NOs: 75, 95,102,123, 128, and 140, respectively;

(12) SEQ ID NOs: 75, 96,102,123, 128, and 140, respectively;

(13) SEQ ID NOs: 75, 97,102,123, 128, and 140, respectively;

(14) SEQ ID NOs: 76, 88,103,115, 129, and 141, respectively;

(15) SEQ ID NOs: 77, 89,104,116, 130, and 142, respectively;

(16) SEQ ID NOs: 78, 90,105,117, 131, and 143, respectively;

(17) SEQ ID NOs: 79, 91,106,118, 132, and 144, respectively;

(18) SEQ ID NOs: 80, 92,107,119, 133, and 145, respectively;

(19) SEQ ID NOs: 81, 93,108,120, 134, and 146, respectively; or

(20) SEQ ID NOs: 82, 94,109,121, 135, and 147, respectively;

wherein the antibody or antigen-binding fragment is capable of specifically binding to PD-L1.

2. The antibody or antigen-binding fragment thereof of claim 1, wherein:

(1) the VH comprises an amino acid sequence that is at least 90% identical to the amino acid sequence of SEQ ID NO:1, and the VL comprises an amino acid sequence that is at least 90% identical to the amino acid sequence of SEQ ID NO:45;

(2) the VH comprises an amino acid sequence that is at least 90% identical to the amino acid sequence of SEQ ID NO:2, and the VL comprises an amino acid sequence that is at least 90% identical to the amino acid sequence of SEQ ID NO:46;

(3) the VH comprises an amino acid sequence that is at least 90% identical to the amino acid sequence of SEQ ID NO:3, and the VL comprises an amino acid sequence that is at least 90% identical to the amino acid sequence of SEQ ID NO:47;

(4) the VH comprises an amino acid sequence that is at least 90% identical to the amino acid sequence of SEQ ID NO:4, and the VL comprises an amino acid sequence that is at least 90% identical to the amino acid sequence of SEQ ID NO:48;

(5) the VH comprises an amino acid sequence that is at least 90% identical to the amino acid sequence of SEQ ID NO:5, and the VL comprises an amino acid sequence that is at least 90% identical to the amino acid sequence of SEQ ID NO:49;

(6) the VH comprises an amino acid sequence that is at least 90% identical to the amino acid sequence of SEQ ID NO:6, and the VL comprises an amino acid sequence that is at least 90% identical to the amino acid sequence of SEQ ID NO:50;

(7) the VH comprises an amino acid sequence that is at least 90% identical to the amino acid sequence of SEQ ID NO:7, and the VL comprises an amino acid sequence that is at least 90% identical to the amino acid sequence of SEQ ID NO:51;

(8) the VH comprises an amino acid sequence that is at least 90% identical to the amino acid sequence of SEQ ID NO:8, and the VL comprises an amino acid sequence that is at least 90% identical to the amino acid sequence of SEQ ID NO:52;

(9) the VH comprises an amino acid sequence that is at least 90% identical to the amino acid sequence of SEQ ID NO:9, and the VL comprises an amino acid sequence that is at least 90% identical to the amino acid sequence of SEQ ID NO:53;

(10) the VH comprises an amino acid sequence that is at least 90% identical to the amino acid sequence of SEQ ID NO:10, and the VL comprises an amino acid sequence that is at least 90% identical to the amino acid sequence of SEQ ID NO:54;

(11) the VH comprises an amino acid sequence that is at least 90% identical to the amino acid sequence of SEQ ID NO:11, and the VL comprises an amino acid sequence that is at least 90% identical to the amino acid sequence of SEQ ID NO:55;

(12) the VH comprises an amino acid sequence that is at least 90% identical to the amino acid sequence of SEQ ID NO:12, and the VL comprises an amino acid sequence that is at least 90% identical to the amino acid sequence of SEQ ID NO:56;

(13) the VH comprises an amino acid sequence that is at least 90% identical to the amino acid sequence of SEQ ID NO:16, and the VL comprises an amino acid sequence that is at least 90% identical to the amino acid sequence of SEQ ID NO:65;

(14) the VH comprises an amino acid sequence that is at least 90% identical to the amino acid sequence of SEQ ID NO:16, and the VL comprises an amino acid sequence that is at least 90% identical to the amino acid sequence of SEQ ID NO:66;

(15) the VH comprises an amino acid sequence that is at least 90% identical to the amino acid sequence of SEQ ID NO:16, and the VL comprises an amino acid sequence that is at least 90% identical to the amino acid sequence of SEQ ID NO:67;

(16) the VH comprises an amino acid sequence that is at least 90% identical to the amino acid sequence of SEQ ID NO:16, and the VL comprises an amino acid sequence that is at least 90% identical to the amino acid sequence of SEQ ID NO:59;

(17) the VH comprises an amino acid sequence that is at least 90% identical to the amino acid sequence of SEQ ID NO:16, and the VL comprises an amino acid sequence that is at least 90% identical to the amino acid sequence of SEQ ID NO:60;

(18) the VH comprises an amino acid sequence that is at least 90% identical to the amino acid sequence of SEQ ID NO:16, and the VL comprises an amino acid sequence that is at least 90% identical to the amino acid sequence of SEQ ID NO:61;

(19) the VH comprises an amino acid sequence that is at least 90% identical to the amino acid sequence of SEQ ID NO:17, and the VL comprises an amino acid sequence that is at least 90% identical to the amino acid sequence of SEQ ID NO:65;

(20) the VH comprises an amino acid sequence that is at least 90% identical to the amino acid sequence of SEQ ID NO:17, and the VL comprises an amino acid sequence that is at least 90% identical to the amino acid sequence of SEQ ID NO:66;

(21) the VH comprises an amino acid sequence that is at least 90% identical to the amino acid sequence of SEQ ID NO:17, and the VL comprises an amino acid sequence that is at least 90% identical to the amino acid sequence of SEQ ID NO:67;

(22) the VH comprises an amino acid sequence that is at least 90% identical to the amino acid sequence of SEQ ID NO:18, and the VL comprises an amino acid sequence that is at least 90% identical to the amino acid sequence of SEQ ID NO:65;

(23) the VH comprises an amino acid sequence that is at least 90% identical to the amino acid sequence of SEQ ID NO:18, and the VL comprises an amino acid sequence that is at least 90% identical to the amino acid sequence of SEQ ID NO:66;

(24) the VH comprises an amino acid sequence that is at least 90% identical to the amino acid sequence of SEQ ID NO:18, and the VL comprises an amino acid sequence that is at least 90% identical to the amino acid sequence of SEQ ID NO:67;

(25) the VH comprises an amino acid sequence that is at least 90% identical to the amino acid sequence of SEQ ID NO:19, and the VL comprises an amino acid sequence that is at least 90% identical to the amino acid sequence of SEQ ID NO:65;

(26) the VH comprises an amino acid sequence that is at least 90% identical to the amino acid sequence of SEQ ID NO:19, and the VL comprises an amino acid sequence that is at least 90% identical to the amino acid sequence of SEQ ID NO:66;

(27) the VH comprises an amino acid sequence that is at least 90% identical to the amino acid sequence of SEQ ID NO:19, and the VL comprises an amino acid sequence that is at least 90% identical to the amino acid sequence of SEQ ID NO:67;

(28) the VH comprises an amino acid sequence that is at least 90% identical to the amino acid sequence of SEQ ID NO:19, and the VL comprises an amino acid sequence that is at least 90% identical to the amino acid sequence of SEQ ID NO:59;

(29) the VH comprises an amino acid sequence that is at least 90% identical to the amino acid sequence of SEQ ID NO:19, and the VL comprises an amino acid sequence that is at least 90% identical to the amino acid sequence of SEQ ID NO:60;

(30) the VH comprises an amino acid sequence that is at least 90% identical to the amino acid sequence of SEQ ID NO:19, and the VL comprises an amino acid sequence that is at least 90% identical to the amino acid sequence of SEQ ID NO:61;

(31) the VH comprises an amino acid sequence that is at least 90% identical to the amino acid sequence of SEQ ID NO:20, and the VL comprises an amino acid sequence that is at least 90% identical to the amino acid sequence of SEQ ID NO:66;

(32) the VH comprises an amino acid sequence that is at least 90% identical to the amino acid sequence of SEQ ID NO:20, and the VL comprises an amino acid sequence that is at least 90% identical to the amino acid sequence of SEQ ID NO:65;

(33) the VH comprises an amino acid sequence that is at least 90% identical to the amino acid sequence of SEQ ID NO:20, and the VL comprises an amino acid sequence that is at least 90% identical to the amino acid sequence of SEQ ID NO:67;

(34) the VH comprises an amino acid sequence that is at least 90% identical to the amino acid sequence of SEQ ID NO:20, and the VL comprises an amino acid sequence that is at least 90% identical to the amino acid sequence of SEQ ID NO:59;

(35) the VH comprises an amino acid sequence that is at least 90% identical to the amino acid sequence of SEQ ID NO:20, and the VL comprises an amino acid sequence that is at least 90% identical to the amino acid sequence of SEQ ID NO:60;

(36) the VH comprises an amino acid sequence that is at least 90% identical to the amino acid sequence of SEQ ID NO:20, and the VL comprises an amino acid sequence that is at least 90% identical to the amino acid sequence of SEQ ID NO:61;

(37) the VH comprises an amino acid sequence that is at least 90% identical to the amino acid sequence of SEQ ID NO:21, and the VL comprises an amino acid sequence that is at least 90% identical to the amino acid sequence of SEQ ID NO:68;

(38) the VH comprises an amino acid sequence that is at least 90% identical to the amino acid sequence of SEQ ID NO:21, and the VL comprises an amino acid sequence that is at least 90% identical to the amino acid sequence of SEQ ID NO:69;

(39) the VH comprises an amino acid sequence that is at least 90% identical to the amino acid sequence of SEQ ID NO:21, and the VL comprises an amino acid sequence that is at least 90% identical to the amino acid sequence of SEQ ID NO:70;

(40) the VH comprises an amino acid sequence that is at least 90% identical to the amino acid sequence of SEQ ID NO:21, and the VL comprises an amino acid sequence that is at least 90% identical to the amino acid sequence of SEQ ID NO:62;

(41) the VH comprises an amino acid sequence that is at least 90% identical to the amino acid sequence of SEQ ID NO:21, and the VL comprises an amino acid sequence that is at least 90% identical to the amino acid sequence of SEQ ID NO:63;

(42) the VH comprises an amino acid sequence that is at least 90% identical to the amino acid sequence of SEQ ID NO:21, and the VL comprises an amino acid sequence that is at least 90% identical to the amino acid sequence of SEQ ID NO:64;

(43) the VH comprises an amino acid sequence that is at least 90% identical to the amino acid sequence of SEQ ID NO:22, and the VL comprises an amino acid sequence that is at least 90% identical to the amino acid sequence of SEQ ID NO:68;

(44) the VH comprises an amino acid sequence that is at least 90% identical to the amino acid sequence of SEQ ID NO:22, and the VL comprises an amino acid sequence that is at least 90% identical to the amino acid sequence of SEQ ID NO:69;

(45) the VH comprises an amino acid sequence that is at least 90% identical to the amino acid sequence of SEQ ID NO:22, and the VL comprises an amino acid sequence that is at least 90% identical to the amino acid sequence of SEQ ID NO:70;

(46) the VH comprises an amino acid sequence that is at least 90% identical to the amino acid sequence of SEQ ID NO:23, and the VL comprises an amino acid sequence that is at least 90% identical to the amino acid sequence of SEQ ID NO:68;

(47) the VH comprises an amino acid sequence that is at least 90% identical to the amino acid sequence of SEQ ID NO:23, and the VL comprises an amino acid sequence that is at least 90% identical to the amino acid sequence of SEQ ID NO:69;

(48) the VH comprises an amino acid sequence that is at least 90% identical to the amino acid sequence of SEQ ID NO:24, and the VL comprises an amino acid sequence that is at least 90% identical to the amino acid sequence of SEQ ID NO:68;

(49) the VH comprises an amino acid sequence that is at least 90% identical to the amino acid sequence of SEQ ID NO:24, and the VL comprises an amino acid sequence that is at least 90% identical to the amino acid sequence of SEQ ID NO:62;

(50) the VH comprises an amino acid sequence that is at least 90% identical to the amino acid sequence of SEQ ID NO:24, and the VL comprises an amino acid sequence that is at least 90% identical to the amino acid sequence of SEQ ID NO:63;

(51) the VH comprises an amino acid sequence that is at least 90% identical to the amino acid sequence of SEQ ID NO:24, and the VL comprises an amino acid sequence that is at least 90% identical to the amino acid sequence of SEQ ID NO:64;

(52) the VH comprises an amino acid sequence that is at least 90% identical to the amino acid sequence of SEQ ID NO:25, and the VL comprises an amino acid sequence that is at least 90% identical to the amino acid sequence of SEQ ID NO:68;

(53) the VH comprises an amino acid sequence that is at least 90% identical to the amino acid sequence of SEQ ID NO:25, and the VL comprises an amino acid sequence that is at least 90% identical to the amino acid sequence of SEQ ID NO:69;

(54) the VH comprises an amino acid sequence that is at least 90% identical to the amino acid sequence of SEQ ID NO:25, and the VL comprises an amino acid sequence that is at least 90% identical to the amino acid sequence of SEQ ID NO:70;

(55) the VH comprises an amino acid sequence that is at least 90% identical to the amino acid sequence of SEQ ID NO:25, and the VL comprises an amino acid sequence that is at least 90% identical to the amino acid sequence of SEQ ID NO:62;

(56) the VH comprises an amino acid sequence that is at least 90% identical to the amino acid sequence of SEQ ID NO:25, and the VL comprises an amino acid sequence that is at least 90% identical to the amino acid sequence of SEQ ID NO:63;

(57) the VH comprises an amino acid sequence that is at least 90% identical to the amino acid sequence of SEQ ID NO:25, and the VL comprises an amino acid sequence that is at least 90% identical to the amino acid sequence of SEQ ID NO:64;

(58) the VH comprises an amino acid sequence that is at least 90% identical to the amino acid sequence of SEQ ID NO:26, and the VL comprises an amino acid sequence that is at least 90% identical to the amino acid sequence of SEQ ID NO:68;

(59) the VH comprises an amino acid sequence that is at least 90% identical to the amino acid sequence of SEQ ID NO:26, and the VL comprises an amino acid sequence that is at least 90% identical to the amino acid sequence of SEQ ID NO:62;

(60) the VH comprises an amino acid sequence that is at least 90% identical to the amino acid sequence of SEQ ID NO:26, and the VL comprises an amino acid sequence that is at least 90% identical to the amino acid sequence of SEQ ID NO:63;

(61) the VH comprises an amino acid sequence that is at least 90% identical to the amino acid sequence of SEQ ID NO:27, and the VL comprises an amino acid sequence that is at least 90% identical to the amino acid sequence of SEQ ID NO:68;

(62) the VH comprises an amino acid sequence that is at least 90% identical to the amino acid sequence of SEQ ID NO:27, and the VL comprises an amino acid sequence that is at least 90% identical to the amino acid sequence of SEQ ID NO:69;

(63) the VH comprises an amino acid sequence that is at least 90% identical to the amino acid sequence of SEQ ID NO:27, and the VL comprises an amino acid sequence that is at least 90% identical to the amino acid sequence of SEQ ID NO:70;

(64) the VH comprises an amino acid sequence that is at least 90% identical to the amino acid sequence of SEQ ID NO:27, and the VL comprises an amino acid sequence that is at least 90% identical to the amino acid sequence of SEQ ID NO:63;
(65) the VH comprises an amino acid sequence that is at least 90% identical to the amino acid sequence of SEQ ID NO:27, and the VL comprises an amino acid sequence that is at least 90% identical to the amino acid sequence of SEQ ID NO:64;
(66) the VH comprises an amino acid sequence that is at least 90% identical to the amino acid sequence of SEQ ID NO:28, and the VL comprises an amino acid sequence that is at least 90% identical to the amino acid sequence of SEQ ID NO:68;
(67) the VH comprises an amino acid sequence that is at least 90% identical to the amino acid sequence of SEQ ID NO:28, and the VL comprises an amino acid sequence that is at least 90% identical to the amino acid sequence of SEQ ID NO:62;
(68) the VH comprises an amino acid sequence that is at least 90% identical to the amino acid sequence of SEQ ID NO:29, and the VL comprises an amino acid sequence that is at least 90% identical to the amino acid sequence of SEQ ID NO:68;
(69) the VH comprises an amino acid sequence that is at least 90% identical to the amino acid sequence of SEQ ID NO:29, and the VL comprises an amino acid sequence that is at least 90% identical to the amino acid sequence of SEQ ID NO:62;
(70) the VH comprises an amino acid sequence that is at least 90% identical to the amino acid sequence of SEQ ID NO:30, and the VL comprises an amino acid sequence that is at least 90% identical to the amino acid sequence of SEQ ID NO:68;
(71) the VH comprises an amino acid sequence that is at least 90% identical to the amino acid sequence of SEQ ID NO:30, and the VL comprises an amino acid sequence that is at least 90% identical to the amino acid sequence of SEQ ID NO:62;
(72) the VH comprises an amino acid sequence that is at least 90% identical to the amino acid sequence of SEQ ID NO:30, and the VL comprises an amino acid sequence that is at least 90% identical to the amino acid sequence of SEQ ID NO:63;
(73) the VH comprises an amino acid sequence that is at least 90% identical to the amino acid sequence of SEQ ID NO:30, and the VL comprises an amino acid sequence that is at least 90% identical to the amino acid sequence of SEQ ID NO:64;
(74) the VH comprises an amino acid sequence that is at least 90% identical to the amino acid sequence of SEQ ID NO:31, and the VL comprises an amino acid sequence that is at least 90% identical to the amino acid sequence of SEQ ID NO:62;
(75) the VH comprises an amino acid sequence that is at least 90% identical to the amino acid sequence of SEQ ID NO:31, and the VL comprises an amino acid sequence that is at least 90% identical to the amino acid sequence of SEQ ID NO:63;
(76) the VH comprises an amino acid sequence that is at least 90% identical to the amino acid sequence of SEQ ID NO:31, and the VL comprises an amino acid sequence that is at least 90% identical to the amino acid sequence of SEQ ID NO:64;
(77) the VH comprises an amino acid sequence that is at least 90% identical to the amino acid sequence of SEQ ID NO:31, and the VL comprises an amino acid sequence that is at least 90% identical to the amino acid sequence of SEQ ID NO:68;
(78) the VH comprises an amino acid sequence that is at least 90% identical to the amino acid sequence of SEQ ID NO:32, and the VL comprises an amino acid sequence that is at least 90% identical to the amino acid sequence of SEQ ID NO:68;
(79) the VH comprises an amino acid sequence that is at least 90% identical to the amino acid sequence of SEQ ID NO:32, and the VL comprises an amino acid sequence that is at least 90% identical to the amino acid sequence of SEQ ID NO:62;
(80) the VH comprises an amino acid sequence that is at least 90% identical to the amino acid sequence of SEQ ID NO:32, and the VL comprises an amino acid sequence that is at least 90% identical to the amino acid sequence of SEQ ID NO:63;
(81) the VH comprises an amino acid sequence that is at least 90% identical to the amino acid sequence of SEQ ID NO:33, and the VL comprises an amino acid sequence that is at least 90% identical to the amino acid sequence of SEQ ID NO:68;
(82) the VH comprises an amino acid sequence that is at least 90% identical to the amino acid sequence of SEQ ID NO:33, and the VL comprises an amino acid sequence that is at least 90% identical to the amino acid sequence of SEQ ID NO:62;
(83) the VH comprises an amino acid sequence that is at least 90% identical to the amino acid sequence of SEQ ID NO:39, and the VL comprises an amino acid sequence that is at least 90% identical to the amino acid sequence of SEQ ID NO:68; or
(84) the VH comprises an amino acid sequence that is at least 90% identical to the amino acid sequence of SEQ ID NO:39, and the VL comprises an amino acid sequence that is at least 90% identical to the amino acid sequence of SEQ ID NO:62.

3. The antibody or antigen-binding fragment thereof of claim 2, wherein:
(1) the VH comprises the amino acid sequence of SEQ ID NO:1, and the VL comprises the amino acid sequence of SEQ ID NO:45;
(2) the VH comprises the amino acid sequence of SEQ ID NO:2, and the VL comprises the amino acid sequence of SEQ ID NO:46;
(3) the VH comprises the amino acid sequence of SEQ ID NO:3, and the VL comprises the amino acid sequence of SEQ ID NO:47;
(4) the VH comprises the amino acid sequence of SEQ ID NO:4, and the VL comprises the amino acid sequence of SEQ ID NO:48;
(5) the VH comprises the amino acid sequence of SEQ ID NO:5, and the VL comprises the amino acid sequence of SEQ ID NO:49;
(6) the VH comprises the amino acid sequence of SEQ ID NO:6, and the VL comprises the amino acid sequence of SEQ ID NO:50;
(7) the VH comprises the amino acid sequence of SEQ ID NO:7, and the VL comprises the amino acid sequence of SEQ ID NO:51;
(8) the VH comprises the amino acid sequence of SEQ ID NO:8, and the VL comprises the amino acid sequence of SEQ ID NO:52;
(9) the VH comprises the amino acid sequence of SEQ ID NO:9, and the VL comprises the amino acid sequence of SEQ ID NO:53;
(10) the VH comprises the amino acid sequence of SEQ ID NO:10, and the VL comprises the amino acid sequence of SEQ ID NO:54;

(11) the VH comprises the amino acid sequence of SEQ ID NO:11, and the VL comprises the amino acid sequence of SEQ ID NO:55;

(12) the VH comprises the amino acid sequence of SEQ ID NO:12, and the VL comprises the amino acid sequence of SEQ ID NO:56;

(13) the VH comprises an amino acid sequence of SEQ ID NO:16, and the VL comprises an amino acid sequence of SEQ ID NO:65;

(14) the VH comprises an amino acid sequence of SEQ ID NO:16, and the VL comprises an amino acid sequence of SEQ ID NO:66;

(15) the VH comprises an amino acid sequence of SEQ ID NO:16, and the VL comprises an amino acid sequence of SEQ ID NO:67;

(16) the VH comprises an amino acid sequence of SEQ ID NO:16, and the VL comprises an amino acid sequence of SEQ ID NO:59;

(17) the VH comprises an amino acid sequence of SEQ ID NO:16, and the VL comprises an amino acid sequence of SEQ ID NO:60;

(18) the VH comprises an amino acid sequence of SEQ ID NO:16, and the VL comprises an amino acid sequence of SEQ ID NO:61;

(19) the VH comprises an amino acid sequence of SEQ ID NO:17, and the VL comprises an amino acid sequence of SEQ ID NO:65;

(20) the VH comprises an amino acid sequence of SEQ ID NO:17, and the VL comprises an amino acid sequence of SEQ ID NO:66;

(21) the VH comprises an amino acid sequence of SEQ ID NO:17, and the VL comprises an amino acid sequence of SEQ ID NO:67;

(22) the VH comprises an amino acid sequence of SEQ ID NO:18, and the VL comprises an amino acid sequence of SEQ ID NO:65;

(23) the VH comprises an amino acid sequence of SEQ ID NO:18, and the VL comprises an amino acid sequence of SEQ ID NO:66;

(24) the VH comprises an amino acid sequence of SEQ ID NO:18, and the VL comprises an amino acid sequence of SEQ ID NO:67;

(25) the VH comprises an amino acid sequence of SEQ ID NO:19, and the VL comprises an amino acid sequence of SEQ ID NO:65;

(26) the VH comprises an amino acid sequence of SEQ ID NO:19, and the VL comprises an amino acid sequence of SEQ ID NO:66;

(27) the VH comprises an amino acid sequence of SEQ ID NO:19, and the VL comprises an amino acid sequence of SEQ ID NO:67;

(28) the VH comprises an amino acid sequence of SEQ ID NO:19, and the VL comprises an amino acid sequence of SEQ ID NO:59;

(29) the VH comprises an amino acid sequence of SEQ ID NO:19, and the VL comprises an amino acid sequence of SEQ ID NO:60;

(30) the VH comprises an amino acid sequence of SEQ ID NO:19, and the VL comprises an amino acid sequence of SEQ ID NO:61;

(31) the VH comprises an amino acid sequence of SEQ ID NO:20, and the VL comprises an amino acid sequence of SEQ ID NO:66;

(32) the VH comprises an amino acid sequence of SEQ ID NO:20, and the VL comprises an amino acid sequence of SEQ ID NO:65;

(33) the VH comprises an amino acid sequence of SEQ ID NO:20, and the VL comprises an amino acid sequence of SEQ ID NO:67;

(34) the VH comprises an amino acid sequence of SEQ ID NO:20, and the VL comprises an amino acid sequence of SEQ ID NO:59;

(35) the VH comprises an amino acid sequence of SEQ ID NO:20, and the VL comprises an amino acid sequence of SEQ ID NO:60;

(36) the VH comprises an amino acid sequence of SEQ ID NO:20, and the VL comprises an amino acid sequence of SEQ ID NO:61;

(37) the VH comprises an amino acid sequence of SEQ ID NO:21, and the VL comprises an amino acid sequence of SEQ ID NO:68;

(38) the VH comprises an amino acid sequence of SEQ ID NO:21, and the VL comprises an amino acid sequence of SEQ ID NO:69;

(39) the VH comprises an amino acid sequence of SEQ ID NO:21, and the VL comprises an amino acid sequence of SEQ ID NO:70;

(40) the VH comprises an amino acid sequence of SEQ ID NO:21, and the VL comprises an amino acid sequence of SEQ ID NO:62;

(41) the VH comprises an amino acid sequence of SEQ ID NO:21, and the VL comprises an amino acid sequence of SEQ ID NO:63;

(42) the VH comprises an amino acid sequence of SEQ ID NO:21, and the VL comprises an amino acid sequence of SEQ ID NO:64;

(43) the VH comprises an amino acid sequence of SEQ ID NO:22, and the VL comprises an amino acid sequence of SEQ ID NO:68;

(44) the VH comprises an amino acid sequence of SEQ ID NO:22, and the VL comprises an amino acid sequence of SEQ ID NO:69;

(45) the VH comprises an amino acid sequence of SEQ ID NO:22, and the VL comprises an amino acid sequence of SEQ ID NO:70;

(46) the VH comprises an amino acid sequence of SEQ ID NO:23, and the VL comprises an amino acid sequence of SEQ ID NO:68;

(47) the VH comprises an amino acid sequence of SEQ ID NO:23, and the VL comprises an amino acid sequence of SEQ ID NO:69;

(48) the VH comprises an amino acid sequence of SEQ ID NO:24, and the VL comprises an amino acid sequence of SEQ ID NO:68;

(49) the VH comprises an amino acid sequence of SEQ ID NO:24, and the VL comprises an amino acid sequence of SEQ ID NO:62;

(50) the VH comprises an amino acid sequence of SEQ ID NO:24, and the VL comprises an amino acid sequence of SEQ ID NO:63;

(51) the VH comprises an amino acid sequence of SEQ ID NO:24, and the VL comprises an amino acid sequence of SEQ ID NO:64;

(52) the VH comprises an amino acid sequence of SEQ ID NO:25, and the VL comprises an amino acid sequence of SEQ ID NO:68;

(53) the VH comprises an amino acid sequence of SEQ ID NO:25, and the VL comprises an amino acid sequence of SEQ ID NO:69;

(54) the VH comprises an amino acid sequence of SEQ ID NO:25, and the VL comprises an amino acid sequence of SEQ ID NO:70;

(55) the VH comprises an amino acid sequence of SEQ ID NO:25, and the VL comprises an amino acid sequence of SEQ ID NO:62;

(56) the VH comprises an amino acid sequence of SEQ ID NO:25, and the VL comprises an amino acid sequence of SEQ ID NO:63;

(57) the VH comprises an amino acid sequence of SEQ ID NO:25, and the VL comprises an amino acid sequence of SEQ ID NO:64;

(58) the VH comprises an amino acid sequence of SEQ ID NO:26, and the VL comprises an amino acid sequence of SEQ ID NO:68;

(59) the VH comprises an amino acid sequence of SEQ ID NO:26, and the VL comprises an amino acid sequence of SEQ ID NO:62;

(60) the VH comprises an amino acid sequence of SEQ ID NO:26, and the VL comprises an amino acid sequence of SEQ ID NO:63;

(61) the VH comprises an amino acid sequence of SEQ ID NO:27, and the VL comprises an amino acid sequence of SEQ ID NO:68;

(62) the VH comprises an amino acid sequence of SEQ ID NO:27, and the VL comprises an amino acid sequence of SEQ ID NO:69;

(63) the VH comprises an amino acid sequence of SEQ ID NO:27, and the VL comprises an amino acid sequence of SEQ ID NO:70;

(64) the VH comprises an amino acid sequence of SEQ ID NO:27, and the VL comprises an amino acid sequence of SEQ ID NO:63;

(65) the VH comprises an amino acid sequence of SEQ ID NO:27, and the VL comprises an amino acid sequence of SEQ ID NO:64;

(66) the VH comprises an amino acid sequence of SEQ ID NO:28, and the VL comprises an amino acid sequence of SEQ ID NO:68;

(67) the VH comprises an amino acid sequence of SEQ ID NO:28, and the VL comprises an amino acid sequence of SEQ ID NO:62;

(68) the VH comprises an amino acid sequence of SEQ ID NO:29, and the VL comprises an amino acid sequence of SEQ ID NO:68;

(69) the VH comprises an amino acid sequence of SEQ ID NO:29, and the VL comprises an amino acid sequence of SEQ ID NO:62;

(70) the VH comprises an amino acid sequence of SEQ ID NO:30, and the VL comprises an amino acid sequence of SEQ ID NO:68;

(71) the VH comprises an amino acid sequence of SEQ ID NO:30, and the VL comprises an amino acid sequence of SEQ ID NO:62;

(72) the VH comprises an amino acid sequence of SEQ ID NO:30, and the VL comprises an amino acid sequence of SEQ ID NO:63;

(73) the VH comprises an amino acid sequence of SEQ ID NO:30, and the VL comprises an amino acid sequence of SEQ ID NO:64;

(74) the VH comprises an amino acid sequence of SEQ ID NO:31, and the VL comprises an amino acid sequence of SEQ ID NO:62;

(75) the VH comprises an amino acid sequence of SEQ ID NO:31, and the VL comprises an amino acid sequence of SEQ ID NO:63;

(76) the VH comprises an amino acid sequence of SEQ ID NO:31, and the VL comprises an amino acid sequence of SEQ ID NO:64;

(77) the VH comprises an amino acid sequence of SEQ ID NO:31, and the VL comprises an amino acid sequence of SEQ ID NO:68;

(78) the VH comprises an amino acid sequence of SEQ ID NO:32, and the VL comprises an amino acid sequence of SEQ ID NO:68;

(79) the VH comprises an amino acid sequence of SEQ ID NO:32, and the VL comprises an amino acid sequence of SEQ ID NO:62;

(80) the VH comprises an amino acid sequence of SEQ ID NO:32, and the VL comprises an amino acid sequence of SEQ ID NO:63;

(81) the VH comprises an amino acid sequence of SEQ ID NO:33, and the VL comprises an amino acid sequence of SEQ ID NO:68;

(82) the VH comprises an amino acid sequence of SEQ ID NO:33, and the VL comprises an amino acid sequence of SEQ ID NO:62;

(83) the VH comprises an amino acid sequence of SEQ ID NO:39, and the VL comprises an amino acid sequence of SEQ ID NO:68; or

(84) the VH comprises an amino acid sequence of SEQ ID NO:39, and the VL comprises an amino acid sequence of SEQ ID NO:62.

4. The antibody or antigen-binding fragment thereof of claim 1, wherein the VH is fused to a heavy chain constant region of an immunoglobulin; and/or the VL is fused to a light chain constant region (CL) of an immunoglobulin.

5. The antibody or antigen-binding fragment thereof of claim 1, wherein the antibody or antigen-binding fragment thereof is a rodent, chimeric, partially humanized, or fully humanized antibody or antigen-binding fragment thereof.

6. The antibody of claim 5, further comprising a constant domain of a human IgG1.

7. The antibody of claim 6, wherein:

(1) the VH comprises the amino acid sequence of SEQ ID NO:278, and the VL comprises the amino acid sequence of SEQ ID NO:322;

(2) the VH comprises the amino acid sequence of SEQ ID NO:279, and the VL comprises the amino acid sequence of SEQ ID NO:323;

(3) the VH comprises the amino acid sequence of SEQ ID NO:280, and the VL comprises the amino acid sequence of SEQ ID NO:324;

(4) the VH comprises the amino acid sequence of SEQ ID NO:281, and the VL comprises the amino acid sequence of SEQ ID NO:325;

(5) the VH comprises the amino acid sequence of SEQ ID NO:282, and the VL comprises the amino acid sequence of SEQ ID NO:326;

(6) the VH comprises the amino acid sequence of SEQ ID NO:283, and the VL comprises the amino acid sequence of SEQ ID NO:327;

(7) the VH comprises the amino acid sequence of SEQ ID NO:284, and the VL comprises the amino acid sequence of SEQ ID NO:328;

(8) the VH comprises the amino acid sequence of SEQ ID NO:285, and the VL comprises the amino acid sequence of SEQ ID NO:329;

(9) the VH comprises the amino acid sequence of SEQ ID NO:286, and the VL comprises the amino acid sequence of SEQ ID NO:330;

(10) the VH comprises the amino acid sequence of SEQ ID NO:287, and the VL comprises the amino acid sequence of SEQ ID NO:331;

(11) the VH comprises the amino acid sequence of SEQ ID NO:288, and the VL comprises the amino acid sequence of SEQ ID NO:332;
(12) the VH comprises the amino acid sequence of SEQ ID NO:289, and the VL comprises the amino acid sequence of SEQ ID NO:333;
(13) the VH comprises an amino acid sequence of SEQ ID NO:293, and the VL comprises an amino acid sequence of SEQ ID NO:342;
(14) the VH comprises an amino acid sequence of SEQ ID NO: 293, and the VL comprises an amino acid sequence of SEQ ID NO:343;
(15) the VH comprises an amino acid sequence of SEQ ID NO: 293, and the VL comprises an amino acid sequence of SEQ ID NO:344;
(16) the VH comprises an amino acid sequence of SEQ ID NO: 293, and the VL comprises an amino acid sequence of SEQ ID NO:336;
(17) the VH comprises an amino acid sequence of SEQ ID NO: 293, and the VL comprises an amino acid sequence of SEQ ID NO:337;
(18) the VH comprises an amino acid sequence of SEQ ID NO: 293, and the VL comprises an amino acid sequence of SEQ ID NO:338;
(19) the VH comprises an amino acid sequence of SEQ ID NO:294, and the VL comprises an amino acid sequence of SEQ ID NO:342;
(20) the VH comprises an amino acid sequence of SEQ ID NO: 294, and the VL comprises an amino acid sequence of SEQ ID NO:343;
(21) the VH comprises an amino acid sequence of SEQ ID NO: 294, and the VL comprises an amino acid sequence of SEQ ID NO:344;
(22) the VH comprises an amino acid sequence of SEQ ID NO:295, and the VL comprises an amino acid sequence of SEQ ID NO:342;
(23) the VH comprises an amino acid sequence of SEQ ID NO: 295, and the VL comprises an amino acid sequence of SEQ ID NO:343;
(24) the VH comprises an amino acid sequence of SEQ ID NO: 295, and the VL comprises an amino acid sequence of SEQ ID NO:344;
(25) the VH comprises an amino acid sequence of SEQ ID NO:296, and the VL comprises an amino acid sequence of SEQ ID NO:342;
(26) the VH comprises an amino acid sequence of SEQ ID NO: 296, and the VL comprises an amino acid sequence of SEQ ID NO:343;
(27) the VH comprises an amino acid sequence of SEQ ID NO: 296, and the VL comprises an amino acid sequence of SEQ ID NO:344;
(28) the VH comprises an amino acid sequence of SEQ ID NO: 296, and the VL comprises an amino acid sequence of SEQ ID NO:336;
(29) the VH comprises an amino acid sequence of SEQ ID NO: 296, and the VL comprises an amino acid sequence of SEQ ID NO:337;
(30) the VH comprises an amino acid sequence of SEQ ID NO: 296, and the VL comprises an amino acid sequence of SEQ ID NO:338;
(31) the VH comprises an amino acid sequence of SEQ ID NO:297, and the VL comprises an amino acid sequence of SEQ ID NO:343;
(32) the VH comprises an amino acid sequence of SEQ ID NO: 297, and the VL comprises an amino acid sequence of SEQ ID NO:342;
(33) the VH comprises an amino acid sequence of SEQ ID NO: 297, and the VL comprises an amino acid sequence of SEQ ID NO:344;
(34) the VH comprises an amino acid sequence of SEQ ID NO: 297, and the VL comprises an amino acid sequence of SEQ ID NO:336;
(35) the VH comprises an amino acid sequence of SEQ ID NO: 297, and the VL comprises an amino acid sequence of SEQ ID NO:337;
(36) the VH comprises an amino acid sequence of SEQ ID NO: 297, and the VL comprises an amino acid sequence of SEQ ID NO:338;
(37) the VH comprises an amino acid sequence of SEQ ID NO:298, and the VL comprises an amino acid sequence of SEQ ID NO:345;
(38) the VH comprises an amino acid sequence of SEQ ID NO: 298, and the VL comprises an amino acid sequence of SEQ ID NO:346;
(39) the VH comprises an amino acid sequence of SEQ ID NO: 298, and the VL comprises an amino acid sequence of SEQ ID NO:347;
(40) the VH comprises an amino acid sequence of SEQ ID NO: 298, and the VL comprises an amino acid sequence of SEQ ID NO:339;
(41) the VH comprises an amino acid sequence of SEQ ID NO: 298, and the VL comprises an amino acid sequence of SEQ ID NO:340;
(42) the VH comprises an amino acid sequence of SEQ ID NO: 298, and the VL comprises an amino acid sequence of SEQ ID NO:341;
(43) the VH comprises an amino acid sequence of SEQ ID NO:299, and the VL comprises an amino acid sequence of SEQ ID NO:345;
(44) the VH comprises an amino acid sequence of SEQ ID NO: 299, and the VL comprises an amino acid sequence of SEQ ID NO:346;
(45) the VH comprises an amino acid sequence of SEQ ID NO: 299, and the VL comprises an amino acid sequence of SEQ ID NO:347;
(46) the VH comprises an amino acid sequence of SEQ ID NO:300, and the VL comprises an amino acid sequence of SEQ ID NO:345;
(47) the VH comprises an amino acid sequence of SEQ ID NO: 300, and the VL comprises an amino acid sequence of SEQ ID NO:346;
(48) the VH comprises an amino acid sequence of SEQ ID NO:301, and the VL comprises an amino acid sequence of SEQ ID NO:345;
(49) the VH comprises an amino acid sequence of SEQ ID NO: 301, and the VL comprises an amino acid sequence of SEQ ID NO:339;
(50) the VH comprises an amino acid sequence of SEQ ID NO: 301, and the VL comprises an amino acid sequence of SEQ ID NO:340;
(51) the VH comprises an amino acid sequence of SEQ ID NO: 301, and the VL comprises an amino acid sequence of SEQ ID NO:341;
(52) the VH comprises an amino acid sequence of SEQ ID NO:302, and the VL comprises an amino acid sequence of SEQ ID NO:345;
(53) the VH comprises an amino acid sequence of SEQ ID NO: 302, and the VL comprises an amino acid sequence of SEQ ID NO:346;
(54) the VH comprises an amino acid sequence of SEQ ID NO: 302, and the VL comprises an amino acid sequence of SEQ ID NO:347;

(55) the VH comprises an amino acid sequence of SEQ ID NO: 302, and the VL comprises an amino acid sequence of SEQ ID NO:339;

(56) the VH comprises an amino acid sequence of SEQ ID NO: 302, and the VL comprises an amino acid sequence of SEQ ID NO:340;

(57) the VH comprises an amino acid sequence of SEQ ID NO: 302, and the VL comprises an amino acid sequence of SEQ ID NO:341;

(58) the VH comprises an amino acid sequence of SEQ ID NO:303, and the VL comprises an amino acid sequence of SEQ ID NO:345;

(59) the VH comprises an amino acid sequence of SEQ ID NO: 303, and the VL comprises an amino acid sequence of SEQ ID NO:339;

(60) the VH comprises an amino acid sequence of SEQ ID NO: 303, and the VL comprises an amino acid sequence of SEQ ID NO:340;

(61) the VH comprises an amino acid sequence of SEQ ID NO:304, and the VL comprises an amino acid sequence of SEQ ID NO:345;

(62) the VH comprises an amino acid sequence of SEQ ID NO: 304, and the VL comprises an amino acid sequence of SEQ ID NO:346;

(63) the VH comprises an amino acid sequence of SEQ ID NO: 304, and the VL comprises an amino acid sequence of SEQ ID NO:347;

(64) the VH comprises an amino acid sequence of SEQ ID NO: 304, and the VL comprises an amino acid sequence of SEQ ID NO:340;

(65) the VH comprises an amino acid sequence of SEQ ID NO: 304, and the VL comprises an amino acid sequence of SEQ ID NO:341;

(66) the VH comprises an amino acid sequence of SEQ ID NO:305, and the VL comprises an amino acid sequence of SEQ ID NO:345;

(67) the VH comprises an amino acid sequence of SEQ ID NO: 305, and the VL comprises an amino acid sequence of SEQ ID NO:339;

(68) the VH comprises an amino acid sequence of SEQ ID NO:306, and the VL comprises an amino acid sequence of SEQ ID NO:345;

(69) the VH comprises an amino acid sequence of SEQ ID NO: 306, and the VL comprises an amino acid sequence of SEQ ID NO:339;

(70) the VH comprises an amino acid sequence of SEQ ID NO:307, and the VL comprises an amino acid sequence of SEQ ID NO:345;

(71) the VH comprises an amino acid sequence of SEQ ID NO: 307, and the VL comprises an amino acid sequence of SEQ ID NO:339;

(72) the VH comprises an amino acid sequence of SEQ ID NO: 307, and the VL comprises an amino acid sequence of SEQ ID NO:340;

(73) the VH comprises an amino acid sequence of SEQ ID NO: 307, and the VL comprises an amino acid sequence of SEQ ID NO:341;

(74) the VH comprises an amino acid sequence of SEQ ID NO:308, and the VL comprises an amino acid sequence of SEQ ID NO:339;

(75) the VH comprises an amino acid sequence of SEQ ID NO: 308, and the VL comprises an amino acid sequence of SEQ ID NO:340;

(76) the VH comprises an amino acid sequence of SEQ ID NO: 308, and the VL comprises an amino acid sequence of SEQ ID NO:341;

(77) the VH comprises an amino acid sequence of SEQ ID NO: 308, and the VL comprises an amino acid sequence of SEQ ID NO:345;

(78) the VH comprises an amino acid sequence of SEQ ID NO:309, and the VL comprises an amino acid sequence of SEQ ID NO:345;

(79) the VH comprises an amino acid sequence of SEQ ID NO: 309, and the VL comprises an amino acid sequence of SEQ ID NO:339;

(80) the VH comprises an amino acid sequence of SEQ ID NO: 309, and the VL comprises an amino acid sequence of SEQ ID NO:340;

(81) the VH comprises an amino acid sequence of SEQ ID NO:310, and the VL comprises an amino acid sequence of SEQ ID NO:345;

(82) the VH comprises an amino acid sequence of SEQ ID NO: 310, and the VL comprises an amino acid sequence of SEQ ID NO:339;

(83) the VH comprises an amino acid sequence of SEQ ID NO:316, and the VL comprises an amino acid sequence of SEQ ID NO:345; or

(84) the VH comprises an amino acid sequence of SEQ ID NO: 316, and the VL comprises an amino acid sequence of SEQ ID NO:339.

8. The antibody or antigen-binding fragment thereof of claim 1, further comprising an additional antibody moiety, wherein the additional antibody moiety is capable of specifically binding to an additional antigen, and wherein the additional antibody moiety is a Fab, a Fab', a $(Fab')_2$, an Fv, a single chain Fv (scFv), an scFv-scFv, a minibody, a diabody, a sdAb, or an antibody mimetic.

9. The antibody or antigen-binding fragment thereof of claim 8, wherein the additional antibody moiety is capable of specifically binding to CTLA-4, TIGIT, TIM-3, or LAG-3, and wherein the additional antibody moiety is a sdAb.

10. The antibody or antigen-binding fragment thereof of claim 9, wherein the antibody or antigen-binding fragment comprises a full-length IgG, wherein the amino-terminus or carboxyl-terminus of the heavy chain or light chain of the full-length IgG capable of specifically recognizing PD-L1 is fused to the carboxyl-terminus or amino-terminus of the sdAb capable of specifically binding to CTLA-4, TIGIT, TIM-3 or LAG-3.

11. The antibody or antigen-binding fragment thereof of claim 10, wherein the full-length IgG capable of specifically recognizing PD-L1 is fused to the sdAb capable of specifically binding to CTLA-4, TIGIT, TIM-3 or LAG-3 via a peptide linker comprising the amino acid sequence of any one of SEQ ID NOs:397-399.

12. The antibody or antigen-binding fragment thereof of claim 1, wherein PD-L1 is a human PD-L1.

13. The antibody or an antigen-binding fragment thereof of claim 1, wherein the HCDR1, HCDR2, HCDR3, LCDR1, LCDR2, and LCDR3 comprise the amino acid sequences of:

(1) SEQ ID NOs: 72, 84, 99,111,125, and 137, respectively; or (2) SEQ ID NOs: 72, 84, 99,122,125, and 137, respectively.

14. The antibody or an antigen-binding fragment thereof of claim 1, wherein the HCDR1, HCDR2, HCDR3, LCDR1, LCDR2, and LCDR3 comprise the amino acid sequences of:

(1) SEQ ID NOs: 75, 87,102,114, 128, and 140, respectively;

(2) SEQ ID NOs: 75, 95,102,114, 128, and 140, respectively;

(3) SEQ ID NOs: 75, 96,102,114, 128, and 140, respectively;

(4) SEQ ID NOs: 75, 97,102,114, 128, and 140, respectively;

(5) SEQ ID NOs: 75, 87,102,123, 128, and 140, respectively;

(6) SEQ ID NOs: 75, 95,102,123, 128, and 140, respectively;

(7) SEQ ID NOs: 75, 96,102,123, 128, and 140, respectively; or (8) SEQ ID NOs: 75, 97,102,123, 128, and 140, respectively.

15. The antibody or an antigen-binding fragment thereof of claim 3, wherein:

(1) the VH comprises an amino acid sequence of SEQ ID NO: 27, and the VL comprises an amino acid sequence of SEQ ID NO: 68;

(2) the VH comprises an amino acid sequence of SEQ ID NO: 31, and the VL comprises an amino acid sequence of SEQ ID NO: 68;

(3) the VH comprises an amino acid sequence of SEQ ID NO: 21, and the VL comprises an amino acid sequence of SEQ ID NO: 68;

(4) the VH comprises an amino acid sequence of SEQ ID NO: 25, and the VL comprises an amino acid sequence of SEQ ID NO: 68;

(5) the VH comprises an amino acid sequence of SEQ ID NO: 16, and the VL comprises an amino acid sequence of SEQ ID NO: 65; or (6) the VH comprises an amino acid sequence of SEQ ID NO: 19, and the VL comprises an amino acid sequence of SEQ ID NO: 65.

16. A nucleic acid molecule, encoding the antibody or an antigen-binding fragment thereof of claim 1.

17. A vector, comprising the nucleic acid molecule of claim 16.

18. A pharmaceutical composition comprising the antibody or antigen-binding fragment thereof of claim 1, and a pharmaceutically acceptable carrier.

19. A method of treating a PD-L1 related disease in a subject in need thereof, the method comprising administering to the subject in need thereof the pharmaceutical composition of claim 18.

20. The method of claim 19, wherein the PD-L1 related disease is a cancer or a pathogenic infection.

21. The method of claim 19, wherein the pharmaceutical composition is administered to the subject in need thereof in combination with an additional cancer therapy, wherein the additional cancer therapy is a surgery, radiation, chemotherapy, immunotherapy, hormone therapy, or a combination thereof.

* * * * *

UNITED STATES PATENT AND TRADEMARK OFFICE

CERTIFICATE OF CORRECTION

PATENT NO. : 12,168,688 B2
APPLICATION NO. : 15/733313
DATED : December 17, 2024
INVENTOR(S) : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 651 days.

Signed and Sealed this
Twenty-fifth Day of March, 2025

Coke Morgan Stewart
*Acting Director of the United States Patent and Trademark Office*